US006617438B1

(12) United States Patent
Beigelman et al.

(10) Patent No.: US 6,617,438 B1
(45) Date of Patent: Sep. 9, 2003

(54) OLIGORIBONUCLEOTIDES WITH ENZYMATIC ACTIVITY

(75) Inventors: Leonid Beigelman, Broomfield, CO (US); Alex B. Burgin, Chula Vista, CA (US); Amber Beaudry, Broomfield, CO (US); Alexander Karpeisky, Lafayette, CO (US); Jasenka Matulic-Adamic, Boulder, CO (US); David Sweedler, Louisville, CO (US); Shawn Zinnen, Denver, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 0 days.

(21) Appl. No.: 09/476,387

(22) Filed: Dec. 30, 1999

Related U.S. Application Data

(63) Continuation-in-part of application No. 09/474,432, filed on Dec. 29, 1999, now Pat. No. 6,528,640, which is a continuation-in-part of application No. 09/301,511, filed on Apr. 28, 1999, now Pat. No. 6,482,932, which is a continuation-in-part of application No. 09/186,675, filed on Nov. 4, 1998, now Pat. No. 6,127,535.

(60) Provisional application No. 60/083,727, filed on Apr. 29, 1998, and provisional application No. 60/064,866, filed on Nov. 5, 1997.

(51) Int. Cl.$^7$ .......... C07H 21/02

(52) U.S. Cl. .......... 536/23.1; 536/25.1; 536/25.3; 536/24.5; 514/44

(58) Field of Search .......... 536/23.1, 25.1, 536/25.3, 24.5; 514/44; 435/91.1, 194, 199, 325

(56) References Cited

U.S. PATENT DOCUMENTS

| | | | | |
|---|---|---|---|---|
| 4,987,071 A | | 1/1991 | Cech et al. | |
| 5,334,711 A | | 8/1994 | Sproat et al. | |
| 5,525,468 A | | 6/1996 | McSwiggen et al. | |
| 5,589,332 A | | 12/1996 | Shih et al. | |
| 5,591,721 A | | 1/1997 | Agrawal et al. | |
| 5,616,459 A | | 4/1997 | Kramer et al. | |
| 5,627,053 A | | 5/1997 | Usman et al. | |
| 5,639,647 A | | 6/1997 | Usman et al. | |
| 5,646,042 A | | 7/1997 | Stinchcomb et al. | |
| 5,652,356 A | | 7/1997 | Agrawal | |
| 5,672,501 A | | 9/1997 | Matulic-Adamic et al. | |
| 5,672,511 A | | 9/1997 | Beigelman et al. | |
| 5,672,695 A | | 9/1997 | Eckstein et al. | |
| 5,691,141 A | | 11/1997 | Koster et al. | |
| 5,716,824 A | | 2/1998 | Beigelman et al. | |
| 5,741,679 A | | 4/1998 | George et al. | |
| 5,767,263 A | | 6/1998 | Usman et al. | |
| 5,834,186 A | | 11/1998 | George et al. | |
| 5,840,876 A | | 11/1998 | Beigelman et al. | |
| 5,871,914 A | | 2/1999 | Nathan et al. | |
| 6,043,084 A | * | 3/2000 | Scanlan et al. | |
| 6,127,535 A | * | 10/2000 | Beigelman et al. | 536/26.26 |
| 6,218,521 B1 | * | 4/2001 | Obata | |
| 6,403,373 B1 | * | 6/2002 | Scanlan et al. | |
| 6,482,932 B1 | * | 11/2002 | Beigelman et al. | 536/23.1 |
| 6,528,640 B1 | * | 3/2003 | Beigelman et al. | 536/25.1 |

FOREIGN PATENT DOCUMENTS

| | | | | |
|---|---|---|---|---|
| DE | 44 24 762 C1 | | 7/1995 | |
| WO | 91/03162 | | 3/1991 | |
| WO | 92/07065 | | 4/1992 | |
| WO | 93/15187 | | 5/1993 | |
| WO | 93/23057 | | 11/1993 | |
| WO | 93/23569 | | 11/1993 | |
| WO | 94/02595 | | 2/1994 | |
| WO | 95/04818 | | 2/1995 | |
| WO | 95/11910 | | 5/1995 | |
| WO | 95/13378 | | 5/1995 | |
| WO | 95/13380 | | 5/1995 | |
| WO | 95/23225 | | 8/1995 | |
| WO | 95/35102 | | 12/1995 | |
| WO | 96/10390 | | 4/1996 | |
| WO | 96/10391 | | 4/1996 | |
| WO | 96/10392 | | 4/1996 | |
| WO | 96/18736 | | 6/1996 | |
| WO | 96/40159 | | 12/1996 | |
| WO | 97/26270 | | 7/1997 | |
| WO | 98/13526 | | 4/1998 | |
| WO | 98/28317 | | 4/1998 | |
| WO | 98/27104 | | 6/1998 | |
| WO | 98/32880 | | 7/1998 | |
| WO | 99/04819 | | 2/1999 | |
| WO | 99/05094 | | 2/1999 | |
| WO | 99/29842 | | 6/1999 | |
| WO | WO 99/33982 A2 | * | 7/1999 | |
| WO | 99/58665 A2 | * | 11/1999 | |
| WO | 00/20621 A1 | * | 4/2000 | |
| WO | 00/24931 | | 5/2000 | |
| WO | 00/26226 | | 5/2000 | |
| WO | 00/58473 A2 | * | 10/2000 | |
| WO | 01/16312 A2 | * | 3/2001 | |
| WO | 01/57058 A2 | * | 8/2001 | |
| WO | 01/64876 A2 | * | 9/2001 | |
| WO | 01/64877 A2 | * | 9/2001 | |

OTHER PUBLICATIONS

U.S. patent application Ser. No. 60/127,607, Shimketts et al., filed Mar. 31, 1999.*

U.S. patent application Ser. No. 09/167,705, Schmidt et al., filed Oct. 6, 1998.*

U.S. patent application Ser. No. 60/085,383, Sikes et al., filed May 14, 1998.*

(List continued on next page.)

*Primary Examiner*—James O. Wilson
*Assistant Examiner*—L E Crane
(74) *Attorney, Agent, or Firm*—McDonnell Boehnen Hulbert & Berghoff

(57) ABSTRACT

Novel nucleotide triphosphates, methods of synthesis and process of incorporating these nucleotide triphosphates into oligonucleotides, and isolation of novel nucleic acid catalysts (e.g., ribozymes) are disclosed. Also, described are the use of novel enzymatic nucleic acid molecules to inhibit HER2/neu/ErbB2 gene expression and their applications in human therapy.

27 Claims, 21 Drawing Sheets

OTHER PUBLICATIONS

Chang et al., "ESX: A Structurally Unique Ets Overexpressed Early During Human Breast Tumorigenesis," *Oncogene, 14*(13), 1617–1622 (Apr. 3, 1997).*

Akhtar and Juliano, "Cellular uptake and intracellular fate of antisense oligonucleotides," *Trends in Cell Biology* 2:139–144 (1992).

Asakura and Robins, "Cerium (IV)–Mediated Halogenation at C–5 of Uracil Derivatives," *J. Org. Chem.* 55: 4928–4933 (1990).

Aurup et al., "2–Fluoro– and 2'–amino–2'–deoxynucleoside 5'–triphosphates as substrates for T7 RNA polymerase," *Biochemistry* 31:9636–9641 (1992) (Issue No. 40, Oct. 13, 1992).

Bartel and Szostak, "Isolation of New Ribozymes From a Large Pool of Random Sequences," *Science* 261:1411–1418 (1993) (Sep. 10, 1993).

Baselga et al., "Recombinant Humanized Anti–HER2 Antibody (Herceptin™) Enhances the Antitumor Activity of Paclitaxel and Doxorubicin against HER2/neu Overexpressing Human Breast Cancer Xenografts," *Cancer Research* 58:2825–2831 (1998).

Beaucage and Iyer, "The Functionalization of Oligonucleotides Via Phosphoramidite Derivatives," *Tetrahedron* 49(10):1925–1963 (1993).

Beaudry and Joyce, "Directed Evolution of an RNA Enzyme," *Science* 257:635–641 (1992) (Jul. 31, 1992).

Beaudry and Joyce, "Minimum Secondary Structure Requirements for Catalytic Activity of a Self–Splicing Group I Intron," *Biochemistry* 29:6534–6539 (1990).

Been et al., "Secondary Structure of the Self–Cleaving RNA of Hepatitis Delta Virus: Applications to Catalytic RNA Design," *Biochemistry* 31:11843–11852 (1992).

Beigelman et al., "Chemical Modification of Hammerhead Ribozymes," *The Journal of Biological Chemistry* 270(43):25702–25708 (1995).

Beigelman et al., "Synthesis of 1–Deoxy–D–Ribofuranose Phosphoramidite and the Incorporation of Abasic Nucleotides in Stem–Loop II of a Hammerhead Ribozyme," *Bioorganic & Medicinal Chemistry Letters* 4(14):1715–1720 (1994).

Bellon et al., "Amino–Linked Ribozymes: Post–Synthetic Conjugation of Half–Ribozymes," *Nucleosides & Nucleotides* 16:951–954 (1997).

Bellon et al., "Post–synthetically Ligated Ribozymes: An Alternative Approach to Iterative Solid Phase Synthesis," *Bioconjugate Chem* 8:204–212 (1997).

Benseler et al., "Hammerhead–like Molecules Containing Non–Nucleoside Linkers are Active RNA Catalysts," *J. Am. Chem. Soc.* 115:8483–8484 (1993).

Berchuk et al., "Overexpression of HER–2/neu Is Associated with Poor Survival in Advanced Epithelial Ovarian Cancer," *Cancer Research* 50:4087–4091 (1990).

Bertram et al., "Reduction of erbB2 gene product in mamma carcinoma call lines by erbB2 mRNA–specific and tyrosine kinase consensus phosphorothioate antisense oligonucleotides," *Biochemical and Biophysical Research Communications* 2000:661–667 (1994).

Beveridge, "Review of clinical studies of CA 27.29 in breast cancer management," *The International Journal of Biological Markers* 14(1):36–39 (1999).

Bonner et al., "Characterization of a set of T7 RNA polymerase active site mutants," *J. Biol. Chem.* 269:25120–25128 (1994) (Issue No. 40, Oct. 7, 1994).

Bonner et al., "Mutations in T7 RNA polymerase that support the proposal for a common polymerase active site structure," *The EMBO Journal* 11(10):3767–3775 (1992).

Breaker and Joyce, "Inventing and improving ribozyme function: rational design versus iterative selection methods," *TIBTECH* 12:268–275 (Jul., 1994).

Breaker, "Are engineered proteins getting competition from RNA?" *Current Opinion in Biotechnology* 7:442–448 (1996).

Brenner et al., "Encoded combinatorial chemistry," *Proc. Natl. Acad. Sci.* 89:5381–5383 (Jun. 15, 1992) (Issue No. 12).

Burgin et al., "Chemically Modified Hammerhead Ribozymes with Improved Catalytic Rates," *Biochemistry* 35:14090–14097 (1996) (Issue No. 45).

Burlina et al., "Chemical Engineering of Rnase Resistant and Catalytically Active Hammerhead Ribozymes," *Bioorganic & Medicinal Chemistry* 5:1999–2010 (1997).

Caruthers et al., "Chemical Synthesis of Deoxyoligonucleotides and Deoxyoligonucleotides Analogs," *Methods in Enzymology* 211:3–19 (1992).

Cech, "Ribozyme engineering," *Current Opinion in Structural Biology* 2:605–609 (1992).

Cech, "Ribozymes and Their Medical Implications," *JAMA* 260:3030–3034 (1988).

Christoffersen and Marr, "Ribozymes as Human Therapeutic Agents," *Journal of Medicinal Chemistry* 38(12):2023–2037 (1995).

Colomer et al., "erbB–2 antisense oligonucleotides inhibit the proliferation of breast carcinoma cells with erbB–2 oncogene amplification," *Br. J. Cancer* 70:819–825 (1994).

Cotten, "The in vivo application of ribozymes," *TIBTECH* 8:174–178 (1990).

Czubayko et al., "Adenovirus–mediated transduction of ribozymes abrogates HER–2/neu and pleiotrophin expression and inhibits tumor cell proliferation," *Gene Therapy* 4:943–949 (1997).

Dewey et al., "New Uridine Derivatives for Systematic Evolution of RNA Ligands by Exponential Enrichment," *J. Am. Chem. Soc.* 117:8474–8475 (1995).

Dhanalekshmi et al., "Electrochemical Behaviour of 3,3–Sigmatropic Systems–Anodic Oxidation of Aryl Allyl Ethers and Ary; Propargyl Ethers," *Tetrahedron Letters* 32:7591–7596 (1991).

Dreyfus, "Restriction Ribozymes?" *The Einstein Quarterly Journal of Biology and Medicine* 6(2):92–93 (1988).

Duval–Valentin, "Specific inhibition of transcription by triple helix–forming oligonucleotides," *Proc. Natl. Acad. Sci. USA* 89:504–508 (Jan. 1992).

Earnshaw et al., "Modified Oligoribonucleotides as Site–Specific Probes of RNA Structure and Function," *Biopolymers* 48:39–55 (1998).

Eaton et al., "Ribonucleosides and RNA," *Annu. Rev. Biochem.* 64:837–863 (1995).

Eaton, "The joys of in vitro selection: Chemically dressing oligonucleotides to satiate protein targets," *Curr. Opin. Chem. Biol.* 1:10–16 (Jun. 1997).

Egholm et al., "PNA hybridizes to complementary oligonucleotides obeying the Watson–Crick hydrogen–bonding rules," *Nature* 365:566–568 (Oct. 7, 1993).

Elkins and Rossi, "Cellular Delivery of Ribozymes," *Delivery Strategies for Antisense Oligonucleotide Therapeutics* ed. Akhtar (1995).

Freier et al., "Improved free–energy parameters for predictions of RNA duplex stability," *Proc. Natl. Acad. Sci. USA* 83:9373–9377 (1986).

Gion et al., "Comparison of the Diagnostic Accuracy of CA27.29 and CA15.3 in Primary Breast Cancer," *Clinical Chemistry* 45(5):630–637 (1999).

Gaur et al., "Novel Solid Phase Synthesis of 2'–O–Methylribonnucleoside 5'–Triphosphates and Their α–Thio Analogues," *Tetrahedron Letters* 33:3301–3304 (1992).

Guo and Collins, "Efficient trans–cleavage of a stem–loop RNA substrate by a ribozyme derived from Neurospora VS RNA," *The EMBO Journal* 14(2):368–376 (1995).

Haselhoff and Gerlach, "Simple RNA enzymes with new and highly specific endoribonuclease activities," *Nature* 334:585–591 (1988).

Hendry et al., "Using linkers to investigate the spatial separation of the conserved nucleotides $A_9$ and $G_{12}$ in the hammerhead ribozyme," *Biochimica et Biophysica Acta* 1219:405–412 (1994).

Hertel et al., "Numbering System for the Hammerhead," *Nucleic Acids Research* 20:3252 (1992).

Hobbs, "Palladium–Catalyzed Synthesis of Alkynylamino Nucleosides. A Universal Linker for Nucleic Acids," *J. Org. Chem.* 54: 3420–3422 (1989).

Huang et al., "Determinants of Ribose Specificity in RNA Polymerization: Effects of $Mn^{2+}$ and Deoxynucleoside Monophosphate Incorporation into Transcripts," Biochemistry 36: 13718–13728 (1997).

Huang et al., "Mechanism of ribose 2' group discrimination by an RNA polymerase," *Biochemistry* 36:8231–8242 (1997).

Hung et al., "HER–2/neu–targeting gene therapy—a review," *Gene* 159:65–71 (1995).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995) (Issue No. 6, Jun. 1995).

Jaeger et al., "Improved predictions of secondary structures for RNA," *Proc. Natl. Acad. Sci. USA* 86:7706–7710 (1989).

Jaeger et al., "[17] Predicting Optimal and Suboptimal Secondary Structure for RNA," *Methods in Enzymology* 183:281–306 (1990).

Jarvis et al., "Inhibition of Vascular Smooth Muscle Cell Proliferation by Hammerhead Ribozymes Targeting C–Myb," Journal of Cellular Biochemistry 19A:221 (1995) (Abstract only XP 002024063).

Jarvis et al., "Optimizing the Cell Efficacy of Synthetic Ribozymes," *Journal of Biological Chemistry* 271:29107–29112 (1996).

Jeffries and Symons, "A catalytic 13–mer ribozyme," *Nucleic Acids Research* 17:1371–1377 (1989).

Joyce et al., "Amplification, mutation and selection of catalytic RNA," *Gene* 82:83–87 (1989).

Joyce, "Choosing the right sugar: How polymerases select a nucleotide substrate," *Proc. Natl. Acad. Sci.* 94:1619–1622 (1997) (Issue No. 5, Mar. 4, 1997).

Joyce, "Directed Molecular Evolution," *Scientific American* 267:90–97 (Dec. 1992).

Kappler et al., "Isozyme–Specific Enzyme Inhibitors. 10 Adenosine 5'–Triphosphate Derivatives as Substrates of Inhibitors of Methioine Adenosyltransferases of Rat Normal and Hepatoma Tissues," *J. Med. Chem.* 29:318–322 (1986).

Karpeisky et al, "Highly Efficient Synthesis of 2'–O–Amino Nucleosides And Their Incorporation in Hammerhead Ribozymes," *Tetrahedron Letters* 39:1131–1134 (1998).

Kim and Cech, "Three–dimensional model of the active site of the self–splicing rRNA precursor of Tetrahymena," *Proc. Natl. Acad. Sci. USA* 84:8788–8792 (1987).

Kovacs and Otvos, "Simple Synthesis of 5–Vinyl– and 5–Ethynyl–2'–Deoxyuridine–5'–Triphosphates," *Tetrahedron Letters* 29:4525–4528 (1988).

Kumar and Ellington, "Artificial evolution and natural ribozymes," *FASEB J.* 9:1183–1195 (Sep. 1995).

Lasic and Needham, "The 'Stealth' Liposome: A Prototypical Biomaterial," *Chemical Reviews* 95:2601–2627 (1995) (Issue No. 8, Dec. 1995).

Lasic and Papahadjopoulos, "Liposomes Revisited," *Science* 267:1275–1276 (Mar. 3, 1995).

Limbach et al., "Summary: the modified nucleosides of RNA," *Nucleic Acids Research* 22(12):2183–2196 (1994) (Issue No. 12).

Lin et al., "Modified RNA sequence pools for in vitro selection," *Nucleic Acids Research* 22:5229–5234 (1994) (Issue No. 24, Dec. 11, 1994).

Liu et al., "Cationic Liposome–mediated Intravenous Gene Delivery," *J. Biol. Chem.* 270(42):24864–24870 (1995) (Oct. 20, 1995).

Long and Uhlenbeck, "Kinetic characterization of intramolecular and intermolecular hammerhead RNAs with stem II deletions," *Proc. Natl. Acad. Sci. USA* 91:6977–6981 (1994).

Lu and Wimmer, "Poliovirus chimeras replicating under the translational control of genetic elements of hepatitis C virus reveal unusual properties of the internal ribosomal entry site of hepatitis C virus," *Proc. Natl. Acad. Sci. USA* 93:1412–1417 (1996).

Ludwig, "A New Route to Nucleoside 5'–Triphosphates," *Acta Biochim. Biophys. Acad. Sci. Hung.* 16:131–133 (1981) (Issue No. 3–4).

Ludwig, "A simple one flask synthesis of nucleoside 5'–triphosphate from unprotected nucleosides via nucleoside 5'–cyclotriphosphates," Biophosphates and Their Analogues–Synthesis, Structure, Metabolism and Activity 201–204 (1987).

Ludwig and Eckstein, "Rapid and Efficient Synthesis of Nucleoside 5'–O–(1–Thiotriphosphates), 5'–Triphosphates and 2',3'–Cyclophosphorothioates Using 2–Chloro–4H–1,3, 2–Benzodioxaphosphorin–4–one," *J. Org. Chem.* 54:631–635 (1989).

Lüftner et al., "c–erbB–2 in serum of patients receiving fractionated paclitaxel chemotherapy," *The International Journal of Biological Markers* 14(2):55–59 (1999).

Maguire et al., "The neu (c–erbB–2) Oncogene," *Seminars in Oncology* 16(2):148–155 (1989).

Matulic–Adamic et al., "Functionalized Nucleoside 5'–triphosphates for In Vitro Selection of New Catalytic Ribonucleic Acids," *Bioorganic & Medicinal Chemistry Letters* 10: 1299–1302 (2000).

Matulic–Adamic et al., "Synthesis of 3–(β–D–Ribofuranosyl)–2–fluoropyridine and 3–(β–D–Ribofuranosyl)–Pyridine–2–one," *Tetrahedron Letter* 38:203–206 (1997) (#2, Jan. 13, 1997).

Matulic–Adamic et al., "Synthesis of 3–(β–D–Ribofuranosyl)–Pyridin–2–one: A 'deletion–modified' analogue of uridine," *Tetrahedron Letter* 38:1669–1672 (1997) (#10, Mar. 10, 1997).

McCall et al., "Minimal sequence requirements for ribozyme activity," *Proc. Natl. Acad. Sci. USA* 89:5710–5714 (1992).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Mitra et al., "A mammalian 2–5A system functions as an antiviral pathway in transgenic plants," *Proc. Natl. Acad. Sci. USA* 93:6780–6785 (1996).

Moore and Sharp, "Site–Specific Modification of Pre–m-RNA: The 2'–Hydroxyl Groups at the Splice Sites," *Science* 256:992–996 (1992).

Mukhopadhyay and Roth, "Antisense Regulation of Oncogenes in Human Cancer," *Critical Reviews in Oncogenesis* 7:151–190 (1996).

Nathans et al., "Restriction Endonucleases in the Analysis and Restructuring of DNA Molecules," *Annual Review of Biochemistry* 44:273–293 (1975).

Nyilas, "Synthesis of pppA2'p5'A2'p5'A y–amidates by one pot procedure form A2'p5'A2'p5'A," *Tetrahedron Letters*. vol. 38, No. 14, 2517–2518 (1997).

Oku et al., "Real–time analysis of liposomal trafficking in tumor–bearing mice by use of positron emission tomography," *Biochemica et Biophysica Acta* 1238:86–90 (1995).

Olsen et al., "Study of a Hammerhead Ribozyme Containing 2'–Modified Adenosine Residues," *Biochemistry* 30:9735–9741 (1991).

Padilla and Sousa, "Efficient synthesis of nucleic acids heavily modified with non–canonical ribose 2'–groups using a mutant T7 RNA polymerase (RNAP)," *Nucleic Acids Research* vol. 27, No. 6 1561–1563 (1999).

Pan et al., "Properties of an In Vitro Selected $Pb^{2+}$ Cleavage Motif," *Biochemistry* 33:9561–9565 (1994).

Pegram et al, "Phase II Study of Receptor–Enhanced Chemosensitivity Using Recombinant Humanized Anti–$p185^{HER/neu}$ Monoclonal Antibody Plus Cisplatin in Patients With HER2/neu–Overexpressing Metastatic Breast Cancer Refractory to Chemotherapy Treatment," *Journal of Clinical Oncology* 16(8):2659–2671 (1998).

Peoc'h et al., "Synthesis and Evaluation of 2'–Modified MMI Linked Dimers in Antisense Constructs," *Nucleosides & Nuclerotides* 16:959–626 (1997).

Perrault et al., "Mixed deoxyribo– and ribo– oligonucleotides with catalytic activity," *Letters to Nature* 344:565–567 (1990).

Pieken et al., "Kinetic Characterization of Ribonuclease–Resistant 2'–Modified Hammerhead Ribozymes," *Science* 253:314–317 (1991).

Player and Torrence, "The 2–5A System: Modulation of Viral and Cellular Processes Through Acceleration of RNA Degradation," *Pharmacol Ther. J*78:55–113 (1998).

Rodriguez de Paterna et al., "Study of serum tumor markers CEA, CA 15.3 and CA 27.29 as diagnostic parameters in patients with breast carcinoma," *The International Journal of Biological Markers* 10(1):24–29 (1995).

Ross et al., "The HER–2/neu Oncogene in Breast Cancer: Prognostic Factor, Predictive Factor, and Target for Therapy," *The Oncologist* 3:237–252 (1998).

Ruffner et al., "Sequence of Requirements of the Hammerhead RNA Self–Cleavage Reaction," *Biochemistry* 29:10695–10702 (1990).

Sakthivel and Barbas, "Expanding the Potential of DNA for Binding and Catalysis: Highly Functionalized dUTP Derivatives That Are Substrates for Thermostable DNA Polymerases," Angew. *Chem. Int. Ed.* 37, No. 20, 2872–2875 (1998).

Sambrook et al., "Molecular Cloning: A Laboratory Manual," *Cold Spring Harbor Laboratory Press*.

Santoro et al., "A general purpose RNA–cleaving DNA enzyme," *Proc. Natl. Acad. Sci. USA* 94:4262–4266 (1997).

Scaringe et al., "Chemical synthesis of biologically active oligoribonucleotides using β–cyanoethyl protected ribonucleoside phosphoramidites," *Nucleic Acids Research* 18:5433–5441 (1990).

Shabarova et al., "Chemical ligation of DNA: The first non–enzymatic assembly of a biologically active gene," *Nucleic Acids Research* 19:4247–4251 (1991).

Silverman et al., "Selective RNA Cleavage by Isolated Rnase L Activated with 2–5A Antisense Chimeric Oligonucleotides," *Methods in Enzymology* 313:522–533 (1999).

Slamon et al., "Human Breast Cancer: Correlation of Relapse and Survival with Amplification of the HER–2/neu Oncogene," *Science* 235:177–182 (1987).

Sousa et al., "A mutant T7 RNA polymerase as a DNA polymerase," *EMBO J.* 14:4609–4621 (1995) (Issue No. 19, Sep. 15, 1995).

Sparano, "Doxorubicin/Taxane Combinations: Cardiac Toxicity and Pharmacokinetics," *Seminars in Oncology* 26(3):14–19 (1999).

Stein and Cheng, "Antisense Oligonucleotides as Therapeutic Agents—Is the Bullet Really Magical?" *Science* 261:1004–1288 (1993) (Aug. 20, 1993).

Stull et al., "Antigene, Ribozyme and Aptamer Nucleic Acid Drugs: Progress and Prospects," *Pharmaceutical Research* 12:465–483 (1995) (Issue No. 4).

Sugiyama et al., "Catalytic activities of hammerhead ribozymes with a triterpenoid linker instead of stem/loop II," *FEBS Letters* 392:215–219 (1996).

Surveillance, Epidemiology and End Results Program (SEER) Cancer Statistics Review: http://www.seer.ims.nci.nih.gov/Publications/CSR1973–1996/.

Suzuki et al., "Anti–cerb–B–2 Ribozyme for Breast Cancer," *Methods in Molecular Medicine: Therapeutic Applications of Ribozymes* 11:223–239.

Szostak, "In Vitro Genetics," *TIBS* 17:89–93 (1993) (Mar. 1992).

Thomson et al., "In vitro selection of hammerhead ribozymes containing a bulged nucleotide in stem II," *Nucleic Acids Research* 24(22):4401–4406 (1996).

Torrence et al., "Targeting RNA for degradation with a (2'–5') oligoadenylate–antisense chimera," *Proc. Natl. Acad. Sci. USA* 90:1300–1304 (1993) (Feb. 1993).

Turner et al., "Free Energy Increments for Hydrogen Bonds in Nucleic Acid Base Pairs," *J. Am. Chem. Soc.* 109:3783–3785 (1987).

Turner et al., "Improved Parameters for Prediction of RNA Structure," *Cold Spring Harbor Symposium on Quantitative Biology* LII:123–133 (1987).

Uhlenbeck, "A small catalytic oligribonucleotide," *Nature* 328:596–600 (1987).

Usman and Cedergren, "Exploiting the chemical synthesis of RNA," *TIBS* 17:334–339 (1992).

Usman and McSwiggen, "Chapter 30. Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of and *Escherichia coli* Formylmethionine tRNA," *Journal of the American Chemical Society* 109:7845–7854 (1987).

Usman et al., "Chemical modification of hammerhead ribozymes: activity and nuclease resistance," *Nucleic Acids Symposium Series* 31:163–164 (1994).

Usman et al., "Hammerhead ribozyme engineering," *Current Opinion in Structural Biology* 1:527–533 (1996).

Vartanian et al., "Hypermutagenic PCR involving all four transitions and a sizeable proportion of transversions," *Nucleic Acids Research* 24:2627–2631 (1996).

Vaughn et al., "Antisense DNA Downregulation of the ERBB2 Oncogene Measured by a Flow Cytometric Assay," *Proc. Natl. Acad. Sci. USA* 92:8338–8342 (1995).

Verma and Eckstein, "Modified Oligonucleotides: Synthesis and Strategy for Users," *Annu. Rev. Biochem.* 67:99–134 (1998).

Wang et al., "Translation of Human Hepatitis C Virus RNA in Cultured Cells is Mediated by an Internal Ribosome––Binding Mechanism," *Journal of Virology* 67:3338–3344 (1993).

Wiechen et al., "Selection of a high activity c–erbB–2 ribozyme using a fusion gene of c–erbB–2 and the enhanced green fluorescent protein," *Cancer Gene Therapy* 5(1):45–51 (1998).

Wieczorek et al., "Evidence that total substitution of adenine with 7–deaza–adenine in the HDV antigenomic ribozyme changes the kinetics of RNA folding," *Bioorganic & Medicinal Chemistry Letters* 4:987–994 (1994) (Issue No. 8).

Williams et al., "Function of specific 2'–hydroxyl groups of guanosines in a hammerhead ribozyme probed by 2' modifications," *Proc. Natl. Acad. Sci. USA* 89:918–921 (1992).

Wincott et al., "Synthesis, deprotection, analysis and purification of RNA and ribozymes," *Nucleic Acids Research* 23:2677–2684 (1995).

Wincott et al., "A Practical Method for the Production of RNA and Ribozymes," *Methods in Molecular Biology* 74:59–69 (1997).

Wright et al., "An intracellular anti–erbB–2 single–chain antibody is specifically cytotoxic to human breast carcinoma cells overexpressing erbB–2," *Gene Therapy* 4:317–322 (1997).

Wu–Pong, "Oligonucleotides: Opportunities for Drug Therapy and Research," *Biopharm* 20–33 (1994).

Yoshikawa et al., "Studies of Phosphorylation. III. Selective Phosphorylation of Unprotected Nucleosides," *Bulletin of the Chemical Society of Japan* 42:3505–3508 (1969).

Zaug et al., "The Tetrahymena ribozyme acts like an RNA restriction endonuclease," *Nature* 324:429–433 (1986).

Zuker, "A comparison of optimal and suboptimal RNA secondary structures predicted by free energy minimization with structures determined by phylogenetic comparison," Nucleic Acids Research, 19: 2707–2714 (1991).

Zuker, "On Finding all Suboptimal Foldings of an RNA Molecule," *Science* 244:48–52 (1989).

Dyer, R.L.; Jones, A.S.; Walker, R.T., "The Synthesis of E–5–(2–Bromovinyll)–2'–deoxyuridine from 2'–Deoxy–5–iodouridine," *Nucleic Acid Chemistry* 79–89 (1991).

Tarasow and Eaton, "Dressed for Success: Realizing the Catalytic Potential of RNA," *Biopolymers* 48: 29–37 (1998).

* cited by examiner

Figure 1: One-Pot Formation of Nucleoside-5'-triphosphates
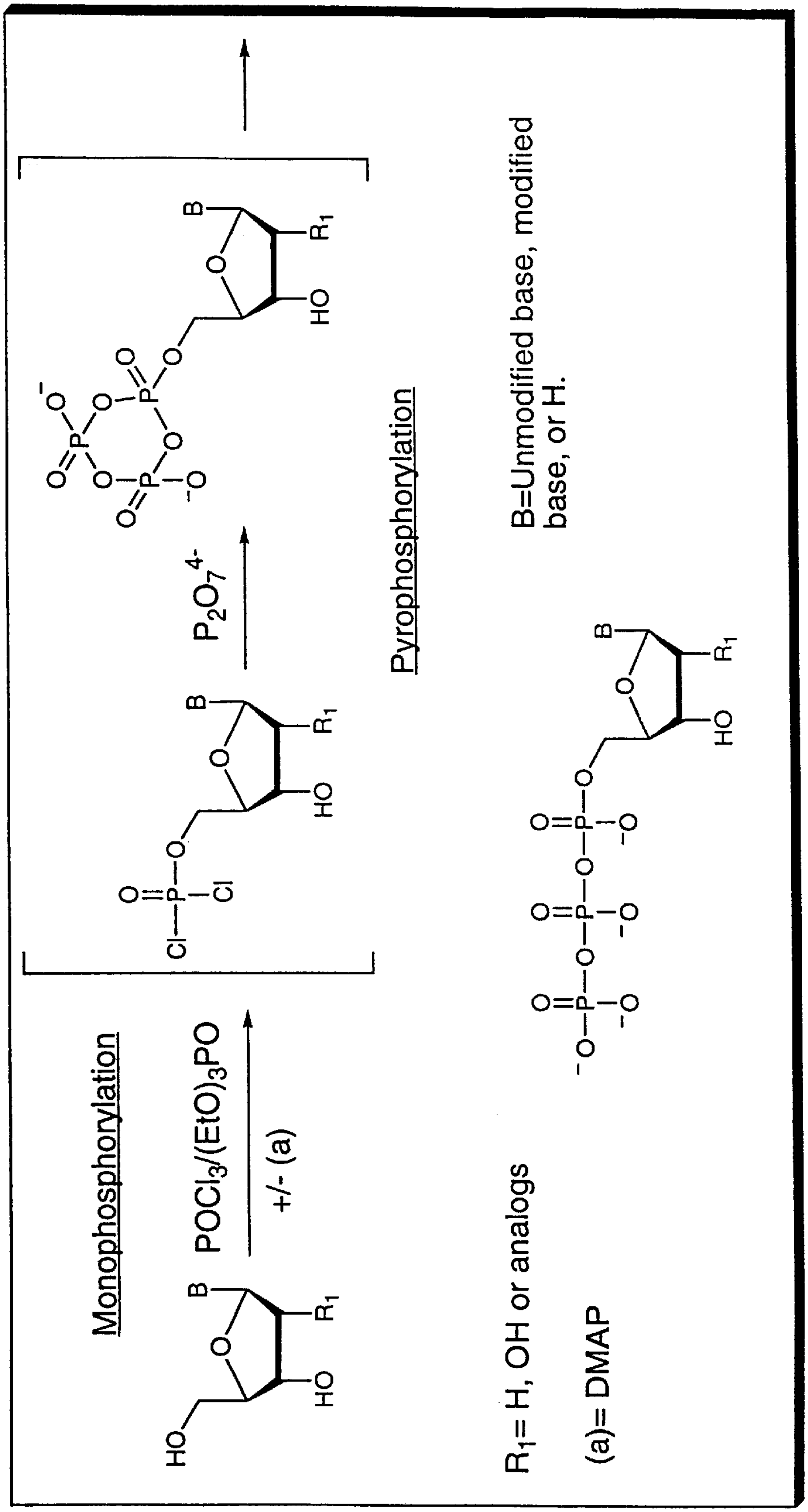

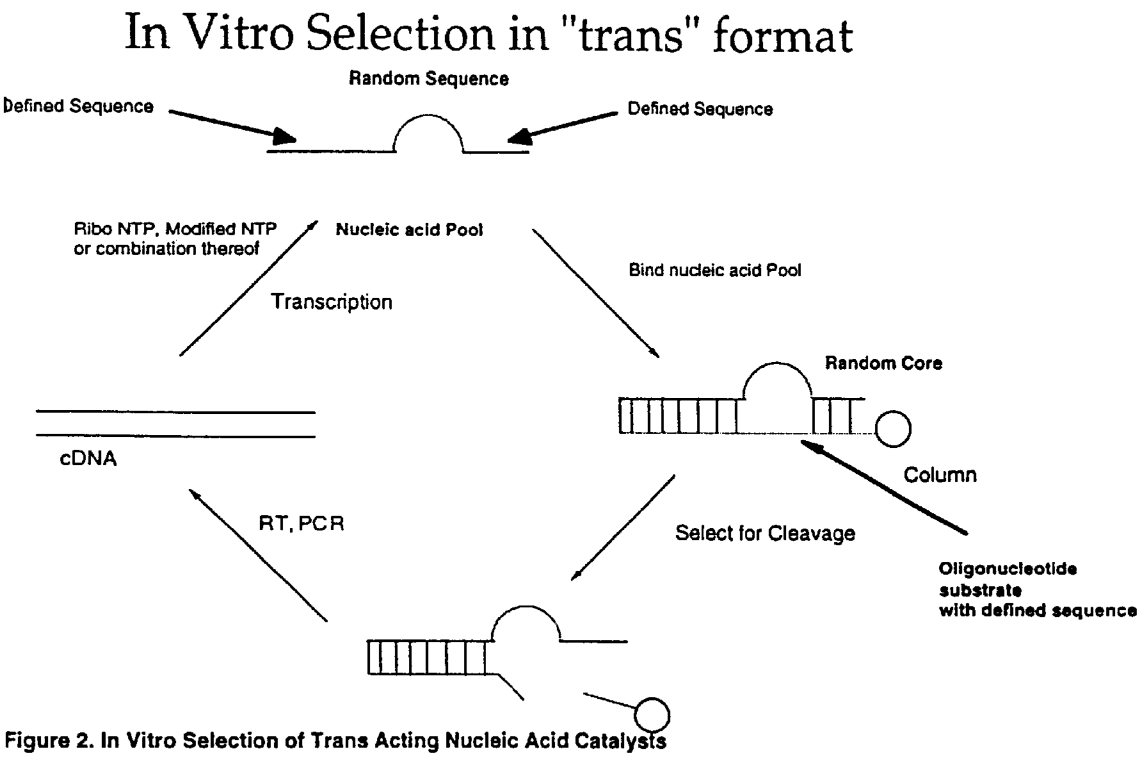
Figure 2. In Vitro Selection of Trans Acting Nucleic Acid Catalysts

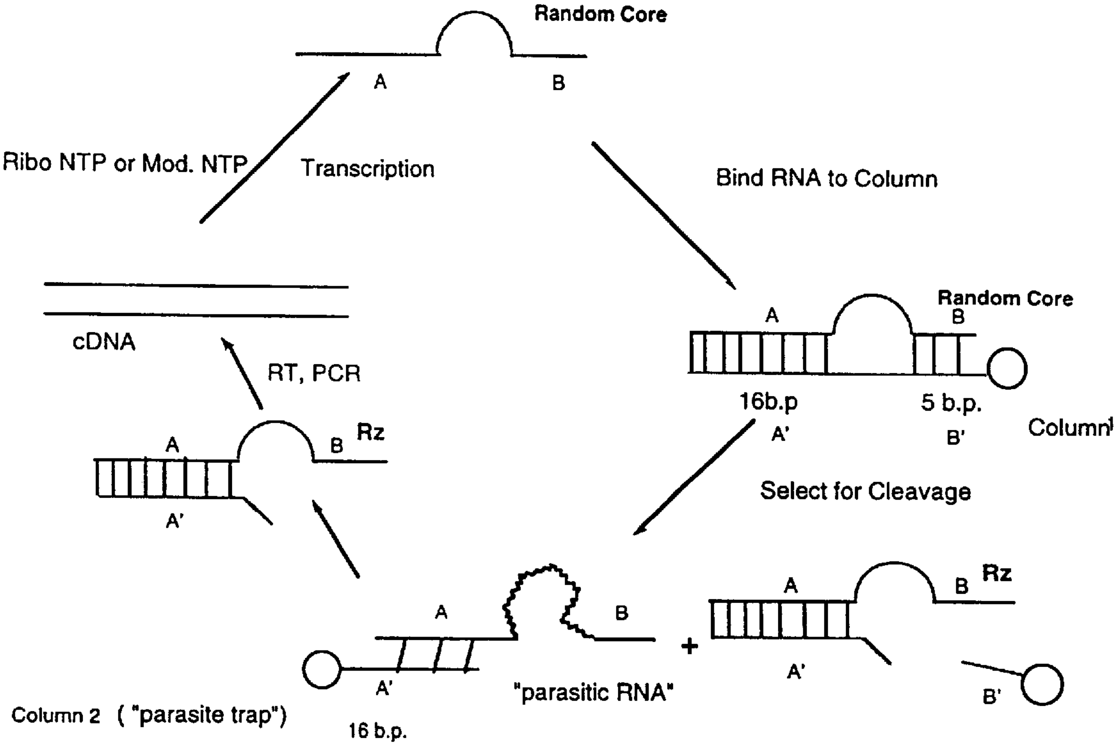
Figure 3. Removal of "parasitic RNA" using a Second Selection column

*Figure 4: 2'-O-Me Stabilization of a Class I Enzymatic Nucleic Acid Motif*
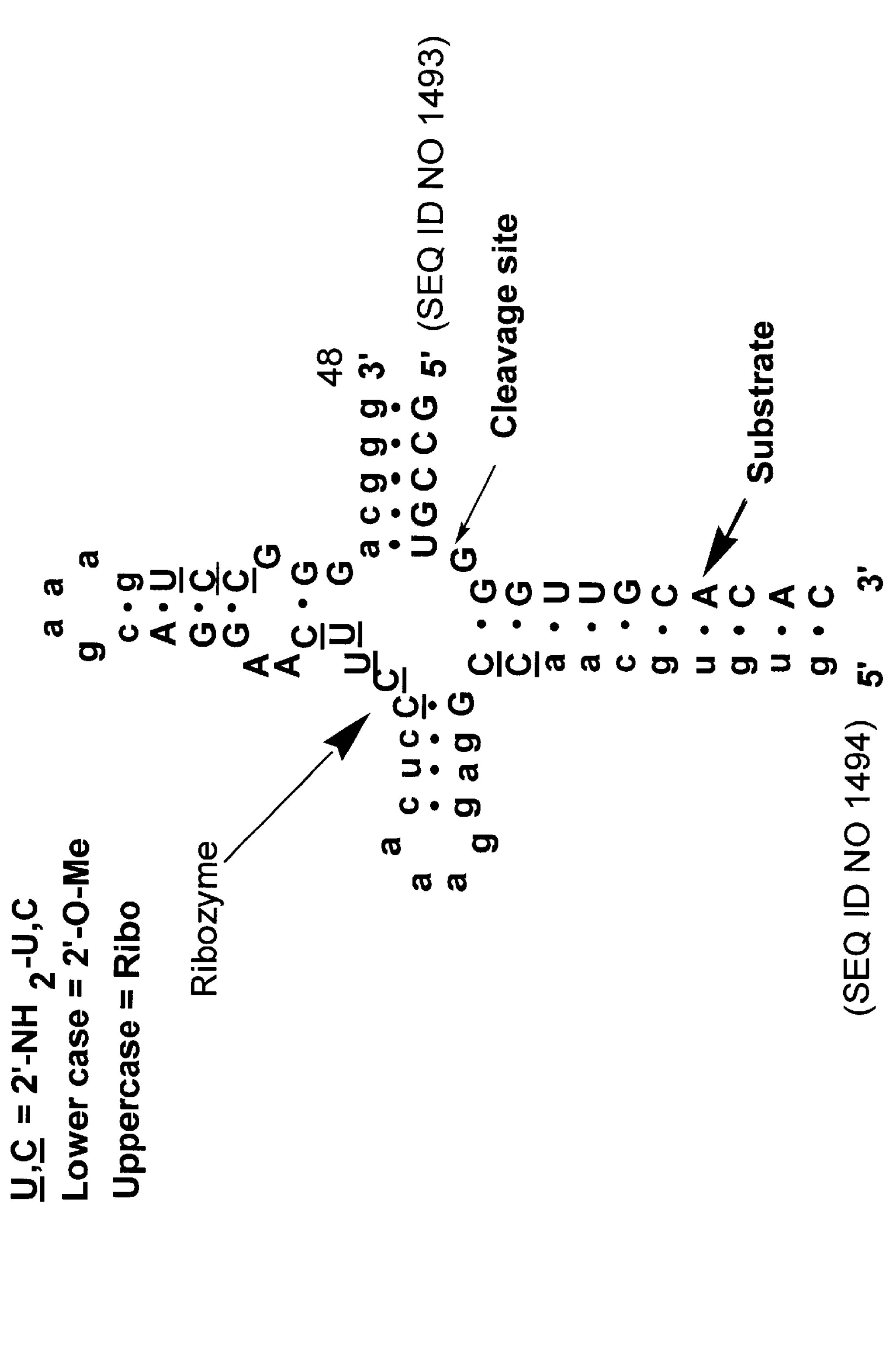

FIGURE 5. Dual Reporter System for Cytoplasmic HCV Target
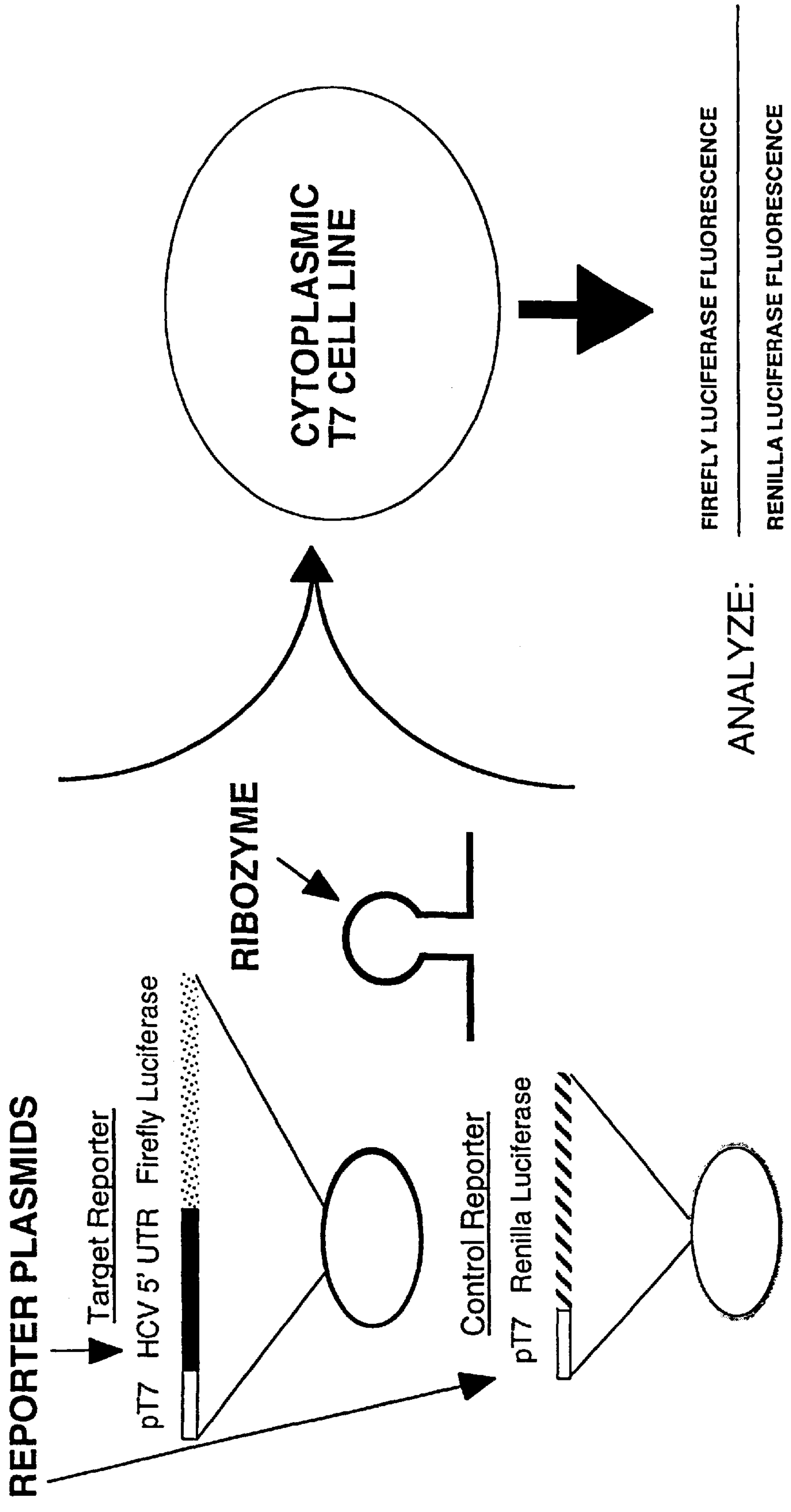

*Figure 6. Dose-dependent inhibition of HCV-IRES mediated luciferase activity*
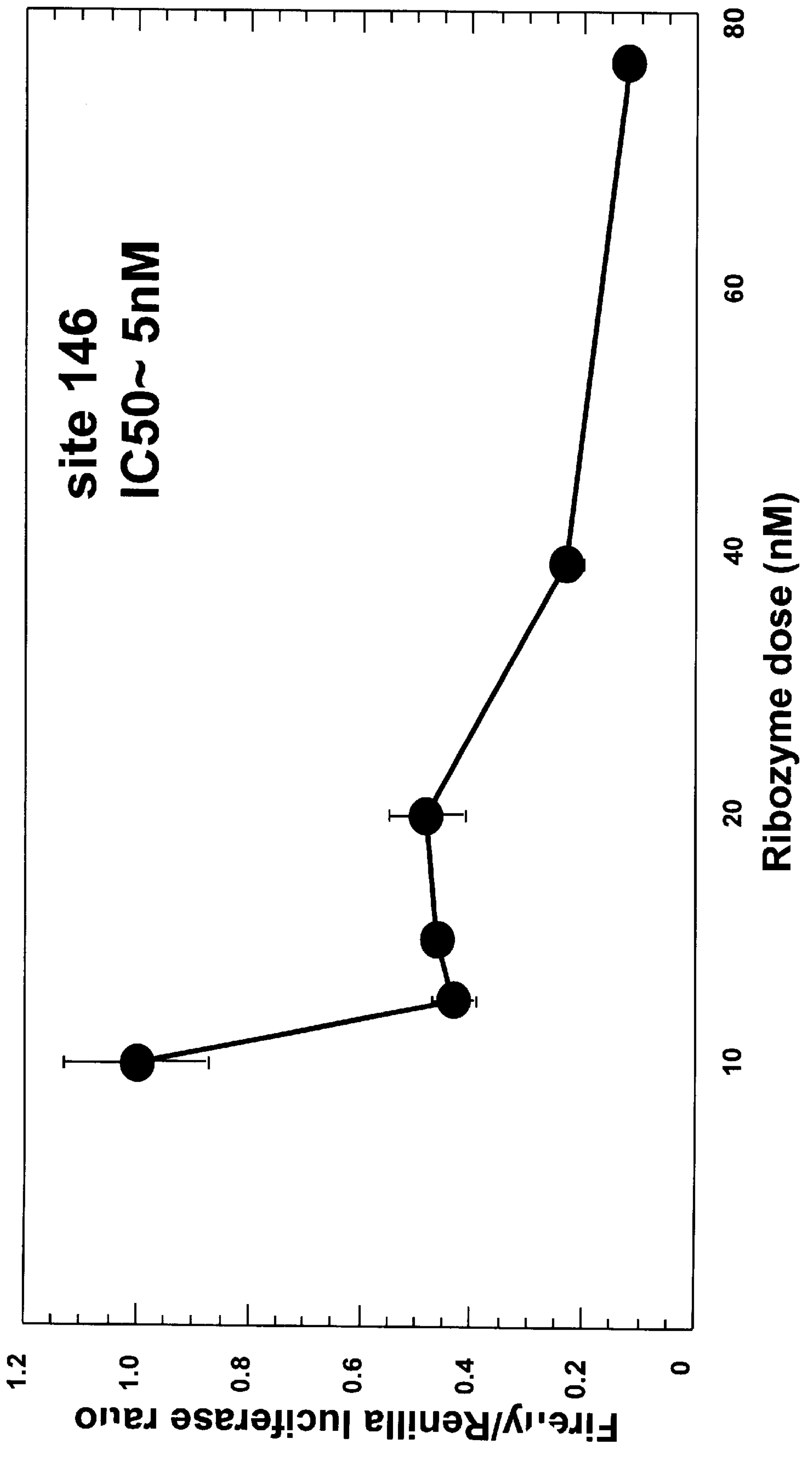

Figure 7. Efficacious Ribozymes Targeting 5'UTR HCV RNA
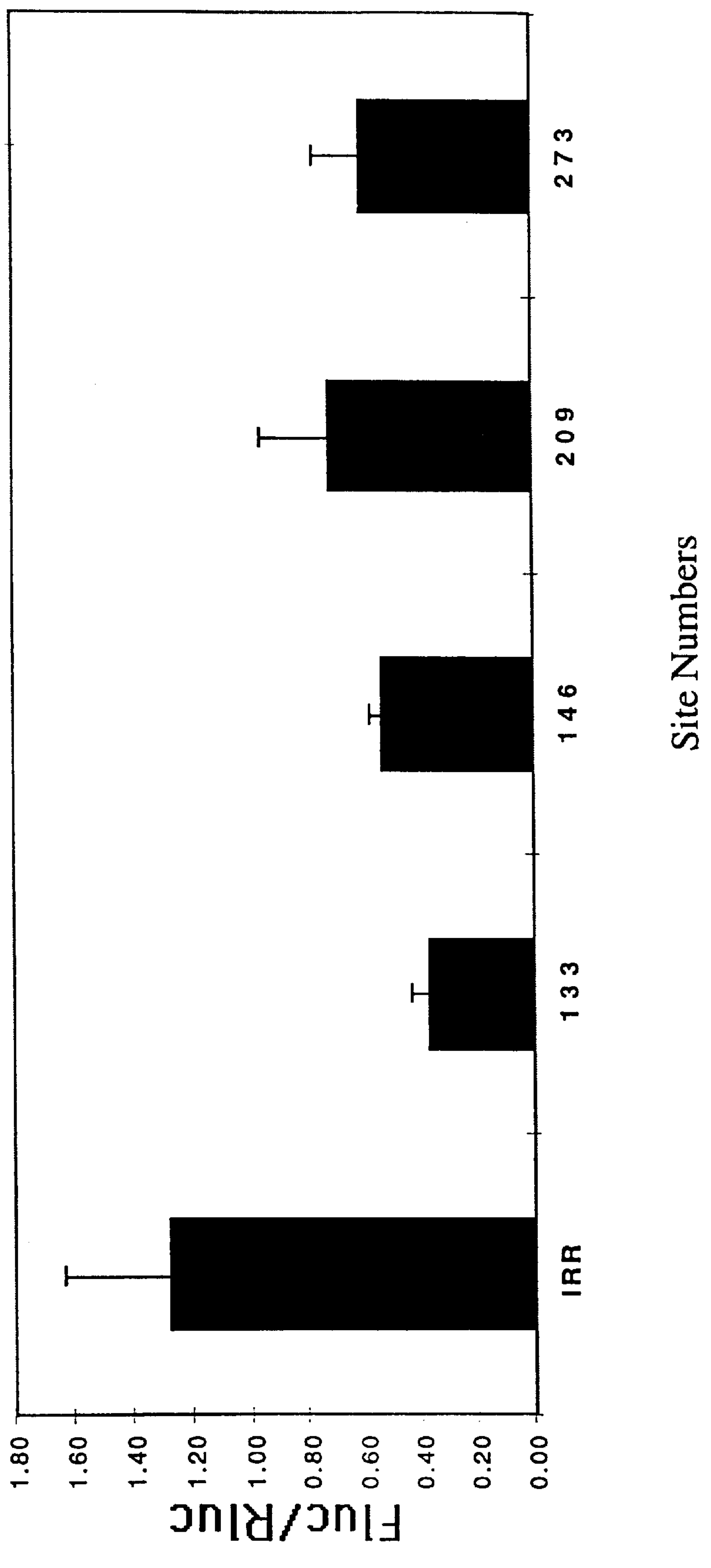
Sequence and chemical compositions for site numbers are given in table XIII

Fig. 8a Class II Enzymatic Nucleic Acid Motifs
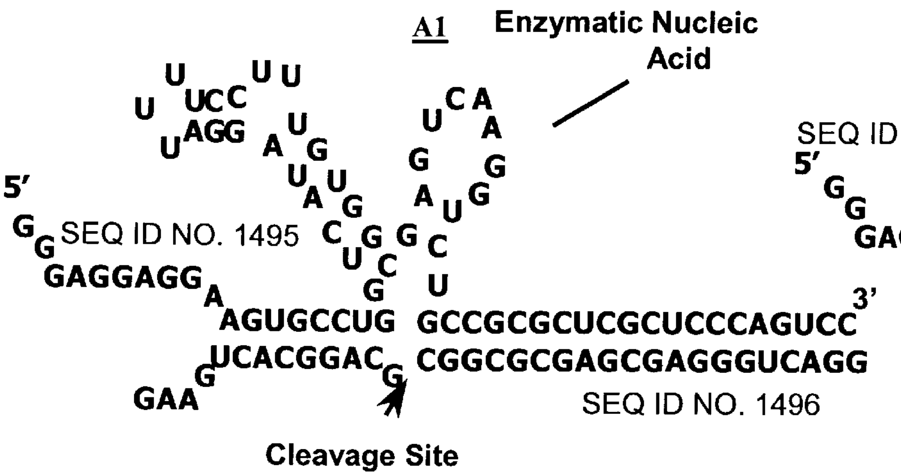
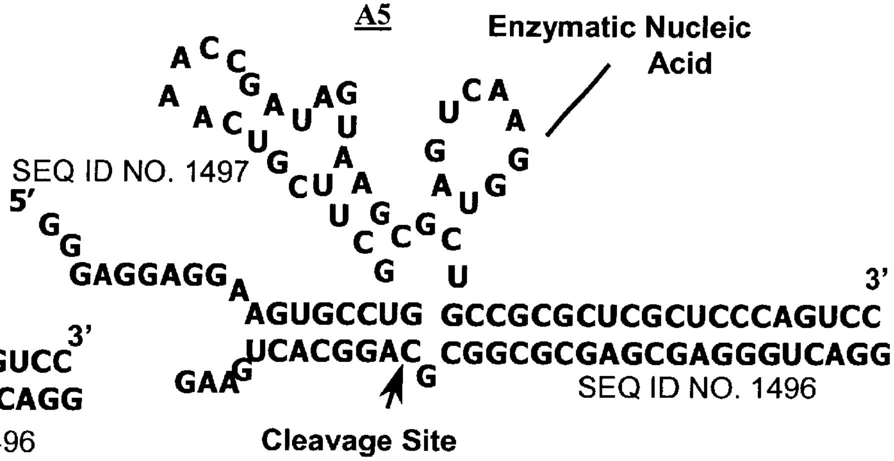
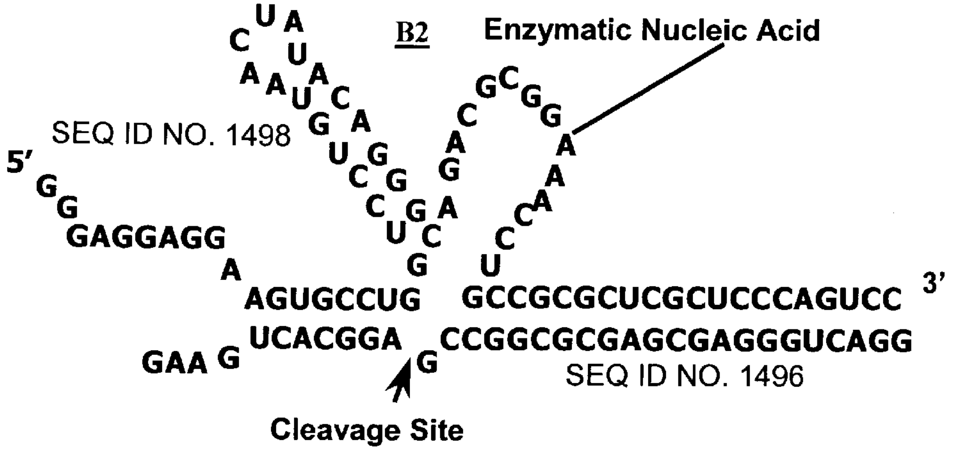
These motifs can all cleave with minimizations in the binding arms (7/7) and not significantly affect rate. All cytosine residues are 2'-$NH_2$ modified.

*Fig. 8b Class II Enzymatic Nucleic Acid Motifs*
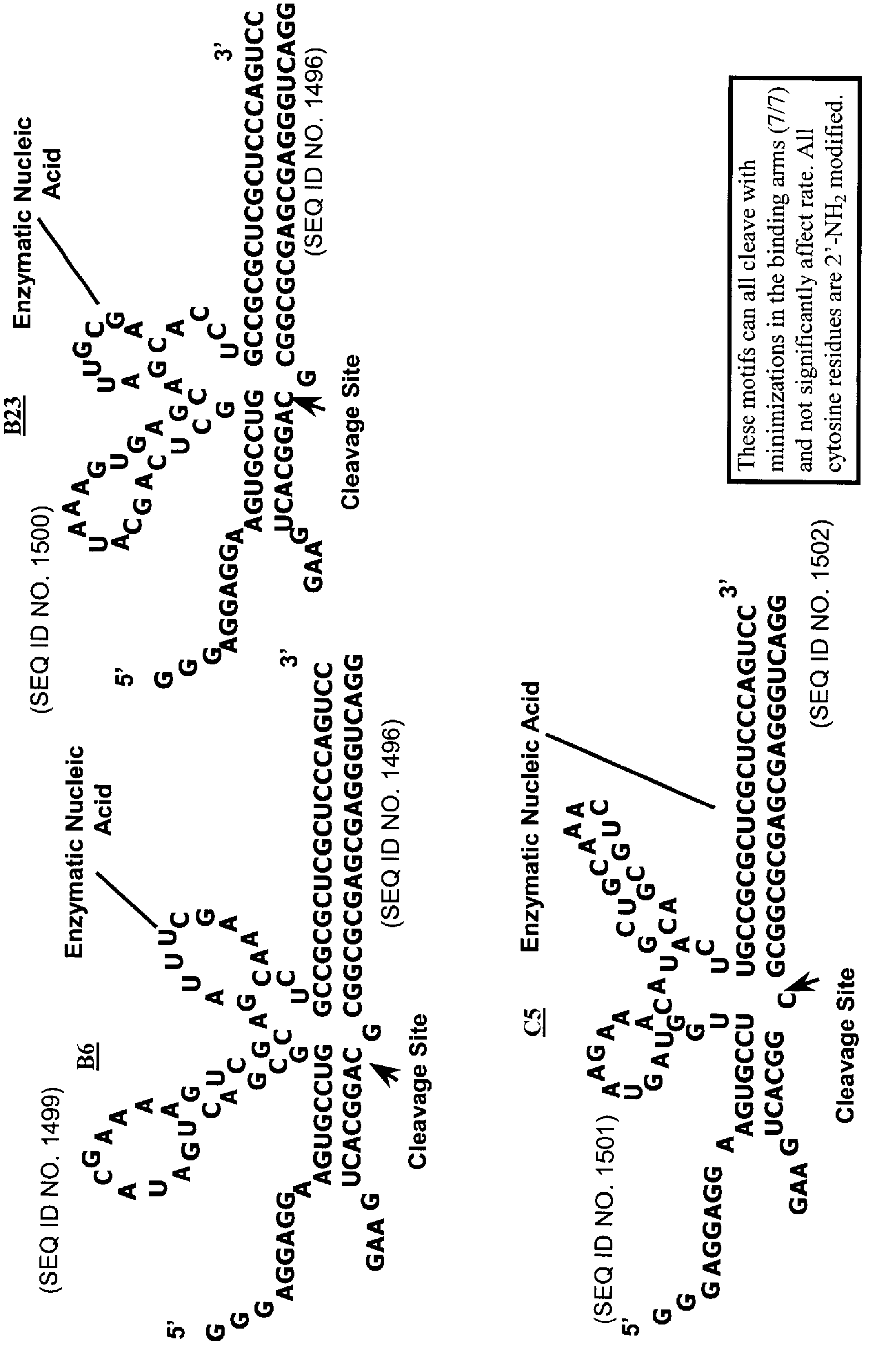

*Figure 9: Chemically Stabilized Class II Motif* 400/009
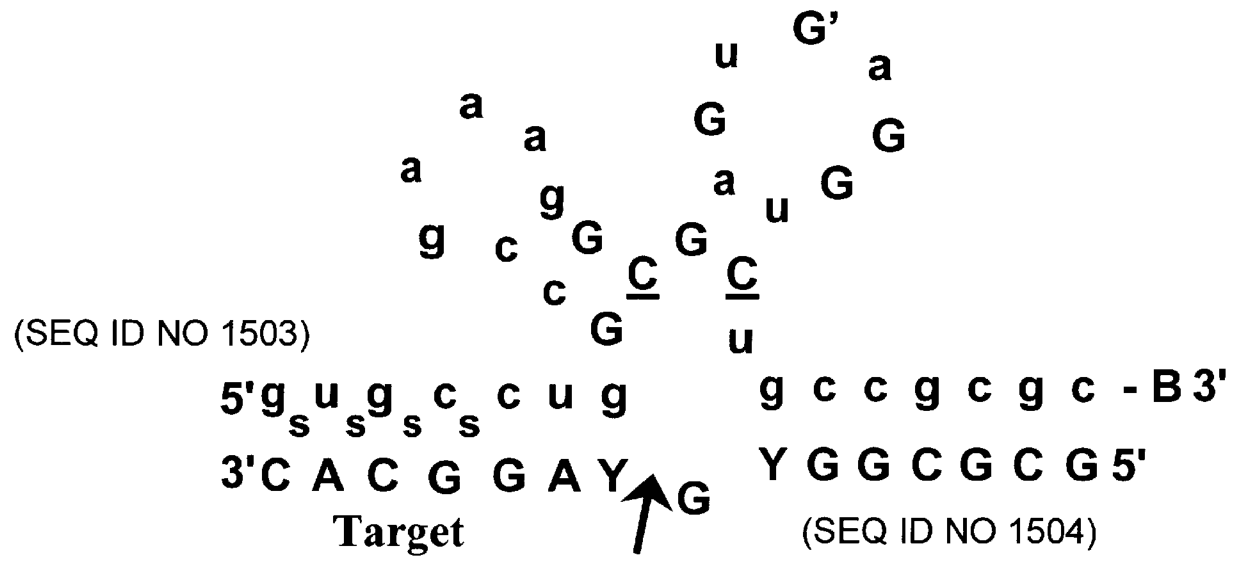
Legend
Uppercase indicates natural ribo residues
C indicates 2'- d-$NH_2$-C
Lowercase: 2'-O-Me
Subscript "s" indicates phosphothioate linkage
B: 3'- 3' abasic moiety
All ribo G's can be replaced with 2'O-methyl G
The gaaa tetraloop can be replaced by 18 atom polyethylene glycol (Spacer)
G' can be G, ca, or caa
Y = U or C Figure 10: Substrate specificities of Class II (zinzyme) ribozymes
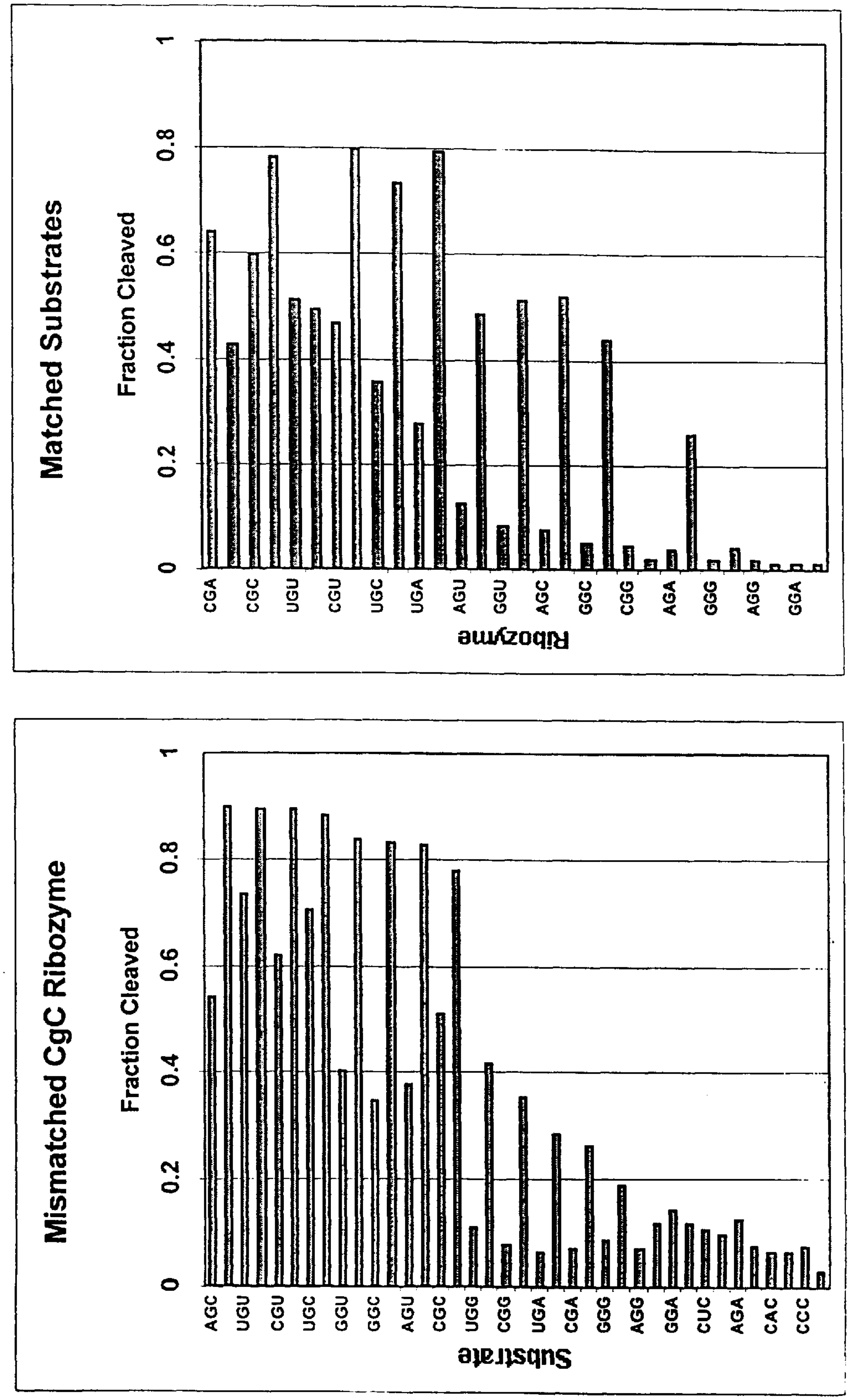

*Figure 11: Representative data of HER2 cell proliferation primary screen of Class II (zinzyme) Ribozymes*
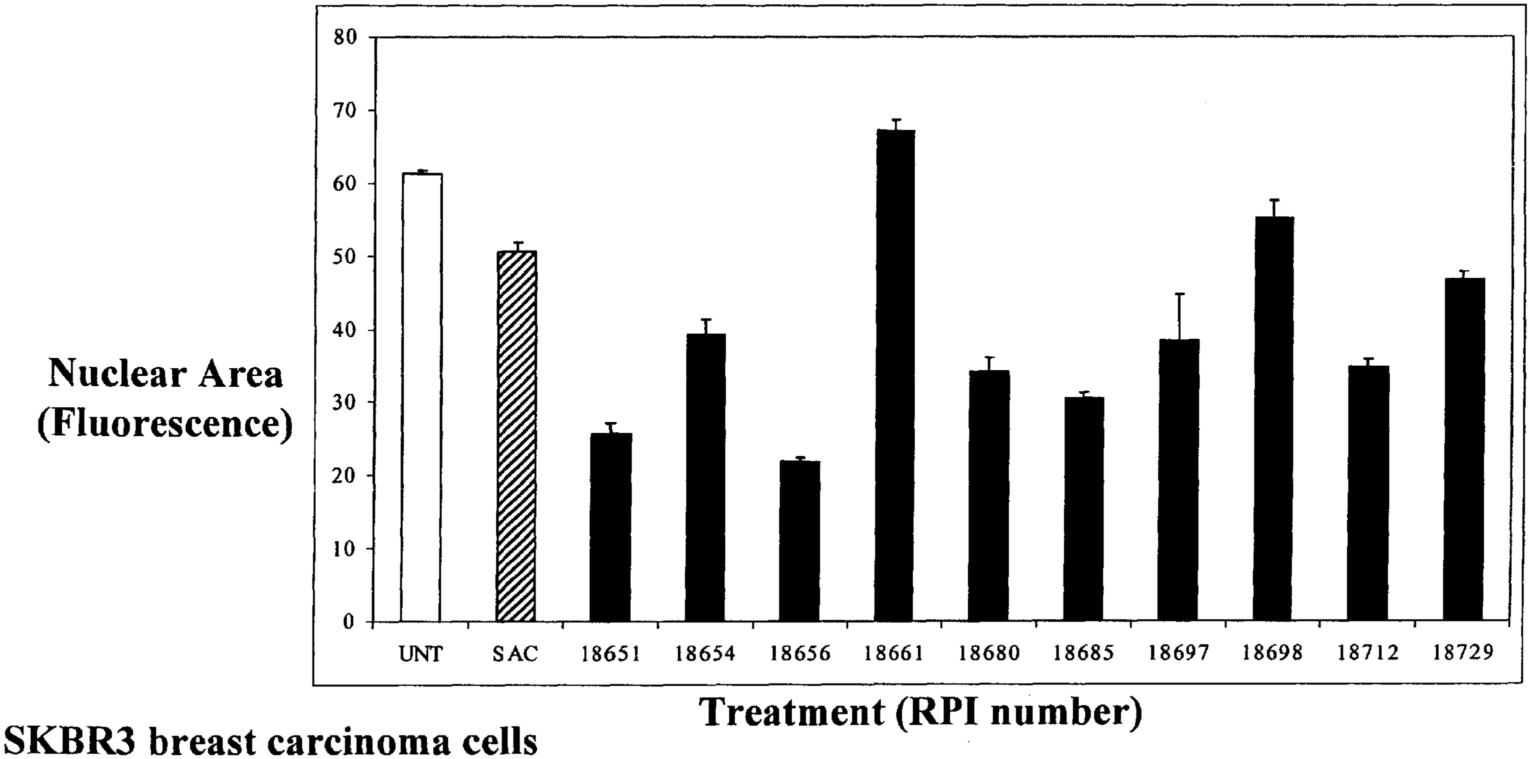
SKBR3 breast carcinoma cells
2 µg/mL RPI.9649 (lipid)
200 nM ribozymes
120 hour timepoint
UNT = untreated
SAC = scrambled attenuated control

Figure 12: Synthesis of 5-[3-aminopropynyl(propyl)]uridine 5'-triphosphates and 4-imidazoleacetic acid conjugates

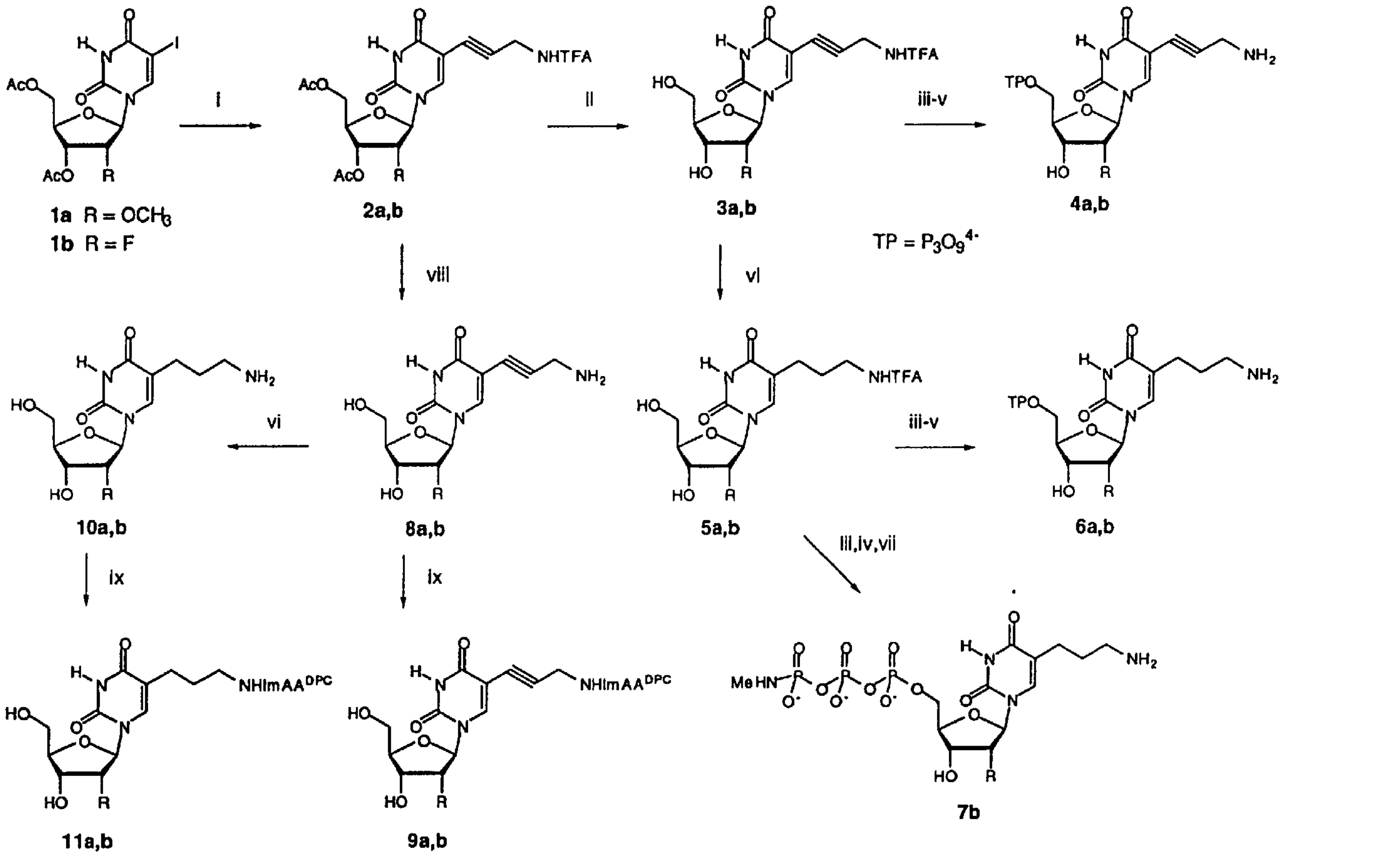

Reagents and Conditions: (I) *N*-TFA propargylamine, CuI, tetrakis($Ph_3P$)Pd(0), $Et_3N$, DMF, 16 h, (ii) aq NaOH, pyr, MeOH, 0 °C, 1 h, (iii) $POCl_3$, Proton-Sponge, $(EtO)_3PO$, 2 h, (iv) *n*-$Bu_3N$ PPi, MeCN, 15 min., (v) 1M $Et_3NH^+HCO_3^-$, then $NH_4OH$, 16 h, (vi) $H_2$, 5% Pd-C, 24 h, 40 psi, (vii) 40% $MeNH_2$, 3 h, (viii) $NH_4OH$, 4 °C, 16 h, (ix) $ImAA^{DPC}$, EDCHCl, DMF, 16 h.

Figure 13: Synthesis of 5-[3-(N-4-imidazoleacetyl0aminopropynyl(propyl)]uridine 5'-triphosphates
9a,b
11a,b
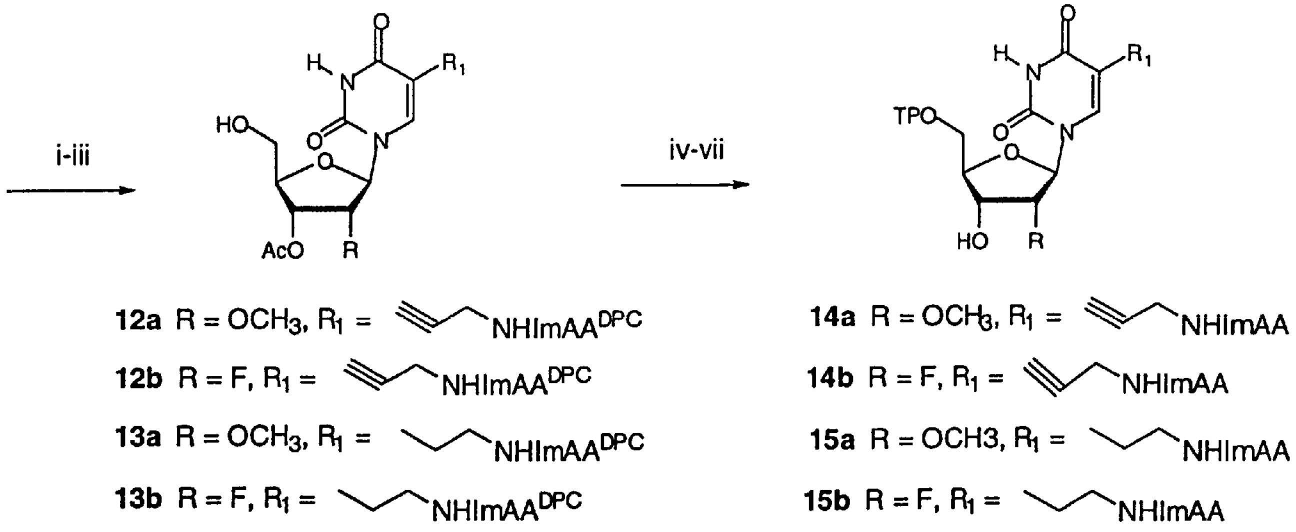
12a R = $OCH_3$, $R_1$ =
12b R = F, $R_1$ =
13a R = $OCH_3$, $R_1$ =
13b R = F, $R_1$ =
14a R = $OCH_3$, $R_1$ =
14b R = F, $R_1$ =
15a R = OCH3, $R_1$ =
15b R = F, $R_1$ =
Reagents and Conditions: (I) DMT-Cl, pyr, 16 h, (ii) $Ac_2O$, pyr, 2 h, (iii) 3%TCA, $CH_2Cl_2$, 2 h, (iv) 2-Cl-4*H*-1,3,2-benzo-dioxaphosphorin-4-one, pyr, dioxane, 30 min., (v) *n*-$Bu_3N$ PPi, DMF, 30 min., (vi) $I_2$, pyr-$H_2O$, 20 min., (vii) $NH_4OH$, 2 h.

Figure 14: Synthesis of Carboxylate tethered uridine 5'-triphosphoates
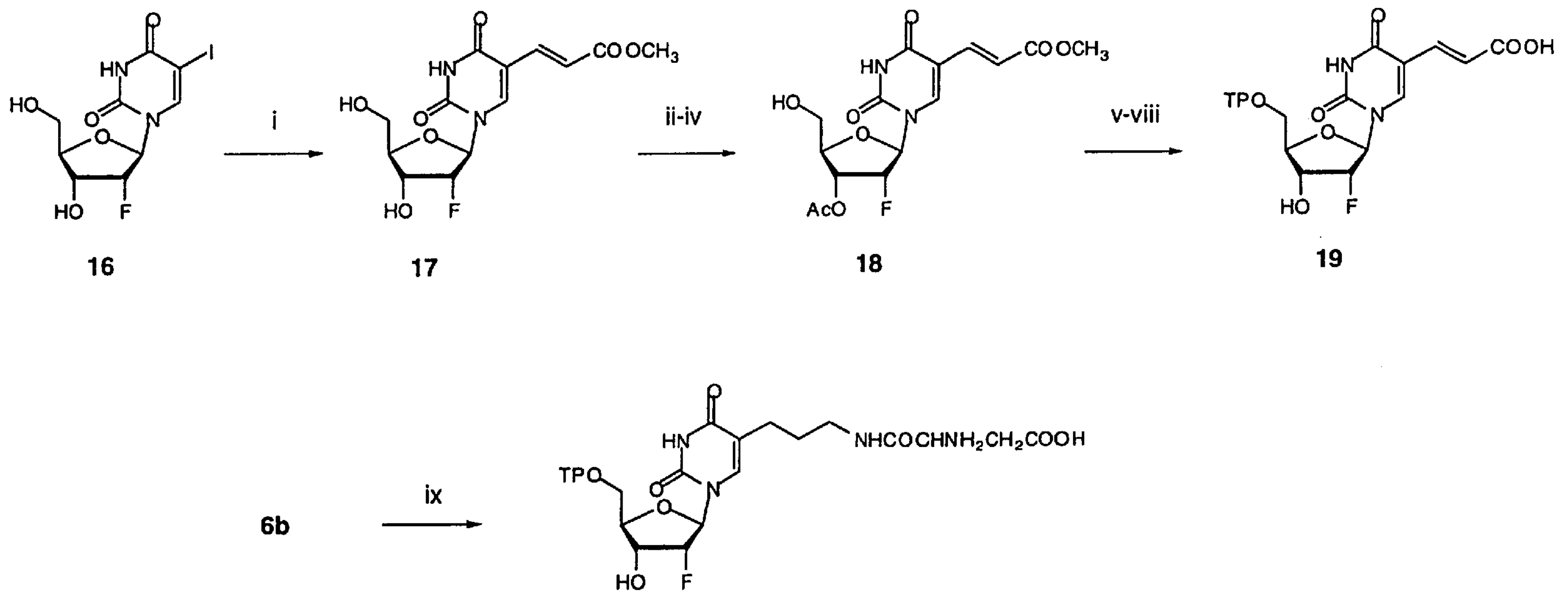
16 17 18 19
6b 20
Reagents and Conditions: (1) methyl acrylate, $Ph_3P$, Pd(II)acetate, $Et_3N$, dioxane, 30 min., reflux, (ii) DMT-Cl, pyr, 16 h. (iii) $Ac_2O$, pyr, 3 h, (iv) 3% TCA, $CH_2Cl_2$, 1 h, (v) 2-Cl-4*H*-1,3,2-benzodioxaphosphorin-4-one, pyr, dioxane, 30 min., (vi) *n*-$Bu_3N$ PPi, DMF, 30 min., (vii) $I_2$, pyr-$H_2O$, 20 min., (viii) 1N NaOH, 5 h,
(ix) Fmoc-Asp-OFm NHS-ester, DMF-0.1M $Na_2B_4O_7$, 16 h, then $Et_2NH$, 3 h.

Figure 15: Synthesis of 5-(3-aminoalkyl) and 5-[3(N-succinyl)aminopropyl] functionalized cytidines

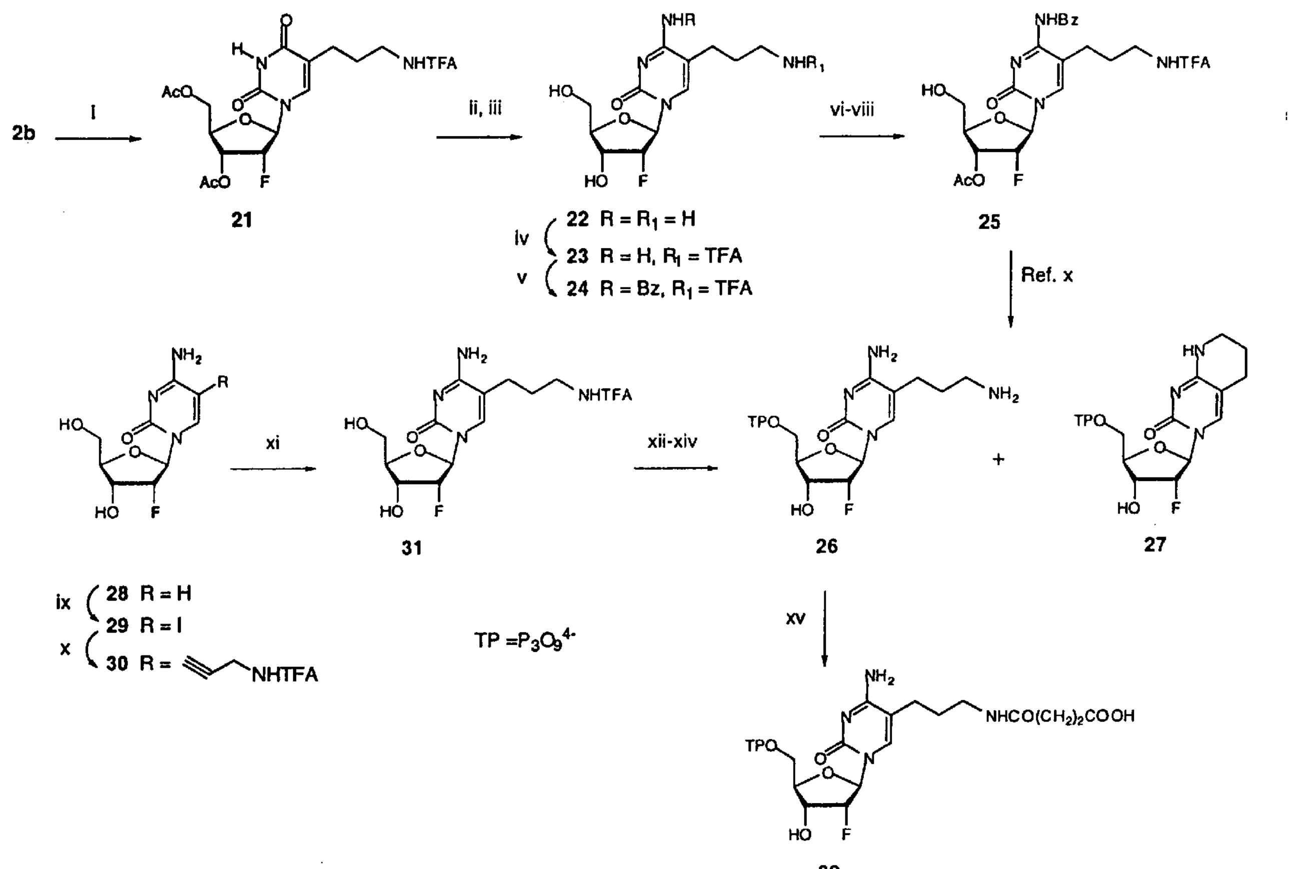

Reagents and Conditions: (i) $H_2$, 5% Pd-C, 24 h, 40 psi, (ii) $POCl_3$, 1,2,4-triazole, $Et_3N$, MeCN, 16 h, (iii), $NH_4OH$, dioxane, 16 h, (iv) $CF_3COOEt$, $Et_3N$, MeOH, reflux, 3 h, (v) $Bz_2O$, EtOH, reflux, 5 h, (vi) DMT-Cl, pyr, 16 h, (vii) $Ac_2O$, pyr, 3 h, (viii) 3% TCA, $CH_2Cl_2$, 3 h, (ix) $HIO_3$, $I_2$, AcOH, $CCl_4$, $H_2O$, 45 °C, 4 h, (x) *N*-TFA propargylamine, CuI, tetrakis($Ph_3P$)Pd(0), $Et_3N$, DMF, 16 h, (xi) $H_2$, 5% Pd-C, MeOH, 72 h, 40 psi, (xii) $POCl_3$, Proton-Sponge, $(MeO)_3PO$, 2 h, (xiii) *n*-$Bu_3N$ PPi, MeCN, 15 min., (xiv) $NH_4OH$, 4 °C, 16 h, (xv) succinic anhydride, DMF-0.1M $Na_2B_4O_7$ 1:1, 16 h.

*Figure 16: Class I ribozyme stem truncation/loop replacement*
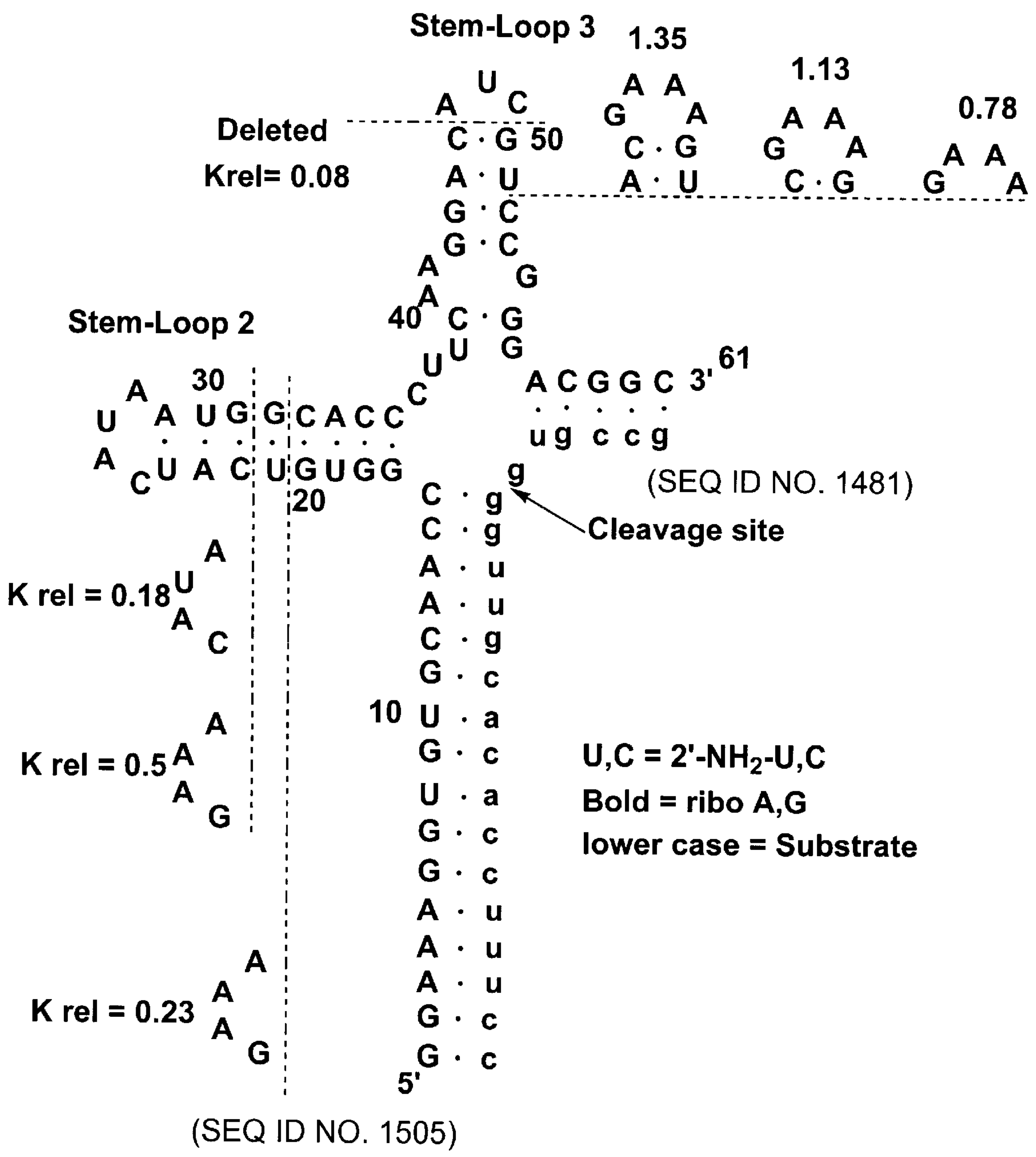

*Figure 17: Class I ribozyme Stem truncation and Loop replacement*
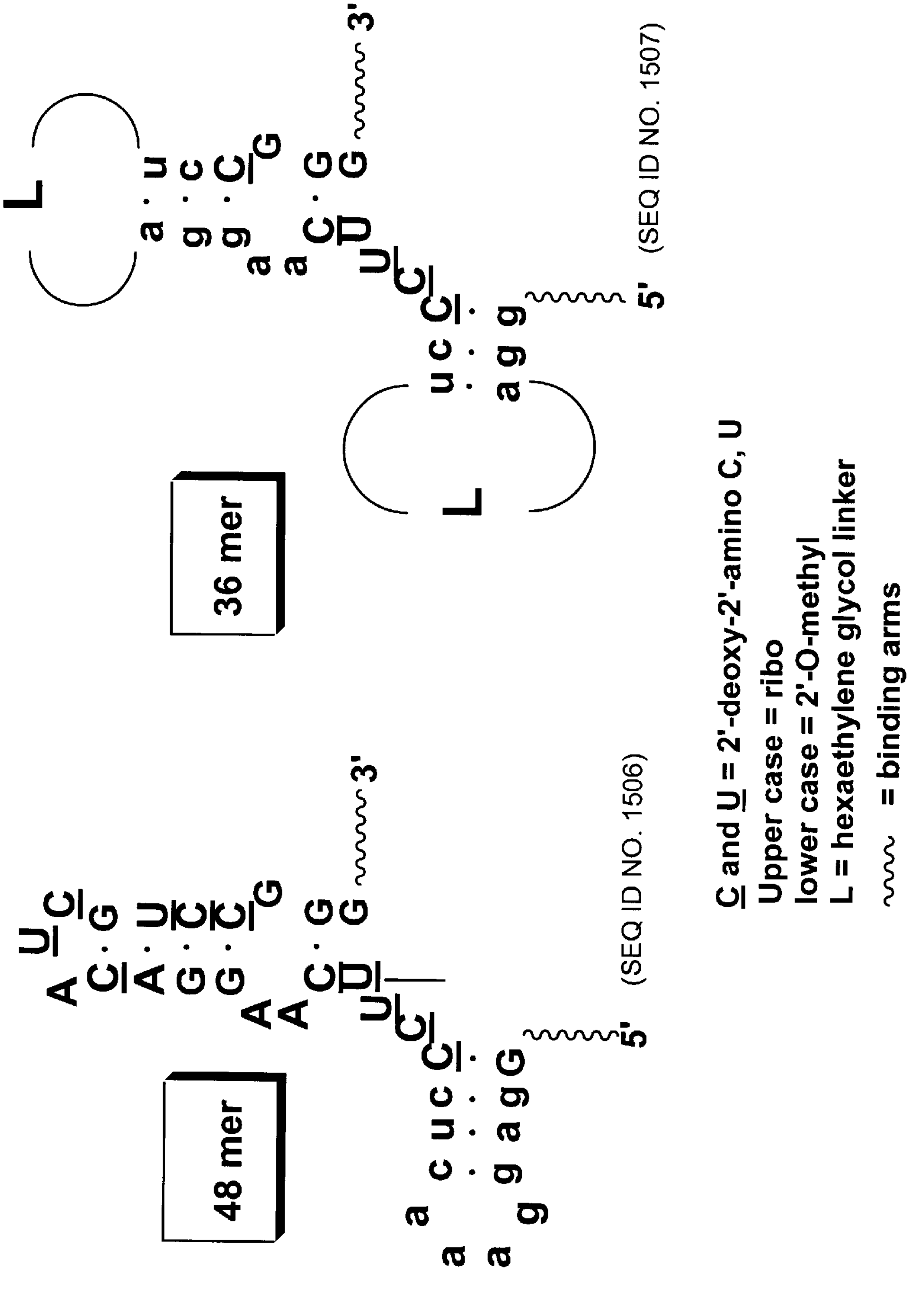

*Figure 18: Non ribo Class II (zinzyme) motifs*

(SEQ ID NO. 1508)

Substrate is the Kras site 521

(SEQ ID NO. 228)

Substrate is the HER2 site 972

Legend

*Italic* indicates natural ribo residues

C indicates 2' - $NH_2$-C

A G C U indicates 2'-*O*Me residues

Subscript s indicates phosphothioate linkage iB indicates inverted deoxy abasic residue Figure 19: Non ribo Class II (zinzyme) cleavage reactions
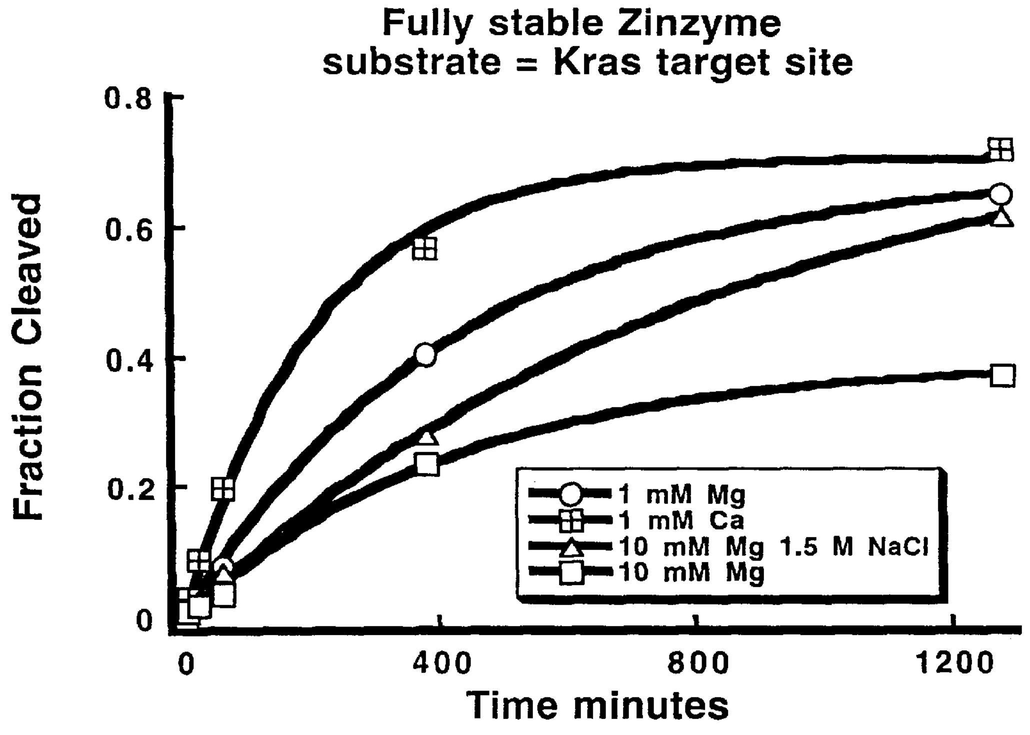

*Figure 20: Positional testing of ribose positions in Class II (zinzyme) nucleic acid catalysts targeting HER2 site 972*
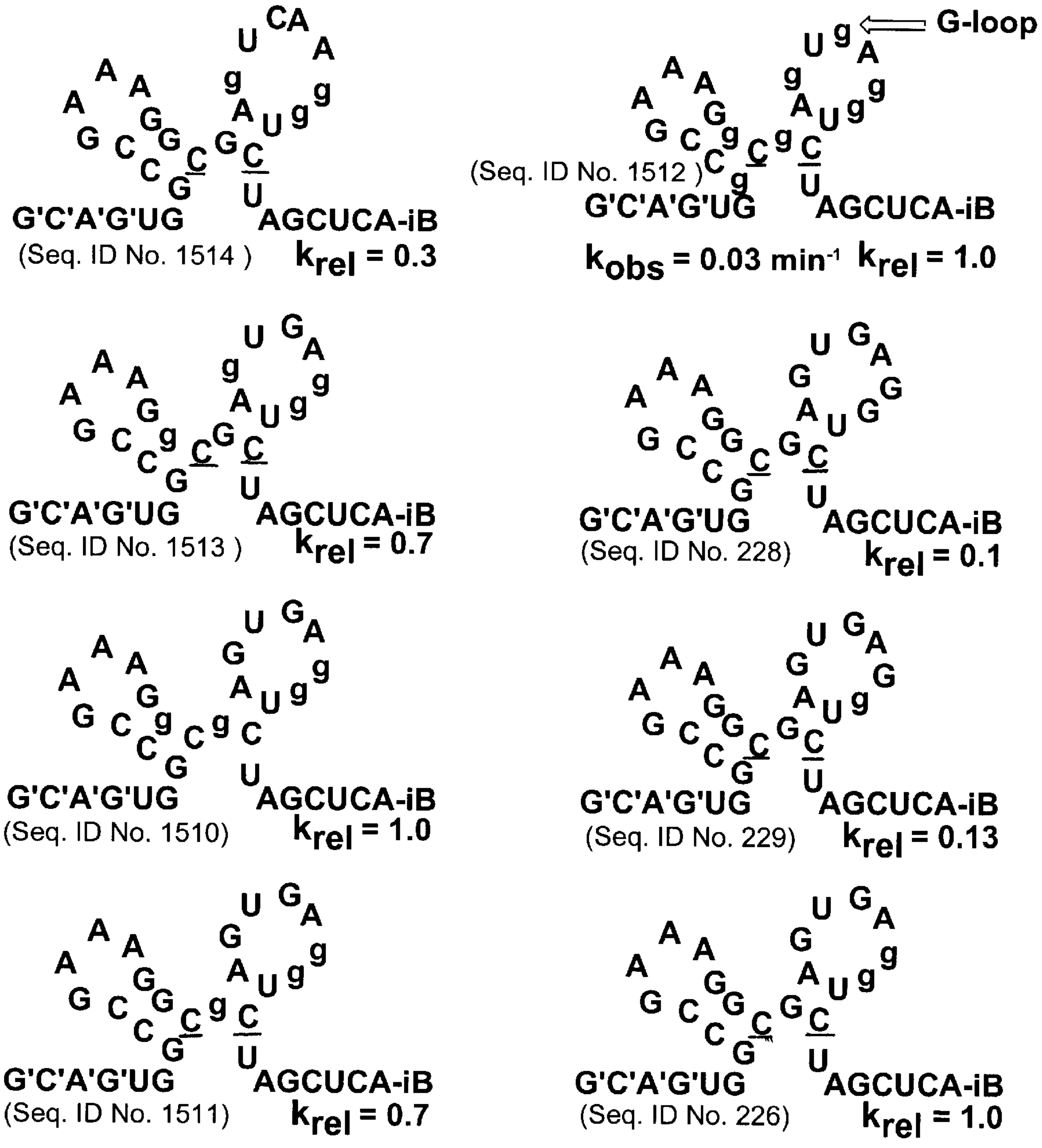
lower case = Ribo
Upper case = 2'-*O*Me
C = 2' $NH_2$
N' = Phosphothioate
iB = inverted abasic

OLIGORIBONUCLEOTIDES WITH ENZYMATIC ACTIVITY

RELATED APPLICATIONS

This patent application is a continuation-in-part of Beigelman et al., U.S. Ser. No. 09/474,432, now U.S. Pat. No. 6,528,640, filed Dec. 29, 1999, which is a continuation-in-part of Beigelman et al., U.S. Ser. No. 09/301,511 filed Apr. 28, 1999, now U.S. Pat. No. 6,482,932, which is a continuation-in-part of Beigelman et al., U.S. Ser. No. 09/186,675, now U.S. Pat. No. 6,127,535, filed Nov. 4, 1998, and claims the benefit of Beigelman et al., U.S. Ser. No. 60/083,727, filed Apr. 29, 1998, and Beigelman et al., U.S. Ser. No. 60/064,866 filed Nov. 5, 1997, all of these earlier applications are entitled "NUCLEOTIDE TRIPHOSPHATES AND THEIR INCORPORATION INTO OLIGONUCLEOTIDES". Each of the published applications and issued patents are hereby incorporated by reference herein in its entirety, including the drawings.

BACKGROUND OF THE INVENTION

This invention relates to novel nucleotide triphosphates (NTPs); methods for synthesizing nucleotide triphosphates; and methods for incorporation of novel nucleotide triphosphates into oligonucleotides. The invention further relates to incorporation of these nucleotide triphosphates into nucleic acid molecules using polymerases under several novel reaction conditions.

The following is a brief description of nucleotide triphosphates. This summary is not meant to be complete, but is provided only to assist understanding of the invention that follows. This summary is not an admission that all of the work described below is prior art to the claimed invention.

The synthesis of nucleotide triphosphates and their incorporation into nucleic acids using polymerase enzymes has greatly assisted in the advancement of nucleic acid research. The polymerase enzyme utilizes nucleotide triphosphates as precursor molecules to assemble oligonucleotides. Each nucleotide is attached by a phosphodiester bond formed through nucleophilic attack by the 3' hydroxyl group of the oligonucleotide's last nucleotide onto the 5' triphosphate of the next nucleotide. Nucleotides are incorporated one at a time into the oligonucleotide in a 5' to 3' direction. This process allows RNA to be produced and amplified from virtually any DNA or RNA templates.

Most natural polymerase enzymes incorporate standard nucleotide triphosphates into nucleic acid. For example, a DNA polymerase incorporates dATP, dTTP, dCTP, and dGTP into DNA and an RNA polymerase generally incorporates ATP, CTP, UTP, and GTP into RNA. There are however, certain polymerases that are capable of incorporating non-standard nucleotide triphosphates into nucleic acids (Joyce, 1997, *PNAS* 94, 1619–1622, Huang et al., *Biochemistry* 36, 8231–8242).

Before nucleosides can be incorporated into RNA transcripts using polymnerase enzymes they must first be converted into nucleotide triphosphates which can be recognized by these enzymes. Phosphorylation of unblocked nucleosides by treatment with $POCl_3$ and trialkyl phosphates was shown to yield nucleoside 5'-phosphorodichloridates (Yoshikawa et al., 1969, *Bull. Chem. Soc.*(Japan) 42, 3505). Adenosine or 2'-deoxyadenosine 5'-triphosphate was synthesized by adding an additional step consisting of treatment with excess tri-n-butylammonium pyrophosphate in DMF followed by hydrolysis (Ludwig, 1981, *Acta Biochim. et Biophys. Acad. Sci. Hung.* 16, 131–133).

Non-standard nucleotide triphosphates are not readily incorporated into RNA transcripts by traditional RNA polymerases. Mutations have been introduced into RNA polymerase to facilitate incorporation of deoxyribonucleotides into RNA (Sousa & Padilla, 1995, *EMBO J.* 14,4609–4621, Bonner et al., 1992, *EMBO J.* 11, 3767–3775, Bonner et al., 1994, *J. Biol. Chem.* 42, 25120–25128, Aurup et al., 1992, *Biochemistry* 31, 9636–9641).

McGee et al., International PCT Publication No. WO 95/35102, describes the incorporation of 2'-$NH_2$-NTP's, 2'-F-NTP's, and 2'-deoxy-2'-benzyloxyanino UTP into RNA using bacteriophage T7 polymerase.

Wieczorek et al., 1994, *Bioorganic & Medicinal Chemistry Letters* 4, 987–994, describes the incorporation of 7-deaza-adenosine triphosphate into an RNA transcript using bacteriophage T7 RNA polymerase.

Lin et al., 1994, *Nucleic Acids Research* 22, 5229–5234, reports the incorporation of 2'-$NH_2$-CTP and 2'-$NH_2$-UTP into RNA using bacteriophage T7 RNA polymerase and polyethylene glycol containing buffer. The article describes the use of the polymerase synthesized RNA for in vitro selection of aptamers to human neutrophil elastase (HNE).

SUMMARY OF THE INVENTION

This invention relates to novel nucleotide triphosphate (NTP) molecules, and their incorporation into nucleic acid molecules, including nucleic acid catalysts. The NTPs of the instant invention are distinct from other NTPs known in the art. The invention further relates to incorporation of these nucleotide triphosphates into oligonucleotides, using an RNA polymerase; the invention further relates to novel transcription conditions for the incorporation of modified (non-standard) and unmodified NTP's, into nucleic acid molecules. Further, the invention relates to methods for synthesis of novel NTP's In a first aspect, the invention features NTP's having the formula triphosphate-OR, for example the following formula I:

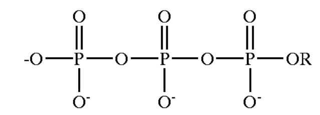

where R is any nucleoside; specifically the nucleosides 2'-O-methyl-2,6-diaminopurine riboside; 2'-deoxy-2'amino-2,6-diaminopurine riboside; 2'-(N-alanyl) amino-2'-deoxy-uridine; 2'-(N-phenylalanyl)amino-2'-deoxy-uridine; 2'-deoxy-2'-(N-β-alanyl) amino ; 2'-deoxy-2'-(lysiyl) amino uridine; 2'-C-allyl uridine; 2'-O-amino-uridine; 2'-O-methylthiomethyl adenosine; 2'-O-methylthiomethyl cytidine ; 2'-O-methylthiomethyl guanosine; 2'-O-methylthiomethyl-uridine; 2'-deoxy-2'-(N-histidyl) amino uridine; 2'-deoxy-2'-amino-5-methyl cytidine; 2'-(N-β-carboxamidine-β-alanyl)amino-2'-deoxy-uridine; 2'-deoxy-2'-(N-β-alanyl)-guanosine; 2'-O-amino-adenosine; 2'-(N-lysyl)amino-2'-deoxy-cytidine; 2'-Deoxy-2'-(L-histidine) amino Cytidine; 5-Imidazoleacetic acid 2'-deoxy uridine, 5-[3-(N-4-imidazoleacetyl)aminopropynyl]-2'-O-methyl uridine, 5-(3-aminopropynyl)-2'-O-methyl uridine, 5-(3-aminopropyl)-2'-O-methyl uridine, 5-[3-(N-4-imidazoleacetyl)aminopropyl]-2'-O-methyl uridine, 5-(3-aminopropyl)-2'-deoxy-2-fluoro uridine, 2'-Deoxy-2'-(β-alanyl-L-histidyl)amino uridine, 2'-deoxy-2'-β-alaninamido-uridine, 3-(2'-deoxy-2'-fluoro-β-D-ribofuranosyl)piperazino[2,3-D] pyrimidine-2-one, 5-[3-(N-4-imidazoleacetyl) aminopropyl]-2'-deoxy-2'-fluoro uridine, 5-[3-(N-4-imidazoleacetyl)aninopropynyl]-2'-deoxy-2'-fluoro uridine, 5-E-(2-carboxyvinyl-2'-deoxy-2'-fluoro uridine, 5-[3-(N-4-aspartyl)aminopropynyl-2'-fluoro uridine, 5-(3-aminopropyl)-2'-deoxy-2-fluoro cytidine, and 5-[3-(N-4-succynyl)aminopropyl-2'-deoxy-2-fluoro cytidine.

In a second aspect, the invention features inorganic and organic salts of the nucleoside triphosphates of the instant invention.

In a third aspect, the invention features a process for the synthesis of pyrimidine nucleotide triphosphate (such as UTP, 2'-O-MTM-UTP, dUTP and the like) including the steps of monophosphorylation where the pyrimidine nucleoside is contacted with a mixture having a phosphorylating agent (such as phosphorus oxychloride, phospho-tris-triazolides, phospho-tris-triimidazolides and the like), trialkyl phosphate (such as triethylphosphate or trimethylphosphate or the like) and a hindered base (such as dimethylaminopyridine, DMAP and the like) under conditions suitable for the formation of pyrimidine monophosphate; and pyrophosphorylation where the pyrimidine monophosphate is contacted with a pyrophosphorylating reagent (such as tributylammonium pyrophosphate) under conditions suitable for the formation of pyrimidine triphosphates.

The term "nucleotide" as used herein is as recognized in the art to include natural bases (standard), and modified bases well known in the art. Such bases are generally located at the 1' position of a sugar moiety. Nucleotides generally include a base, a sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187. There are several examples of modified nucleic acid bases known in the art, e.g., as recently summarized by Limbach et al., 1994, *Nucleic Acids Res.* 22, 2183. Some of the non-limiting examples of base modifications that can be introduced into nucleic acids without significantly effecting their catalytic activity include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine thymine and uracil at 1' position or their equivalents; such bases may be used within the catalytic core of an enzymatic nucleic acid molecule and/or in the substrate-binding regions of such a molecule. Such modified nucleotides include dideoxynucleotides which have pharmaceutical utility well known in the art, as well as utility in basic molecular biology methods such as sequencing.

By "ribonucleotide" is meant a nucleotide with a hydroxyl group at the 2' position of a β-D-ribo-furanose moiety.

By "unmodified nucleoside" or "unmodified nucleotide" is meant one of the bases adenine, cytosine, guanine, uracil joined to the 1' carbon of β-D-ribo-furanose with no substitutions on either moiety.

By "modified nucleoside" or "modified nucleotide" is meant any nucleotide base which contains a modification in the chemical structure of an unmodified nucleotide base, sugar and/or phosphate.

By "pyrimidines" is meant nucleotides comprising modified or unmodified derivatives of a six membered pyrimidine ring. An example of a pyrimidine is modified or unmodified uridine.

By "nucleotide triphosphate" or "NTP" is meant a nucleoside bound to three inorganic phosphate groups at the 5' hydroxyl group of the modified or unmodified ribose or deoxyribose sugar where the 1' position of the sugar may comprise a nucleic acid base or hydrogen. The triphosphate portion may be modified to include chemical moieties which do not destroy the functionality of the group (i.e., allow incorporation into an RNA molecule).

In another preferred embodiment, nucleotide triphosphates (NTPs) of the instant invention are incorporated into an oligonucleotide using an RNA polymerase enzyme. RNA polymerases include but are not limited to mutated and wild type versions of bacteriophage T7, SP6, or T3 RNA polymerases. Applicant has also found that the NTPs of the present invention can be incorporated into oligonucleotides using certain DNA polymerases, such as Taq polymerase.

In yet another preferred embodiment, the invention features a process for incorporating modified NTP's into an oligonucleotide including the step of incubating a mixture having a DNA template, RNA polymerase, NTP, and an enhancer of modified NTP incorporation under conditions suitable for the incorporation of the modified NTP into the oligonucleotide.

By "enhancer of modified NTP incorporation" is meant a reagent which facilitates the incorporation of modified nucleotides into a nucleic acid transcript by an RNA polymerase. Such reagents include but are not limited to methanol; LiCl; polyethylene glycol (PEG); diethyl ether; propanol; methyl amine; ethanol and the like.

In another preferred embodiment, the modified nucleotide triphosphates can be incorporated by transcription into a nucleic acid molecules including enzymatic nucleic acid, antisense, 2–5A antisense chimera, oligonucleotides, triplex forming oligonucleotide (TFO), aptamers and the like (Stull et al., 1995 *Pharmaceutical Res.* 12, 465).

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004; Agrawal et al., U.S. Pat. No. 5,591,721; Agrawal, U.S. Pat. No. 5,652,356). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A- dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89,504).

By "oligonucleotide" as used herein is meant a molecule having two or more nucleotides. The polynucleotide can be single, double or multiple stranded and may have modified or unmodified nucleotides or non-nucleotides or various mixtures and combinations thereof.

In a related aspect, the invention provides a nucleic acid catalyst containing a histidyl modification, and able to catalyze an endonuclease cleavage reaction, where the catalyst contain at least one histidyl modification. Preferably the nucleic acid catalyst catalyze an endonuclease reaction (either intramolecularly or intermolecularly cleave RNA or DNA) in the absence of a metal ion co-factor. Examples of such histidyl-modified nucleotides and their incorporation into nucleic acid catalyst are provided in the Examples. Preferably the catalyst includes at least nucleotide with a histidyl modification at the 2'-position of the sugar moiety. In yet another embodiment, such modified nucleic acid catalysts contain at least one ribonucleotide.

By "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme, finderon or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, 260 *JAMA* 3030).

By "enzymatic portion" or "catalytic domain" is meant that portion/region of the enzymatic nucleic acid molecule essential for cleavage of a nucleic acid substrate.

By "substrate binding arm" or "substrate binding domain" is meant that portion/region of an enzymatic nucleic acid molecule which is complementary to (i.e., able to base-pair with) a portion of its substrate. Generally, such complementarity is 100%, but can be less if desired. For example, as few as 10 bases out of 14 may be base-paired. That is, these arms contain sequences within a enzymatic nucleic acid molecule which are intended to bring enzymatic nucleic acid molecule and target together through complementary base-pairing interactions. The enzymatic nucleic acid molecule of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If two binding arms are chosen, the design is such that the length of the binding arms are symmetrical (i.e., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

By "nucleic acid molecule" as used herein is meant a molecule having nucleotides. The nucleic acid can be single, double or multiple stranded and may comprise modified or unmodified nucleotides or non-nucleotides or various mixtures and combinations thereof. An example of a nucleic acid molecule according to the invention is a gene which encodes for a macromolecule such as a protein.

In preferred embodiments of the present invention, a nucleic acid molecule, e.g., an antisense molecule, a triplex DNA, or an enzymatic nucleic acid molecule, is 13 to 100 nucleotides in length, e.g., in specific embodiments 35, 36, 37, or 38 nucleotides in length (e.g., for particular ribozymes). In particular embodiments, the nucleic acid molecule is 15–100, 17–100, 20–100, 21–100, 23–100, 25–100, 27–100, 30–100, 32–100, 35–100, 40–100, 50–100, 60–100, 70–100, or 80–100 nucleotides in length. Instead of 100 nucleotides being the upper limit on the length ranges specified above, the upper limit of the length range can be, for example, 30, 40, 50, 60, 70, or 80 nucleotides. Thus, for any of the length ranges, the length range for particular embodiments has lower limit as specified, with an upper limit as specified which is greater than the lower limit. For example, in a particular embodiment, the length range can be 35–50 nucleotides in length. All such ranges are expressly included. Also in particular embodiments, a nucleic acid molecule can have a length which is any of the lengths specified above, for example, 21 nucleotides in length.

By "complementarity" is meant that a nucleic acid can form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well-known in the art (see, e.g., Turner et al., 1987, CSH *Symp. Quant. Biol.* LII pp.123–133; Frier et al., 1986*, Proc. Nat. Acad. Sci. USA* 83:9373–9377; Turner et al., 1987*, J Am. Chem. Soc.* 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

In yet another preferred embodiment, the modified nucleotide triphosphates of the instant invention can be used for combinatorial chemistry or in vitro selection of nucleic acid molecules with novel function. Modified oligonucleotides can be enzymatically synthesized to generate libraries for screening.

In another preferred embodiment, the invention features nucleic acid based techniques (e.g., enzymatic nucleic acid molecules), antisense nucleic acids, 2–5A antisense chimeras, triplex DNA, antisense nucleic acids containing RNA cleaving chemical groups) isolated using the methods described in this invention and methods for their use to diagnose, down regulate or inhibit gene expression.

In yet another perferred embodiment, the invention features enzymatic nucleic acid molecules targeted against HER2 RNA, specifically including ribozymes in the class II (zinzyme) motif.

Targets, for example HER2, for useful ribozymes and antisense nucleic acids can be determined, for example, as described in Draper et al, WO 93/23569; Sullivan et al., WO 93/23057; Thompson et al, WO 94/02595; Draper et al., WO 95/04818; McSwiggen et al., U.S. Pat. Nos. 5,525,468 and 5,646,042, both of which are hereby incorporated by reference herein in their totality. Other examples include the following PCT applications, which concern inactivation of expression of disease-related genes: WO 95/23225, WO 95/13380, WO 94/02595.

By "inhibit" it is meant that the activity of target genes or level of mRNAs or equivalent RNAs encoding target genes is reduced below that observed in the absence of the nucleic acid molecules of the instant invention (e.g., enzymatic nucleic acid molecules), antisense nucleic acids, 2–5A antisense chimeras, triplex DNA, antisense nucleic acids containing RNA cleaving chemical groups). In one embodiment, inhibition with enzymatic nucleic acid molecule preferably is below that level observed in the presence of an enzymatically attenuated nucleic acid molecule that is able to bind to the same site on the mRNA, but is unable to cleave that RNA. In another embodiment, inhibition with nucleic acid molecules, including enzymatic nucleic acid and antisense molecules, is preferably greater than that observed in the presence of for example, an oligonucleotide with scrambled sequence or with mismatches. In another embodiment, inhibition of target genes with the nucleic acid molecule of the instant invention is greater than in the presence of the nucleic acid molecule than in its absence.

In yet another preferred embodiment, the invention features a process for incorporating a plurality of compounds of formula I.

In yet another embodiment, the invention features a nucleic acid molecule with catalytic activity having formula II:

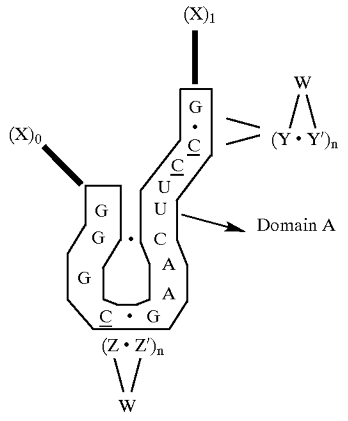

In the formula shown above X, Y, and Z represent independently a nucleotide or a non-nucleotide linker, which may be same or different; • indicates hydrogen bond formation between two adjacent nucleotides which may or may not be present; Y'is a nucleotide complementary to Y; Z' is a nucleotide complementary to Z; l is an integer greater than or equal to 3 and preferably less than 20, more specifically 4, 5, 6, 7, 8, 9, 10, 11, 12, or 15; m is an integer greater than 1 and preferably less than 10, more specifically 2, 3, 4, 5, 6, or 7; n is an integer greater than 1 and preferably less than 10, more specifically 3, 4, 5, 6, or 7; o is an integer greater than or equal to 3 and preferably less than 20, more specifically 3, 4, 5, 6, 7, 8, 9, 10, 11, 12, or 15; l and o may be the same length (l=o) or different lengths (l≠o); each X(l) and X(o) are oligonucleotides which are of sufficient length to stably interact independently with a target nucleic acid sequence (the target can be an RNA, DNA or RNA/DNA mixed polymers); W is a linker of ≧2 nucleotides in length or may be a non-nucleotide linker; A, U, C, and G represent the nucleotides; G is a nucleotide, preferably 2'-O-methyl or ribo; A is a nucleotide, preferably 2'-O-methyl or ribo; U is a nucleotide, preferably 2'-amino (e.g., $2'-NH_2$ or $2'-O-NH_2$), 2'-O-methyl or ribo; C represents a nucleotide, preferably 2'-amino (e.g., $2'-NH_2$ or $2'-O-NH_2$), and represents a chemical linkage (e.g. a phosphate ester linkage, amide linkage, phosphorothioate, phosphorodithioate or others known in the art).

In yet another embodiment, the invention features a nucleic acid molecule with catalytic activity having formula III:

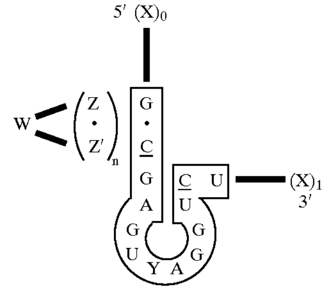

In the formula shown above X, Y, and Z represent independently a nucleotide or a non-nucleotide linker, which may be same or different; • indicates hydrogen bond formation between two adjacent nucleotides which may or may not be present; Z' is a nucleotide complementary to Z; l is an integer greater than or equal to 3 and preferably less than 20, more specifically 4, 5, 6, 7, 8, 9, 10, 11, 12, or 15; n is an integer greater than 1 and preferably less than 10, more specifically 3, 4, 5, 6, or 7; o is an integer greater than or equal to 3 and preferably less than 20, more specifically 3, 4, 5, 6, 7, 8, 9, 10, 11, 12, or 15; l and o may be the same length (l=o) or different lengths (l≠o); each X(l) and X(o) are oligonucleotides which are of sufficient length to stably interact independently with a target nucleic acid sequence (the target can be an RNA, DNA or RNA/DNA mixed polymers); X(o) preferably has a G at the 3'-end, X(l) preferably has a G at the 5'-end; W is a linker of ≧2 nucleotides in length or may be a non-nucleotide linker; Y is a linker of ≧1 nucleotides in length, preferably G, 5'-CA-3', or 5'-CAA-3', or may be a non-nucleotide linker; A, U, C, and G represent the nucleotides; G is a nucleotide, preferably 2'-O-methyl, 2'-deozy-2'-fluoro, or 2'-OH; A is a nucleotide, preferably 2'-O-methyl, 2'-deozy-2'-fluoro, or 2'-OH; U is a nucleotide, preferably 2'-O-methyl, 2'-deozy-2'-fluoro, or 2'-OH; C represents a nucleotide, preferably 2'-amino (e.g., $2'-NH_2$ or $2'-O-NH_2$, and represents a chemical linkage (e.g. a phosphate ester linkage, amide linkage, phosphorothioate, phosphorodithioate or others known in the art).

The enzymatic nucleic acid molecules of Formula II and Formula III may independently comprise a cap structure which may independently be present or absent.

By "sufficient length" is meant an oligonucleotide of greater than or equal to 3 nucleotides that is of a length great enough to provide the intended finction under the expected condition. For example, for binding arms of enzymatic nucleic acid "sufficient length" means that the binding arm sequence is long enough to provide stable binding to a target site under the expected binding conditions. Preferably, the binding arms are not so long as to prevent useful turnover.

By "stably interact" is meant, interaction of the oligonucleotides with target nucleic acid (e.g., by forming hydrogen bonds with complementary nucleotides in the target under physiological conditions).

By "chimeric nucleic acid molecule" or "chimeric oligonucleotide" is meant that, the molecule may be comprised of both modified or unmodified DNA or RNA.

By "cap structure" is meant chemical modifications, which have been incorporated at a terminus of the oligonucleotide. These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both termini. In non-limiting examples the 5'-cap is selected from the group comprising inverted abasic residue (moiety), 4',5'-methylene nucleotide, 1-(beta-D-erythrofuranosyl) nucleotide, 4'-thio nucleotide, carbocyclic nucleotide; 1,5-anhydrohexitol nucleotide; L-nucleotides; alpha-nucleotides, modified base nucleotide, phosphorodithioate linkage, threo-pentofuranosyl nucleotide, acyclic 3',4'-seco nucleotide, acyclic 3,4-dihydroxybutyl nucleotide, acyclic 3,5-dihydroxypentyl nucleotide, 3'-3'-inverted nucleotide moiety, 3'-3'-inverted abasic moiety; 3'-2'-inverted nucleotide moiety; 3'-2'-inverted abasic moiety; 1,4-butanediol phosphate, 3'-phosphoramidate, hexylphosphate, aminohexyl phosphate; 3'-phosphate, 3'-phosphorothioate, phosphorodithioate, or bridging or non-bridging methylphosphonate moiety (for more details see Beigelman et al., International PCT publication No. WO 97/26270, incorporated by reference herein). In yet another preferred embodiment the 3'-cap is selected from a group comprising, 4',5'-methylene nucleotide, 1-(beta-D-erythrofuranosyl) nucleotide, 4'-thio nucleotide, carbocyclic nucleotide, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,5-anhydrohexitol nucleotide, L-nucleotide, alpha-nucleotide, modified base nucleotide, phosphorodithioate, threo-pentofuranosyl nucleotide, acyclic 3',4'-seco nucleotide, 3,4-dihydroxybutyl nucleotide, 3,5-dihydroxypentyl nucleotide, 5'-5'-inverted nucleotide moiety, 5'-5'-inverted abasic moiety, 5'-phosphoramidate, 5'-phosphorothioate, 1,4-butanediol phosphate, 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein). By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The terms "abasic" or "abasic nucleotide" as used herein encompass sugar moieties lacking a base or having other chemical groups in place of base at the 1' position.

In connection with 2'-modified nucleotides as described for the present invention, by "amino" is meant 2'-$NH_2$ or 2'-O-$NH_2$, which may be modified or unmodified. Such modified groups are described, for example, in Eckstein et al., U.S. Pat. No. 5,672,695, incorporated by reference in its entirety, and Matulic-Adamic et al., WO 98/28317, respectively.

DESCRIPTION OF THE PREFERRED EMBODIMENTS

The drawings will first briefly be described.

Drawings:

FIG. 1 displays a schematic representation of NTP synthesis using nucleoside substrates.

FIG. 2 shows a scheme for an in vitro selection method. A pool of nucleic acid molecules is generated with a random core region and one or more region(s) with a defined sequence. These nucleic acid molecules are bound to a column containing immobilized oligonucleotide with a defined sequence, where the defined sequence is complementary to region(s) of defined sequence of nucleic acid molecules in the pool. Those nucleic acid molecules capable of cleaving the immobilized oligonucleotide (target) in the column are isolated and converted to complementary DNA (cDNA), followed by transcription using NTPs to form a new nucleic acid pool.

FIG. 3 shows a scheme for a two column in vitro selection method. A pool of nucleic acid molecules is generated with a random core and two flanking regions (region A and region B) with defined sequences. The pool is passed through a column which has immobilized oligonucleotides with regions A' and B' that are complementary to regions A and B of the nucleic acid molecules in the pool, respectively. The column is subjected to conditions sufficient to facilitate cleavage of the immobilized oligonucleotide target. The molecules in the pool that cleave the target (active molecules) have A' region of the target bound to their A region, whereas the B region is free. The column is washed to isolate the active molecules with the bound A' region of the target. This pool of active molecules may also contain some molecules that are not active to cleave the target (inactive molecules) but have dissociated from the column. To separate the contaminating inactive molecules from the active molecules, the pool is passed through a second column (column 2) which contains immobilized oligonucleotides with the A' sequence but not the B' sequence. The inactive molecules will bind to column 2 but the active molecules will not bind to column 2 because their A region is occupied by the A' region of the target oligonucleotide from column 1. Column 2 is washed to isolate the active molecules for further processing as described in the scheme shown in FIG. 2.

FIG. 4 is a diagram of a novel 48 nucleotide enzymatic nucleic acid motif which was identified using in vitro methods described in the instant invention. The molecule shown is only exemplary. The 5' and 3' terminal nucleotides (referring to the nucleotides of the substrate binding arms rather than merely the single terminal nucleotide on the 5' and 3' ends) can be varied so long as those portions can base-pair with target substrate sequence. In addition, the guanosine (G) shown at the cleavage site of the substrate can be changed to other nucleotides so long as the change does not eliminate the ability of enzymatic nucleic acid molecules to cleave the target sequence. Substitutions in the nucleic acid molecule and/or in the substrate sequence can be readily tested, for example, as described herein.

FIG. 5 is a schematic diagram of HCV luciferase assay used to demonstrate efficacy of class I enzymatic nucleic acid molecule motif.

FIG. 6 is a graph indicating the dose curve of an enzymatic nucleic acid molecule targeting site 146 on HCV RNA.

FIG. 7 is a bar graph showing enzymatic nucleic acid molecules targeting 4 sites within the HCV RNA are able to reduce RNA levels in cells.

Figure 18A:
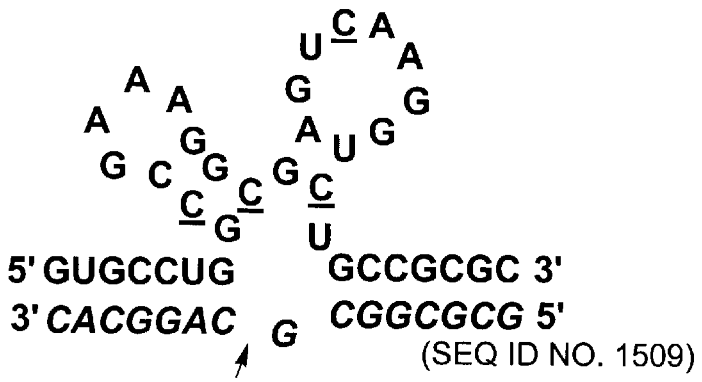

FIGS. 8*a* and 8*b* show secondary structures for characterized Class II enzymatic nucleic acid motifs. Cleavage rates ($min^{-1}$) for FIG. 8*a*: Molecule A1=0.05, Molecule A5=0.03, Molecule B2=0.11; FIG. 8*b*: Molecule B6=0.10, Molecule B23=0.05, Molecule C5=0.01. The NTP used in these assays was 2'-$NH_2$-CTP.

FIG. 9 is a diagram of a novel 35 nucleotide enzymatic nucleic acid motif which was identified using in vitro methods described in the instant invention. The molecule shown is only exemplary. The 5' and 3' terminal nucleotides (referring to the nucleotides of the substrate binding arms rather than merely the single terminal nucleotide on the 5' and 3' ends) can be varied so long as those portions can base-pair with target substrate sequence. In addition, the guanosine (G) shown at the cleavage site of the substrate can be changed to other nucleotides so long as the change does not eliminate the ability of enzymatic nucleic acid molecules to cleave the target sequence. Substitutions in the nucleic acid molecule and/or in the substrate sequence can be readily tested, for example, as described herein.

FIG. 10 is a bar graph showing substrate specificities for Class II (zinzyme) ribozymes.

FIG. 11 is a bar graph showing Class II enzymatic nucleic acid molecules targeting 10 representative sites within the HER2 RNA in a cellular proliferation screen.

FIG. 12 is a synthetic scheme outlining the synthesis of 5-[3-aminopropynyl(propyl)]uridine 5'-triphosphates and 4-imidazoleaceticacid conjugates.

FIG. 13 is a synthetic scheme outlining the synthesis of 5-[3-(N-4-imidazoleacetyl)aminopropynyl(propyl)]uridine 5'-triphosphates.

FIG. 14 is a synthetic scheme outlining the synthesis of carboxylate tethered uridine 5'-triphosphoates.

FIG. 15 is a synthetic scheme outlining the synthesis of 5-(3-aminoalkyl) and 5-[3(N-succinyl)aminopropyl] functionalized cytidines.

FIG. 16 is a diagram of a class I ribozyme stem truncation and loop replacement analysis.

FIG. 17 is a diagram of class I ribozymes with truncated stem(s) and/or non-nucleotide linkers used in loop structures.

FIG. 18 is a diagram of "no-ribo" class II ribozymes.

FIG. 19 is a graph showing cleavage reactions with class II ribozymes under differing divalent metal concentrations.

FIG. 20 is a diagram of differing class II ribozymes with varying ribo content and their relative rates of catalysis.

NUCLEOTIDE SYNTHESIS

Addition of dimethylaminopyridine (DMAP) to the phosphorylation protocols known in the art can greatly increase the yield of nucleotide monophosphates while decreasing the reaction time (FIG. 1). Synthesis of the nucleosides of the invention have been described in several publications and Applicants previous applications (Beigelman et al., International PCT publication No. WO 96/18736; Dudzcy et al., Int. PCT Pub. No. WO 95/11910; Usman et al., Int. PCT Pub. No. WO 95/13378; Matulic-Adamic et al., 1997, *Tetrahedron Lett*. 38, 203; Matulic-Adamic et al., 1997, *Tetrahedron Lett*. 38, 1669; all of which are incorporated herein by reference). These nucleosides are dissolved in triethyl phosphate and chilled in an ice bath. Phosphorus oxychloride ($POCl_3$) is then added followed by the introduction of DMAP. The reaction is then warmed to room temperature and allowed to proceed for 5 hours. This reaction allows the formation of nucleotide monophosphates which can then be used in the formation of nucleotide triphosphates. Tributylamine is added followed by the addition of anhydrous acetonitrile and tributylammonium pyrophosphate. The reaction is then quenched with TEAB and stirred overnight at room temperature (about 20° C.). The triphosphate is purified using Sephadex® column purification or equivalent and/or HPLC and the chemical structure is confirmed using NMR analysis. Those skilled in the art will recognize that the reagents, temperatures of the reaction, and purification methods can easily be alternated with substitutes and equivalents and still obtain the desired product.

Nucleotide Triphosphates

The invention provides nucleotide triphosphates which can be used for a number of different functions. The nucleotide triphosphates formed from nucleosides found in Table I are unique and distinct from other nucleotide triphosphates known in the art. Incorporation of modified nucleotides into DNA or RNA oligonucleotides can alter the properties of the molecule. For example, modified nucleotides can hinder binding of nucleases, thus increasing the chemical half-life of the molecule. This is especially important if the molecule is to be used for cell culture or in vivo. It is known in the art that the introduction of modified nucleotides into these molecules can greatly increase the stability and thereby the effectiveness of the molecules (Burgin et al., 1996, *Biochemistry* 35, 14090–14097; Usman et al., 1996, *Curr. Opin. Struct. Biol*. 6, 527–533).

Modified nucleotides are incorporated using either wild type or mutant polymerases. For example, mutant T7 polymerase is used in the presence of modified nucleotide triphosphate(s), DNA template and suitable buffers. Those skilled in the art will recognize that other polymerases and their respective mutant versions can also be utilized for the incorporation of NTP's of the invention. Nucleic acid transcripts were detected by incorporating radiolabelled nucleotides (($\alpha$-$^{32}$P NTP). The radiolabeled NTP contained the same base as the modified triphosphate being tested. The effects of methanol, PEG and LiCl were tested by adding these compounds independently or in combination. Detection and quantitation of the nucleic acid transcripts was performed using a Molecular Dynamics Phosphorlmager. Efficiency of transcription was assessed by comparing modified nucleotide triphosphate incorporation with all-ribonucleotide incorporation control. Wild-type polymerase was used to incorporate NTP's using the manufacturer's buffers and instructions (Boehringer Mannheim).

Transcription Conditions

Incorporation rates of modified nucleotide triphosphates into oligonucleotides can be increased by adding to traditional buffer conditions, several different enhancers of modified NTP incorporation. Applicant has utilized methanol and LiCl in an attempt to increase incorporation rates of dNTP using RNA polymerase. These enhancers of modified NTP incorporation can be used in different combinations and ratios to optimize transcription. Optimal reaction conditions differ between nucleotide triphosphates and can readily be determined by standard experimentation. Overall, however, Applicant has found that inclusion of enhancers of modified NTP incorporation such as methanol or inorganic compound such as lithium chloride increase the mean transcription rates.

Mechanism of Action of Nucleic Acid Molecules of the Invention

Antisense: Antisense molecules may be modified or unmodified RNA, DNA, or mixed polymer oligonucleotides and primarily function by specifically binding to matching sequences resulting in inhibition of peptide synthesis (Wu-Pong, Nov 1994*, BioPharm*, 20–33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996*, Crit. Rev. in Oncogenesis* 7, 151–190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates and phosphorodithioates. Recently, it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526;

Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Triplex Forming Oligonucleotides (TFO): Single stranded DNA may be designed to bind to genomic DNA in a sequence specific manner. TFOs are comprised of pyrimidine-rich oligonucleotides which bind DNA helices through Hoogsteen Base-pairing (Wu-Pong, supra). The resulting triple helix composed of the DNA sense, DNA antisense, and TFO disrupts RNA synthesis by RNA polymerase. The TFO mechanism may result in gene expression or cell death since binding may be irreversible (Mukhopadhyay & Roth, supra)

2-5A Antisense Chimera: The 2-5A system is an interferon-mediated mechanism for RNA degradation found in higher vertebrates (Mitra et al., 1996*, Proc Nat Acad Sci USA* 93, 6780–6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L which has the ability to cleave single stranded RNA. The ability to form 2-5A structures with double stranded RNA makes this system particularly useful for inhibition of viral replication.

(2'-5') oligoadenylate structures may be covalently linked to antisense molecules to form chimeric oligonucleotides capable of RNA cleavage (Torrence, supra). These molecules putatively bind and activate a 2-5A dependent RNase, the oligonucleotide/enzyme complex then binds to a target RNA molecule which can then be cleaved by the RNase enzyme.

Enzymatic Nucleic Acid: In general, enzymatic nucleic acids act by first binding to a target RNA. Such binding occurs through the target-binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of an enzymatic nucleic acid has significant advantages, such as the concentration of enzymatic nucleic acid molecules necessary to affect a therapeutic treatment is lower. This advantage reflects the ability of the enzymatic nucleic acid molecules to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of enzymatic nucleic acid molecules.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and efficient cleavage achieved in vitro (Zaug et al., 324*, Nature* 429 1986; Uhlenbeck, 1987 *Nature* 328, 596; Kim et al., 84 *Proc. Natl. Acad. Sci. USA* 8788, 1987; Dreyfus, 1988*, Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 infra).

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

Synthesis of Nucleic acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs no more than 100 nucleotides in length, preferably no more than 80 nucleotides in length, and most preferably no more than 50 nucleotides in length; e.g., antisense oligonucleotides, hammerhead or the hairpin ribozymes) are preferably used for exogenous delivery. The simple structure of these molecules increases the ability of the nucleic acid to invade targeted regions of RNA structure. Exemplary molecules of the instant invention were chemically synthesized, and others can similarly be synthesized. Oligodeoxyribonucleotides were synthesized using standard protocols as described in Caruthers et al., 1992*, Methods in Enzymology* 211, 3–19, which is incorporated herein by reference.

The method of synthesis used for normal RNA including certain enzymatic nucleic acid molecules follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677–2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses were conducted on a 394 Applied Biosystems, Inc. synthesizer using a 0.2 $\mu$mol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 $\mu$mol scale can be done on a 96-well plate synthesizer, such as the instrument produced by Protogene (Palo Alto, Calif.) with minimal modification to the cycle. A 33-fold excess (60 $\mu$L of 0.11 M=6.6 $\mu$mol) of 2'-O-methyl phosphoramidite and a 75-fold excess of S-ethyl tetrazole (60 $\mu$L of 0.25 M=15 $\mu$mol) can be used in each coupling cycle of 2'-O-methyl residues relative to polymer-bound 5'-hydroxyl. A 66-fold excess (120 liL of 0.11 M=13.2 $\mu$mol) of alkylsilyl (ribo) protected phosphoramidite and a 150-fold excess of S-ethyl tetrazole (120 $\mu$L of 0.25 M=30 $\mu$mol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer; detritylation solution was 3% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (PERSEPTIVE™). Burdick & Jackson Synthesis Grade acetonitrile was used directly from the reagent bottle. S-Ethyltetrazole solution (0.25 M in acetonitrile) was made up from the solid obtained from American International Chemical, Inc.

Deprotection of the RNA was performed using either a two-pot or one-pot protocol. For the two-pot protocol, the polymer-bound trityl-on oligoribonucleotide was transferred to a 4 mL glass screw top vial and suspended in a solution of 40% aq. methylamine (1 mL) at 65° C. for 10 min. After cooling to −20° C., the supernatant was removed from the polymer support. The support was washed three times with 1.0 mL of EtOH:MeCN:H20/3:1:1, vortexed and the supernatant was then added to the first supernatant. The combined supernatants, containing the oligoribonucleotide, were dried to a white powder. The base deprotected oligoribonucleotide was resuspended in anhydrous TEA/HF/NMP solution (300 $\mu$L of a solution of 1.5 mL N-methylpyrrolidinone, 750 $\mu$L TEA and 1 mL TEA-3.HF to provide a 1.4 M HF concentration) and heated to 65° C. After 1.5 h, the oligomer was quenched with 1.5 M $NH_4HCO_3$.

Alternatively, for the one-pot protocol, the polymer-bound trityl-on oligoribonucleotide was transferred to a 4 mL glass screw top vial and suspended in a solution of 33% ethanolic methylamine/DMSO: 1/1 (0.8 mL) at 65° C. for 15 min. The vial was brought to r.t. TEA.3HF (0.1 mL) was added and the vial was heated at 65° C. for 15 min. The sample was cooled at −20° C. and then quenched with 1.5 M $NH_4HCO_3$.

For purification of the trityl-on oligomers, the quenched $NH_4HCO_3$ solution was loaded onto a C-18 containing cartridge that had been prewashed with acetonitrile followed by 50 mM TEAA. After washing the loaded cartridge with water, the RNA was detritylated with 0.5% TFA for 13 min. The cartridge was then washed again with water, salt exchanged with 1 M NaCl and washed with water again. The oligonucleotide was then eluted with 30% acetonitrile.

Inactive hammerhead ribozymes or binding attenuated control (BAC) oligonucleotides) were synthesized by substituting a U for $G_5$ and a U for $A_{14}$ (numbering from Hertel, K. J., et al., 1992, *Nucleic Acids Res.*, 20, 3252). Similarly, one or more nucleotide substitutions can be introduced in other enzymatic nucleic acid molecules to inactivate the molecule and such molecules can serve as a negative control.

The average stepwise coupling yields were >98% (Wincott et al., 1995 *Nucleic Acids Res.* 23, 2677–2684). Those of ordinary skill in the art will recognize that the scale of synthesis can be adapted to be larger or smaller than the example described above including but not limited to 96-well format, all that is important is the ratio of chemicals used in the reaction.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204).

The nucleic acid molecules of the present invention are modified extensively to enhance stability by modification with nuclease resistant groups, for example, 2'-amino, 2'-C-allyl, 2'-flouro, 2'-O-methyl, 2'-H (for a review see Usman and Cedergren, 1992, *TIBS* 17, 34; Usman et al., 1994, *Nucleic Acids Symp.* Ser. 31, 163). Ribozymes are purified by gel electrophoresis using general methods or are purified by high pressure liquid chromatography (HPLC; See Wincott et al., supra, the totality of which is hereby incorporated herein by reference) and are re-suspended in water.

The sequences of the ribozymes and antisense constructs that are chemically synthesized, useful in this study, are shown in Tables XII to XV. Those in the art will recognize that these sequences are representative only of many more such sequences where the enzymatic portion of the ribozyme (all but the binding arms) is altered to affect activity. The ribozyme and antisense construct sequences listed in Tables XIII to XV may be formed of ribonucleotides or other nucleotides or non-nucleotides. Such ribozymes with enzymatic activity are equivalent to the ribozymes described specifically in the Tables.

In Tables XIII, XV, and XVI, substrate sequences are also shown. The cleavage site is indicated as "nucleotide position", or "NT Pos", or "Pos". Generally, cleavage occurs at or after the indicated nucleotide. In Tables XV and XVI, the specified nucleotide position is shown in the sequence separated from the other nucleotides.

Optimizing Nucleic Acid Catalyst Activity

Catalytic activity of the enzymatic nucleic acid molecules described and identified using the methods of the instant invention, can be optimized as described by Draper et al., supra and using the methods well known in the art. The details will not be repeated here, but include altering the length of the enzymatic nucleic acid molecules' binding arms, or chemically synthesizing enzymatic nucleic acid molecules with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; Rossi et al., International Publication No. WO 91/03162; Sproat, U.S. Pat. No. 5,334,711, incorporated herein by reference in its entirety; and Burgin et al., supra; all of these describe various chemical modifications that can be made to the base, phosphate and/or sugar moieties of enzymatic nucleic acid molecules). Modifications which enhance their efficacy in cells, and removal of bases from stem loop structures to shorten synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992*, TIBS.* 17, 34; Usman et al., 1994*, Nucleic Acids Symp. Ser.* 31, 163; Burgin et al., 1996*, Biochemistry*, 35, 14090). Sugar modification of nucleic acid molecules have been extensively described in the art (see Eckstein et al., *International Publication* PCT No. WO 92/07065; Perrault et al. *Nature*, 1990, 344, 565–568; Pieken et al. *Science*, 1991, 253, 314–317; Usman and Cedergren, *Trends in Biochem. Sci.*, 1992, 17, 334–339; Usman et al. *International Publication* PCT No. WO 93/15187; Sproat, U.S. Pat. No. 5,334,711 and Beigelman et al., 1995*, J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998*, Tetrahedron Lett.*, 39, 1131; Earnshaw and Gait, 1998*, Biopolymers* (*Nucleic acid Sciences*), 48, 39–55; Verma and Eckstein, 1998*, Annu. Rev. Biochem.*, 67, 99–134; and Burlina et al., 1997*, Bioorg. Med. Chem.*, 5, 1999–2010; each of the U.S. Patents are hereby incorporated by reference herein in their totalities). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorodithioate, and/or 5'-methylphosphonate linkages improves stability, too many of these modifications may cause some toxicity. Therefore, when designing nucleic acid molecules, the amount of these internucleotide linkages should be minimized, but can be balanced to provide acceptable stability while reducing potential toxicity. The reduction in the concentration of these linkages should lower toxicity resulting in increased efficacy and higher specificity of these molecules.

Nucleic acid catalysts having chemical modifications which maintain or enhance enzymatic activity are provided. Such nucleic acid molecules are generally more resistant to nucleases than unmodified nucleic acid. Thus, in a cell and/or in vivo the activity may not be significantly lowered. As exemplified herein, such enzymatic nucleic acid molecules are useful in a cell and/or in vivo even if activity over all is reduced 10-fold (Burgin et al., 1996*, Biochemistry*, 35, 14090). Such enzymatic nucleic acid molecules herein are said to "maintain" the enzymatic activity.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

The invention also provides cells, preferably mammalian cells, containing the enzymatic nucleic acid molecules or nucleic acid catalysts described herein. The invention also provides non-human organisms, preferable animals, more preferably mammals, containing such cells.

As used in herein "cell" is used in its usual biological sense, and does not refer to an entire multicellular organism, e.g., specifically does not refer to a human. The cell may be present in a non-human multicellular organism, e.g., birds, and mammals such as cows, sheep, apes, monkeys, swine, dogs, and cats.

By "enhanced enzymatic activity" is meant to include activity measured in cells and/or in vivo where the activity is a reflection of both catalytic activity and enzymatic nucleic acid molecules stability. In this invention, the product of these properties is increased or not significantly (less than 10-fold) decreased in vivo compared to unmodified enzymatic nucleic acid molecules.

In yet another preferred embodiment, nucleic acid catalysts having chemical modifications, which maintain or enhance enzymatic activity are provided. Such nucleic acid is also generally more resistant to nucleases than unmodified nucleic acid. Thus, in a cell and/or in vivo the activity may not be significantly lowered. As exemplified herein, such enzymatic nucleic acid molecules are useful in a cell and/or in vivo even if activity over all is reduced 10-fold (Burgin et al., 1996*, Biochemistry*, 35, 14090). Such enzymatic nucleic acid molecules herein are said to "maintain" the enzymatic activity on all RNA enzymatic nucleic acid molecule.

Use of these molecules will lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecules motifs) and/or other chemical or biological molecules). The treatment of patients with nucleic acid molecules may also include combinations of different types of nucleic acid molecules. Therapies may be devised which include a mixture of enzymatic nucleic acid molecules (including different enzymatic nucleic acid molecules motifs), antisense and/or 2-5A chimera molecules to one or more targets to alleviate symptoms of a disease.

Administration of Nucleotide Mono, Di or Triphosphates and Nucleic Acid Molecules Methods for the delivery of nucleic acid molecules are described in Akhtar et al., 1992*, Trends Cell Bio.*, 2, 139; and

*Delivery Strategies for Antisense Oligonucleotide Therapeutics*, ed. Akhtar, 1995. Sullivan et al., PCT WO 94/02595, further describes the general methods for delivery of enzymatic RNA molecules. These protocols may be utilized for the delivery of virtually any nucleic acid molecule. Nucleic acid molecules may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, nucleic acid molecules may be directly delivered ex vivo to cells or tissues with or without the aforementioned vehicles. Alternatively, the nucleic acid/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of nucleic acid delivery and administration are provided in Sullivan et al., supra, Draper et al., PCT W093/23569, Beigelman et al., PCT WO99/05094, and Klimuk et al., PCT WO99/04819.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged nucleotide mono, di or triphosphates of the invention can be administered and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., ammonium, sodium, calcium, magnesium, lithium, tributylammoniun, and potassium salts.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitations: intravenous, subcutaneous, intraperitoneal, inhalation, oral, intrapulmonary and intramuscular. Each of these administration routes expose the desired negatively charged polymers, e.g., NTP's, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as cancer cells.

The invention also features the use of a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995*, Biochim. Biophys. Acta*, 1238, 86–90). The long-circulating liposomes enhance the pharmacokinetics and pharmacodynamics of drugs, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues, such as the liver and spleen.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used.

By "patient" is meant an organism which is a donor or recipient of explanted cells or the cells themselves. "Patient" also refers to an organism to which the compounds of the invention can be administered. Preferably, a patient is a mammal, e.g., a human, primate, bovine, porcine, dog, cat, or rodent.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required.

The nucleic acid molecules of the present invention may also be administered to a patient in combination with other therapeutic compounds to increase the overall therapeutic effect. The use of multiple compounds to treat an indication may increase the beneficial effects while reducing the presence of side effects.

EXAMPLES

The following are non-limiting examples showing the synthesis, incorporation and analysis of nucleotide triphosphates and activity of enzymatic nucleic acids of the instant invention.

Applicant synthesized pyrimidine nucleotide triphosphates using DMAP in the reaction. For purines, applicant utilized standard protocols previously described in the art (Yoshikawa et al supra;. Ludwig, supra). Described below is one example of a pyrimdine nucleotide triphosphate and one purine nucleotide triphosphate synthesis.

Example 1

Synthesis of Purine Nucleotide Triphosphates: 2'-O-methyl-guanosine-5'-Triphosphate 2'-O-methyl guanosine nucleoside (0.25 grams, 0.84 mmol) was dissolved in triethyl phosphate (5.0) ml by heating to 100° C. for 5 minutes. The resulting clear, colorless solution was cooled to 0° C. using an ice bath under an argon atmosphere. Phosphorous oxychloride (1.8 eq., 0.141 ml) was then added to the reaction mixture with vigorous stirring. The reaction was monitored by HPLC, using a sodium perchlorate gradient. After 5 hours at 0° C., tributylamine (0.65 ml) was added followed by the addition of anhydrous acetonitrile (10.0 ml), and after 5 minutes (reequilibration to 0° C.) tributylammonium pyrophosphate (4.0 eq., 1.53 g) was added. The reaction mixture was quenched with 20 ml of 2M TEAB after 15 minutes at 0° C. (HPLC analysis with above conditions showed consumption of monophosphate at 10 minutes) then stirred overnight at room temperature, the mixture was evaporated in vacuo with methanol co-evaporation (4×) then diluted in 50 ml 0.05M TEAB. DEAE sephadex purification was used with a gradient of 0.05 to 0.6 M TEAB to obtain pure triphosphate (0.52 g, 66.0% yield) (elutes around 0.3M TEAB); the purity was confirmed by HPLC and NMR analysis.

Example 2

Synthesis of Pyrimdine Nucleotide Triphosphates: 2'-O-methylthiomethyl-uridine-5 '-triphosphate 2'-O-methylthiomethyl uridine nucleoside (0.27 grams, 1.0 mmol) was dissolved in triethyl phosphate (5.0 ml). The resulting clear, colorless solution was cooled to 0° C. with an ice bath under an argon atmosphere. Phosphorus oxychloride (2.0 eq., 0.190 ml) was then added to the reaction mixture with vigorous stirring. Dimethylaminopyridine (DMAP, 0.2eq., 25 mg) was added, the solution warmed to room temperature and the reaction was monitored by HPLC, using a sodium perchlorate gradient. After 5 hours at 20° C., tributylamine (1.0 ml) was added followed by anhydrous acetonitrile (10.0 ml), and after 5 minutes tributylammonium pyrophosphate (4.0 eq., 1.8 g) was added. The reaction mixture was quenched with 20 ml of 2M TEAB after 15 minutes at 20° C. (HPLC analysis with above conditions showed consumption of monophosphate at 10 minutes) then stirred overnight at room temperature. The mixture was evaporated in vacuo with methanol co-evaporation (4×) then diluted in 50 ml 0.05M TEAB. DEAE fast flow Sepharose purification with a gradient of 0.05 to 1.0 M TEAB was used to obtain pure triphosphate (0.40 g, 44% yield) (elutes around 0.3M TEAB) as determined by HPLC and NMR analysis.

Example 3

Utilization of DMAP in Uridine 5'-Triphosphate Synthesis

The reactions were performed on 20 mg aliquots of nucleoside dissolved in 1 ml of triethyl phosphate and 19 ul of phosphorus oxychloride. The reactions were monitored at 40 minute intervals automatically by HPLC to generate yield-of-product curves at times up to 18 hours. A reverse phase column and ammonium acetate/sodium acetate buffer system (50 mM & 100 mM respectively at pH 4.2) was used to separate the 5', 3', 2' monophosphates (the monophosphates elute in that order) from the 5'-triphosphate and the starting nucleoside. The data is shown in Table III. These conditions doubled the product yield and resulted in a 10-fold improvement in the reaction time to maximum yield (1200 minutes down to 120 minutes for a 90% yield). Selectivity for 5'-monophosphorylation was observed for all reactions. Subsequent triphosphorylation occurred in nearly quantitative yield.

Materials Used in Bacteriophage T7 RNA Polymerase Reactions

Buffer 1: Reagents are mixed together to form a 10×stock solution of buffer 1 (400 mM Tris-Cl [pH 8.1], 200 mM $MgCl_2$, 100 mM DTT, 50 mM spermidine, and 0.1% triton® X-100). Prior to initiation of the polymerase reaction methanol, LiCl is added and the buffer is diluted such that the final reaction conditions for condition 1 consisted of: 40 mM tris (pH 8.1), 20 mM $MgCl_2$, 10 mM DTT, 5 mM spermidine, 0.01% triton® X-100, 10% methanol, and 1 mM LiCl.

BUFFER 2: Reagents are mixed together to form a 10×stock solution of buffer 2 (400 mM Tris-Cl [pH 8.1], 200 mM $MgCl_2$, 100 mM DTT, 50 mM spernidine, and 0.1% triton® X-100). Prior to initiation of the polymerase reaction PEG, LiCl is added and the buffer is diluted such that the final reaction conditions for buffer 2 consisted of: 40 mM tris (pH 8.1), 20 mM $MgCl_2$, 10 mM DTT, 5 mM spermidine, 0.01% triton® X-100, 4% PEG, and 1 mM LiCl.

BUFFER 3: Reagents are mixed together to form a 10×stock solution of buffer 3 (400 mM Tris-Ci [pH 8.0], 120 mM $MgCl_2$, 50 mM DTT, 10 mM spermidine and 0.02% triton® X-100). Prior to initiation of the polymerase reaction PEG is added and the buffer is diluted such that the final reaction conditions for buffer 3 consisted of: 40 mM tris (pH 8.0), 12 mM $MgCl_2$, 5 mM DTT, 1 mM spermidine, 0.002% triton® X-100, and 4% PEG.

BUFFER 4: Reagents are mixed together to form a 10×stock solution of buffer 4 (400 mM Tris-Cl [pH 8.0], 120 mM $MgCl_2$, 50 mM DTT, 10 mM spermidine and 0.02% triton® X-100). Prior to initiation of the polymerase reaction PEG, methanol is added and the buffer is diluted such that the final reaction conditions for buffer 4 consisted of: 40 mM tris (pH 8.0), 12 mM $MgCl_2$, 5 mM DTT, 1 mM spermidine, 0.002% triton® X-100, 10% methanol, and 4% PEG.

BUFFER 5: Reagents are mixed together to form a lOX stock solution of buffer 5 (400 mM Tris-Cl [pH 8.0], 120 mM $MgCl_2$, 50 mM DTT, 10 mM spermidine and 0.02% triton® X-100). Prior to initiation of the polymerase reaction PEG, LiCl is added and the buffer is diluted such that the final reaction conditions for buffer S consisted of: 40 mM tris (pH 8.0), 12 mM $MgCl_2$, 5 mM DTT, 1 mM spermidine, 0.002% triton® X-100, 1 mM LiCl and 4% PEG.

BUFFER 6: Reagents are mixed together to form a 10×stock solution of buffer 6 (400 mM Tris-Cl [pH 8.0], 120 mM $MgCl_2$, 50 mM DTT, 10 mM spermidine and 0.02% triton® X-100). Prior to initiation of the polymerase reaction PEG, methanol is added and the buffer is diluted such that the final reaction conditions for buffer 6 consisted of: 40 mM tris (pH 8.0), 12 mM $MgCl_2$, 5 mM DTT, 1 mM spermidine, 0.002% triton® X-100, 10% methanol, and 4% PEG.

BUFFER 7: Reagents are mixed together to form a 10×stock solution of buffer 6 (400 mM Tris-Cl [pH 8.0], 120 mM $MgCl_2$, 50 mM DTT, 10 mM spermidine and 0.02% triton® X-100). Prior to initiation of the polymerase reaction PEG, methanol and LiCl is added and the buffer is diluted such that the final reaction conditions for buffer 6 consisted of: 40 mM tris (pH 8.0), 12 mM $MgCl_2$, 5 mM DTT, 1 mM spermidine, 0.002% triton® X-100, 10% methanol, 4% PEG, and 1 mM LiCl.

Example 4

Screening of Modified Nucleotide Triphosphates with Mutant T7 RNA

Polymerase

Modified nucleotide triphosphates were tested in buffers 1 through 6 at two different temperatures (25 and 37° C.). Buffers 1–6 tested at 25° C. were designated conditions 1–6 and buffers 1–6 tested at 37° C. were designated conditions 7–12 (Table IV). In each condition, Y639F mutant T7 polymerase (Sousa and Padilla, supra) (0.3–2 mg/20 ml reaction), NTP's (2 mM each), DNA template (10 pmol), inorganic pyrophosphatase (5 U/ml) and $\alpha$-$^{32}$P NTP (0.8 mCi/pmol template) were combined and heated at the designated temperatures for 1–2 hours. The radiolabeled NTP used was different from the modified triphosphate being testing. The samples were resolved by polyacrylamide gel electrophoresis. Using a phosphorimager (Molecular Dynamics, Sunnyvale, Calif.), the amount of full-length transcript was quantified and compared with an all-RNA control reaction. The data is presented in Table V; results in each reaction are expressed as a percent compared to the all-ribonucleotide triphosphate (rNTP) control. The control was run with the mutant T7 polymerase using commercially available polymerase buffer (Boehringer Mannheim, Indianapolis, Ind.).

Example 5

Incorporation of Modified NTP's Using Wild-type T7 RNA Polymerase

Bacteriophage T7 RNA polymerase was purchased from Boehringer Mannheim at 0.4 U/$\mu$L concentration. Applicant used the commercial buffer supplied with the enzyme and 0.2 $\mu$Ci alpha-$^{32}$P NTP in a 50 $\mu$L reaction with nucleotides triphosphates at 2 mM each. The template was a double-stranded PCR fragment, which was used in previous screens. Reactions were carried out at 37° C. for 1 hour. Ten $\mu$L of the sample was run on a 7.5% analytical PAGE and bands were quantitated using a Phosphorlmager. Results are calculated as a comparison to an "all ribo" control (non-modified nucleotide triphosphates) and the results are in Table VI.

Example 6

Incorporation of Multiple Modified Nucleotide Triphosphates Into Oligonucleotides Combinations of modified nucleotide triphosphates were tested with the transcription protocol described in example 4, to determine the rates of incorporation of two or more of these triphosphates. Incorporation of 2'-Deoxy-2'-(L-histidine) amino uridine (2'-his-$NH_2$-UTP) was tested with unmodified cytidine nucleotide triphosphates, rATP and rGTP in reaction condition number 9. The data is presented as a percentage of incorporation of modified NTP's compared to the all rNTP control and is shown in Table VII a.

Two modified cytidines (2'-$NH_2$-CTP or 2'dCTP) were incorporated along with 2'-his-$NH_2$-UTP with identical efficiencies. 2'-his-$NH_2$-UTP and 2'-$NH_2$-CTP were then tested with various unmodified and modified adenosine triphosphates in the same buffer (Table VII b). The best modified adenosine triphosphate for incorporation with both 2'-his-$NH_2$-UTP and 2'-$NH_2$-CTP was 2'-$NH_2$-DAPTP.

Example 7

Optimization of Reaction Conditions for Incorporation of Modified Nucleotide Triphosphate The combination of 2'-his-$NH_2$-UTP, 2'-$NH_2$-CTP, 2'-$NH_2$-DAP, and rGTP was tested in several reaction conditions (Table VIII) using the incorporation protocol described in example 9. The results demonstrate that of the buffer conditions tested, incorporation of these modified nucleotide triphosphates occur in the presence of both methanol and LiCl.

Example 8

Selection of Novel Enzymatic Nucleic Acid Molecule Motifs Using 2'-deoxy-2'amino Modified GTP and CTP For selection of new enzymatic nucleic acid molecule motifs, pools of enzymatic nucleic acid molecules were designed to have two substrate binding arms (5 and 16 nucleotides long) and a random region in the middle. The substrate has a biotin on the 5' end, 5 nucleotides complementary to the short binding arm of the pool, an unpaired G (the desired cleavage site), and 16 nucleotides complementary to the long binding arm of the pool. The substrate was bound to column resin through an avidin-biotin complex. The general process for selection is shown in FIG. 2. The protocols described below represent one possible method that may be utilized for selection of enzymatic nucleic acid molecules and are given as a non-limiting example of enzymatic nucleic acid molecule selection with combinatorial libraries.

Construction of Libraries: The oligonucleotides listed below were synthesized by Operon Technologies (Alameda, Calif.). Templates were gel purified and then run through a Sep-Pak™ cartridge (Waters, Millford, Mass.) using the manufacturers protocol. Primers (MST3, MST7c, MST3del) were used without purification.

| Primers: | | |
|---|---|---|
| MST3 (30 mer): | 5'-CAC TTA GCA TTA ACC CTC ACT AAA GGC CGT-3' | (SEQ ID NO. 1515) |
| MST7c (33 mer): | 5'-TAA TAC GAC TCA CTA TAG GAA AGG TGT GCAACC-3' | (SEQ ID NO. 1516) |
| MST3del (18 mer): | 5'-ACC CTC ACT AAA GGC CGT-3' | (SEQ ID NO. 1517) |
| Templates: | | |
| MSN60c (93 mer): | 5'-ACC CTC ACT AAA GGC CGT (N)60 GGT TGC ACA CCT TTG-3' | (SEQ ID NO. 1518) |
| MSN40c (73 mer): | 5'-ACC CTC ACT AAA GGC CGT (N)40 GGT TGC ACA CCT TTG-3' | (SEQ ID NO. 1519) |
| MSN20c (53 mer): | 5'-ACC CTC ACT AAA GGC CGT (N)20 GGT TGC ACA CCT TTG-3' | (SEQ ID NO. 1520) |

N60 library was constructed using MSN60c as a template and MST3/MST7c as primers. N40 and N20 libraries were constructed using MSN40c (or MSN20c) as template and MST3deV/MST7c as primers.

Single-stranded templates were converted into double-stranded DNA by the following protocol: 5 nmol template, 10 nmol each primer, in 10 ml reaction volume using standard PCR buffer, dNTP's, and taq DNA polymerase (all reagents from Boerhinger Mannheim). Synthesis cycle conditions were 94° C., 4 minutes; (94° C., 1 minute; 42° C., 1 minute; 72° C., 2 minutes) x 4; 72° C., 10 minutes. Products were checked on agarose gel to confirm the length of each fragment (N60=123 bp, N40=91 bp, N20=71 bp) and then were phenouchloroform extracted and ethanol precipitated. The concentration of the double-stranded product was 25 $\mu$M.

Transcription of the initial pools was performed in a 1 ml volume comprising: 500 pmol double-stranded template ($3\times10^{14}$ molecules), 40 mM tris-HCl (pH 8.0), 12 mM $MgCl_2$, 1 mM spermidine, 5 mM DTT, 0.002% triton X-100, 1 mM LiCl, 4% PEG 8000, 10% methanol, 2 mM ATP (Pharmacia), 2 mM GTP (Pharmacia), 2 mM 2'-deoxy-2'-amino-CTP (USB), 2 mM 2'-deoxy-2'-amino-UTP (USB), 5 U/ml inorganic pyrophosphatase (Sigma), 5 U/$\mu$l T7 RNA polymerase (USB; Y639F mutant was used in some cases at 0.1 mg/ml (Sousa and Padilla, supra)), 37° C., 2 hours. Transcribed libraries were purified by denaturing PAGE (N60=106 ntds, N40=74, N20=54) and the resulting product was desalted using Sep-Pak™ columns and then ethanol precipitated.

Initial column-Selection: The following biotinylated substrate was synthesized using standard protocols (Usman el al., 1987 *J. Am. Chem. Soc.*, 109, 7845; Scaringe et al., 1990 *Nucleic Acids Res.*, 18, 5433; and Wincott et al., 1995 *Nucleic Acids Res.*, 23, 2677–2684):

5'-biotin-C18 spacer-GCC GUG GGU UGC ACA CCU UUC C-C18 spacer-thiol-modifier C6 S-S-inverted abasic-3' (SEQ ID NO. 1521).

Substrate was purified by denaturing PAGE and ethanol precipitated. 10 nmol of substrate was linked to a NeutrAvidin™ column using the following protocol: 400 $\mu$l UltraLink Immobilized NeutrAvidin™ slurry (200 $\mu$l beads, Pierce, Rockford, Ill.) were loaded into a polystyrene column (Pierce). The column was washed twice with 1 ml of binding buffer (20 mM $NaPO_4$ (pH 7.5), 150 mM NaCl) and then capped off (i.e., a cap was put on the bottom of the column to stop the flow). 200 $\mu$l of the substrate suspended in binding buffer was applied and allowed to incubate at room temperature for 30 minutes with occasional vortexing to ensure even linking and distribution of the solution to the resin. After the incubation, the cap was removed and the column was washed with 1 ml binding buffer followed by 1 ml column buffer (50 mM tris-HCL (pH 8.5), 100 mM NaCl, 50 mM KCl). The column was then ready for use and capped off. 1 nmol of the initial pool RNA was loaded on the column in a volume of 200 $\mu$l column buffer. It was allowed to bind the substrate by incubating for 30 minutes at room temperature with occasional vortexing. After the incubation, the cap was removed and the column was washed twice with 1 ml column buffer and capped off. 200 $\mu$l of elution buffer (50 mM tris-HCl (pH 8.5), 100 mM NaCl, 50 mM KCl, 25 mM $MgCl_2$) was applied to the column followed by 30 minute incubation at room temperature with occasional vortexing. The cap was removed and four 200 $\mu$l fractions were collected using elution buffer.

Second-column-(counter-selection): A diagram for events in the second column is generally shown in FIG. 3 and substrate oligonucleotide used is shown below:

5'-GGU UGC ACA CCU UUC C-C18 spacer-biotin-inverted abasic-3' (SEQ ID NO. 1522).

This column substrate was linked to UltraLink NeutrAvidin™ resin as previously described (40 pmol) which was washed twice with elution buffer. The eluent from the first column purification was then run On the second column. The use of this column allowed for binding of RNA that non-specifically diluted from the first column, while RNA that performed a catalytic event and had product bound to it, flowed through the second column. The fractions were ethanol precipitated using glycogen as carrier and rehydrated in sterile water for amplification.

Amplification: RNA and primer MST3 (10–100 pmol) were denatured at 90° C. for 3 minutes in water and then snap-cooled on ice for one minute. The following reagents were added to the tube (final concentrations given): 1×PCR buffer (Boerhinger Mannheim), 1 mM dNTP's (for PCR, Boerhinger Mannheim), 2 U/$\mu$l RNase-Inhibitor (Boerhinger Mannheim), 10 U/$\mu$l Superscript™ II Reverse Transcriptase (BRL). The reaction was incubated for 1 hour at 42° C., then at 95° C. for 5 minutes in order to destroy the Superscript™. The following reagents were then added to the tube to increase the volume five-fold for the PCR step (final concentrations/amounts given): MST7c primer (10–100 pmol, same amount as in RT step), 1×PCR buffer, taq DNA polymerase (0.025–0.05 U/$\mu$l, Boerhinger Mannheim). The reaction was cycled as follows: 94° C., 4 minutes; (94° C., 30 s; 42–54° C., 30 s; 72° C., 1 minute)× 4–30 cycles; 72° C., 5 minutes; 30° C., 30 minutes. Cycle number and annealing temperature were decided on a round by round basis. In cases where heteroduplex was observed, the reaction was diluted five-fold with fresh reagents and allowed to progress through 2 more amplification cycles. Resulting products were analyzed for size on an agarose gel (N60=123 bp, N40=103 bp, N20=83 bp) and then ethanol precipitated.

Transcriptions: Transcription of amplified products was done using the conditions described above with the following modifications: 10–20% of the amplification reaction was used as template, reaction volume was 100–500 $\mu$l, and the products sizes varied slightly (N60=106 ntds, N40=86, N20=66). A small amount of $^{32}$P-GTP was added to the reactions for quantitation purposes.

Subsequent rounds: Subsequent rounds of selection used 20 pmols of input RNA and 40 pmol of the 22 nucleotide substrate on the column.

Activity of pools: Pools were assayed for activity under single turnover conditions every three to four rounds. Activity assay conditions were as follows: 50 mM tris-HCl (pH 8.5), 25 mM MgCl$_2$, 100 mM NaCl, 50 mM KCl, trace $^{32}$P-labeled substrate, 10 nM RNA pool. 2×pool in buffer and, separately, 2×substrate in buffer were incubated at 90° C. for 3 minutes, then at 37° C. for 3 minutes. Equal volume 2×substrate was then added the 2×pool tube (t=0). Initial assay time points were taken at 4 and 24 hours: 5 µl was removed and quenched in 8 µl cold Stop buffer (96% formamide, 20 mM EDTA, 0.05% bromphenyl blue/xylene cyanol). Samples were heated 90° C., 3 minutes, and loaded on a 20% sequencing gel. Quantitation was performed using a Molecular Dynamics Phosphorimager and ImageQuaNT™ software. The data is shown in Table IX.

Samples from the pools of oligonucleotide were cloned into vectors and sequenced using standard protocols (Sambrook et al., *Molecular Cloning: A Laboratory Manual*, Cold Spring Harbor Laboratory Press). The enzymatic nucleic acid molecules were transcribed from a representative number of these clones using methods described in this application. Individuals from each pool were tested for RNA cleavage from N60 and N40 by incubating the enzymatic nucleic acid molecules from the clones with 5/16 substrate in 2mM MgCl2, pH 7.5, 10 mM KCl at 37° C. The data in Table XI shows that the enzymatic nucleic acid molecules isolated from the pool are individually active.

Kinetic Activity: Kinetic activity of the enzymatic nucleic acid molecule shown in Table XI, was determined by incubating enzymatic nucleic acid molecule (10 nM) with substrate in a cleavage buffer (pH 8.5, 25 mM MgCl$_2$, 100 mM NaCl, 50 mM KCl) at 37° C.

Magnesium Dependence: Magnesium dependence of round 15 of N20 was tested by varying MgCl$_2$ while other conditions were held constant (50 mM tris [pH 8.0], 100 mM NaCl, 50 mM KCl, single turnover, 10 nM pool). The data is shown in Table XII, which demonstrates increased activity with increased magnesium concentrations.

Example 9

Selection of Novel Enzymatic Nucleic Acid Molecule Motifs Using 2'-Deoxy-2'-(N-histidyl) Amino UTP, 2'-Fluoro-ATP, and 2'-deoxy-2'-amino CTP and GTP The method described in example 8 was repeated using 2'-Deoxy-2'-(N-histidyl) amino UTP, 2'-Fluoro-ATP, and 2'-deoxy-2'-amino CTP and GTP. However, rather than causing cleavage on the initial column with MgCl$_2$, the initial random modified-RNA pool was loaded onto substrate-resin in the following buffer; 5 mM NaOAc pH 5.2, 1 M NaCl at 4° C. After ample washing, the resin was moved to 22° C. and the buffer switch 20 mM HEPES pH 7.4, 140 mM KCl, 10 mM NaCl, 1 mM CaCl$_2$, 1 mM MgCl$_2$. In one selection of N60 oligonucleotides, no divalent cations (MgCl$_2$, CaCl$_2$) was used. The resin was incubated for 10 minutes to allow reaction and the eluant collected.

The enzymatic nucleic acid molecule pools were capable of cleaving 1–3% of the present substrate even in the absense of divalent cations, the background (in the absence of modified pools) was 0.2–0.4%.

Example 10

Synthesis of 5-substituted 2'-modified Nucleosides

When designing monomeric nucleoside triphosphates for selection of therapeutic catalytic RNAs, one has to take into account nuclease stability of such molecules in biological sera. A common approach to increase RNA stability is to replace the sugar 2'-OH group with other groups like 2'-fluoro, 2'-O-methyl or 2'-amino. Fortunately such 2'-modified pyrimidine 5'triphosphates are shown to be substrates for RNA polymerases.[5,7] On the other hand it was shown that variety of substituents at pyrimidine 5-position is well tolerated by T7 RNA polymerase,[1] most likely because the natural hydrogen-bonding pattern of these nucleotides is preserved. We have chosen 2'-fluoro and 2'-O-methyl pyrimidine nucleosides as starting materials for attachment of different functionalities to the 5-position of the base. Both rigid (alkynyl) and flexible (alkyl) spacers are used. The choice of imidazole, amino and carboxylate pendant groups is based on their ability to act as general acids, general bases, nucleophiles and metal ligands, all of which can improve the catalytic effectiveness of selected nucleic acids. FIGS. 12–15 relate to the synthesis of these compounds.

2'-O-methyluridine was 3',5'-bis-acetylated using acetic anhydride in pyridine and then converted to its 5-iodo derivative 1a using I$_2$/ceric ammonium nitrate reagent[8] (Scheme 1). Both reactions proceeded in a quantitative yield and no chromatographic purifications were needed. Coupling between 1 and N-trifluoroacetyl propargylamine using copper(I) iodide and tetrakis(triphenylphosphine)palladium (0) catalyst as described by Hobbs[9] yielded 2a in 89% yield. Selective O-deacylation with aqueous NaOH afforded 3a which was phosphorylated with POCl$_3$/triethylphosphate (TEP) in the presence of 1,8-bis(dimethylamino) naphthalene (Proton-Sponge) (Method A).[10] The intermediate nucleoside phosphorodichloridate was condensed in situ with tri-n-butylammonium pyrophosphate. At the end, the N-TFA group was removed with concentrated ammonia. 5'-Triphosphate was purified on Sephadex® DEAE A-25 ion exchange column using a linear gradient of 0.1–0.8M triethylammonium bicarbonate (TEAB) for elution. Traces of contaminating inorganic pyrophosphate are removed using C-18 RP HPLC to afford analytically pure material. Conversion into Na-salt was achieved by passing the aqueous solution of triphosphate through Dowex 50WX8 ion exchange resin in Na$^+$ form to afford 4a in 45% yield. When Proton-Sponge was omitted in the first phosphorylation step, yields were reduced to 10–20%. Catalytic hydrogenation of 3a yielded 5-aminopropyl derivative 5a which was phosphorylated under conditions identical to those described for propynyl derivative 3a to afford triphosphate 6a in 50% yield.

For the preparation of imidazole derivatized triphosphates 9a and 11a, we developed an efficient synthesis of N-diphenylcarbamoyl 4-imidazoleacetic acid (ImAA$^{DPC}$): Transient protection of carboxyl group as TMS-ester using TMS-Cl/pyridine followed by DPC-Cl allowed for a clean and quantitative conversion of 4-imidazoleacetic acid (ImAA) to its N-DPC protected derivative.

Complete deacylation of 2a afforded 5-(3-aminopropynyl) derivative 8a which was condensed with 4-imidazoleacetic acid in the presence of 1-(3-dimethylaminopropyl)-3-ethylcarbodiimide (EDC) to afford 9a in 68% yield. Catalytic hydrogenation of 8a yielded 5-(3-aminopropyl) derivative 10a which was condensed with ImAA$^{DPC}$ to yield conjugate 11a in 32% yield. Yields in these couplings were greatly improved when 5'-OH was protected with DMT group (not shown) thus efficiently preventing undesired 5'-O-esterification. Both 9a and 11a failed to yield triphosphate products in reaction with $POCl_3$/TEP/Proton-Sponge.

On the contrary, phosphorylation of 3'-O-acetylated derivatives 12a and 13a using 2-chloro-4H-1,3,2-benzodioxaphosphorin-4-one followed by pyrophosphate addition and oxidation (Method B,[11] Scheme 2) afforded the desired triphosphates 14a and 15a in 57% yield, respectively.

2'-Deoxy-2'-fluoro nucleoside 5'-triphosphates containing amino-(4b, 6b) and imidazole-(14b,15b) linked groups were synthesized in a manner analogous to that described for the preparation of 2'-O-methyl nucleoside 5'-triphosphates (Schemes 1 and 2). Again, only Ludwig-Eckstein's phosphorylation worked for the preparation of 4-imidazoleacetyl derivatized triphosphates.

It is worth noting that when “one-pot-two-steps” phosphorylation reaction[10] of 5b was quenched with 40% aqueous methylamine instead of TEAB or $H_2O$, the—amidate 7b was generated as the only detectable product. Similar reaction was reported recently for the preparation of the γ-amidate of pppA2'p5'A2'p5'A.[12]

Carboxylate group was introduced into 5-position of uridine both on the nucleoside level and post-synthetically (Method C) (Scheme 3). 5-Iodo-2'-deoxy-2'-fluorouridine (16) was coupled with methyl acrylate using modified Heck reaction,[3] to yield 17 in 85% yield. 5'-O-Dimethoxytritylation, followed by in situ 3'-O-acetylation and subsequent detritylation afforded 3'-protected derivative 18. Phosphorylation using 2-chloro-4H-1,3,2-benzodioxaphosphorin-4-one followed by pyrophosphate addition and oxidation [1] afforded the desired triphosphate in 54% yield. On the other hand, 5-(3-aminopropyl)uridine 5'-triphosphate 6b was coupled with N-hydroxysuccinimide ester of Fmoc-Asp-OFm to afford, after removal of Fmoc and Fm groups with diethylamine, the desired aminoacyl conjugate 20 in 50% yield.

Cytidine derivatives comprising 3-aminopropyl and 3(N-succinyl)aminopropyl groups were synthesized according to Scheme 4. Peracylated 5-(3-aminopropynyl)uracil derivative 2b is reduced using catalytic hydrogenation and then converted in seven steps and 5% overall yield into 3'-acetylated cytidine derivative 25. This synthesis was plagued by poor solubility of intermediates and formation of the $N^4$-cyclized byproduct during ammonia treatment of the 4-triazolyl intermediate. Phosphorylation of 25 as described in reference 11 yielded triphosphate 26 and $N^4$-cyclized product 27 in 1:1 ratio. They were easily separated on Sephadex DEAE A-25 ion exchange column using 0.1–0.8M TEAB gradient. It appears that under basic conditions the free primary amine can displace any remaining intact 4-NHBz group leading to the cyclized product. This is similar to displacement of 4-triazolyl group by primary amine as mentioned above.

We reasoned that utilization of $N^4$-unprotected cytidine will solve this problem. This lead to an improved synthesis of 26: Iodination of 2'-deoxy-2'-fluorocytidine (28) provided the 5-iodo derivative 29 in 58% yield. This compound was then smoothly converted into 5-(3-aminopropynyl) derivative 30. Hydrogenation afforded 5-(3-aminopropyl) derivative 31 which was phosphorylated directly with $POCl_3$/PPi to afford 26 in 37% yield. Coupling of the 5'-triphosphate 26 with succinic anhydride yielded succinylated derivative 32 in 36% yield.

References

1. Tarasow, T. M.; Eaton, B. E. *Biopolymers* 1998, 48, 29.
2. Eaton, B. E.; Pieken, W. A. *Annu. Rev. Biochem.* 1995, 64, 837.
3. Eaton, B. E. *Curr. Opin. Chem. Biol.* 1997, 1, 10.
4. Dewey, T. M.; Mundt, A. A.; Crouch, G. J.; Zyzniewski, M. C., Eaton, B. E. *J. Am. Chem. Soc.* 1995, 32, 8475.
5. Aurup, H.; Williams, D. M.; Eckstein, F. *Biochemistry* 1992, 31, 9637.
6. Sakthivel, K.; Barbas III, C. F. *Angew. Chem. Int.* Ed. 1998, 37, 2872.
7. Padilla, R.; Sousa, R. *Nucleic Acids Res.* 1999, 27, 1561.
8. Asakura, J.; Robins, M. J. *J. Org. Chem.* 1990, 55, 4928.
9. Hobbs, F. W.,Jr. *J. Org. Chem.* 1989, 54, 3420.
10. Kovácz, T; Ötvös, L. Tetrahedron Lett. 1988, 29, 4525.
11. Ludwig, J.; Eckstein, F. *J. Org. Chem.* 1989, 54, 631.
12. Nyilas, A. *Tetrahedron Lett.* 1997, 38, 2517.
13. Dyer, R. L.; Jones, A. S.; Walker, R. T. in *Nucleic Acid Chemistry*; Townsend, L. B. and Tipson, R. T., Ed.; John Wiley & Sons, Inc., New, York, 1991; p. 79.

Example 11

Synthesis of 5-Imidazoleacetic Acid 2'-deoxy-5'-triphosphate Uridine 5-dintrophenylimidazoleacetic acid 2'-deoxy uridine nucleoside (80 mg) was dissolved in 5 ml of triethylphosphate while stirring under argon, and the reaction mixture was cooled to 0° C. Phosphorous oxychloride (1.8 eq, 22 ml) was added to the reaction mixture at 0° C., three more aliquots were added over the course of 48 hours at room temperature. The reaction mixture was then diluted with anhydrous MeCN (5 ml) and cooled to 0° C., followed by the addition of tributylamine (0.65 ml) and tributylammonium pyrophosphate (4.0 eq, 0.24 g). After 45 minutes, the reaction was quenched with 10 ml aq. methyl amine for four hours. After co-evaporation with MeOH (3×), purified material on DEAE Sephadex followed by RP chromatography to afford 15 mg of triphosphate.

Example 12

Synthesis of 2'-(N-lysyl)-amino-2'-deoxy-cytidine Triphosphate

2'-(N-lysyl)-amino-2'-deoxy cytidine (0.180 g, 0.22 mmol) was dissolved in triethyl phosphate (2.00 ml) under Ar. The solution was cooled to 0° C. in an ice bath. Phosphorus oxychloride (99.999%, 3 eq., 0.0672 mL) was added to the solution and the reaction was stirred for two hours at 0° C. Tributylammonium pyrophosphate (4 eq., 0.400 g) was dissolved in 3.42 mL of acetonitrile and tribuytylamine (0.165 mL).

Acetonitrile (1 mL) was added to the monophosphate solution followed by the pyrophosphate solution which was added dropwise. The resulting solution was clear. The reaction was allowed to warm up to room temperature. After stirring for 45 minutes, methylamine (5 mL) was added and the reaction and stirred at room temperature for 2 hours. A biphasic mixture appeared (little beads at the bottom of the flask). TLC (7:1:2 iPrOH:$NH_4OH$:$H_2O$) showed the appearance of triphosphate material. The solution was concentrated, dissolved in water and loaded on a newly prepared DEAE Sephadex A-25 column. The column was washed with a gradient up to 0.6 M TEAB buffer and the product eluted off in fractions 90–95. The fractions were analyzed by ion exchange HPLC. Each fraction showed one triphosphate peak that eluted at ~4.000 minutes. The fractions were combined and pumped down from methanol to remove buffer salt to yield 15.7 mg of product.

Example 13

Synthesis of 2'-deoxy-2'-(L-histidine)amino Cytidine Triphosphate

2'-[N-Fmoc, $N^{imid}$-dinitrophenyl-histidyl]amino-2'-cytidine (0.310 g, 4.04 mmol) was dissolved in triethyl phosphate (3 ml) under Ar. The solution was cooled to 0° C. Phosphorus oxychloride (1.8 eq., 0.068 mL) was added to the solution and stored overnight in the freezer. The next morning TLC (10% MeOH in $CH_2Cl_2$) showed significant starting material, one more equivalent of $POCl_3$ was added. After two hours, TLC still showed starting material. Tributylamine (0.303 mL) and Tributylammonium pyrophosphate (4 eq., 0.734 g) dissolved in 6.3 mL of acetonitrile (added dropwise) were added to the monophosphate solution. The reaction was allowed to warm up to room temperature. After stirring for 15 min, methylamine (10 mL) was added at room temperature and stirring continued for 2 hours. TLC (7:1:2 iPrOH:$NH_4OH$:$H_2O$) showed the appearance of triphosphate material. The solution was concentrated, dissolved in water and loaded on a DEAE Sephadex A-25 column. The column was washed with a gradient up to 0.6 M TEAB buffer and the product eluted off in fractions 170–179. The fractions were analyzed by ion exchange HPLC. Each fraction showed one triphosphate peak that eluted at ~6.77 minutes. The fractions were combined and pumped down from methanol to remove buffer salt to afford 17 mg of product.

Example 14

Screening for Novel Enzymatic Nucleic Acid Molecule Motifs Using Modified NTPs (Class I Motif)

Our initial pool contained $3\times10^{14}$ individual sequences of 2'-amino-dCTP/2'-amino-dUTP RNA. We optimized transcription conditions in order to increase the amount of RNA product by inclusion of methanol and lithium chloride. 2'-amino-2'-deoxynucleotides do not interfere with the reverse transcription and amplification steps of selection and confer nuclease resistance. We designed the pool to have two binding arms complementary to the substrate, separated by the random 40 nucleotide region. The 16-mer substrate had two domains, 5 and 10 nucleotides long, that bind the pool, separated by an unpaired guanosine. On the 5' end of the substrate was a biotin attached by a C18 linker. This enabled us to link the substrate to a NeutrAvidin™ resin in a column format. The desired reaction would be cleavage at the unpaired G upon addition of magnesium cofactor followed by dissociation from the column due to instability of the 5 base pair helix. A detailed protocol follows:

Enzymatic nucleic acid molecule Pool Prep: The initial pool DNA was prepared by converting the following template oligonucleotides into double-stranded DNA by filling in with taq polymerase. (template=5'-ACC CTC ACT AAA GGC CGT $(N)_{40}$ GGT TGC ACA CCT TTC-3' (SEQ ID NO. 1523); primer 1=5'-CAC TTA GCA TTA ACC CTC ACT AAA GGC CGT-3' (SEQ ID NO. 1515); primer 2=5'-TAA TAC GAC TCA CTA TAG GAA AGG TGT GCA ACC-3' (SEQ ID NO. 1516)). All DNA oligonucleotides were synthesized by Operon technologies. Template oligos were purified by denaturing PAGE and Sep-pak chromatography columns (Waters). RNA substrate oligos were using standard solid phase chemistry and purified by denaturing PAGE followed by ethanol precipitation. Substrates for in vitro cleavage assays were 5'-end labeled with gamma-$^{32}$P-ATP and T4 polynucleotide kinase followed by denaturing PAGE purification and ethanol precipitation.

5 nmole of template, 10 nmole of each primer and 250 U taq polymerase were incubated in a 10 ml volume with 1×PCR buffer (10 mM tris-HCl (pH 8.3), 1.5 mM $MgCl_2$, 50 mM KCl) and 0.2 mM each dNTP as follows: 94° C., 4 minutes; (94° C., 1 min; 42° C., 1 min; 72° C., 2 min) through four cycles; and then 72° C., for 10 minutes. The product was analyzed on 2% Separide T agarose gel for size and then was extracted twice with buffered phenol, then chloroform-isoamyl alcohol, and ethanol precipitated. The initial RNA pool was made by transcription of 500 pmole ($3\times10^{14}$ molecules) of this DNA as follows. Template DNA was added to 40 mM tris-HCl (pH 8.0),12 mM $MgCl_2$, 5 mM dithiothreitol (DTT), 1 mM spermidine, 0.002% triton X-100, 1 mM LiCi, 4% PEG-8000, 10% methanol, 2 mM ATP, 2 mM GTP, 2 mM 2'-amino-dCTP, 2 mM 2'-amino-dUTP, 5 U/ml inorganic pyrophosphatase, and 5 U/μl T7 RNA polymerase at room temperature for a total volume of 1 ml. A separate reaction contained a trace amount of alpha-$^{32}$P-GTP for detection. Transcriptions were incubated at 37° C. for 2 hours followed by addition of equal volume STOP buffer (94% formamide, 20 mM EDTA, 0.05% bromophenol blue). The resulting RNA was purified by 6% denaturing PAGE gel, Sep-pak™ chromatography, and ethanol precipitated.

INITIAL SELECTION: 2 nmole of 16 mer 5'-biotinylated substrate (Biotin-C18 linker-5'-GCC GUG GGU UGC ACA C-3' (SEQ ID NO: 1493) was linked to 200 μl UltraLink Immobilized NeutrAvidin™ resin (400 μl slurry, Pierce) in binding buffer (20 mM $NaPO_4$ (pH 7.5), 150 mM NaCl) for 30 minutes at room temperature. The resulting substrate column was washed with 2 ml binding buffer followed by 2 ml column buffer (50 mM tris-HCl (pH 8.5), 100 mM NaCl, 50 mM KCl). The flow was capped off and 1000 pmole of initial pool RNA in 200 μl column buffer was added to the column and incubated 30 minutes at room temperature. The column was uncapped and washed with 2 ml column buffer, then capped off. 200 μl elution buffer (=column buffer+25 mM $MgCl_2$) was added to the column and allowed to incubate 30 minutes at room temperature. The column was uncapped and eluent collected followed by three 200 μl elution buffer washes. The eluent/washes were ethanol precipitated using glycogen as carrier and rehydrated in 50 μl sterile $H_2O$. The eluted RNA was amplified by standard reverse transcription/PCR amplification techniques. 5–31 μl RNA was incubated with 20 pmol of primer 1 in 14 μl volume 90° for 3 min then placed on ice for 1 minute. The following reagent were added (final concentrations noted): 1×PCR buffer, 1 mM each dNTP, 2 U/μl RNase Inhibitor, 10 U/μl SuperScript™ II reverse transcriptase. The reaction was incubated 42° for 1 hour followed by 95° for 5 min in order to inactivate the reverse transcriptase. The volume was then increased to 100 μl by adding water and reagents for PCR: 1×PCR buffer, 20 pmol primer 2, and 2.5 U taq DNA polymerase. The reaction was cycled in a Hybaid thermocycler: 94°, 4 min; (94° C., 30 sec; 54° C., 30 sec; 72° C., 1 min)×25; 72° C., 5 min. Products were analyzed on agarose gel for size and ethanol precipitated. One-third to one-fifth of the PCR DNA was used to transcribe the next generation, in 100 μl volume, as described above. Subsequent rounds used 20 pmol RNA for the column with 40 pmol substrate.

TWO COLUMN SELECTION: At generation 8 (G8), the column selection was changed to the two column format.

200 pmoles of 22 mer 5'-biotinylated substrate (Biotin-C18 linker-5'-GCC GUG GGU UGC ACA CCU UUC C-3' (SEQ ID NO: 1481)-C18 linker-thiol modifier C6 S-S-inverted abasic') was used in the selection column as described above. Elution was in 200 μl elution buffer followed by a 1 ml elution buffer wash. The 1200 μl eluent was passed through a product trap column by gravity. The product trap column was prepared as follows: 200 pmol 16 mer 5'-biotinylated "product" (5'-GGU UGC ACA CCU UUC C-3' (SEQ ID NO: 1521)-C18 linker-biotin') was linked to the column as described above and the column was equilibrated in elution buffer. Eluent from the product column was precipitated as previously described. The products were amplified as above only with 2.5-fold more volume and 100 pmol each primer. 100 μl of the PCR reaction was used to do a cycle course; the remaining fraction was amplified the minimal number of cycles needed for product. After 3 rounds (G11), there was visible activity in a single turnover cleavage assay. By generation 13, 45% of the substrate was cleaved a hours; $k_{obs}$ of the pool was 0.037 $min^{-1}$ in 25 mM $MgCl_2$. We subcloned and sequenced generation 13; the pool was still very diverse. Since our goal was a enzymatic nucleic acid molecule that would work in a physiological environment, we decided to change selection presure rather than exhaustively catalog G13.

Reselection of the N40 pool was started from G12 DNA. Part of the G12 DNA was subjected to hypermutagenic PCR (Vartanian et al., 1996, *Nucleic Acids Research* 24, 2627–2631) to introduce a 10% per position mutation frequency and was designated N40H. At round 19, part of the DNA was hypermutagenized again, giving N40M and N40HM (a total of 4 parallel pools). The column substrates remained the same; buffers were changed and temperature of binding and elution was raised to 37° C. Column buffer was replaced by physiological buffer (50 mM tris-HCl (pH 7.5), 140 mM KCl, 10 mM NaCl) and elution buffer was replaced by 1 mM Mg buffer (physiological buffer +1 mM $MgCl_2$). Amount of time allowed for the pool to bind the column was eventually reduced to 10 min and elution time was gradually reduced from 30 min to 20 sec. Between rounds 18 and 23, $k_{obs}$ for the N40 pool stayed relatively constant at 0.035–0.04 $min^{-1}$. Generation 22 from each of the 4 pools was cloned and sequenced.

CLONING AND SEQUENCING: Generations 13 and 22 were cloned using Novagen's Perfectly Blunt™ Cloning kit (pT7Blue-3 vector) following the kit protocol. Clones were screened for insert by PCR amplification using vector-specific primers. Positive clones were sequenced using ABI Prism 7700 sequence detection system and vector-specific primer. Sequences were aligned using MacVector software; two-dimensional folding was performed using Mulfold software (Zuker, 1989, *Science* 244, 48–52; Jaeger et al., 1989, *Biochemistry* 86, 7706–7710; Jaeger et al., 1989, R. F. Doolittle ed., *Methods in Enzymology*, 183, 281–306). Individual clone transcription units were constructed by PCR amplification with 50 pmol each primer 1 and primer 2 in 1×PCR buffer, 0.2 mM each dNTP, and 2.5 U of taq polymerase in 100 μl volume cycled as follows: 94° C., 4 min; (94° C., 30 sec; 54° C., 30 sec; 72° C., 1 min)×20; 72° C., 5 min. Transcription units were ethanol precipitated, rehydrated in 30 μl H2O, and 10 μl was transcribed in 100 μl volume and purified as previously described.

Thirty-six clones from each pool were sequenced and were found to be variations of the same consensus motif. Unique clones were assayed for activity in 1 mM $MgCl_2$ and physiological conditions; nine clones represented the consensus sequence and were used in subsequent experiments. There were no mutations that significantly increased activity; most of the mutations were in regions believed to be duplex, based on the proposed secondary structure. In order to make the motif shorter, we deleted the 3'-terminal 25 nucleotides necessary to bind the primer for amplification. The measured rates of the full length and truncated molecules were both 0.04 $min^{-1}$; thus we were able reduce the size of the motif from 86 to 61 nucleotides. The molecule was shortened even further by truncating base pairs in the stem loop structures as well as the substrate recognition arms to yield a 48 nucleotide molecule. In addition, many of the ribonucleotides were replaced with 2O-methyl modified nucleotides to stabilize the molecule. An example of the new motif is given in FIG. 4. Those of ordinary skill in the art will recognize that the molecule is not limited to the chemical modifications shown in the figure and that it represents only one possible chemically modified molecule.

Kinetic Analysis

Single turnover kinetics were performed with trace amounts of 5'-$^{32}$P-labeled substrate and 10–1000 nM pool of enzymatic nucleic acid molecule. 2x substrate in 1x buffer and 2x pool/enzymatic nucleic acid molecule in 1x buffer were incubated separately 90° for 3 min followed by equilibration to 37° for 3 min. Equal volume of 2x substrate was added to pool/enzymatic nucleic acid molecule at $t_0$ and the reaction was incubated at 37° C. Time points were quenched in 1.2 vol STOP buffer on ice. Samples were heated to 90° C. for 3 min prior to separation on 15% sequencing gels. Gels were imaged using a PhosphorImager and quantitated using ImageQuant™ software (Molecular Dynamics). Curves were fit to double-exponential decay in most cases, although some of the curves required linear fits.

STABILITY: Serum stability assays were performed as previously described (Beigelman et al., 1995, *J. Biol. Chem.* 270, 25702–25708). 1 μg of 5'-$^{32}$P-labeled synthetic enzymatic nucleic acid molecule was added to 13 μl cold and assayed for decay in human serum. Gels and quantitation were as described in kinetics section.

SUBSTRATE REQUIREMENTS: Table XVII outlines the substrate requirements for Class I motif. Substrates maintained Watson-Crick or wobble base pairing with mutant Class I constructs. Activity in single turnover kinetic assay is shown relative to wild type Class I and 22 mer substrate (50 mM Tris-HCL (pH 7.5), 140 mM KCl, 10 mM NaCl, 1 mM $MgCl_2$, 100 nM ribozyme, 5 nM substrate, 37° C.).

RANDOM REGION MUTATION ALIGNMENT: Table XVII outlines the random region alignment of 134 clones from generation 22 (1.x=N40, 2.x=N40M, 3.x=N40H, 4.x=N40HM). The number of copies of each mutant is in parenthesis in the table, deviations from consensus are shown. Mutations that maintain base pair U19:A34 are shown in italic. Activity in single turnover kinetic assay is shown relative to the G22 pool rate (50 mM Tris-HCL pH 7.5, 140 mM KCl, 10 mM NaCl, 1 mM $MgCl_2$, 100 nM ribozyme, trace substrate, 37° C.).

STEM TRUNCATION AND LOOP REPLACEMENT ANALYSIS: FIG. 16 shows a representation of Class I ribozyme stem truncation and loop replacement analysis. The $K_{re1}$ is compared to a 61 mer Class I ribozyme measured as described above. FIG. 17 shows examples of Class I ribozymes with truncated stem(s) and/or non-nucleotide linker replaced loop structures.

Example 15

Inhibition of HCV Using Class I (Amberzme) Motif

During HCV infection, viral RNA is present as a potential target for enzymatic nucleic acid molecule cleavage at several processes: uncoating, translation, RNA replication and packaging. Target RNA may be more or less accessible to enzymatic nucleic acid molecule cleavage at any one of these steps. Although the association between the HCV initial ribosome entry site (IRES) and the translation apparatus is mimicked in the HCV 5'UTR/luciferase reporter system (example 9), these other viral processes are not represented in the OST7 system. The resulting RNA/protein complexes associated with the target viral RNA are also absent. Moreover, these processes may be coupled in an HCV-infected cell which could further impact target RNA accessibility. Therefore, we tested whether enzymatic nucleic acid molecules designed to cleave the HCV 5'UTR could effect a replicating viral system.

Recently, Lu and Wimmer characterized an HCV-poliovirus chimera in which the poliovirus IRES was replaced by the IRES from HCV (Lu & Wimmer, 1996, *Proc. Natl. Acad. Sci. USA*. 93, 1412–1417). Poliovirus (PV) is a positive strand RNA virus like HCV, but unlike HCV is non-enveloped and replicates efficiently in cell culture. The HCV-PV chimera expresses a stable, small plaque phenotype relative to wild type PV.

The capability of the new enzymatic nucleic acid molecule motifs to inhibit HCV RNA intracellularly was tested using a dual reporter system that utilizes both firefly and Renilla luciferase (FIG. 5). A number of enzymatic nucleic acid molecules having the new class I motif (Amberzyme) were designed and tested (Table XIII). The Amberzyme ribozymes were targeted to the 5' HCV UTR region, which when cleaved, would prevent the translation of the transcript into luciferase. OST-7 cells were plated at 12,500 cells per well in black walled 96-well plates (Packard) in medium DMEM containing 10% fetal bovine serum, 1% pen/strep, and 1% L-glutamine and incubated at 37° C. overnight. A plasmid containing T7 promoter expressing 5' HCV UTR and firefly luciferase (T7C1-341 (Wang et al., 1993, *J. of Virol*. 67, 3338–3344)) was mixed with a pRLSV40 Renilla control plasmid (Promega Corporation) followed by enzymatic nucleic acid molecule, and cationic lipid to make a 5×concentration of the reagents (T7C1-341 (4 μg/ml), pRLSV40 renilla luciferase control (6 μg/ml), enzymatic nucleic acid molecule (250 nM), transfection reagent (28.5 μg/ml).

The complex mixture was incubated at 37° C. for 20 minutes. The media was removed from the cells and 120 μl of Opti-mem media was added to the well followed by 30 μl of the 5×complex mixture. 150 μl of Opti-mem was added to the wells holding the untreated cells. The complex mixture was incubated on OST-7 cells for 4 hours, lysed with passive lysis buffer (Promega Corporation) and luminescent signals were quantified using the Dual Luciferase Assay Kit using the manufacturer's protocol (Promega Corporation). The data shown in FIG. 6 is a dose curve of enzymatic nucleic acid molecule targeting site 146 of the HCV RNA and is presented as a ratio between the firefly and Renilla luciferase fluorescence. The enzymatic nucleic acid molecule was able to reduce the quantity of HCV RNA at all enzymatic nucleic acid molecule concentrations yielding an IC 50 of approximately 5 nM. Other sites were also efficacious (FIG. 7), in particular enzymatic nucleic acid molecules targeting sitesl33, 209, and 273 were also able to reduce HCV RNA compared to the irrelevant (IRR) controls.

Example 16

Cleavage of Substrates Using Completely Modified class I (Amberzvme) Enzymatic Nucleic Acid Molecule The ability of an enzymatic nucleic acid, which is modified at every 2' position to cleave a target RNA was tested to determine if any ribonucleotide positions are necessary in the Amberzyme motif. Enzymatic nucleic acid molecules were constructed with 2'-O-methyl, and 2'-amino ($NH_2$) nucleotides and included no ribonucleotides (Table XIII; gene name: no ribo) and kinetic analysis was performed as described in example 13. 100 nM enzymatic nucleic acid was mixed with trace amounts of substrate in the presence of 1 mM $MgCl_2$ at physiological conditions (37° C.). The Amberzyme with no ribonucleotide present in it has a $K_{rel}$ of 0.13 compared to the enzymatic nucleic acid with a few ribonucleotides present in the molecule shown in Table XIII (ribo). This shows that Amberzyme enzymatic nucleic acid molecule may not require the presence of 2'-OH groups within the molecule for activity.

Example 17

Substrate Recognition Rules for Class II (Zinzyme) Enzymatic Nucleic Acid Molecules Class II (zinzyme) ribozymes were tested for their ability to cleave base-paired substrates with all sixteen possible combinations of bases immediately 5' and 3' proximal to the bulged cleavage site G. Ribozymes were identical in all remaining positions of their 7 base pair binding arms. Activity was assessed at two and twenty-four hour time points under standard reaction conditions [20 mM HEPES pH 7.4, 140 mM KCl, 10 mM NaCl, 1 mM $MgCl_2$, 1 mM $CaCi_2$—37° C.]. FIG. 10 shows the results of this study. Base paired substrate UGG (not shown in the figure) cleaved as poorly as CGG shown in the figure. The figure shows the cleavage site substrate triplet in the 5'-3' direction and 2 and 24 hour time points are shown top to bottom respectively. The results indicate the cleavage site triplet is most active with a 5'-Y-G-H-3' (where Y is C or U and H is A, C or U with cleavage between G and H); however activity is detected particularly with the 24 hour time point for most paired substrates. All positions outside of the cleavage triplet were found to tolerate any base pairings (data not shown).

All possible mispairs immediately 5' and 3' proximal to the bulged cleavage site G were tested to a class II ribozyme designed to cleave a 5'-C-G-C-3'. It was observed the 5' and 3' proximal sites are as active with G:U wobble pairs, in addition, the 5' proximal site will tolerate a mismatch with only a slight reduction in activity [data not shown].

Example 18

Screening for Novel Enzymatic Nucleic Acid Molecule Motifs (Class II Motifs)

The selections were initiated with pools of >$10^{14}$ modified RNA's of the following sequence: 5'-GGGAGGAGGAAGUGCCU-$(N)_{35}$-UGCCGCGCUCGCUCCCAGUCC-3' (SEQ ID NO: 1524). The RNA was enzymatically generated using the mutant T7 Y639F RNA polymerase prepared by Rui Souza (1997, *Biochemistry* 36(44):13718–28). The following modified NTP's were incorporated: 2'-deoxy-2'-fluoro-adenine triphosphate, 2'-deoxy-2'-fluoro-uridine triphosphate or 2'-deoxy-2'-fluoro-5-[(N-imidazole-4acetyl)propyl amine] uridine triphosphate, and 2'-deoxy-2'-amino-cytidine triphosphate; natural guanidine triphosphate was used in all selections so that alpha—$^{32}P$-GTP could be used to label pool RNA's. RNA pools were purified by denaturing gel electrophoresus 8% polyacrilamide 7 M Urea.

The following target RNA (resin A) was synthesized and coupled to lodoacetyl Ultralink™ resin (Pierce) by the supplier's procedure: 5'-b-L-GGACUGGGAGCGAGCGC- GGCGCAGGCACUGAAG-L-S-B-3' (SEQ ID NO: 1496); where b is biotin (Glenn Research cat# 10–1953-nn), L is polyethylene glycol spacer (Glenn Research cat# 10–1918-nn), S is thiol-modifier C6 S-S (Glenn Research cat# 10–1936-nn), B is a standard inverted deoxy abasic.

RNA pools were added to 100 ul of 5 uM Resin A in the buffer A (20 mM HEPES pH 7.4, 140 mM KCL, 10 mM NaCl) and incubated at 22° C. for 5 minutes. The temperature was then raised to 37° C. for 10 minutes. The resin was washed with 5 ml buffer A. Reaction was triggered by the addition of buffer B(20 mM HEPES pH 7.4, 140 mM KCL, 10 mM NaCl, 1 mM $MgCl_2$, 1 mM $CaCl_2$). Incubation proceeded for 20 minutes in the first generation and was reduced progressively to 1 minute in the final generations; with 13 total generations. The reaction eluant was collected in 5 M NaCl to give a final concentration of 2 M NaCl. To this was added 100 $\mu$l of 50% slurry Ultralink NeutraAvidin™ (Pierce). Binding of cleaved biotin product to the avidin resin was allowed by 20 minute incubation at 22° C. The resin was subsequently washed with 5 ml of 20 mM HEPES pH 7.4, 2 M NaCl. Desired RNA's were removed by a 1.2 ml denaturing wash 1M NaCl, 10 M Urea at 94° C. over 10 minutes. RNA's were double precipitated in 0.3 M sodium acetate to remove $Cl^-$ ions inhibitory to reverse transcription. Standard protocols of reverse transcription and PCR amplification were performed. RNA's were again transcribed with the modified NTP's described above. After 13 generations cloning and sequencing provided 14 sequences which were able to cleave the target substrate. Six sequences were characterized to determine secondary structure and kinetic cleavage rates. The structures and kinetic data are given in FIG. 8. The sequences of eight other enzymatic nucleic acid molecule sequences are given in Table XIV. The size, sequence, and chemical compositions of these molecules can be modified as described under example 13 or using other techniques well known in the art.

Nucleic Acid Catalyst Engineering

Sequence, chemical and structural variants of Class I and Class II enzymatic nucleic acid molecule can be engineered and re-engineered using the techniques shown in this application and known in the art. For example, the size of class I and class II enzymatic nucleic acid molecules can, be reduced or increased using the techniques known in the art (Zaug et al., 1986*, Nature*, 324, 429; Ruffnier et al., 1990*, Biochem*., 29, 10695; Beaudry et al., 1990*, Biochem*., 29, 6534; McCall et al., 1992*, Proc. Natl. Acad. Sci., USA*., 89, 5710; Long et al., 1994, supra; Hendry et al., 1994*, BBA* 1219, 405; Benseler et al., 1993*, JACS*, 115, 8483; Thompson et al., 1996*, Nucl. Acids Res*., 24, 4401; Michels et al., 1995*, Biochem*., 34, 2965; Been et al., 1992*, Biochem*., 31, 11843; Guo et al., 1995*, EMBO. J*., 14, 368; Pan et al., 1994*, Biochem*., 33, 9561; Cech, 1992*, Curr. Op. Struc. Bio*., 2, 605; Sugiyama et al., 1996*, FEBS Lett*., 392, 215; Beigelman et al., 1994*, Bioorg. Med. Chem*., 4, 1715; Santoro et al., 1997*, PNAS* 94, 4262; all are incorporated in their totality by reference herein), to the extent that the overall catalytic activity of the ribozyme is not significantly decreased.

Further rounds of in vitro selection strategies described herein and variations thereof can be readily used by a person skilled in the art to evolve additional nucleic acid catalysts and such new catalysts are within the scope of the instant invention.

Example 19

Activity of Class II (Zinzyme) Nucleic Acid Catalysts to Inhibit HER2 Gene Expression HER2 (also known as neu, erbB2 and c-erbB2) is an oncogene that encodes a 185-kDa transmembrane tyrosine kinase receptor. HER2 is a member of the epidermal growth factor receptor (EGFR) family and shares partial homology with other family members. In normal adult tissues HER2 expression is low. However, HER2 is overexpressed in at least 25–30% of breast (McGuire & Greene, 1989) and ovarian cancers (Berchuck, et al., 1990). Furthermore, overexpression of HER2 in malignant breast tumors has been correlated with increased metastasis, chemoresistance and poor survival rates (Slamon et al., 1987 Science 235: 177–182). Because HER2 expression is high in aggressive human breast and ovarian cancers, but low in normal adult tissues, it is an attractive target for ribozyme-mediated therapy (Thompson et al., supra).

Cell Culture Review

The greatest HER2 specific effects have been observed in cancer cell lines that express high levels of HER2 protein (as measured by ELISA). Specifically, in one study that treated five human breast cancer cell lines with the HER2 antibody (anti-erbB2-sFv), the greatest inhibition of cell growth was seen in three cell lines (MDA-MB-361, SKBR-3 and BT-474) that express high levels of HER2 protein. No inhibition of cell growth was observed in two cell lines (MDA-MB-231 and MCF-7) that express low levels of HER2 protein (Wright et al., 1997). Another group successfully used SKBR-3 cells to show HER2 antisense oligonucleotide-mediated inhibition of. HER2 protein expression and HER2 RNA knockdown (Vaughn et al., 1995). Other groups have also demonstrated a decrease in the levels of HER2 protein, HER2 mRNA and/or cell proliferation in cultured cells using anti-HER2 ribozymes or antisense molecules (Suzuki, T. et al., 1997; Weichen, et al., 1997; Czubayko, F. et al., 1997; Colomer, et al., 1994; Betram et al., 1994). Because cell lines that express higher levels of HER2 have been more sensitive to anti-HER2 agents, we prefer using several medium to high expressing cell lines, including SKBR-3 and T47D, for ribozyme screens in cell culture.

A variety of endpoints have been used in cell culture models to look at HER2-mediated effects after treatment with anti-HER2 agents. Phenotypic endpoints include inhibition of cell proliferation, apoptosis assays and reduction of HER2 protein expression. Because overexpression of HER2 is directly associated with increased proliferation of breast and ovarian tumor cells, a proliferation endpoint for cell culture assays will preferably be used as the primary screen. There are several methods by which this endpoint can be measured. Following treatment of cells with ribozymes, cells are allowed to grow (typically 5 days) after which either the cell viability, the incorporation of [$^3$H] thymidine into cellular DNA and/or the cell density can be measured. The assay of cell density is very straightforward and can be done in a 96-well format using commercially available fluorescent nucleic acid stains (such as Syto® 13 or CyQuant®). The assay using CyQuant® is described herein and is currently being employed to screen 100 ribozymes targeting HER2 (details below).

As a secondary, confirmatory endpoint a ribozyme-mediated decrease in the level of HER2 protein expression can be evaluated using a HER2-specific ELISA.

Validation of Cell Lines and Ribozyme Treatment Conditions

Two human breast cancer cell lines (T47D and SKBR-3) that are known to express medium to high levels of HER2 protein, respectively, were considered for ribozyme screening. In order to validate these cell lines for HER2-mediated sensitivity, both cell lines were treated with the HER2 specific antibody, Herceptin® (Genentech) and its effect on cell proliferation was determined. Herceptin® was added to cells at concentrations ranging from 0–8 $\mu$M in medium containing either no serum (OptiMem), 0.1% or 0.5% FBS and efficacy was determined via cell proliferation. Maximal inhibition of proliferation (~50%) in both cell lines was observed after addition of Herceptin® at 0.5 nM in medium containing 0.1% or no FBS. The fact that both cell lines are sensitive to an anti-HER2 agent (Herceptin®) supports their use in experiments testing anti-HER2 ribozymes.

Prior to ribozyme screening, the choice of the optimal lipid(s) and conditions for ribozyme delivery was determined empirically for each cell line. Applicant has established a panel of cationic lipids (lipids as described in PCT application W099/05094) that can be used to deliver ribozymes to cultured cells and are very useful for cell proliferation assays that are typically 3–5 days in length. (Additional description of useful lipids is provided above, and those skilled in the art are also familiar with a variety of lipids that can be used for delivery of oligonucleotide to cells in culture.) Initially, this panel of lipid delivery vehicles was screened in SKBR-3 and T47D cells using previously established control oligonucleotides. Specific lipids and conditions for optimal delivery were selected for each cell line based on these screens. These conditions were used to deliver HER2 specific ribozymes to cells for primary (inhibition of cell proliferation) and secondary (decrease in HER2 protein) efficacy endpoints.

Primary Screen: Inhibition of Cell Proliferation

Although optimal ribozyme delivery conditions were determined for two cell lines, the SKBR-3 cell line was used for the initial screen because it has the higher level of HER2 protein, and thus should be most susceptible to a HER2-specific ribozyme. Follow-up studies can be carried out in T47D cells to confirm delivery and activity results as necessary.

Ribozyme screens were be performed using an automated, high throughput 96-well cell proliferation assay. Cell proliferation was measured over a 5-day treatment period using the nucleic acid stain CyQuant® for determining cell density. The growth of cells treated with ribozyme/lipid complexes were compared to both untreated cells and to cells treated with Scrambled-arm Attenuated core Controls (SAC; FIG. 11). SACs can no longer bind to the target site due to the scrambled arm sequence and have nucleotide changes in the core that greatly diminish ribozyme cleavage. These SACs are used to determine non-specific inhibition of cell growth caused by ribozyme chemistry (i.e. multiple 2'O-Me modified nucleotides, a single 2'C-allyl uridine, 4 phosphorothioates and a 3' inverted abasic). Lead ribozymes are chosen from the primary screen based on their ability to inhibit cell proliferation in a specific manner. Dose response assays are carried out on these leads and a subset was advanced into a secondary screen using the level of HER2 protein as an endpoint.

Secondary Screen: Decrease in HER2 Protein

A secondary screen that measures the effect of anti-HER2 ribozymes on HER2 protein levels is used to affirm preliminary findings. A robust HER2 ELISA for both T47D and SKBR-3 cells has been established and is available for use as an additional endpoint.

Ribozyme Mechanism Assays

A Taqman® assay for measuring the ribozyme-mediated decrease in HER2 RNA has also been established. This assay is based on PCR technology and can measure in real time the production of HER2 mRNA relative to a standard cellular MRNA such as GAPDH. This RNA assay is used to establish proof that lead ribozymes are working through an RNA cleavage mechanism and result in a decrease in the level of HER2 mRNA, thus leading to a decrease in cell surface HER2 protein receptors and a subsequent decrease in tumor cell proliferation.

Animal Models

Evaluating the efficacy of anti-HER2 agents in animal models is an important prerequisite to human clinical trials. As in cell culture models, the most HER2 sensitive mouse tumor xenografts are those derived from human breast carcinoma cells that express high levels of HER2 protein. In a recent study, nude mice bearing BT-474 xenografts were sensitive to the anti-HER2 humanized monoclonal antibody Herceptin®, resulting in an 80% inhibition of tumor growth at a 1 mg kg dose (ip, 2x week for 4–5 weeks). Tumor eradication was observed in 3 of 8 mice treated in this manner (Baselga et al., 1998). This same study compared the efficacy of Herceptin® alone or in combination with the commonly used chemotherapeutics, paclitaxel or doxorubicin. Although, all three anti-HER2 agents caused modest inhibition of tumor growth, the greatest antitumor activity was produced by the combination of Herceptin® and paclitaxel (93% inhibition of tumor growth vs 35% with paclitaxel alone). The above studies provide proof that inhibition of HER2 expression by anti-HER2 agents causes inhibition of tumor growth in animals. Lead anti-HER2 ribozymes chosen from in vitro assays are further tested in mouse xenograft models. Ribozymes are first tested alone and then in combination with standard chemotherapies.

Animal Model Development

Three human breast tumor cell lines (T47D, SKBR-3 and BT-474) were characterized to establish their growth curves in mice. These three cell lines have been implanted into the mammary papillae of both nude and SClD mice and primary tumor volumes are being measured 3 times per week. Growth characteristics of these tumor lines using a Matrigel implantation format can also be established. In addition, the use of two other breast cell lines that have been engineered to express high levels of HER2 can also be used. The tumor cell line(s) and implantation method that supports the most consistent and reliable tumor growth is used in animal studies testing the lead HER2 ribozyme(s). Ribozyme are administered by daily subcutaneous injection or by continuous subcutaneous infusion from Alzet mini osmotic pumps beginning 3 days after tumor implantation and continuing for the duration of the study. Group sizes of at least 10 animals are employed. Efficacy is determined by statistical comparison of tumor volume of ribozyme-treated animals to a control group of animals treated with saline alone. Because the growth of these tumors is generally slow (45–60 days), an initial endpoint will be the time in days it takes to establish an easily measurable primary tumor (i.e. 50–100 $mm^3$) in the presence or absence of ribozyme treatment.

Clinical Summary

Overview

Breast cancer is a common cancer in women and also occurs in men to a lesser degree. The incidence of breast cancer in the United States is ~180,000 cases per year and ~46,000 die each year of the disease. In addition, 21,000 new cases of ovarian cancer per year lead to ~13,000 deaths (data from Hung et al., 1995 and the Surveillance, Epidemiology and End Results Program, NCI). Ovarian cancer is a potential secondary indication for anti-HER2 ribozyme therapy.

A full review of breast cancer is given in the NCI PDQ for Breast Cancer. A brief overview is given here. Breast cancer is evaluated or "staged" on the basis of tumor size, and whether it has spread to lymph nodes and/or other parts of the body. In Stage I breast cancer, the cancer is no larger than 2 centimeters and has not spread outside of the breast. In Stage II, the patient's tumor is 2–5 centimeters but cancer may have spread to the axillary lymph nodes. By Stage III, metastasis to the lymph nodes is typical, and tumors are $\geqq 5$ centimeters. Additional tissue involvement (skin, chest wall, ribs, muscles etc.) may also be noted. Once cancer has spread to additional organs of the body, it is classed as Stage IV.

Almost all breast cancers (>90%) are detected at Stage I or II, but 31% of these are already lymph node positive. The 5-year survival rate for node negative patients (with standard surgery/radiation/chemotherapy /hormone regimens) is 97%; however, involvement of the lymph nodes reduces the 5-year survival to only 77%. Involvement of other organs ($\geqq$Stage III) drastically reduces the overall survival, to 22% at 5 years. Thus, chance of recovery from breast cancer is highly dependent on early detection. Because up to 10% of breast cancers are hereditary, those with a family history are considered to be at high risk for breast cancer and should be monitored very closely.

Therapy

Breast cancer is highly treatable and often curable when detected in the early stages. (For a complete review of breast cancer treatments, see the NCI PDQ for Breast Cancer.) Common therapies include surgery, radiation therapy, chemotherapy and hormonal therapy. Depending upon many factors, including the tumor size, lymph node involvement and location of the lesion, surgical removal varies from lumpectomy (removal of the tumor and some surrounding tissue) to mastectomy (removal of the breast, lymph nodes and some or all of the underlying chest muscle). Even with successful surgical resection, as many as 21% of the patients may ultimately relapse (10–20 years). Thus, once local disease is controlled by surgery, adjuvant radiation treatments, chemotherapies and/or hormonal therapies are typically used to reduce the rate of recurrence and improve survival. The therapy regimen employed depends not only on the stage of the cancer at its time of removal, but other variables such the type of cancer (ductal or lobular), whether lymph nodes were involved and removed, age and general health of the patient and if other organs are involved.

Common chemotherapies include various combinations cytotoxic drugs to kill the cancer cells. These drugs include paclitaxel (Taxol), docetaxel, cisplatin, methotrexate, cyclophosphamide, doxorubin, fluorouracil etc. Significant toxicities are associated with these cytotoxic therapies. Well-characterized toxicities include nausea and vomiting, myelosuppression, alopecia and mucosity. Serious cardiac problems are also associated with certain of the combinations, e.g. doxorubin and paclitaxel, but are less common.

Testing for estrogen and progesterone receptors helps to determine whether certain anti-hormone therapies might be helpful in inhibiting tumor growth. If either or both receptors are present, therapies to interfere with the action of the hormone ligands, can be given in combination with chemotherapy and are generally continued for several years. These adjuvant therapies are called SERMs, selective estrogen receptor modulators, and they can give beneficial estrogen-like effects on bone and lipid metabolism while antagonizing estrogen in reproductive tissues. Tamoxifen is one such compound. The primary toxic effect associated with the use of tamoxifen is a 2 to 7-fold increase in the rate of endometrial cancer. Blood clots in the legs and lung and the possibility of stroke are additional side effects. However, tamoxifen has been determined to reduce breast cancer incidence by 49% in high-risk patients and an extensive, somewhat controversial, clinical study is underway to expand the prophylactic use of tamoxifen. Another SERM, raloxifene, was also shown to reduce the incidence of breast cancer in a large clinical trial where it was being used to treat osteoporosis. In additional studies, removal of the ovaries and/or drugs to keep the ovaries from working are being tested.

Bone marrow transplantation is being studied in clinical trials for breast cancers that have become resistant to traditional chemotherapies or where >3 lymph nodes are involved. Marrow is removed from the patient prior to high-dose chemotherapy to protect it from being destroyed, and then replaced after the chemotherapy. Another type of "transplant" involves the exogenous treatment of peripheral blood stem cells with drugs to kill cancer cells prior to replacing the treated cells in the bloodstream.

One biological treatment, a humanized monoclonal anti-HER2 antibody, Herceptin® (Genentech) has been approved by the FDA as an additional treatment for HER2 positive tumors. Herceptin® binds with high affinity to the extracellular domain of HER2 and thus blocks its signaling action. Herceptin® can be used alone or in combination with chemotherapeutics (i.e. paclitaxel, docetaxel, cisplatin, etc.) (Pegram, et al., 1998). In Phase III studies, Herceptin® significantly improved the response rate to chemotherapy as well as improving the time to progression (Ross & Fletcher, 1998). The most common side effects attributed to Herceptin® are fever and chills, pain, asthenia, nausea, vomiting, increased cough, diarrhea, headache, dyspnea, infection, rhinitis, and insomnia. Herceptin® in combination with chemotherapy (paclitaxel) can lead to cardiotoxicity (Sparano, 1999), leukopenia, anemia, diarrhea, abdominal pain and infection.

HER2 Protein Levels for Patient Screening and as a Potential Endpoint

Because elevated HER2 levels can be detected in at least 30% of breast cancers, breast cancer patients can be pre-screened for elevated HER2 prior to admission to initial clinical trials testing an anti-HER2 ribozyme. Initial HER2 levels can be determined (by ELISA) from tumor biopsies or resected tumor samples.

During clinical trials, it may be possible to monitor circulating HER2 protein by ELISA (Ross and Fletcher, 1998). Evaluation of serial blood/serum samples over the course of the anti-HER2 ribozyme treatment period could be useful in determining early indications of efficacy. In fact, the clinical course of Stage IV breast cancer was correlated with shed HER2 protein fragment following a dose-intensified paclitaxel monotherapy. In all responders, the HER2 serum level decreased below the detection limit (Luftner et al.).

Two cancer-associated antigens, CA27.29 and CA15.3, can also be measured in the serum. Both of these glycoproteins have been used as diagnostic markers for breast cancer. CA27.29 levels are higher than CA15.3 in breast cancer patients; the reverse is true in healthy individuals. Of these two markers, CA27.29 was found to better discriminate primary cancer from healthy subjects. In addition, a statistically significant and direct relationship was shown between CA27.29 and large vs small tumors and node postive vs node negative disease (Gion, et al., 1999). Moreover, both cancer antigens were found to be suitable for the detection of possible metastases during follow-up (Rodriguez de Paterna et al., 1999). Thus, blocking breast tumor growth may be reflected in lower CA27.29 and/or CA15.3 levels compared to a control group. FDA submissions for the use of CA27.29 and CA1 5.3 for monitoring metastatic breast cancer patients have been filed (reviewed in Beveridge, 1999). Fully automated methods for measurement of either of these markers are commercially available.

References

Baselga, J., Norton, L. Albanell, J., Kim, Y. M. and Mendelsohn, J. (1998) Recombinant humanized anti-HER2 antibody (Herceptin) enhances the antitumor activity of paclitaxel and doxorubicin against HER2/neu overexpressing human breast cancer xenografts. *Cancer Res*. 15: 2825–2831.

Berchuck, A. Kamel, A., Whitaker, R. et al. (1990) Overexpression of her-2/neu is associated with poor survival in advanced epithelial ovarian cancer. *Cancer Research* 50: 4087–4091.

Bertram, J. Killian, M., Brysch, W., Schlingensiepen, K. -H., and Kneba, M. (1994) Reduction of erbB2 gene product in mamma carcinoma cell lines by erbB2 mRNA-specific and tyrosine kinase consensus phosphorothioate antisense oligonucleotides. *Biochem. BioPhys. Res. Comm*. 200: 661–667.

Beveridge, R. A. (1999) Review of clinical studies of CA27.29 in breast cancer management. *Int. J. Biol, Markers* 14: 36–39.

Colomer, R., Lupu, R., Bacus, S. S. and Gelmann, E. P. (1994) erbB-2 antisense oligonucloetides inhibit the proliferation of breast carcinoma cells with erbB-2 oncogene amplification. *British J. Cancer* 70: 819–825.

Czubayko, F., Downing, S. G., Hsieh, S. S., Goldstein, D. J., Lu P. Y., Trapnell, B. C. and Wellstein, A. (1997) Adenovirus-mediated transduction of ribozymes abrogates HER-2/neu and pleiotrophin expression and inhibits tumor cell proliferation. *Gene Ther*. 4: 943–949.

Gion, M., Mione, R., Leon, A. E. and Dittadi, R. (1999) Comparison of the diagnostic accuracy of CA27.29 and CA15.3 in primary breast cancer. *Clin. Chem*. 45: 630–637.

Hung, M. -C., Matin, A., Zhang, Y., Xing, X., Sorgi, F., Huang, L. and Yu, D. (1995) HER-2/neu-targeting gene therapy—a review. *Gene* 159: 65–71.

Luftner, D., Schnabel. S. and Possinger, K. (1999) c-erbB-2 in serum of patients receiving fractionated paclitaxel chemotherapy. *Int. J. Biol. Markers* 14: 55–59.

McGuire, H. C. and Greene, M. I. (1989) The neu (c-erbB-2) oncogene. *Semin. Oncol*. 16: 148–155.

NCI PDQ/Treatment/Health Professionals/Breast Cancer: http://cancemet.nci.nih.gov/clinpdq/soa/Breast_cancer_Physician.html NCl PDQ/Treatment/Patients/Breast Cancer:

http://cancernet.nci.nih.gov/clinpdg/pif/Breast_cancer_Patient.html

Pegram, M. D., Lipton, A., Hayes, D. F., Weber, B. L., Baselga, J. M., Tripathy, D., Baly, D., Baughman, S. A., Twaddell, T., Glaspy, J. A. and Slamon, D. J. (1998) Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. *J. Clin. Oncol*. 16: 2659–2671.

Rodriguez de Patema, L., Arnaiz, F., Estenoz, J. Ortuno, B. and Lanzos E. (1999) Study of serum tumor markers CEA, CA15.3, CA27.29 as diagnostic parameters in patients with breast carcinoma. *Int. J. Biol. Markers* 10: 24–29.

Ross, J. S. and Fletcher, J. A. (1998) The HER-2/neu oncogene in breast cancer: Prognostic factor, predictive factor and target for therapy. *Oncologist* 3: 1998.

Slamon, D. J., Clark, G. M., Wong, S. G., Levin, W. J., Ullrich, A. and McGuire, W. L. (1987) Human breast cancer: correlation of relapse and survival with amplification of the HER-2/neu oncogene. *Science* 235: 177–1821.

Sparano, J.A. (1999) Doxorubicin/taxane combinations: Cardiac toxicity and pharmacokinetics. *Semin. Oncol*. 26: 14–19.

Surveillance, Epidemiology and End Results Program (SEER) Cancer Statistics Review: http://www.seer.ims.nci.nih.gov/Publications/CSR1973_1996/

Suzuki T., Curcio, L.D., Tsai, J. and Kashani-Sabet M. (1997) Anti-c-erb-B-2 Ribozyme for Breast Cancer. In *Methods in Molecular Medicine*, Vol. 11, Therapeutic Applications of Ribozmes, Human Press, Inc., Totowa, N.J.

Vaughn, J. P., Iglehart, J. D., Demirdji, S., Davis, P., Babiss, L. E., Caruthers, M. H., Marks, J. R. (1995) Antisense DNA downregulation of the ERBB2 oncogene measured by a flow cytometric assay. *Proc Natl Acad Sci USA* 92: 8338–8342.

Weichen, K., Zimmer, C. and Dietel, M. (1997) Selection of a high activity c-erbB-2 ribozyme using a fusion gene of c-erbB-2 and the enhanced green fluorescent protein. *Cancer Gene Therapy* 5: 45–51.

Wright, M., Grim, J., Deshane, J., Kim, M., Strong, T. V., Siegel, G. P., Curiel, D. T. (1997) An intracellular anti-erbB-2 single-chain antibody is specifically cytotoxic to human breast carcinoma cells overexpressing erbB-2. *Gene Therapy* 4: 317–322.

Applicant has designed, synthesized and tested several class II (zinzyme) ribozymes targeted against HER2 RNA (see for example Tables XV and XVI) in cell proliferation assays.

Proliferation assay: The model proliferation assay used in the study requires a cell-plating density of 2000 cells/well in 96-well plates and at least 2 cell doublings over a 5-day treatment period. To calculate cell density for proliferation assays, the FIPS (fluoro-imaging processing system) method well known in the art was used. This method allows for cell density measurements after nucleic acids are stained with CyQuant® dye, and has the advantage of accurately measuring cell densities over a very wide range 1,000–100,000 cells/well in 96-well format.

Ribozymes (50–200 nM) were delivered in the presence of cationic lipid at 2.0 μg/mL and inhibition of proliferation was determined on day S post-treatment. Two full ribozyme screens were completed resulting in the selection of 14 ribozymes. Class II (zinzyme) ribozymes against sites, 314 (RPI No. 18653), 443 (RPI No. 18680), 597 (RPI No. 18697), 659 (RPI No. 18682), 878 (RPI Nos. 18683 and 18654), 881 (RPI Nos. 18684 and 18685) 934 (RPI No. 18651), 972 (RPI No. 18656, 19292, 19727, and 19728), 1292 (RPI No. 18726), 1541 (RPI No. 18687), 2116 (RPI No. 18729), 2932 (RPI No. 18678), 2540 (RPI No. 18715), and 3504 (RPI No. 18710) caused inhibition of proliferation ranging from 25–80% as compared to a scrambled control ribozyme. An example of results from a cell culture assay is shown in FIG. 11. Referring to FIG. 11, Class II ribozymes targeted against HER2 RNA are shown to cause significant inhibition of proliferation of cells. This shows that ribozymes, for instance the Class II (zinzyme) ribozymes are capable of inhibiting HER2 gene expression in mammalian cells.

Example 20

Reduction of Ribose Residues in Class II (Zinzyme) Nucleic Acid Catalysts

Class II (zinzyme) nucleic acid catalysts were tested for their activity as a function ribonucleotide content. A Zinzyme having no ribonucleotide residue (ie., no 2'-OH group at the 2' position of the nucleotide sugar) against the K-Ras site 521 was designed. This molecules were tested utilizing the chemistry shown in FIG. 18*a*. The in vitro catalytic activity zinzyme construct was not significantly effected (the cleavage rate reduced only 10 fold).

The Kras zinzyme shown in FIG. 18*a* was tested in physiological buffer with the divalent concentrations as indicated in the legend (high NaCl is an altered monovalent condition shown) of FIG. 19. The 1 mM $Ca^{++}$ condition yielded a rate of 0.005 $min^{-1}$ while the 1 mM $Mg^{++}$ condition yielded a rate of 0.002 $min^{-1}$. The ribose containing wild type yields a rate of 0.05 $min^{-1}$ while substrate in the absence of zinzyme demonstrates less than 2% degradation at the longest time point under reaction conditions shown. This illustrates a well-behaved cleavage reaction done by a non-ribose containing catalyst with only a 10-fold reduced cleavage as compared to ribonucleotide-containing zinzyme and vastly above non-catalyzed degradation.

Figure 18B:
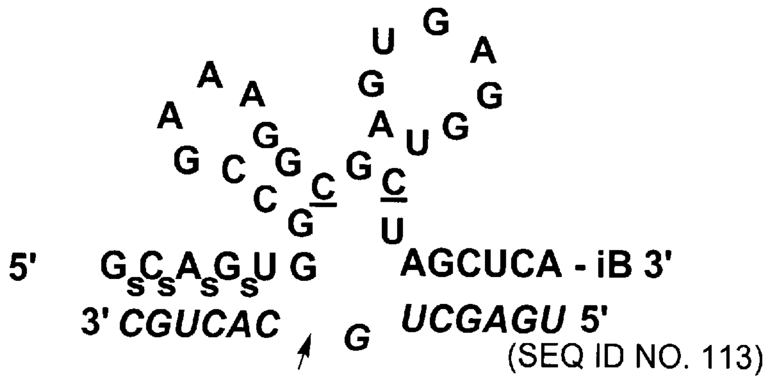

A more detailed investigation into the role of ribose positions in the Class II (zinzyme) motif was carried out in the context of the HER2 site 972 (Applicant has further designed a fully modified Zinzyme as shown in FIG. 18*b* targeting the HER2 RNA site 972). FIG. 20 is a diagram of the alternate formats tested and their relative rates of catalysis. The effect of substitution of ribose G for the 2'-O-methyl C-2'-O-methyl A in the loop of Zinzyme was insignificant when assayed with the Kras target but showed a modest rate enhancement in the HER2 assays. The activity of all Zinzyme motifs, including the fully stabilized "0 ribose" are well above background noise level degradation. Zinzyme with only two ribose positions are sufficient to restore "wild-type" activity. Motifs containing 3, 4 or 5 ribose positions demonstrated a greater extent of cleavage and profiles almost identical to the 2 ribose motif. Applicant has thus demonstrated that a Zinzyme with no ribonucleotides present at any position can catalyze efficient RNA cleavage activity. Thus, Zinzyme enzymatic nucleic acid molecules do not require the presence of 2'-OH group within the molecule for catalytic activity.

Example 21

Activity of Reduced Ribose Containing Class II (Zinzyme) Nucleic Acid Catalysts to Inhibit HER2 Gene Expression A cell proliferation assay for testing reduced ribo class II (zinzyme) nucleic acid catalysts (100–200 nM) targeting HER2 site 972 was performed as described in example 19. Single ribonucleotide containing Zinzyme (RPI No 19728) showed cell proliferation inhibition of between 37% and 67%, and fully stabilized non-ribonucleotide containing Zinzyme (RPI No. 19727) showed cell proliferation inhibition of between 38% and 65% compared to scrambled attenuated controls. The seven-ribonucleotide Zinzyme (RPI No. 19292) demonstrated the same level of inhibition as the single ribo/non-ribo derivatives. These results indicate significant inhibition of HER2 gene expression using stabilized Class II (zinzyme) motifs, including one ribo and non-ribo containing nucleic acid catalysts.

Applications

The use of NTP's described in this invention have several research and commercial applications. These modified nucleotide triphosphates can be used for in vitro selection (evolution) of oligonucleotides with novel functions. Examples of in vitro selection protocols are incorporated herein by reference (Joyce, 1989*, Gene*, 82, 83–87; Beaudry et al., 1992*, Science* 257, 635–641; Joyce, 1992*, Scientific American* 267, 90–97; Breaker et al., 1994*, TIBTECH* 12, 268; Bartel et al., 1993*, Science* 261:1411–1418; Szostak, 1993*, TIBS* 17, 89–93; Kumar et al., 1995*, FASEB J.*, 9, 1183; Breaker, 1996*, Curr. Op. Biotech.*, 7, 442).

Additionally, these modified nucleotide triphosphates can be employed to generate modified oligonucleotide combinatorial chemistry libraries. Several references for this technology exist (Brenner et al., 1992*, PNAS* 89, 5381–5383, Eaton, 1997*, Curr. Opin. Chem. Biol.* 1, 10–16).

Diagnostic Uses

Enzymatic nucleic acid molecules of this invention may be used as diagnostic tools to examine genetic drift and mutations within diseased cells or to detect the presence of specific RNA in a cell. The close relationship between enzymatic nucleic acid molecule activity and the structure of the target RNA allows the detection of mutations in any region of the molecule which alters the base-pairing and three-dimensional structure of the target RNA. By using multiple enzymatic nucleic acid molecules described in this invention, one may map nucleotide changes which are important to RNA structure and function in vitro, as well as in cells and tissues. Cleavage of target RNAs with enzymatic nucleic acid molecules may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple enzymatic nucleic acid molecules targeted to different genes, enzymatic nucleic acid molecules coupled with known small molecule inhibitors, radiation or intermittent treatment with combinations of enzymatic nucleic acid molecules and/or other chemical or biological molecules). Other in vitro uses of enzymatic nucleic acid molecules of this invention are well known in the art, and include detection of the presence of mRNAs associated with related conditions. Such RNA is detected by determining the presence of a cleavage product after treatment with a enzymatic nucleic acid molecule using standard methodology.

In a specific example, enzymatic nucleic acid molecules which can cleave only wild-type or mutant forms of the target RNA are used for the assay. The first enzymatic nucleic acid molecule is used to identify wild-type RNA present in the sample and the second enzymatic nucleic acid molecule will be used to identify mutant RNA in the sample.

As reaction controls, synthetic substrates of both wild-type and mutant RNA will be cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates will also serve to generate size markers for the analysis of wild type and mutant RNAs in the sample population. Thus each analysis can involve two enzymatic nucleic acid molecules, two substrates and one unknown sample which can be combined into six reactions. The presence of cleavage products can be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention can have many of the same applications for the study of RNA that DNA restriction endonucleases have for the study of DNA (Nathans et al., 1975 *Ann. Rev. Biochem.* 44:273). For example, the pattern of restriction fragments can be used to establish sequence relationships between two related RNAs, and large RNAs could be specifically cleaved to fragments of a size more useful for study. The ability to engineer sequence specificity of the enzymatic nucleic acid molecule is ideal for cleavage of RNAs of unknown sequence. Applicant describes the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains. All U.S. patents and published patent applications cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative. of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims

TABLE I

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 1 | 2'-O-methyl-2,6-diaminopurine riboside | 2'-O-Me-DAP | 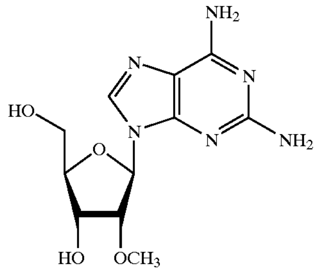 |

TABLE I-continued
NUCLEOSIDES USED FOR CHEMICAL SYNTHESIS OF MODIFIED NUCLEOTIDE TRIPHOSPHATES
| | NUCLEOSIDES | Abbreviation | CHEMICAL STRUCTURE |
|---|---|---|---|
| 2 | 2'-deoxy-2'amino-2,6-diaminopurine riboside | 2'-$NH_2$-DAP | 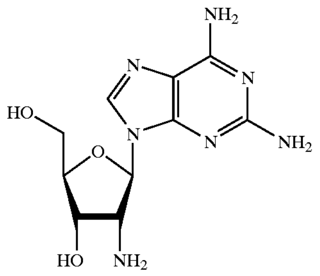 |
| 3 | 2'-(N-alanyl)amino-2'-deoxy-uridine | ala-2'-$NH_2$ U | 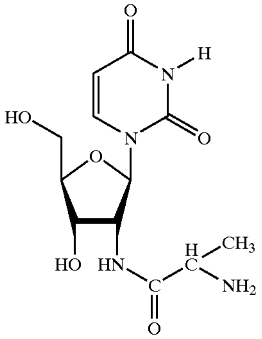 |
| 4 | 2'-(N-phenylalanyl)amino-2'-deoxy-uridine | phe-2'-$NH_2$-U | 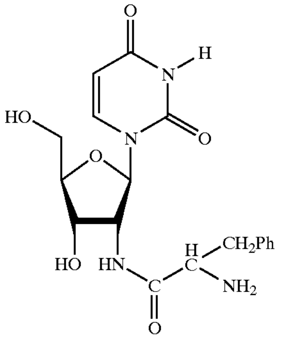 |
| 5 | 2'-(N-β-alanyl)amino-2'-deoxy uridine | 2'-β-Ala-$NH_2$-U | 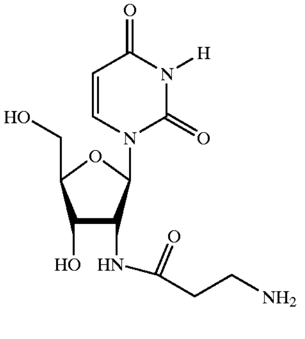 |

TABLE I-continued
NUCLEOSIDES USED FOR CHEMICAL SYNTHESIS OF MODIFIED NUCLEOTIDE TRIPHOSPHATES
| | NUCLEOSIDES | Abbreviation | CHEMICAL STRUCTURE |
|---|---|---|---|
| 6 | 2'-Deoxy-2'-(lysiyl) amino uridine | 2'-L-lys-$NH_2$-U | 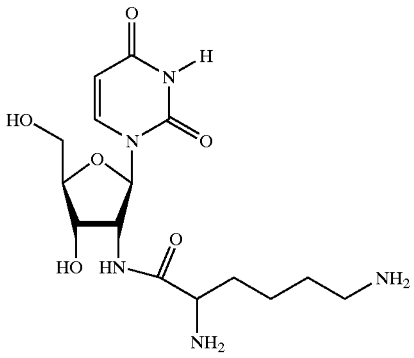 |
| 7 | 2'-C-allyl uridine | 2'-C-allyl-U | 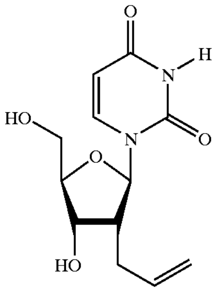 |
| 8 | 2'-O-amino-uridine | 2'-O-$NH_2$-U | 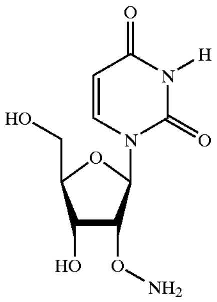 |
| 9 | 2'-O-methylthiomethyl adenosine | 2'-O-MTM-A | 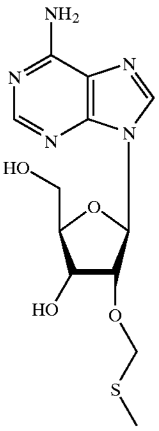 |

TABLE I-continued
NUCLEOSIDES USED FOR CHEMICAL SYNTHESIS OF MODIFIED NUCLEOTIDE TRIPHOSPHATES
| | NUCLEOSIDES | Abbreviation | CHEMICAL STRUCTURE |
|---|---|---|---|
| 10 | 2'-O-methylthiomethyl cytidine | 2'-O-MTM-C | 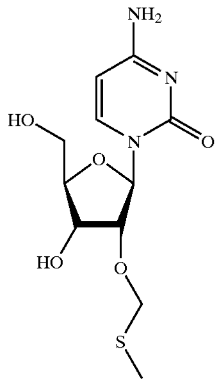 |
| 11 | 2'-O-methylthiomethyl guanosine | 2'-O-MTM-G | 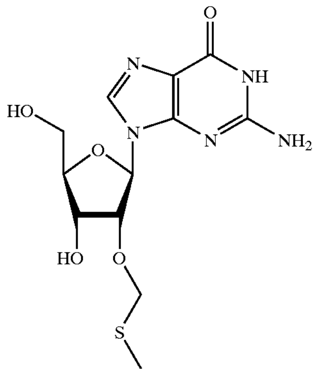 |
| 12 | 2'-O-methylthiomethyl-uridine | 2'-O-MTM-U | 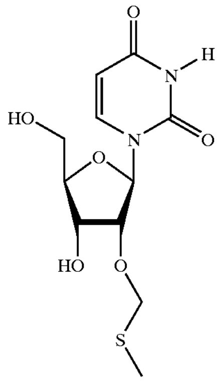 |
| 13 | 2'-(N-histidyl)amino uridine | 2'-his-$NH_2$-U | 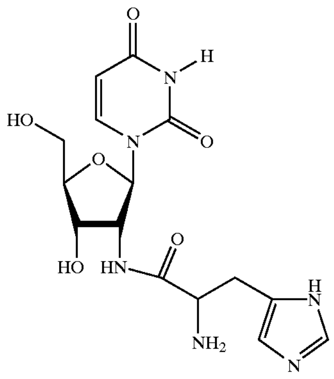 |

TABLE I-continued
NUCLEOSIDES USED FOR CHEMICAL SYNTHESIS OF MODIFIED NUCLEOTIDE TRIPHOSPHATES
| | NUCLEOSIDES | Abbreviation | CHEMICAL STRUCTURE |
|---|---|---|---|
| 14 | 2'-Deoxy-2'-amino-5-methyl cytidine | 5-Me-2'-$NH_2$-C | 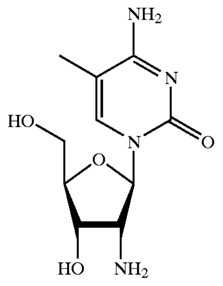 |
| 15 | 2'-(N-β-carboxamidine-β-alanyl)amino-2'-deoxy-uridine | β-ala-CA-NH2-U | 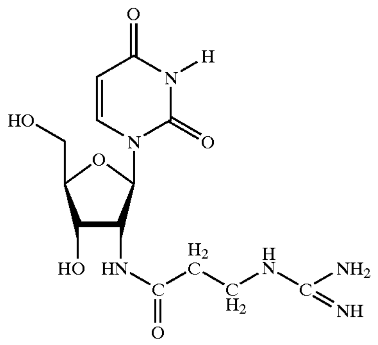 |
| 16 | 2'-(N-β-alanyl) guanosine | β-Ala-$NH_2$-G | 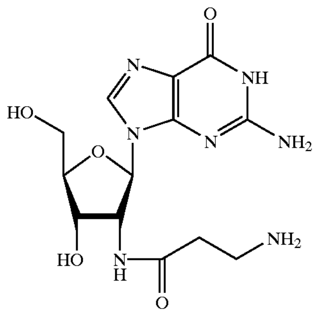 |
| 17 | 2'-O-Amino-Uridine | 2'-O-$NH_2$-U | 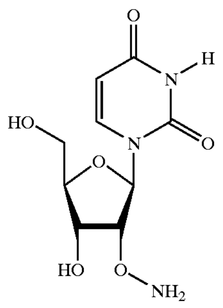 |

TABLE I-continued
NUCLEOSIDES USED FOR CHEMICAL SYNTHESIS OF MODIFIED NUCLEOTIDE TRIPHOSPHATES
| | NUCLEOSIDES | Abbreviation | CHEMICAL STRUCTURE |
|---|---|---|---|
| 18 | 2'-(N-lysyl)amino-2'-deoxy-cytidine | 2'-$NH_2$-lys-C | 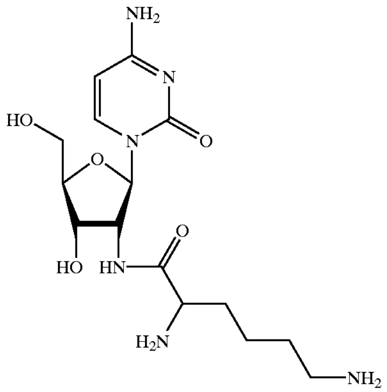 |
| 19 | 2'-Deoxy-2'-(L-histidine)amino Cytidine | 2'-$NH_2$-his-C | 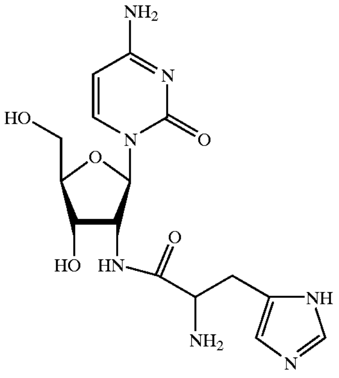 |
| 20 | 5-Imidazoleacetic acid 2'-deoxy uridine | 5-IAA-U | 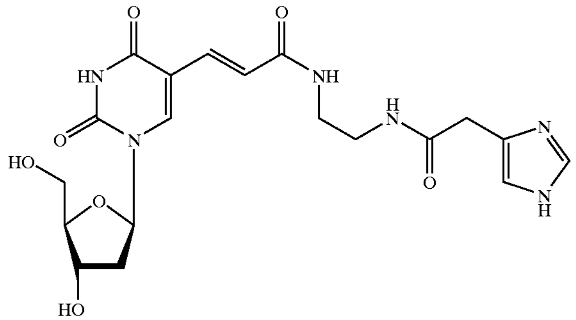 |
| 21 | 5-[3-(N-4-imidazoleacetyl)amino propynyl]-2'-O-methyl uridine | 5-IAA-propynylamino-2'-OMe U | 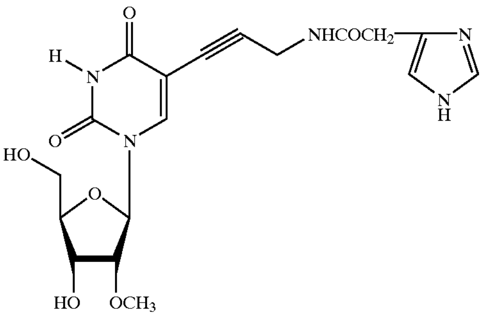 |

TABLE I-continued

| | NUCLEOSIDES USED FOR CHEMICAL SYNTHESIS OF MODIFIED NUCLEOTIDE TRIPHOSPHATES | | |
|---|---|---|---|
| | NUCLEOSIDES | Abbreviation | CHEMICAL STRUCTURE |
| 22 | 5-(3-aminopropynyl)-2'-O-methyl uridine | 5-aminopropynyl-2'-OMe U | 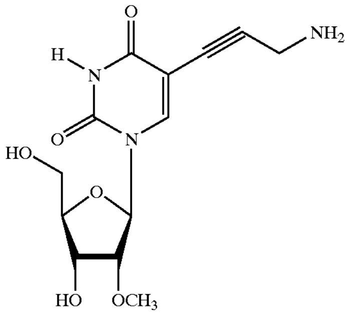 |
| 23 | 5-(3-aminopropyl)-2'-O-methyl uridine | 5-aminopropyl-2'-OMe U | 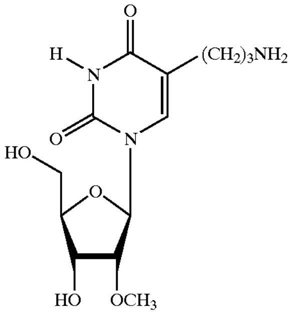 |
| 24 | 5-[3-(N-4-imidazoleacetyl)amino propyl]-2'-O-methyl Uridine | 5-IAA-propylamino-2'-OMe U | 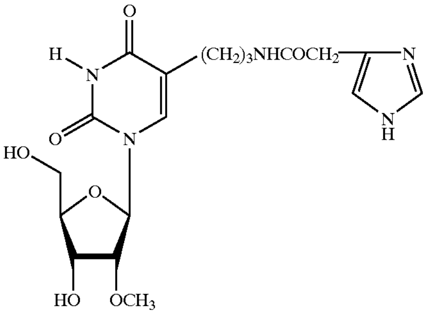 |
| 25 | 5-(3-aminopropyl)-2'-deoxy-2-fluoro uridine | 5-aminopropyl-2'-F dU | 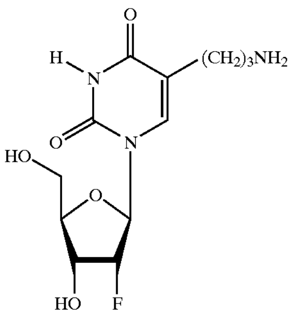 |

TABLE I-continued

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 26 | 2'-Deoxy-2'-(β-alanyl-L-histidyl)amino Uridine | 2'-amino-β-ALA-HIS dU | 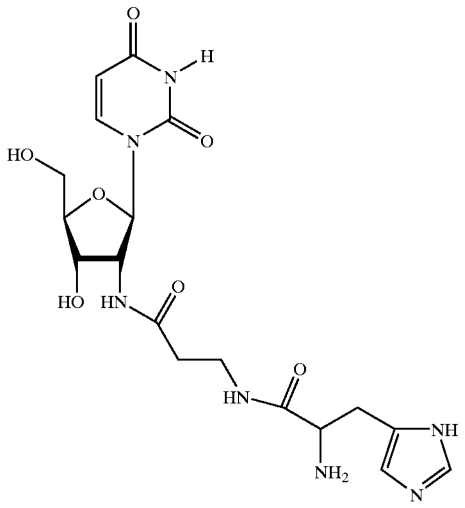 |
| 27 | 2'-deoxy-2'-β-alaninamido-uridine | 2'-β-ALA dU | 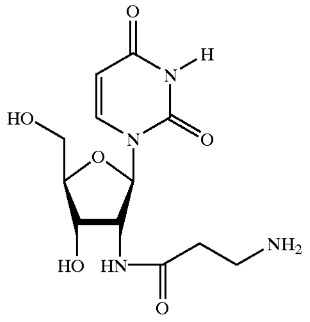 |
| 28 | 3-(2'-deoxy-2'-fluoro-β-D-ribofuranosyl)piperazino [2,3-D]pyrimidine-2-one | 2'-F piperazino-pyrimidinone | 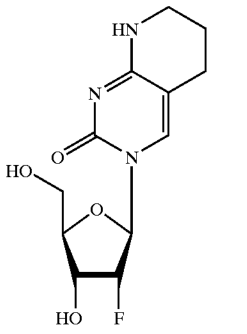 |
| 29 | 5-[3-(N-4-imidazoleacetyl)amino propyl]-2'-deoxy-2'-fluoro Uridine | 5-IAA-propylamino-2'-F dU | 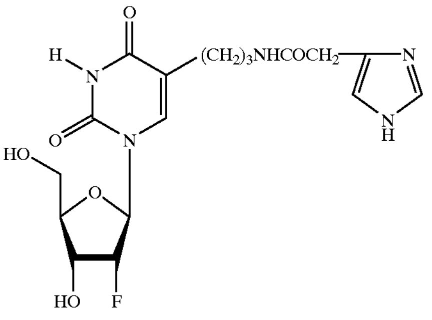 |

TABLE I-continued

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 30 | 5-[3-(N-4-imidazoleacetyl)amino propynyl]-2'-deoxy-2'-fluoro uridine | 5-IAA-propynylamino-2'-F dU | 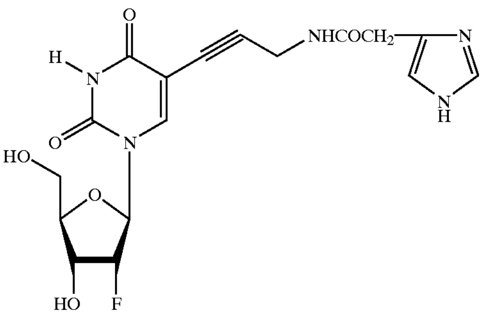 |
| 31 | 5-E-(2-carboxyvinyl-2'-deoxy-2'-fluoro uridine | 5-carboxyvinyl-2'-F dU | 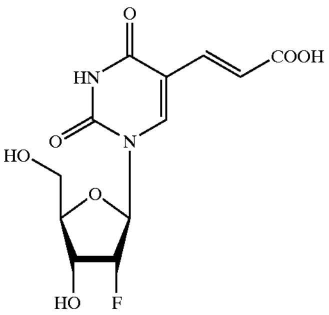 |
| 32 | 5-[3-(N-4-aspartyl)aminopropynyl-2'-fluoro uridine | 5-ASP-aminopropyl-2'-F-dU | 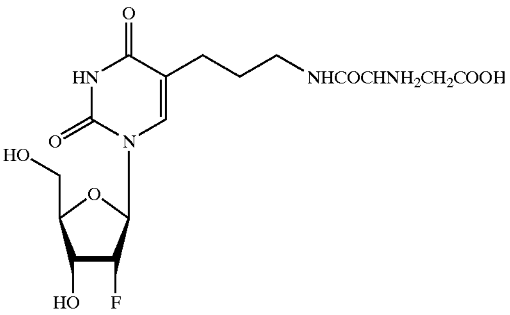 |
| 33 | 5-(3-aminopropyl)-2'-deoxy-2-fluoro cytidine | 5-aminopropyl-2'-F dC | 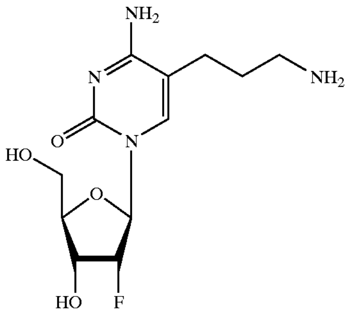 |

TABLE I-continued

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 34 | 5-[3-(N-4-succynyl)aminopropyl-2'-deoxy-2-fluoro cytidine | 5-succynylamino-propyl-2'-F dC | 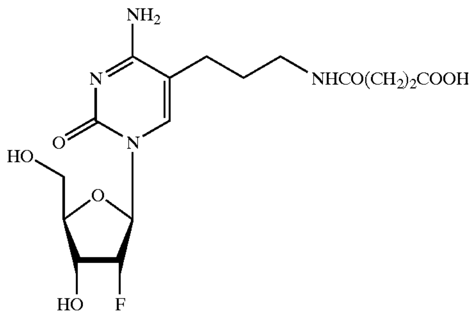 |

TABLE II

A. 2.5 μmol Synthesis Cycle ABI 394 Instrument

| Reagent | Equivalents | Amount | Wait Time* 2'-O-methyl | Wait Time* RNA |
|---|---|---|---|---|
| Phosphoramidites | 6.5 | 163 μL | 2.5 min | 7.5 |
| S-Ethyl Tetrazole | 23.8 | 238 μL | 2.5 min | 7.5 |
| Acetic Anhydride | 100 | 233 μL | 5 sec | 5 sec |
| N-Methyl Imidazole | 186 | 233 μL | 5 sec | 5 sec |
| TCA | 110.1 | 2.3 mL | 21 sec | 21 sec |
| Iodine | 11.2 | 1.7 mL | 45 sec | 45 sec |
| Acetonitrile | NA | 6.67 mL | NA | NA |

B. 0.2 μmol Synthesis Cycle ABI 394 Instrument

| Reagent | Equivalents | Amount | Wait Time* 2'-O-methyl | Wait Time* RNA |
|---|---|---|---|---|
| Phosphoramidites | 15 | 31 μL | 233 sec | 465 sec |
| S-Ethyl Tetrazole | 38.7 | 31 μL | 233 min | 465 sec |
| Acetic Anhydride | 655 | 124 μL | 5 sec | 5 sec |
| N-Methyl Imidazole | 1245 | 124 μL | 5 sec | 5 sec |
| TCA | 700 | 732 μL | 10 sec | 10 sec |
| Iodine | 20.6 | 244 μL | 15 sec | 15 sec |
| Acetonitrile | NA | 2.64 mL | NA | NA |

C. 0.2 μmol Synthesis Cycle 96 well Instrument

| Reagent | Equivalents 2'-O-methyl/Ribo | Amount 2'-O-methyl/Ribo | Wait Time* 2'-O-methyl | Wait Time* Ribo |
|---|---|---|---|---|
| Phosphoramidites | 33/66 | 60/120 μL | 233 sec | 465 sec |
| S-Ethyl Tetrazole | 75/150 | 60/120 μL | 233 min | 465 sec |
| Acetic Anhydride | 50/50 | 50/50 μL | 10 sec | 10 sec |
| N-Methyl Imidazole | 502/502 | 50/50 μL | 10 sec | 10 sec |
| TCA | 16,000/16,000 | 500/500 μL | 15 sec | 15 sec |
| Iodine | 6.8/6.8 | 80/80 μL | 30 sec | 30 sec |
| Acetonitrile | NA | 850/850 μL | NA | NA |

*Wait time does not include contact time during delivery.

TABLE III

PHOSPHORYLATION OF URIDINE IN THE PRESENCE OF DMAP

| 0 equiv. DMAP | | 0.2 equiv. DMAP | | 0.5 equiv. DMAP | | 1.0 equiv. DMAP | |
|---|---|---|---|---|---|---|---|
| Time (min) | Product % | Time (min) | Product % | Time (min) | Product % | Time (min) | Product % |
| 0 | 1 | 0 | 0 | 0 | 0 | 0 | 0 |
| 40 | 7 | 10 | 8 | 20 | 27 | 30 | 74 |
| 80 | 10 | 50 | 24 | 60 | 46 | 70 | 77 |

TABLE III-continued

PHOSPHORYLATION OF URIDINE IN THE PRESENCE OF DMAP

| 0 equiv. DMAP | | 0.2 equiv. DMAP | | 0.5 equiv. DMAP | | 1.0 equiv. DMAP | |
|---|---|---|---|---|---|---|---|
| Time (min) | Product % | Time (min) | Product % | Time (min) | Product % | Time (min) | Product % |
| 120 | 12 | 90 | 33 | 100 | 57 | 110 | 84 |
| 160 | 14 | 130 | 39 | 140 | 63 | 150 | 83 |
| 200 | 17 | 170 | 43 | 180 | 63 | 190 | 84 |
| 240 | 19 | 210 | 47 | 220 | 64 | 230 | 77 |
| 320 | 20 | 250 | 48 | 260 | 68 | 270 | 79 |
| 1130 | 48 | 290 | 49 | 300 | 64 | 310 | 77 |
| 1200 | 46 | 1140 | 68 | 1150 | 76 | 1160 | 72 |
| | | 1210 | 69 | 1220 | 76 | 1230 | 74 |

TABLE IV

Detailed Description of the NTP Incorporation Reaction Conditions

| Condition No. | TRIS-HCL (mM) | $MgCl_2$ (mM) | DTT (mM) | Spermidine (mM) | Triton X-100 (%) | METHANOL (%) | LiCl (mM) | PEG (%) | Temp (° C.) |
|---|---|---|---|---|---|---|---|---|---|
| 1 | 40 (pH 8.0) | 20 | 10 | 5 | 0.01 | 10 | 1 | — | 25 |
| 2 | 40 (pH 8.0) | 20 | 10 | 5 | 0.01 | 10 | 1 | 4 | 25 |
| 3 | 40 (pH 8.1) | 12 | 5 | 1 | 0.002 | — | — | 4 | 25 |
| 4 | 40 (pH 8.1) | 12 | 5 | 1 | 0.002 | 10 | — | 4 | 25 |
| 5 | 40 (pH 8.1) | 12 | 5 | 1 | 0.002 | — | 1 | 4 | 25 |
| 6 | 40 (pH 8.1) | 12 | 5 | 1 | 0.002 | 10 | 1 | 4 | 25 |
| 7 | 40 (pH 8.0) | 20 | 10 | 5 | 0.01 | 10 | 1 | — | 37 |
| 8 | 40 (pH 8.0) | 20 | 10 | 5 | 0.01 | 10 | 1 | 4 | 37 |
| 9 | 40 (pH 8.1) | 12 | 5 | 1 | 0.002 | — | — | 4 | 37 |
| 10 | 40 (pH 8.1) | 12 | 5 | 1 | 0.002 | 10 | — | 4 | 37 |
| 11 | 40 (pH 8.1) | 12 | 5 | 1 | 0.002 | — | 1 | 4 | 37 |
| 12 | 40 (pH 8.1) | 12 | 5 | 1 | 0.002 | 10 | 1 | 4 | 37 |

TABLE V

INCORPORATION OF MODIFIED NUCLEOTIDE TRIPHOSPHATES

| Modification | COND# 1 | COND# 2 | COND# 3 | COND# 4 | COND# 5 | COND# 6 | COND# 7 | COND# 8 | COND# 9 | COND# 10 | COND# 11 | COND# 12 |
|---|---|---|---|---|---|---|---|---|---|---|---|---|
| 2'-$NH_2$—ATP | 1 | 2 | 3 | 5 | 2 | 4 | 1 | 2 | 10 | 11 | 5 | 9 |
| 2'-$NH_2$—CTP | 11 | 37 | 45 | 64 | 25 | 70 | 26 | 54 | 292 | 264 | 109 | 244 |
| 2'-$NH_2$—GTP | 4 | 7 | 6 | 14 | 5 | 17 | 3 | 16 | 10 | 21 | 9 | 16 |
| 2'-$NH_2$—UTP | 14 | 45 | 4 | 100 | 85 | 82 | 48 | 88 | 20 | 418 | 429 | 440 |
| 2'-dATP | 9 | 3 | 19 | 23 | 9 | 24 | 6 | 3 | 84 | 70 | 28 | 51 |
| 2'-dCTP | 1 | 10 | 43 | 46 | 35 | 47 | 27 | 127 | 204 | 212 | 230 | 235 |
| 2'-dGTP | 6 | 10 | 9 | 15 | 9 | 12 | 8 | 34 | 38 | 122 | 31 | 46 |
| 2'-dTTP | 9 | 9 | 14 | 18 | 13 | 18 | 8 | 15 | 116 | 114 | 59 | 130 |
| 2'-O—Me—ATP | 0 | 0 | 0 | 0 | 0 | 0 | 1 | 1 | 2 | 2 | 2 | 2 |
| 2'-O—Me—CTP | no data compared to ribo; incorporates at low level | | | | | | | | | | | |
| 2'-O—Me—GTP | 4 | 3 | 4 | 4 | 4 | 4 | 2 | 4 | 4 | 5 | 4 | 5 |
| 2'-O—Me—UTP | 55 | 52 | 39 | 38 | 41 | 48 | 55 | 71 | 93 | 103 | 81 | 77 |
| 2'-O—Me—DAP | 4 | 4 | 3 | 4 | 4 | 5 | 4 | 3 | 4 | 5 | 5 | 5 |
| 2'-$NH_2$—DAP | 0 | 0 | 1 | 1 | 1 | 1 | 1 | 0 | 0 | 0 | 0 | 0 |
| ala-2'-$NH_2$—UTP | 2 | 2 | 2 | 2 | 3 | 4 | 14 | 18 | 15 | 20 | 13 | 14 |
| phe-2'-$NH_2$—UTP | 8 | 12 | 7 | 7 | 8 | 8 | 4 | 10 | 6 | 6 | 10 | 6 |
| 2'-β $NH_2$-ala-UTP | 65 | 48 | 25 | 17 | 21 | 21 | 220 | 223 | 265 | 300 | 275 | 248 |
| 2'-F—ATP | 227 | 252 | 98 | 103 | 100 | 116 | 288 | 278 | 471 | 198 | 317 | 185 |
| 2'-F—GTP | 39 | 44 | 17 | 30 | 17 | 26 | 172 | 130 | 375 | 447 | 377 | 438 |
| 2'-C-allyl-UTP | 3 | 2 | 2 | 3 | 3 | 2 | 3 | 3 | 3 | 2 | 3 | 3 |
| 2'-O—$NH_2$—UTP | 6 | 8 | 5 | 5 | 4 | 5 | 16 | 23 | 24 | 24 | 19 | 24 |
| 2'-O—MTM—ATP | 0 | 1 | 0 | 0 | 0 | 0 | 1 | 0 | 0 | 0 | 0 | 0 |
| 2'-O—MTM—CTP | 2 | 2 | 1 | 1 | 1 | 1 | 3 | 4 | 5 | 4 | 5 | 3 |
| 2'-O—MTM—GTP | 6 | 1 | 1 | 3 | 1 | 2 | 0 | 1 | 1 | 3 | 1 | 4 |
| 2'-F—CTP | | | | | | | | | 100 | | | |
| 2'-F—UTP | | | | | | | | | 100 | | | |
| 2'-F—TTP | | | | | | | | | 50 | | | |
| 2'-F-C5-carboxyvinyl UTP | | | | | | | | | 100 | | | |
| 2'-F-C5-aspartyl-aminopropyl UTP | | | | | | | | | 100 | | | |
| 2'-F-C5-propylamine CTP | | | | | | | | | 100 | | | |

TABLE V-continued

| INCORPORATION OF MODIFIED NUCLEOTIDE TRIPHOSPHATES | | | | | | | | | | | | |
|---|---|---|---|---|---|---|---|---|---|---|---|---|
| Modification | COND# 1 | COND# 2 | COND# 3 | COND# 4 | COND# 5 | COND# 6 | COND# 7 | COND# 8 | COND# 9 | COND# 10 | COND# 11 | COND# 12 |
| 2'-O—Me CTP | | | | | | | | | 0 | | | |
| 2'-O—Me UTP | | | | | | | | | 25 | | | |
| 2'-O—Me 5-3-aminopropyl UTP | | | | | | | | | 4 | | | |
| 2'-O—Me 5-3-aminopropyl UTP | | | | | | | | | 10 | | | |

TABLE VI

Table VI: INCORPORATION OF MODIFIED NUCLEOTIDE TRIPHOSPHATES USING WILD TYPE BACTERIOPHAGE T7 POLYMERASE

| Modification | label | % ribo control |
|---|---|---|
| 2'-$NH_2$-GTP | ATP | 4% |
| 2'-dGTP | ATP | 3% |
| 2'-O-Me-GTP | ATP | 3% |
| 2'-F-GTP | ATP | 4% |
| 2'-O-MTM-GTP | ATP | 3% |
| 2'-$NH_2$-UTP | ATP | 39% |
| 2'-dTTP | ATP | 5% |
| 2'-O-Me-UTP | ATP | 3% |
| ala-2'-$NH_2$-UTP | ATP | 2% |
| phe-2'-$NH_2$-UTP | ATP | 1% |
| 2'-β-ala-$NH_2$-UTP | ATP | 3% |
| 2'-C-allyl-UTP | ATP | 2% |
| 2'-O-$NH_2$-UTP | ATP | 1% |
| 2'-O-MTM-UTP | ATP | 64% |
| 2'-$NH_2$-ATP | GTP | 1% |
| 2'-O-MTM-ATP | GTP | 1% |
| 2'-$NH_2$-CTP | GTP | 59% |
| 2'-dCTP | GTP | 40% |
| 2'-F-CTP | GTP | 100% |
| 2'-F-UTP | GTP | 100% |
| 2'-F-TTP | GTP | 0% |
| 2'-F-C5-carboxyvinyl UTP | GTP | 100% |
| 2'-F-C5-aspartyl-aminopropyl UTP | GTP | 100% |
| 2'-F-C5-propylamine CTP | GTP | 100% |
| 2'-O-Me CTP | GTP | 0% |
| 2'-O-Me UTP | GTP | 0% |
| 2'-O-Me 5-3-aminopropyl UTP | GTP | 0% |
| 2'-O-Me 5-3-aminopropyl UTP | GTP | 0% |

TABLE VII

Table VII a: Incorporation of 2'-his-UTP and Modified CTP's

| modification | 2'-his-UTP | rUTP |
|---|---|---|
| CTP | 16.1 | 100 |
| 2'-amino-CTP | **9.5*** | 232.7 |
| 2'-deoxy-CTP | **9.6*** | 130.1 |
| 2'-OMe-CTP | 1.9 | 6.2 |
| 2'-MTM-CTP | 5.9 | 5.1 |
| control | 1.2 | |

Table VII b: Incorporation of 2'-his-UTP, 2-amino CTP, and Modified ATP's

| modification | 2'-his-UTP and 2'-amino-CTP | rUTP and rCTP |
|---|---|---|
| ATP | 15.7 | 100 |
| 2'-amino-ATP | 2.4 | 28.9 |
| 2'-deoxy-ATP | 2.3 | 146.3 |
| 2'-OMe-ATP | 2.7 | 15 |
| 2'-F-ATP | 4 | 222.6 |
| 2'-MTM-ATP | 4.7 | 15.3 |
| 2'-OMe-DAP | 1.9 | 5.7 |
| 2'-amino-DAP | **8.9*** | 9.6 |

Numbers shown are a percentage of incorporation compared to the all-RNA control
*Bold number indicates best observed rate of modified nucleotide triphosphate incorporation

TABLE VIII

Table VIII: INCORPORATION OF 2'-his-UTP, 2'-$NH_2$-CTP, 2'-$NH_2$-DAP, and rGTP USING VARIOUS REACTION CONDITIONS

| Conditions | compared to all rNTP |
|---|---|
| 7 | 8.7* |
| 8 | 7* |
| 9 | 2.3 |
| 10 | 2.7 |
| 11 | 1.6 |
| 12 | 2.5 |

Numbers shown are a percentage of incorporation compared to the all-RNA control
*Two highest levels of incorporation contained both methanol and LiCl

TABLE IX

Selection of Oligonucleotides with Ribozyme Activity

| pool | Generation | time | substrate remaining (%) | time | Substrate remaining (%) |
|---|---|---|---|---|---|
| N60 | 0 | 4 hr | 100.00 | 24 hr | 100.98 |
| N60 | 14 | 4 hr | 99.67 | 24 hr | 97.51 |
| N60 | 15 | 4 hr | 98.76 | 24 hr | 96.76 |
| N60 | 16 | 4 hr | 97.09 | 24 hr | 96.60 |
| N60 | 17 | 4 hr | 79.50 | 24 hr | 64.01 |
| N40 | 0 | 4 hr | 99.89 | 24 hr | 99.78 |
| N40 | 10 | 4 hr | 99.74 | 24 hr | 99.42 |
| N40 | 11 | 4 hr | 97.18 | 24 hr | 90.38 |
| N40 | 12 | 4 hr | 61.64 | 24 hr | 44.54 |
| N40 | 13 | 4 hr | 54.28 | 24 hr | 36.46 |
| N20 | 0 | 4 hr | 99.18 | 24 hr | 100.00 |
| N20 | 11 | 4 hr | 100.00 | 24 hr | 100.00 |
| N20 | 12 | 4 hr | 99.51 | 24 hr | 100.00 |
| N20 | 13 | 4 hr | 90.63 | 24 hr | 84.89 |
| N20 | 14 | 4 hr | 91.16 | 24 hr | 85.92 |
| N60B | 0 | 4 hr | 100.00 | 24 hr | 100.00 |
| N60B | 1 | 4 hr | 100.00 | 24 hr | 100.00 |
| N60B | 2 | 4 hr | 100.00 | 24 hr | 100.00 |
| N60B | 3 | 4 hr | 100.00 | 24 hr | 100.00 |
| N60B | 4 | 4 hr | 99.24 | 24 hr | 100.00 |
| N60B | 5 | 4 hr | 97.81 | 24 hr | 96.65 |
| N60B | 6 | 4 hr | 89.95 | 24 hr | 77.14 |

TABLE X

Table X: Kinetic Activity of Combinatorial Libraries

| Pool | Generation | $k_{obs}$ ($min^{-1}$) |
|---|---|---|
| N60 | 17 | 0.0372 |
| | 18 | 0.0953 |
| | 19 | 0.0827 |
| N40 | 12 | 0.0474 |
| | 13 | 0.037 |
| | 14 | 0.065 |
| | 15 | 0.0254 |
| N20 | 13 | 0.0359 |
| | 14 | 0.0597 |
| | 15 | 0.0549 |
| | 16 | 0.0477 |
| N60B | 6 | 0.0209 |
| | 7 | 0.0715 |
| | 8 | 0.0379 |

TABLE XI

Table XI: Kinetic Activity of Clones within N60 and N40 Combinatorial Libraries

| clone | library | activity($min^{-1}$) | $k_{ref}$ |
|---|---|---|---|
| G18 | N60 | 0.00226 | 1.00 |
| 0-2 | N60 | 0.0389 | 17.21 |
| 0-3 | N60 | 0.000609 | 0.27 |
| 0-5 | N60 | 0.000673 | 0.30 |
| 0-7 | N60 | 0.00104 | 0.46 |
| 0-8 | N60 | 0.000739 | 0.33 |
| 0-11 | N60 | 0.0106 | 4.69 |

TABLE XI-continued

Table XI: Kinetic Activity of Clones within N60 and N40 Combinatorial Libraries

| clone | library | activity($min^{-1}$) | $k_{ref}$ |
|---|---|---|---|
| 0-12 | N60 | 0.00224 | 0.99 |
| 0-13 | N60 | 0.0255 | 11.28 |
| 0-14 | N60 | 0.000878 | 0.39 |
| 0-15 | N60 | 0.0000686 | 0.03 |
| 0-21 | N60 | 0.0109 | 4.82 |
| 0-22 | N60 | 0.000835 | 0.37 |
| 0-24 | N60 | 0.000658 | 0.29 |
| 0-28 | N40 | 0.000741 | 0.33 |
| 0-35 | N40 | 0.00658 | 2.91 |
| 3-1 | N40 | 0.0264 | 11.68 |
| 3-3 | N40 | 0.000451 | 0.20 |
| 3-7 | N40 | 0.000854 | 0.38 |
| 3-15 | N40 | 0.000832 | 0.37 |

TABLE XII

Table XII: Effect of Magnesium Concentration of the Cleavage Rate of N20

| [$Mg^{++}$] | $k_{obs}$($min^{-1}$) |
|---|---|
| 25 | 0.0259 |
| 20 | 0.0223 |
| 15 | 0.0182 |
| 10 | 0.0208 |
| 5 | 0.0121 |
| 2 | 0.00319 |
| 2 | 0.00226 |

TABLE XIII

Class I Enzymatic Nucleic Acid Motifs Targeting HCV

| Pos | Target | Seq ID | Alias | | Sequence | Rz Seq ID |
|---|---|---|---|---|---|---|
| 6 | AUGGGGGCGACACUCC | 1 | HCV.R1A-6 | Amb.Rz-10/5 | ggagugucgc Ggaggaaacuc**C** **CU** **UC**AAGGACA**UCGUCC**GGG cccau B | 39 |
| 56 | UUCACGCAGAAAGCGU | 2 | HCV.R1A-56 | Amb.Rz-10/5 | acgcuuucug Ggaggaaacuc**C** **CU** **UC**AAGGACA**UCGUCC**GGG gugaa B | 40 |
| 75 | GCCAUGGCGUUAGUAU | 3 | HCV.R1A-75 | Amb.Rz-10/5 | auacuaacgc Ggaggaaacuc**C** **CU** **UC**AAGGACA**UCGUCC**GGG auggc B | 41 |
| 76 | CCAUGGCGUUAGUAUG | 4 | HCV.R1A-76 | Amb.Rz-10/5 | cauacuaacg Ggaggaaacuc**C** **CU** **UC**AAGGACA**UCGUCC**GGG caugg B | 42 |
| 95 | GUCGUGCAGCCUCCAG | 5 | HCV.R1A-95 | Amb.Rz-10/5 | cuggaggcug Ggaggaaacuc**C** **CU** **UC**AAGGACA**UCGUCC**GGG acgac B | 43 |
| 138 | GGUCUGCGGAACCGGU | 6 | HCV.R1A-138 | Amb.Rz-10/5 | accgguuccg Ggaggaaacuc**C** **CU** **UC**AAGGACA**UCGUCC**GGG agacc B | 44 |
| 146 | GAACCGGUGAGUACAC | 7 | HCV.R1A-146 | Amb.Rz-10/5 | guguacucac Ggaggaaacuc**C** **CU** **UC**AAGGACA**UCGUCC**GGG gguuc B | 45 |
| 158 | ACACCGGAAUUGCCAG | 8 | HCV.R1A-158 | Amb.Rz-10/5 | cuggcaauuc Ggaggaaacuc**C** **CU** **UC**AAGGACA**UCGUCC**GGG ggugu B | 46 |
| 164 | GAAUUGCCAGGACGAC | 9 | HCV.R1A-164 | Amb.Rz-10/5 | gucguccugg Ggaggaaacuc**C** **CU** **UC**AAGGACA**UCGUCC**GGG aauuc B | 47 |
| 176 | CGACCGGGUCCUUUCU | 10 | HCV.R1A-176 | Amb.Rz-10/5 | agaaaggacc Ggaggaaacuc**C** **CU** **UC**AAGGACA**UCGUCC**GGG ggucg B | 48 |
| 177 | GACCGGGUCCUUUCUU | 11 | HCV.R1A-177 | Amb.Rz-10/5 | aagaaaggac Ggaggaaacuc**C** **CU** **UC**AAGGACA**UCGUCC**GGG cgguc B | 49 |
| 209 | UGCCUGGAGAUUUGGG | 12 | HCV.R1A-209 | Amb.Rz-10/5 | cccaaaucuc Ggaggaaacuc**C** **CU** **UC**AAGGACA**UCGUCC**GGG aggca B | 50 |
| 237 | AGACUGCUAGCCGAGU | 13 | HCV.R1A-237 | Amb.Rz-10/5 | acucggcuag Ggaggaaacuc**C** **CU** **UC**AAGGACA**UCGUCC**GGG agucu B | 51 |
| 254 | GUGUUGGGUCGCGAAA | 14 | HCV.R1A-254 | Amb.Rz-10/5 | uuucgcgacc Ggaggaaacuc**C** **CU** **UC**AAGGACA**UCGUCC**GGG aacac B | 52 |
| 255 | UGUUGGGUCGCGAAAG | 15 | HCV.R1A-255 | Amb.Rz-10/5 | cuuucgcgac Ggaggaaacuc**C** **CU** **UC**AAGGACA**UCGUCC**GGG caaca B | 53 |
| 259 | GGGUCGCGAAAGGCCU | 16 | HCV.R1A-259 | Amb.Rz-10/5 | aggccuuucg Ggaggaaacuc**C** **CU** **UC**AAGGACA**UCGUCC**GGG gaccc B | 54 |
| 266 | GAAAGGCCUUGUGGUA | 17 | HCV.R1A-266 | Amb.Rz-10/5 | uaccacaagg Ggaggaaacuc**C** **CU** **UC**AAGGACA**UCGUCC**GGG cuuuc B | 55 |
| 273 | CUUGUGGUACUGCCUG | 18 | HCV.R1A-273 | Amb.Rz-10/5 | caggcaguac Ggaggaaacuc**C** **CU** **UC**AAGGACA**UCGUCC**GGG acaag B | 56 |
| 288 | GAUAGGGUGCUUGCGA | 19 | HCV.R1A-288 | Amb.Rz-10/5 | ucgcaagcac Ggaggaaacuc**C** **CU** **UC**AAGGACA**UCGUCC**GGG cuauc B | 57 |
| 291 | AGGGUGCUUGCGAGUG | 20 | HCV.R1A-291 | Amb.Rz-10/5 | cacucgcaag Ggaggaaacuc**C** **CU** **UC**AAGGACA**UCGUCC**GGG acccu B | 58 |
| 7 | UGGGGGCGACACUCCA | 21 | HCV.R1A-7 | Amb.Rz-10/5 | uggagugucg Ggaggaaacuc**C** **CU** **UC**AAGGACA**UCGUCC**GGG cccca B | 59 |
| 119 | CUCCCGGGAGAGCCAU | 22 | HCV.R1A-119 | Amb.Rz-10/5 | auggcucucc Ggaggaaacuc**C** **CU** **UC**AAGGACA**UCGUCC**GGG gggag B | 60 |
| 120 | UCCCGGGAGAGCCAUA | 23 | HCV.R1A-120 | Amb.Rz-10/5 | uauggcucuc Ggaggaaacuc**C** **CU** **UC**AAGGACA**UCGUCC**GGG cggga B | 61 |
| 133 | AUAGUGGUCUGCGGAA | 24 | HCV.R1A-133 | Amb.Rz-10/5 | uuccgcagac Ggaggaaacuc**C** **CU** **UC**AAGGACA**UCGUCC**GGG acuau B | 62 |
| 140 | UCUGCGGAACCGGUGA | 25 | HCV.R1A-140 | Amb.Rz-10/5 | ucaccgguuc Ggaggaaacuc**C** **CU** **UC**AAGGACA**UCGUCC**GGG gcaga B | 63 |
| 188 | UUCUUGGAUAACCCCG | 26 | HCV.R1A-188 | Amb.Rz-10/5 | cgggguuauc Ggaggaaacuc**C** **CU** **UC**AAGGACA**UCGUCC**GGG aagaa B | 64 |
| 198 | ACCCCGCUCAAUGCCU | 27 | HCV.R1A-198 | Amb.Rz-10/5 | aggcauugag Ggaggaaacuc**C** **CU** **UC**AAGGACA**UCGUCC**GGG ggggu B | 65 |
| 205 | UCAAUGCCUGGAGAUU | 28 | HCV.R1A-205 | Amb.Rz-10/5 | aaucuccagg Ggaggaaacuc**C** **CU** **UC**AAGGACA**UCGUCC**GGG auuga B | 66 |
| 217 | GAUUUGGGCGUGCCCC | 29 | HCV.R1A-217 | Amb.Rz-10/5 | ggggcacgcc Ggaggaaacuc**C** **CU** **UC**AAGGACA**UCGUCC**GGG aaauc B | 67 |
| 218 | AUUUGGGCGUGCCCCC | 30 | HCV.R1A-218 | Amb.Rz-10/5 | gggggcacgc Ggaggaaacuc**C** **CU** **UC**AAGGACA**UCGUCC**GGG caaau B | 68 |
| 219 | UUUGGGCGUGCCCCCG | 31 | HCV.R1A-219 | Amb.Rz-10/5 | cgggggcacg Ggaggaaacuc**C** **CU** **UC**AAGGACA**UCGUCC**GGG ccaaa B | 69 |

TABLE XIII-continued

Class I Enzymatic Nucleic Acid Motifs Targeting HCV

| Pos | Target | Seq ID | Alias | Sequence | Rz Seq ID |
|---|---|---|---|---|---|
| 223 | GGCGUGCCCCCGCAAG | 32 | HCV.R1A-223 Amb.Rz-10/5 | cuugcggggg Ggaggaaacuc**C** **CU** **UC**AAGGACA**UC**G**UCC**GGG acgcc B | 70 |
| 229 | CCCCCGCAAGACUGCU | 33 | HCV.R1A-229 Amb.Rz-10/5 | agcagucuug Ggaggaaacuc**C** **CU** **UC**AAGGACA**UC**G**UCC**GGG ggggg B | 71 |
| 279 | GUACUGCCUGAUAGGG | 34 | HCV.R1A-279 Amb.Rz-10/5 | cccuaucagg Ggaggaaacuc**C** **CU** **UC**AAGGACA**UC**G**UCC**GGG aguac B | 72 |
| 295 | UGCUUGCGAGUGCCCC | 35 | HCV.R1A-295 Amb.Rz-10/5 | ggggcacucg Ggaggaaacuc**C** **CU** **UC**AAGGACA**UC**G**UCC**GGG aagca B | 73 |
| 301 | CGAGUGCCCCGGGAGG | 36 | HCV.R1A-301 Amb.Rz-10/5 | ccucccgggg Ggaggaaacuc**C** **CU** **UC**AAGGACA**UC**G**UCC**GGG acucg B | 74 |
| 306 | GCCCCGGGAGGUCUCG | 37 | HCV.R1A-306 Amb.Rz-10/5 | cgagaccucc Ggaggaaacuc**C** **CU** **UC**AAGGACA**UC**G**UCC**GGG ggggc B | 75 |
| 307 | CCCCGGGAGGUCUCGU | 38 | HCV.R1A-307 Amb.Rz-10/5 | acgagaccuc Ggaggaaacuc**C** **CU** **UC**AAGGACA**UC**G**UCC**GGG cgggg B | 76 |
| No Ribo | | | | Ggaaaggugugcaaccggagucaucauaauggcuuc**CCUUC**aaggaCa**UC**g**CC** g ggacggc**B** | 77 |
| Ribo | | | | GGAAAGG**UGU**G**C**AA**CC**GGAG**UC**A**UC**A**U**AA**U**GG**CUCCCUUC**AAGGA**C**A**UC**G**UCC** GGGA**C**GG**CB** | 78 |

lower case =]2'-O-methyl
U, C = 2'-deoxy-2'-amino U, = 2'-deoxy-2'-amino C
G,A = ribo G, A
B = inverted deoxyabasic

TABLE XIV

Additional Class II enzymatic nucleic acid Motifs

| Class II Motif ID | Sequence | Seq ID No. | Kinetic Rate |
|---|---|---|---|
| A2 | GGGAGGAGGAAGUGCCUGGUCAGUCACACCGAGACUGGCAGACGCUGAAACC GCCGCGCUCGCUCCCAGUCC | 79 | UNK |
| A12 | GGGAGGAGGAAGUGCCUGGUAGUAAUAUAAUCGUUACUACGAGUGCAAGGUC GCCGCGCUCGCUCCCAGUCC | 80 | UNK |
| A11 | GGGAGGAGGAAGUGCCUGGUAGUUGCCCGAACUGUGACUACGAGUGAGGUC GCCGCGCUCGCUCCCAGUCC | 81 | UNK |
| B14 | GGGAGGAGGAAGUGCCUGGCGAUCAGAUGAGAUGAUGGCAGACGCAGAGACC GCCGCGCUCGCUCCCAGUCC | 82 | UNK |
| B10 | GGGAGGAGGAAGUGCCUGGCGACUGAUACGAAAAGUCGCAGUUUCGAAACC GCCGCGCUCGCUCCCAGUCC | 83 | UNK |
| B21 | GGGAGGAGGAAGUGCCUGGCGACUGAUACGAAAAGUCGCAGGUUUCGAAACC GCCGCGCUCGCUCCCAGUCC | 84 | UNK |
| B7 | GGGAGGAGGAAGUGCCUUGGCUCAGCAUAAGUGAGCAGAUUGCGACACC GCCGCGCUCGCUCCCAGUCC | 85 | UNK |
| C8 | GGGAGGAGGAAGUGCCUUGGUCAUUAGGAUGACAAACGUAUACUGAACACU GCCGCGCUCGCUCCCAGUCC | 86 | 0.01 $MIN^{-1}$ |

TABLE XV

Human Her2 Class II Ribozyme and Target Sequence

| RPI# | NT Pos | Substrate | Seq ID No | Ribozyme Alias | Ribozyme Sequence | Seq ID No |
|---|---|---|---|---|---|---|
| 18722 | 180 | CAUGGA G CUGGCG | 87 | erbB2-180 Zin.Rz-6 amino stab1 | $c_sg_sc_sc_s$ag GccgaaagG**C**GaGucaaGGu**C**u uccaug B | 196 |
| 18835 | 184 | GAGCUG G CGGCCU | 88 | erbB2-184 Zin.Rz-6 amino stab1 | $a_sg_sg_sc_s$cg GccgaaagG**C**GaGucaaGGu**C**u cagcuc B | 197 |
| 18828 | 276 | AGCUGCG G CUCCCUG | 89 | erbB2-276 Zin.Rz-7 amino stab1 | $c_sa_sg_sg_s$gag GccgaaagG**C**GaGucaaGGu**C**u cgcagcu B | 198 |
| 18653 | 314 | UGCUCC G CCACCU | 90 | erbB2-314 Zin.Rz-6 amino stab1 | $a_sg_sg_su_s$gg GccgaaagG**C**GaGucaaGGu**C**u ggagca B | 199 |
| 18825 | 314 | AUGCUCC G CCACCUC | 91 | erbB2-314 Zin.Rz-7 amino stab1 | $g_sa_sg_sg_s$ugg GccgaaagG**C**GaGucaaGGu**C**u ggagcau B | 200 |
| 18831 | 379 | ACCAAU G CCAGCC | 92 | erbB2-379 Zin.Rz-6 amino stab1 | $g_sg_sc_su_s$gg GccgaaagG**C**GaGucaaGGu**C**u auuggu B | 201 |
| 18680 | 433 | GCUCAUC G CUCACAA | 93 | erbB2-433 Zin.Rz-7 amino stab1 | $u_su_sg_su_s$gag GccgaaagG**C**GaGucaaGGu**C**u gaugagc B | 202 |
| 18711 | 594 | GGAGCU G CAGCUU | 94 | erbB2-594 Zin.Rz-6 amino stab1 | $a_sa_sg_sc_s$ug GccgaaagG**C**GaGucaaGGu**C**u agcucc B | 203 |
| 18681 | 594 | GGGAGCU G CAGCUUC | 95 | erbB2-594 Zin.Rz-7 amino stab1 | $g_sa_sa_sg_s$cug GccgaaagG**C**GaGucaaGGu**C**u agcuccc B | 204 |
| 18697 | 597 | GCUGCA G CUUCGA | 96 | erbB2-597 Zin.Rz-6 amino stab1 | $u_sc_sg_sa_s$ag GccgaaagG**C**GaGucaaGGu**C**u ugcagc B | 205 |

TABLE XV-continued

Human Her2 Class II Ribozyme and Target Sequence

| RPI# | NT Pos | Substrate | Seq ID No | Ribozyme Alias | Ribozyme Sequence | Seq ID No |
|---|---|---|---|---|---|---|
| 18665 | 597 | AGCUGCA G CUUCGAA | 97 | erbB2-597 Zin.Rz-7 amino stab1 | $u_s u_s c_s g_s$aag GccgaaagG**C**GaGucaaGGu**C**u ugcagcu B | 206 |
| 18712 | 659 | AGCUCU G CUACCA | 98 | erbB2-659 Zin.Rz-6 amino stab1 | $u_s g_s g_s u_s$ag GccgaaagG**C**GaGucaaGGu**C**u agagcu B | 207 |
| 18682 | 659 | CAGCUCU G CUACCAG | 99 | erbB2-659 Zin.Rz-7 amino stab1 | $c_s u_s g_s g_s$uag GccgaaagG**C**GaGucaaGGu**C**u agagcug B | 208 |
| 18683 | 878 | CUGACU G CUGCCA | 100 | erbB2-878 Zin.Rz-6 amino stab1 | $u_s g_s g_s c_s a_s$ GccgaaagG**C**GaGucaaGGu**C**u agucag B | 209 |
| 18654 | 878 | ACUGACU G CUGCCAU | 101 | erbB2-878 Zin.Rz-7 amino stab1 | $a_s u_s g_s g_s$cag GccgaaagG**C**GaGucaaGGu**C**u agucagu B | 210 |
| 18685 | 881 | ACUGCU G CCAUGA | 102 | erbB2-881 Zin.Rz-6 amino stab1 | $u_s c_s a_s u_s$gg GccgaaagG**C**GaGucaaGGu**C**u agcagu B | 211 |
| 18684 | 881 | GACUGCU G CCAUGAG | 103 | erbB2-881 Zin.Rz-7 amino stab1 | $c_s u_s c_s a_s$ugg GccgaaagG**C**GaGucaaGGu**C**u agcaguc B | 212 |
| 18723 | 888 | GCCAUGA G CAGUGUG | 104 | erbB2-888 Zin.Rz-7 amino stab1 | $c_s a_s c_s a_s$cug GccgaaagG**C**GaGucaaGGu**C**u ucauggc B | 213 |
| 18686 | 929 | CUGACU G CCUGGC | 105 | erbB2-929 Zin.Rz-6 amino stab1 | $g_s c_s c_s a_s$gg GccgaaagG**C**GaGucaaGGu**C**u agucag B | 214 |
| 18648 | 929 | UCUGACU G CCUGGCC | 106 | erbB2-929 Zin.Rz-7 amino stab1 | $g_s g_s c_s c_s$agg GccgaaagG**C**GaGucaaGGu**C**u agucaga B | 215 |
| 18666 | 934 | UGCCUG G CCUGCC | 107 | erbB2-934 Zin.Rz-6 amino stab1 | $g_s g_s c_s a_s$gg GccgaaagG**C**GaGucaaGGu**C**u caggca B | 216 |
| 18651 | 934 | CUGCCUG G CCUGCCU | 108 | erbB2-934 Zin.Rz-7 amino stab1 | $a_s g_s g_s c_s$agg GccgaaagG**C**GaGucaaGGu**C**u caggcag B | 217 |
| 18655 | 938 | UGGCCU G CCUCCA | 109 | erbB2-938 Zin.Rz-6 amino stab1 | $u_s g_s g_s a_s$gg GccgaaagG**C**GaGucaaGGu**C**u aggcca B | 218 |
| 18649 | 938 | CUGGCCU G CCUCCAC | 110 | erbB2-938 Zin.Rz-7 amino stab1 | $g_s u_s g_s g_s$agg GccgaaagG**C**GaGucaaGGu**C**u aggccag B | 219 |
| 18667 | 969 | CUGUGA G CUGCAC | 111 | erbB2-969 Zin.Rz-6 amino stab1 | $g_s u_s g_s c_s$ag GccgaaagG**C**GaGucaaGGu**C**u ucacag B | 220 |
| 18668 | 969 | UCUGUGA G CUGCACU | 112 | erbB2-969 Zin.Rz-7 amino stab1 | $a_s g_s u_s g_s$cag GccgaaagG**C**GaGucaaGGu**C**u ucacaga B | 221 |
| 18656 | 972 | UGAGCU G CACUGC | 113 | erbB2-972 Zin.Rz-6 amino stab1 | $g_s c_s a_s g_s$ug GccgaaagG**C**GaGucaaGGu**C**u agcuca B | 222 |
| 18657 | 972 | GUGAGCU G CACUGCC | 114 | erbB2-972 Zin.Rz-7 amino stab1 | $g_s g_s c_s a_s$gug GccgaaagG**C**GaGucaaGGu**C**u agcucac B | 223 |
| 19294 | 972 | UGAGCU G CACUGC | 113 | erbB2-972 Zin.Rz-6 amino stab1 | $g_s c_s a_s g_s$ug GcccaauuugugG**C**GaGucaaGGu**C**u agcuca B | 224 |
| 19295 | 972 | UGAGCU G CACUGC | 113 | erbB2-972 Zin.Rz-6 amino stab1 | $g_s c_s a_s g_s$ug GccAAuuuGuGG**C**GaGucaaGGu**C**u agcuca B | 225 |
| 19293 | 972 | UGAGCU G CACUGC | 113 | erbB2-972 Zin.Rz-6 amino stab1 | $g_s c_s a_s g_s$ug GccgaaagG**C**GaGuGaGGu**C**u agcuca B | 226 |
| 19292 | 972 | UGAGCU G CACUGC | 113 | erbB2-972 Zin.Rz-6 amino stab1 | $g_s c_s a_s g_s$ug GccgaaagG**C**GaGuGaGGu**C**u agcuca B | 226 |
| 19296 | 972 | UGAGCU G CACUGC | 113 | erbB2-972 Zin.Rz-6 amino stab1 | $g_s c_s a_s g_s$ug GccacAAuuuGuGGcagG**C**GaGucaaGGu**C**u agcuca B | 227 |
| 19727 | 972 | UGAGCU G CACUGC | 113 | erbB2-972 Zin.Rz-6 amino stab1 | $g_s c_s a_s g_s$ug gccgaaagg**C**gagugaggu**C**u agcuca B | 228 |
| 19728 | 972 | UGAGCU G CACUGC | 113 | erbB2-972 Zin.Rz-6 amino stab1 | $g_s c_s a_s g_s$ug gccgaaagg**C**gagugaggu**C**u agcuca B | 229 |
| 18659 | 1199 | GAGUGU G CUAUGG | 115 | erbB2-1199 Zin.Rz-6 amino stab1 | $c_s c_s a_s u_s$ag GccgaaagG**C**GaGucaaGGu**C**u acacuc B | 230 |
| 18658 | 1199 | CGAGUGU G CUAUGGU | 116 | erbB2-1199 Zin.Rz-7 amino stab1 | $a_s c_s c_s a_s$uag GccgaaagG**C**GaGucaaGGu**C**u acacucg B | 231 |
| 18724 | 1205 | GCUAUG G UCUGGG | 117 | erbB2-1205 Zin.Rz-6 amino stab1 | $c_s c_s c_s a_s$ga GccgaaagG**C**GaGucaaGGu**C**u cauagc B | 232 |
| 18669 | 1205 | UGCUAUG G UCUGGGC | 118 | erbB2-1205 Zin.Rz-7 amino stab1 | $g_s c_s c_s c_s$aga GccgaaagG**C**GaGucaaGGu**C**u cauagca B | 233 |
| 18725 | 1211 | GUCUGG G CAUGGA | 119 | erbB2-1211 Zin.Rz-6 amino stab1 | $u_s c_s c_s a_s$ug GccgaaagG**C**GaGucaaGGu**C**u ccagac B | 234 |
| 18726 | 1292 | UUGGGA G CCUGGC | 120 | erbB2-1292 Zin.Rz-6 amino stab1 | $g_s c_s c_s a_s$gg GccgaaagG**C**GaGucaaGGu**C**u ucccaa B | 235 |
| 18698 | 1292 | UUUGGGA G CCUGGCA | 121 | erbB2-1292 Zin.Rz-7 amino stab1 | $u_s g_s c_s c_s$agg GccgaaagG**C**GaGucaaGGu**C**u ucccaaa B | 236 |
| 18727 | 1313 | CCGGAGA G CUUUGAU | 122 | erbB2-1313 Zin.Rz-7 amino stab1 | $a_s u_s c_s a_s$aag GccgaaagG**C**GaGucaaGGu**C**u ucuccgg B | 237 |
| 18699 | 1397 | UCACAG G UUACCU | 123 | erbB2-1397 Zin.Rz-6 amino stab1 | $a_s g_s g_s u_s a_s$a GccgaaagG**C**GaGucaaGGu**C**u cuguga B | 238 |
| 18728 | 1414 | AUCUCA G CAUGGC | 124 | erbB2-1414 Zin.Rz-6 amino stab1 | $g_s c_s c_s a_s$ug GccgaaagG**C**GaGucaaGGu**C**u ugagau B | 239 |
| 18670 | 1414 | CAUCUCA G CAUGGCC | 125 | erbB2-1414 Zin.Rz-7 amino stab1 | $g_s g_s c_s c_s$aug GccgaaagG**C**GaGucaaGGu**C**u ugagaug B | 240 |

TABLE XV-continued

Human Her2 Class II Ribozyme and Target Sequence

| RPI# | NT Pos | Substrate | Seq ID No | Ribozyme Alias | Ribozyme Sequence | Seq ID No |
|---|---|---|---|---|---|---|
| 18671 | 1536 | GCUGGG G CUGCGC | 126 | erbB2-1536 Zin.Rz-6 amino stab1 | $g_sc_sg_sc_s$ag GccgaaagG**C**GaGucaaGGu**C**u cccagc B | 241 |
| 18687 | 1541 | GGCUGC G CUCACU | 127 | erbB2-1541 Zin.Rz-6 amino stab1 | $a_sg_su_sg_s$ag GccgaaagG**C**GaGucaaGGu**C**u gcagcc B | 242 |
| 18829 | 1562 | CUGGGCA G UGGACUG | 128 | erbB2-1562 Zin.Rz-7 amino stab1 | $c_sa_sg_su_s$cca GccgaaagG**C**GaGucaaGGu**C**u ugcccag B | 243 |
| 18830 | 1626 | GGGACCA G CUCUUUC | 129 | erbB2-1626 Zin.Rz-7 amino stab1 | $g_sa_sa_sa_s$gag GccgaaagG**C**GaGucaaGGu**C**u uggucccB | 244 |
| 18700 | 1755 | CACCCA G UGUGUC | 130 | erbB2-1755 Zin.Rz-6 amino stab1 | $g_sa_sc_sa_s$ca GccgaaagG**C**GaGucaaGGu**C**u ugggug B | 245 |
| 18672 | 1755 | CCACCCA G UGUGUCA | 131 | erbB2-1755 Zin.Rz-7 amino stab1 | $u_sg_sa_sc_s$aca GccgaaagG**C**GaGucaaGGu**C**u uggguggB | 246 |
| 18688 | 1757 | CCCAGU G UGUCAA | 132 | erbB2-1757 Zin.Rz-6 amino stab1 | $u_su_sg_sa_s$ca GccgaaagG**C**GaGucaaGGu**C**u acuggg B | 247 |
| 18660 | 1757 | ACCCAGU G UGUCAAC | 133 | erbB2-1757 Zin.Rz-7 amino stab1 | $g_su_su_sg_s$aca GccgaaagG**C**GaGucaaGGu**C**u acugggu B | 248 |
| 18689 | 1759 | CAGUGU G UCAACU | 134 | erbB2-1759 Zin.Rz-6 amino stab1 | $a_sg_su_su_s$ga GccgaaagG**C**GaGucaaGGu**C**u acacug B | 249 |
| 18690 | 1759 | CCAGUGU G UCAACUG | 135 | erbB2-1759 Zin.Rz-7 amino stab1 | $c_sa_sg_su_s$uga GccgaaagG**C**GaGucaaGGu**C**u acacugg B | 250 |
| 18701 | 1784 | UUCGGG G CCAGGA | 136 | erbB2-1784 Zin.Rz-6 amino stab1 | $u_sc_sc_su_s$gg GccgaaagG**C**GaGucaaGGu**C**u cccgaa B | 251 |
| 18673 | 1784 | CUUCGGG G CCAGGAG | 137 | erbB2-1784 Zin.Rz-7 amino stab1 | $c_su_sc_sc_s$ugg GccgaaagG**C**GaGucaaGGu**C**u cccgaag B | 252 |
| 18691 | 2063 | UCAACU G CACCCA | 138 | erbB2-2063 Zin.Rz-6 amino stab1 | $u_sg_sg_sg_s$ug GccgaaagG**C**GaGucaaGGu**C**u aguuga B | 253 |
| 18661 | 2063 | AUCAACU G CACCCAC | 139 | erbB2-2063 Zin.Rz-7 amino stab1 | $g_su_sg_sg_s$gug GccgaaagG**C**GaGucaaGGu**C**u aguugau B | 254 |
| 18692 | 2075 | ACUCCU G UGUGGA | 140 | erbB2-2075 Zin.Rz-6 amino stab1 | $u_sc_sc_sa_s$ca GccgaaagG**C**GaGucaaGGu**C**u aggagu B | 255 |
| 18729 | 2116 | CAGAGA G CCAGCC | 141 | erbB2-2116 Zin.Rz-6 amino stab1 | $g_sg_sc_su_s$gg GccgaaagG**C**GaGucaaGGu**C**u ucucug B | 256 |
| 18832 | 2247 | GACUGCU G CAGGAAA | 142 | erbB2-2247 Zin.Rz-7 amino stab1 | $u_su_su_sc_s$cug GccgaaagG**C**GaGucaaGGu**C**u agcaguc B | 257 |
| 18833 | 2271 | UGGAGCC G CUGACAC | 143 | erbB2-2271 Zin.Rz-7 amino stab1 | $g_su_sg_su_s$cag GccgaaagG**C**GaGucaaGGu**C**u ggcucca B | 258 |
| 18702 | 2341 | AGGAAG G UGAAGG | 144 | erbB2-2341 Zin.Rz-6 amino stab1 | $c_sc_su_su_s$ca GccgaaagG**C**GaGucaaGGu**C**u cuuccu B | 259 |
| 18730 | 2347 | GUGAAG G UGCUUG | 145 | erbB2-2347 Zin.Rz-6 amino stab1 | $c_sa_sa_sg_s$ca GccgaaagG**C**GaGucaaGGu**C**u cuucac B | 260 |
| 18674 | 2347 | GGUGAAG G UGCUUGG | 146 | erbB2-2347 Zin.Rz-7 amino stab1 | $c_sc_sa_sa_s$gca GccgaaagG**C**GaGucaaGGu**C**u cuucacc B | 261 |
| 18713 | 2349 | GAAGGU G CUUGGA | 147 | erbB2-2349 Zin.Rz-6 amino stab1 | $u_sc_sc_sa_s$ag GccgaaagG**C**GaGucaaGGu**C**u accuuc B | 262 |
| 18693 | 2349 | UGAAGGU G CUUGGAU | 148 | erbB2-2349 Zin.Rz-7 amino stab1 | $a_su_sc_sc_s$aag GccgaaagG**C**GaGucaaGGu**C**u accuuca B | 263 |
| 18731 | 2384 | UACAAGG G CAUCUGG | 149 | erbB2-2384 Zin.Rz-7 amino stab1 | $c_sc_sa_sg_s$aug GccgaaagG**C**GaGucaaGGu**C**u ccuugua B | 264 |
| 18714 | 2410 | GGAGAAU G UGAAAAU | 150 | erbB2-2410 Zin.Rz-7 amino stab1 | $a_su_su_su_s$uca GccgaaagG**C**GaGucaaGGu**C**u auucucc B | 265 |
| 18732 | 2497 | GUGAUG G CUGGUG | 151 | erbB2-2497 Zin.Rz-6 amino stab1 | $c_sa_sc_sc_s$ag GccgaaagG**C**GaGucaaGGu**C**u caucac B | 266 |
| 18703 | 2501 | UGGCUG G UGUGGG | 152 | erbB2-2501 Zin.Rz-6 amino stab1 | $c_sc_sc_sa_s$ca GccgaaagG**C**GaGucaaGGu**C**u cagcca B | 267 |
| 18715 | 2540 | GCAUCU G CCUGAC | 153 | erbB2-2540 Zin.Rz-6 amino stab1 | $g_su_sc_sa_s$gg GccgaaagG**C**GaGucaaGGu**C**u agaugc B | 268 |
| 18733 | 2563 | CAGCUG G UGACAC | 154 | erbB2-2563 Zin.Rz-6 amino stab1 | $g_su_sg_su_s$ca GccgaaagG**C**GaGucaaGGu**C**u cagcug B | 269 |
| 18734 | 2571 | GACACA G CUUAUG | 155 | erbB2-2571 Zin.Rz-6 amino stab1 | $c_sa_su_sa_s$ag GccgaaagG**C**GaGucaaGGu**C**u uguguc B | 270 |
| 18675 | 2571 | UGACACA G CUUAUGC | 156 | erbB2-2571 Zin.Rz-7 amino stab1 | $g_sc_sa_su_s$aag GccgaaagG**C**GaGucaaGGu**C**u uguguca B | 271 |
| 18716 | 2662 | CAGAUU G CCAAGG | 157 | erbB2-2662 Zin.Rz-6 amino stab1 | $c_sc_su_su_s$gg GccgaaagG**C**GaGucaaGGu**C**u aaucug B | 272 |
| 18704 | 2675 | GGAUGA G CUACCU | 158 | erbB2-2675 Zin.Rz-6 amino stab1 | $a_sg_sg_su_s$ag GccgaaagG**C**GaGucaaGGu**C**u ucaucc B | 273 |
| 18676 | 2675 | GGGAUGA G CUACCUG | 159 | erbB2-2675 Zin.Rz-7 amino stab1 | $c_sa_sg_sg_s$uag GccgaaagG**C**GaGucaaGGu**C**u ucauccc B | 274 |
| 18735 | 2738 | GUCAAGA G UCCCAAC | 160 | erbB2-2738 Zin.Rz-7 amino stab1 | $g_su_su_sg_s$gga GccgaaagG**C**GaGucaaGGu**C**u ucuugac B | 275 |
| 18705 | 2773 | GGGCUG G CUCGGC | 161 | erbB2-2773 Zin.Rz-6 amino stab1 | $g_sc_sc_sg_s$ag GccgaaagG**C**GaGucaaGGu**C**u cagccc B | 276 |

TABLE XV-continued

Human Her2 Class II Ribozyme and Target Sequence

| RPI# | NT Pos | Substrate | Seq ID No | Ribozyme Alias | Ribozyme Sequence | Seq ID No |
|---|---|---|---|---|---|---|
| 18836 | 2778 | UGGCUCG G CUGCUGG | 162 | erbB2-2778 Zin.Rz-7 amino stab1 | $c_sc_sa_sg_s$cag GccgaaagG**C**GaGucaaGGu**C**u cgagcca B | 277 |
| 18694 | 2781 | UCGGCU G CUGGAC | 163 | erbB2-2781 Zin.Rz-6 amino stab1 | $g_su_sc_sc_s$ag GccgaaagG**C**GaGucaaGGu**C**u agccga B | 278 |
| 18662 | 2781 | CUCGGCU G CUGGACA | 164 | erbB2-2781 Zin.Rz-7 amino stab1 | $u_sg_su_sc_s$cag GccgaaagG**C**GaGucaaGGu**C**u agccgag B | 279 |
| 18737 | 2802 | GACAGA G UACCAU | 165 | erbB2-2802 Zin.Rz-6 amino stab1 | $a_su_sg_sg_s$ua GccgaaagG**C**GaGucaaGGu**C**u ucuguc B | 280 |
| 18736 | 2802 | AGACAGA G UACCAUG | 166 | erbB2-2802 Zin.Rz-7 amino stab1 | $c_sa_su_sg_s$gua GccgaaagG**C**GaGucaaGGu**C**u ucugucu B | 281 |
| 18717 | 2809 | GUACCAU G CAGAUGG | 167 | erbB2-2809 Zin.Rz-7 amino stab1 | $c_sc_sa_su_s$cug GccgaaagG**C**GaGucaaGGu**C**u augguac B | 282 |
| 18738 | 2819 | AUGGGG G CAAGGU | 168 | erbB2-2819 Zin.Rz-6 amino stab1 | $a_sc_sc_su_s$ug GccgaaagG**C**GaGucaaGGu**C**u ccccau B | 283 |
| 18706 | 2819 | GAUGGGG G CAAGGUG | 169 | erbB2-2819 Zin.Rz-7 amino stab1 | $c_sa_sc_sc_s$uug GccgaaagG**C**GaGucaaGGu**C**u ccccauc B | 284 |
| 18695 | 2887 | GAGUGAU G UGUGGAG | 170 | erbB2-2887 Zin.Rz-7 amino stab1 | $c_su_sc_sc_s$aca GccgaaagG**C**GaGucaaGGu**C**u aucacuc B | 285 |
| 18663 | 2908 | GUGACU G UGUGGG | 171 | erbB2-2908 Zin.Rz-6 amino stab1 | $c_sc_sc_sa_s$ca GccgaaagG**C**GaGucaaGGu**C**u agucac B | 286 |
| 18826 | 2908 | UGUGACU G UGUGGGA | 172 | erbB2-2908 Zin.Rz-7 amino stab1 | $u_sc_sc_sc_s$aca GccgaaagG**C**GaGucaaGGu**C**u agucaca B | 287 |
| 18664 | 2910 | GACUGU G UGGGAG | 173 | erbB2-2910 Zin.Rz-6 amino stab1 | $c_su_sc_sc_s$ca GccgaaagG**C**GaGucaaGGu**C**u acaguc B | 288 |
| 18650 | 2910 | UGACUGU G UGGGAGC | 174 | erbB2-2910 Zin.Rz-7 amino stab1 | $g_sc_su_sc_s$cca GccgaaagG**C**GaGucaaGGu**C**u acaguca B | 289 |
| 18677 | 2916 | GUGGGA G CUGAUG | 175 | erbB2-2916 Zin.Rz-6 amino stab1 | $c_sa_su_sc_s$ag GccgaaagG**C**GaGucaaGGu**C**u ucccac B | 290 |
| 18652 | 2916 | UGUGGGA G CUGAUGA | 176 | erbB2-2916 Zin.Rz-7 amino stab1 | $u_sc_sa_su_s$cag GccgaaagG**C**GaGucaaGGu**C**u ucccaca B | 291 |
| 18707 | 2932 | UUUGGG G CCAAAC | 177 | erbB2-2932 Zin.Rz-6 amino stab1 | $g_su_su_su_s$gg GccgaaagG**C**GaGucaaGGu**C**u cccaaa B | 292 |
| 18678 | 2932 | UUUUGGG G CCAAACC | 178 | erbB2-2932 Zin.Rz-7 amino stab1 | $g_sg_su_su_s$ugg GccgaaagG**C**GaGucaaGGu**C**u cccaaaa B | 293 |
| 18719 | 3025 | AUUGAU G UCUACA | 179 | erbB2-3025 Zin.Rz-6 amino stab1 | $u_sg_su_sa_s$ga GccgaaagG**C**GaGucaaGGu**C**u aucaau B | 294 |
| 18718 | 3025 | CAUUGAU G UCUACAU | 180 | erbB2-3025 Zin.Rz-7 amino stab1 | $a_su_sg_su_s$aga GccgaaagG**C**GaGucaaGGu**C**u aucaaug B | 295 |
| 18720 | 3047 | UCAAAU G UUGGAU | 181 | erbB2-3047 Zin.Rz-6 amino stab1 | $a_su_sc_sc_s$aa GccgaaagG**C**GaGucaaGGu**C**u auuuga B | 296 |
| 18696 | 3047 | GUCAAAU G UUGGAUG | 182 | erbB2-3047 Zin.Rz-7 amino stab1 | $c_sa_su_sc_s$caa GccgaaagG**C**GaGucaaGGu**C**u auuugac B | 297 |
| 18739 | 3087 | CCGGGA G UUGGUG | 183 | erbB2-3087 Zin.Rz-6 amino stab1 | $c_sa_sc_sc_s$aa GccgaaagG**C**GaGucaaGGu**C**u ucccgg B | 298 |
| 18708 | 3087 | UCCGGGA G UUGGUGU | 184 | erbB2-3087 Zin.Rz-7 amino stab1 | $a_sc_sa_sc_s$caa GccgaaagG**C**GaGucaaGGu**C**u ucccgga B | 299 |
| 18740 | 3415 | GAAGGG G CUGGCU | 185 | erbB2-3415 Zin.Rz-6 amino stab1 | $a_sg_sc_sc_s$ag GccgaaagG**C**GaGucaaGGu**C**u cccuuc B | 300 |
| 18741 | 3419 | GGGCUG G CUCCGA | 186 | erbB2-3419 Zin.Rz-6 amino stab1 | $u_sc_sg_sg_s$ag GccgaaagG**C**GaGucaaGGu**C**u cagccc B | 301 |
| 18837 | 3419 | GGGGCUG G CUCCGAU | 187 | erbB2-3419 Zin.Rz-7 amino stab1 | $a_su_sc_sg_s$gag GccgaaagG**C**GaGucaaGGu**C**u cagcccc B | 302 |
| 18709 | 3437 | UUGAUG G UGACCU | 188 | erbB2-3437 Zin.Rz-6 amino stab1 | $a_sg_sg_su_s$ca GccgaaagG**C**GaGucaaGGu**C**u caucaa B | 303 |
| 18679 | 3437 | UUUGAUG G UGACCUG | 189 | erbB2-3437 Zin.Rz-7 amino stab1 | $c_sa_sg_sg_s$uca GccgaaagG**C**GaGucaaGGu**C**u caucaaa B | 304 |
| 18823 | 3504 | UCUACA G CGGUAC | 190 | erbB2-3504 Zin.Rz-6 amino stab1 | $g_su_sa_sc_s$cg GccgaaagG**C**GaGucaaGGu**C**u uguaga B | 305 |
| 18710 | 3504 | CUCUACA G CGGUACA | 191 | erbB2-3504 Zin.Rz-7 amino stab1 | $u_sg_su_sa_s$ccg GccgaaagG**C**GaGucaaGGu**C**u uguagag B | 306 |
| 18721 | 3724 | CAAAGAC G UUUUUGC | 192 | erbB2-3724 Zin.Rz-7 amino stab1 | $g_sc_sa_sa_s$aaa GccgaaagG**C**GaGucaaGGu**C**u gucuuug B | 307 |
| 18834 | 3808 | CCUCCU G CCUUCA | 193 | erbB2-3808 Zin.Rz-6 amino stab1 | $u_sg_sa_sa_s$gg GccgaaagG**C**GaGucaaGGu**C**u aggagg B | 308 |
| 18827 | 3808 | UCCUCCU G CCUUCAG | 194 | erbB2-3808 Zin.Rz-7 amino stab1 | $c_su_sg_sa_s$agg GccgaaagG**C**GaGucaaGGu**C**u aggagga B | 309 |
| 18824 | 3996 | GGGAAG G CCUGAC | 195 | erbB2-3996 Zin.Rz-6 amino stab1 | $g_su_sc_sa_s$gg GccgaaagG**C**GaGucaaGGu**C**u cuuccc B | 310 |

UPPER CASE = RIBO
Lower case = 2'-O-methyl
C= 2'-deoxy-2'-amino Cytidine
s = phosphorothioate
B = inverted deoxyabasic

TABLE XVI

Human HER2 Class II (zinzyme) Ribozyme and Target Sequence

| Pos | Substrate | Seq ID | Ribozyme | Seq ID |
|---|---|---|---|---|
| 46 | GGGCAGCC G CGCGCCCC | 311 | GGGGCGCG GCCGAAAGGCGAGUCAAGGUCU GGCUGCCC | 896 |
| 48 | GCAGCCGC G CGCCCCUU | 312 | AAGGGGCG GCCGAAAGGCGAGUCAAGGUCU GCGGCUGC | 897 |
| 50 | AGCCGCGC G CCCCUUCC | 313 | GGAAGGGG GCCGAAAGGCGAGUCAAGGUCU GCGCGGCU | 898 |
| 75 | CCUUUACU G CGCCGCGC | 314 | GCGCGGCG GCCGAAAGGCGAGUCAAGGUCU AGUAAAGG | 899 |
| 77 | UUUACUGC G CCGCGCGC | 315 | GCGCGCGG GCCGAAAGGCGAGUCAAGGUCU GCAGUAAA | 900 |
| 80 | ACUGCGCC G CGCGCCCG | 316 | CGGGCGCG GCCGAAAGGCGAGUCAAGGUCU GGCGCAGU | 901 |
| 82 | UGCGCCGC G CGCCCGGC | 317 | GCCGGGCG GCCGAAAGGCGAGUCAAGGUCU GCGGCGCA | 902 |
| 84 | CGCCGCGC G CCCGGCCC | 318 | GGGCCGGG GCCGAAAGGCGAGUCAAGGUCU GCGCGGCG | 903 |
| 102 | CACCCCUC G CAGCACCC | 319 | GGGUGCUG GCCGAAAGGCGAGUCAAGGUCU GAGGGGUG | 904 |
| 112 | AGCACCCC G CGCCCCGC | 320 | GCGGGGCG GCCGAAAGGCGAGUCAAGGUCU GGGGUGCU | 905 |
| 114 | CACCCCGC G CCCCGCGC | 321 | GCGCGGGG GCCGAAAGGCGAGUCAAGGUCU GCGGGGUG | 906 |
| 119 | CGCGCCCC G CGCCCUCC | 322 | GGAGGGCG GCCGAAAGGCGAGUCAAGGUCU GGGGCGCG | 907 |
| 121 | CGCCCCGC G CCCUCCCA | 323 | UGGGAGGG GCCGAAAGGCGAGUCAAGGUCU GCGGGGCG | 908 |
| 163 | CCGGAGCC G CAGUGAGC | 324 | GCUCACUG GCCGAAAGGCGAGUCAAGGUCU GGCUCCGG | 909 |
| 194 | GGCCUUGU G CCGCUGGG | 325 | CCCAGCGG GCCGAAAGGCGAGUCAAGGUCU ACAAGGCC | 910 |
| 197 | CUUGUGCC G CUGGGGGC | 326 | GCCCCCAG GCCGAAAGGCGAGUCAAGGUCU GGCACAAG | 911 |
| 214 | UCCUCCUC G CCCUCUUG | 327 | CAAGAGGG GCCGAAAGGCGAGUCAAGGUCU GAGGAGGA | 912 |
| 222 | GCCCUCUU G CCCCCCGG | 328 | CCGGGGGG GCCGAAAGGCGAGUCAAGGUCU AAGAGGGC | 913 |
| 235 | CCGGAGCC G CGAGCACC | 329 | GGUGCUCG GCCGAAAGGCGAGUCAAGGUCU GGCUCCGG | 914 |
| 251 | CCAAGUGU G CACCGGCA | 330 | UGCCGGUG GCCGAAAGGCGAGUCAAGGUCU ACACUUGG | 915 |
| 273 | AUGAAGCU G CGGCUCCC | 331 | GGGAGCCG GCCGAAAGGCGAGUCAAGGUCU AGCUUCAU | 916 |
| 283 | GGCUCCCU G CCAGUCCC | 332 | GGGACUGG GCCGAAAGGCGAGUCAAGGUCU AGGGAGCC | 917 |
| 309 | CUGGACAU G CUCCGCCA | 333 | UGGCGGAG GCCGAAAGGCGAGUCAAGGUCU AUGUCCAG | 918 |
| 314 | CAUGCUCC G CCACCUCU | 334 | AGAGGUGG GCCGAAAGGCGAGUCAAGGUCU GGAGCAUG | 919 |
| 332 | CCAGGGCU G CCAGGUGG | 335 | CCACCUGG GCCGAAAGGCGAGUCAAGGUCU AGCCCUGG | 920 |
| 342 | CAGGUGGU G CAGGGAAA | 336 | UUUCCCUG GCCGAAAGGCGAGUCAAGGUCU ACCACCUG | 921 |
| 369 | ACCUACCU G CCCACCAA | 337 | UUGGUGGG GCCGAAAGGCGAGUCAAGGUCU AGGUAGGU | 922 |
| 379 | CCACCAAU G CCAGCCUG | 338 | CAGGCUGG GCCGAAAGGCGAGUCAAGGUCU AUUGGUGG | 923 |
| 396 | UCCUUCCU G CAGGAUAU | 339 | AUAUCCUG GCCGAAAGGCGAGUCAAGGUCU AGGAAGGA | 924 |
| 414 | CAGGAGGU G CAGGGCUA | 340 | UAGCCCUG GCCGAAAGGCGAGUCAAGGUCU ACCUCCUG | 925 |
| 426 | GGCUACGU G CUCAUCGC | 341 | GCGAUGAG GCCGAAAGGCGAGUCAAGGUCU ACGUAGCC | 926 |
| 433 | UGCUCAUC G CUCACAAC | 342 | GUUGUGAG GCCGAAAGGCGAGUCAAGGUCU GAUGAGCA | 927 |
| 462 | GUCCCACU G CAGAGGCU | 343 | AGCCUCUG GCCGAAAGGCGAGUCAAGGUCU AGUGGGAC | 928 |
| 471 | CAGAGGCU G CGGAUUGU | 344 | ACAAUCCG GCCGAAAGGCGAGUCAAGGUCU AGCCUCUG | 929 |
| 480 | CGGAUUGU G CGAGGCAC | 345 | GUGCCUCG GCCGAAAGGCGAGUCAAGGUCU ACAAUCCG | 930 |
| 511 | ACAACUAU G CCCUGGCC | 346 | GGCCAGGG GCCGAAAGGCGAGUCAAGGUCU AUAGUUGU | 931 |
| 522 | CUGGCCGU G CUAGACAA | 347 | UUGUCUAG GCCGAAAGGCGAGUCAAGGUCU ACGGCCAG | 932 |
| 540 | GGAGACCC G CUGAACAA | 348 | UUGUUCAG GCCGAAAGGCGAGUCAAGGUCU GGGUCUCC | 933 |
| 585 | GGAGGCCU G CGGGAGCU | 349 | AGCUCCCG GCCGAAAGGCGAGUCAAGGUCU AGGCCUCC | 934 |
| 594 | CGGGAGCU G CAGCUUCG | 350 | CGAAGCUG GCCGAAAGGCGAGUCAAGGUCU AGCUCCCG | 935 |
| 659 | CCAGCUCU G CUACCAGG | 351 | CCUGGUAG GCCGAAAGGCGAGUCAAGGUCU AGAGCUGG | 936 |
| 737 | CACCAACC G CUCUCGGG | 352 | CCCGAGAG GCCGAAAGGCGAGUCAAGGUCU GGUUGGUG | 937 |
| 749 | UCGGGCCU G CCACCCCU | 353 | AGGGGUGG GCCGAAAGGCGAGUCAAGGUCU AGGCCCGA | 938 |
| 782 | GGGCUCCC G CUGCUGGG | 354 | CCCAGCAG GCCGAAAGGCGAGUCAAGGUCU GGGAGCCC | 939 |
| 785 | CUCCCGCU G CUGGGGAG | 355 | CUCCCCAG GCCGAAAGGCGAGUCAAGGUCU AGCGGGAG | 940 |
| 822 | AGCCUGAC G CGCACUGU | 356 | ACAGUGCG GCCGAAAGGCGAGUCAAGGUCU GUCAGGCU | 941 |
| 824 | CCUGACGC G CACUGUCU | 357 | AGACAGUG GCCGAAAGGCGAGUCAAGGUCU GCGUCAGG | 942 |
| 835 | CUGUCUGU G CCGGUGGC | 358 | GCCACCGG GCCGAAAGGCGAGUCAAGGUCU ACAGACAG | 943 |
| 847 | GUGGCUGU G CCCGCUGC | 359 | GCAGCGGG GCCGAAAGGCGAGUCAAGGUCU ACAGCCAC | 944 |
| 851 | CUGUGCCC G CUGCAAGG | 360 | CCUUGCAG GCCGAAAGGCGAGUCAAGGUCU GGGCACAG | 945 |
| 854 | UGCCCGCU G CAAGGGGC | 361 | GCCCCUUG GCCGAAAGGCGAGUCAAGGUCU AGCGGGCA | 946 |
| 867 | GGGCCACU G CCCACUGA | 362 | UCAGUGGG GCCGAAAGGCGAGUCAAGGUCU AGUGGCCC | 947 |
| 878 | CACUGACU G CUGCCAUG | 363 | CAUGGCAG GCCGAAAGGCGAGUCAAGGUCU AGUCAGUG | 948 |
| 881 | UGACUGCU G CCAUGAGC | 364 | GCUCAUGG GCCGAAAGGCGAGUCAAGGUCU AGCAGUCA | 949 |
| 895 | AGCAGUGU G CUGCCGGC | 365 | GCCGGCAG GCCGAAAGGCGAGUCAAGGUCU ACACUGCU | 950 |
| 898 | AGUGUGCU G CCGGCUGC | 366 | GCAGCCGG GCCGAAAGGCGAGUCAAGGUCU AGCACACU | 951 |
| 905 | UGCCGGCU G CACGGGCC | 367 | GGCCCGUG GCCGAAAGGCGAGUCAAGGUCU AGCCGGCA | 952 |
| 929 | CUCUGACU G CCUGGCCU | 368 | AGGCCAGG GCCGAAAGGCGAGUCAAGGUCU AGUCAGAG | 953 |
| 938 | CCUGGCCU G CCUCCACU | 369 | AGUGGAGG GCCGAAAGGCGAGUCAAGGUCU AGGCCAGG | 954 |
| 972 | UGUGAGCU G CACUGCCC | 370 | GGGCAGUG GCCGAAAGGCGAGUCAAGGUCU AGCUCACA | 955 |
| 977 | GCUGCACU G CCCAGCCC | 371 | GGGCUGGG GCCGAAAGGCGAGUCAAGGUCU AGUGCAGC | 956 |
| 1020 | GAGUCCAU G CCCAAUCC | 372 | GGAUUGGG GCCGAAAGGCGAGUCAAGGUCU AUGGACUC | 957 |
| 1051 | CAUUCGGC G CCAGCUGU | 373 | ACAGCUGG GCCGAAAGGCGAGUCAAGGUCU GCCGAAUG | 958 |
| 1066 | GUGUGACU G CCUGUCCC | 374 | GGGACAGG GCCGAAAGGCGAGUCAAGGUCU AGUCACAC | 959 |
| 1106 | GGGAUCCU G CACCCUCG | 375 | CGAGGGUG GCCGAAAGGCGAGUCAAGGUCU AGGAUCCC | 960 |
| 1118 | CCUCGUCU G CCCCCUGC | 376 | GCAGGGGG GCCGAAAGGCGAGUCAAGGUCU AGACGAGG | 961 |
| 1125 | UGCCCCCU G CACAACCA | 377 | UGGUUGUG GCCGAAAGGCGAGUCAAGGUCU AGGGGGCA | 962 |
| 1175 | UGAGAAGU G CAGCAAGC | 378 | GCUUGCUG GCCGAAAGGCGAGUCAAGGUCU ACUUCUCA | 963 |
| 1189 | AGCCCUGU G CCCGAGUG | 379 | CACUCGGG GCCGAAAGGCGAGUCAAGGUCU ACAGGGCU | 964 |
| 1199 | CCGAGUGU G CUAUGGUC | 380 | GACCAUAG GCCGAAAGGCGAGUCAAGGUCU ACACUCGG | 965 |
| 1224 | GAGCACUU G CGAGAGGU | 381 | ACCUCUCG GCCGAAAGGCGAGUCAAGGUCU AAGUGCUC | 966 |
| 1249 | UUACCAGU G CCAAUAUC | 382 | GAUAUUGG GCCGAAAGGCGAGUCAAGGUCU ACUGGUAA | 967 |
| 1267 | AGGAGUUU G CUGGCUGC | 383 | GCAGCCAG GCCGAAAGGCGAGUCAAGGUCU AAACUCCU | 968 |
| 1274 | UGCUGGCU G CAAGAAGA | 384 | UCUUCUUG GCCGAAAGGCGAGUCAAGGUCU AGCCAGCA | 969 |
| 1305 | GCAUUUCU G CCGGAGAG | 385 | CUCUCCGG GCCGAAAGGCGAGUCAAGGUCU AGAAAUGC | 970 |

TABLE XVI-continued

Human HER2 Class II (zinzyme) Ribozyme and Target Sequence

| Pos | Substrate | Seq ID | Ribozyme | Seq ID |
|---|---|---|---|---|
| 1342 | CCAACACU G CCCCGCUC | 386 | GAGCGGGG GCCGAAAGGCGAGUCAAGGUCU AGUGUUGG | 971 |
| 1347 | ACUGCCCC G CUCCAGCC | 387 | GGCUGGAG GCCGAAAGGCGAGUCAAGGUCU GGGGCAGU | 972 |
| 1431 | GACAGCCU G CCUGACCU | 388 | AGGUCAGG GCCGAAAGGCGAGUCAAGGUCU AGGCUGUC | 973 |
| 1458 | CAGAACCU G CAAGUAAU | 389 | AUUACUUG GCCGAAAGGCGAGUCAAGGUCU AGGUUCUG | 974 |
| 1482 | CGAAUUCU G CACAAUGG | 390 | CCAUUGUG GCCGAAAGGCGAGUCAAGGUCU AGAAUUCG | 975 |
| 1492 | ACAAUGGC G CCUACUCG | 391 | CGAGUAGG GCCGAAAGGCGAGUCAAGGUCU GCCAUUGU | 976 |
| 1500 | GCCUACUC G CUGACCCU | 392 | AGGGUCAG GCCGAAAGGCGAGUCAAGGUCU GAGUAGGC | 977 |
| 1509 | CUGACCCU G CAAGGGCU | 393 | AGCCCUUG GCCGAAAGGCGAGUCAAGGUCU AGGGUCAG | 978 |
| 1539 | CUGGGGCU G CGCUCACU | 394 | AGUGAGCG GCCGAAAGGCGAGUCAAGGUCU AGCCCCAG | 979 |
| 1541 | GGGGCUGC G CUCACUGA | 395 | UCAGUGAG GCCGAAAGGCGAGUCAAGGUCU GCAGCCCC | 980 |
| 1598 | CCACCUCU G CUUCGUGC | 396 | GCACGAAG GCCGAAAGGCGAGUCAAGGUCU AGAGGUGG | 981 |
| 1605 | UGCUUCGU G CACACGGU | 397 | ACCGUGUG GCCGAAAGGCGAGUCAAGGUCU ACGAAGCA | 982 |
| 1614 | CACACGGU G CCCUGGGA | 398 | UCCCAGGG GCCGAAAGGCGAGUCAAGGUCU ACCGUGUG | 983 |
| 1641 | CGGAACCC G CACCAAGC | 399 | GCUUGGUG GCCGAAAGGCGAGUCAAGGUCU GGGUUCCG | 984 |
| 1653 | CAAGCUCU G CUCCACAC | 400 | GUGUGGAG GCCGAAAGGCGAGUCAAGGUCU AGAGCUUG | 985 |
| 1663 | UCCACACU G CCAACCGG | 401 | CCGGUUGG GCCGAAAGGCGAGUCAAGGUCU AGUGUGGA | 986 |
| 1706 | CCUGGCCU G CCACCAGC | 402 | GCUGGUGG GCCGAAAGGCGAGUCAAGGUCU AGGCCAGG | 987 |
| 1718 | CCAGCUGU G CGCCCGAG | 403 | CUCGGGCG GCCGAAAGGCGAGUCAAGGUCU ACAGCUGG | 988 |
| 1720 | AGCUGUGC G CCCGAGGG | 404 | CCCUCGGG GCCGAAAGGCGAGUCAAGGUCU GCACAGCU | 989 |
| 1733 | AGGGCACU G CUGGGGUC | 405 | GACCCCAG GCCGAAAGGCGAGUCAAGGUCU AGUGCCCU | 990 |
| 1766 | UGUCAACU G CAGCCAGU | 406 | ACUGGCUG GCCGAAAGGCGAGUCAAGGUCU AGUUGACA | 991 |
| 1793 | CCAGGAGU G CGUGGAGG | 407 | CCUCCACG GCCGAAAGGCGAGUCAAGGUCU ACUCCUGG | 992 |
| 1805 | GGAGGAAU G CCGAGUAC | 408 | GUACUCGG GCCGAAAGGCGAGUCAAGGUCU AUUCCUCC | 993 |
| 1815 | CGAGUACU G CAGGGGCU | 409 | AGCCCCUG GCCGAAAGGCGAGUCAAGGUCU AGUACUCG | 994 |
| 1843 | AUGUGAAU G CCAGGCAC | 410 | GUGCCUGG GCCGAAAGGCGAGUCAAGGUCU AUUCACAU | 995 |
| 1857 | CACUGUUU G CCGUGCCA | 411 | UGGCACGG GCCGAAAGGCGAGUCAAGGUCU AAACAGUG | 996 |
| 1862 | UUUGCCGU G CCACCCUG | 412 | CAGGGUGG GCCGAAAGGCGAGUCAAGGUCU ACGGCAAA | 997 |
| 1936 | UGGCCUGU G CCCACUAU | 413 | AUAGUGGG GCCGAAAGGCGAGUCAAGGUCU ACAGGCCA | 998 |
| 1961 | UCCCUUCU G CGUGGCCC | 414 | GGGCCACG GCCGAAAGGCGAGUCAAGGUCU AGAAGGGA | 999 |
| 1970 | CGUGGCCC G CUGCCCCA | 415 | UGGGGCAG GCCGAAAGGCGAGUCAAGGUCU GGGCCACG | 1000 |
| 1973 | GGCCCGCU G CCCCAGCG | 416 | CGCUGGGG GCCGAAAGGCGAGUCAAGGUCU AGCGGGCC | 1001 |
| 2007 | UCCUACAU G CCCAUCUG | 417 | CAGAUGGG GCCGAAAGGCGAGUCAAGGUCU AUGUAGGA | 1002 |
| 2038 | AGGAGGGC G CAUGCCAG | 418 | CUGGCAUG GCCGAAAGGCGAGUCAAGGUCU GCCCUCCU | 1003 |
| 2042 | GGGCGCAU G CCAGCCUU | 419 | AAGGCUGG GCCGAAAGGCGAGUCAAGGUCU AUGCGCCC | 1004 |
| 2051 | CCAGCCUU G CCCCAUCA | 420 | UGAUGGGG GCCGAAAGGCGAGUCAAGGUCU AAGGCUGG | 1005 |
| 2063 | CAUCAACU G CACCCACU | 421 | AGUGGGUG GCCGAAAGGCGAGUCAAGGUCU AGUUGAUG | 1006 |
| 2099 | CAAGGGCU G CCCCGCCG | 422 | CGGCGGGG GCCGAAAGGCGAGUCAAGGUCU AGCCCUUG | 1007 |
| 2104 | GCUGCCCC G CCGAGCAG | 423 | CUGCUCGG GCCGAAAGGCGAGUCAAGGUCU GGGGCAGC | 1008 |
| 2143 | UCAUCUCU G CGGUGGUU | 424 | AACCACCG GCCGAAAGGCGAGUCAAGGUCU AGAGAUGA | 1009 |
| 2160 | GGCAUUCU G CUGGUCGU | 425 | ACGACCAG GCCGAAAGGCGAGUCAAGGUCU AGAAUGCC | 1010 |
| 2235 | UACACGAU G CGGAGACU | 426 | AGUCUCCG GCCGAAAGGCGAGUCAAGGUCU AUCGUGUA | 1011 |
| 2244 | CGGAGACU G CUGCAGGA | 427 | UCCUGCAG GCCGAAAGGCGAGUCAAGGUCU AGUCUCCG | 1012 |
| 2247 | AGACUGCU G CAGGAAAC | 428 | GUUUCCUG GCCGAAAGGCGAGUCAAGGUCU AGCAGUCU | 1013 |
| 2271 | GUGGAGCC G CUGACACC | 429 | GGUGUCAG GCCGAAAGGCGAGUCAAGGUCU GGCUCCAC | 1014 |
| 2292 | GGAGCGAU G CCCAACCA | 430 | UGGUUGGG GCCGAAAGGCGAGUCAAGGUCU AUCGCUCC | 1015 |
| 2304 | AACCAGGC G CAGAUGCG | 431 | CGCAUCUG GCCGAAAGGCGAGUCAAGGUCU GCCUGGUU | 1016 |
| 2310 | GCGCAGAU G CGGAUCCU | 432 | AGGAUCCG GCCGAAAGGCGAGUCAAGGUCU AUCUGCGC | 1017 |
| 2349 | GUGAAGGU G CUUGGAUC | 433 | GAUCCAAG GCCGAAAGGCGAGUCAAGGUCU ACCUUCAC | 1018 |
| 2362 | GAUCUGGC G CUUUUGGC | 434 | GCCAAAAG GCCGAAAGGCGAGUCAAGGUCU GCCAGAUC | 1019 |
| 2525 | UGUCUCCC G CCUUCUGG | 435 | CCAGAAGG GCCGAAAGGCGAGUCAAGGUCU GGGAGACA | 1020 |
| 2540 | GGGCAUCU G CCUGACAU | 436 | AUGUCAGG GCCGAAAGGCGAGUCAAGGUCU AGAUGCCC | 1021 |
| 2556 | UCCACGGU G CAGCUGGU | 437 | ACCAGCUG GCCGAAAGGCGAGUCAAGGUCU ACCGUGGA | 1022 |
| 2577 | CAGCUUAU G CCCUAUGG | 438 | CCAUAGGG GCCGAAAGGCGAGUCAAGGUCU AUAAGCUG | 1023 |
| 2588 | CUAUGGCU G CCUCUUAG | 439 | CUAAGAGG GCCGAAAGGCGAGUCAAGGUCU AGCCAUAG | 1024 |
| 2615 | GGAAAACC G CGGACGCC | 440 | GGCGUCCG GCCGAAAGGCGAGUCAAGGUCU GGUUUUCC | 1025 |
| 2621 | CCGCGGAC G CCUGGGCU | 441 | AGCCCAGG GCCGAAAGGCGAGUCAAGGUCU GUCCGCGG | 1026 |
| 2640 | CAGGACCU G CUGAACUG | 442 | CAGUUCAG GCCGAAAGGCGAGUCAAGGUCU AGGUCCUG | 1027 |
| 2655 | UGGUGUAU G CAGAUUGC | 443 | GCAAUCUG GCCGAAAGGCGAGUCAAGGUCU AUACACCA | 1028 |
| 2662 | UGCAGAUU G CCAAGGGG | 444 | CCCCUUGG GCCGAAAGGCGAGUCAAGGUCU AAUCUGCA | 1029 |
| 2691 | GAGGAUGU G CGGCUCGU | 445 | ACGAGCCG GCCGAAAGGCGAGUCAAGGUCU ACAUCCUC | 1030 |
| 2716 | ACUUGGCC G CUCGGAAC | 446 | GUUCCGAG GCCGAAAGGCGAGUCAAGGUCU GGCCAAGU | 1031 |
| 2727 | CGGAACGU G CUGGUCAA | 447 | UUGACCAG GCCGAAAGGCGAGUCAAGGUCU ACGUUCCG | 1032 |
| 2781 | GCUCGGCU G CUGGACAU | 448 | AUGUCCAG GCCGAAAGGCGAGUCAAGGUCU AGCCGAGC | 1033 |
| 2809 | AGUACCAU G CAGAUGGG | 449 | CCCAUCUG GCCGAAAGGCGAGUCAAGGUCU AUGGUACU | 1034 |
| 2826 | GGCAAGGU G CCCAUCAA | 450 | UUGAUGGG GCCGAAAGGCGAGUCAAGGUCU ACCUUGCC | 1035 |
| 2844 | UGGAUGGC G CUGGAGUC | 451 | GACUCCAG GCCGAAAGGCGAGUCAAGGUCU GCCAUCCA | 1036 |
| 2861 | CAUUCUCC G CCGGCGGU | 452 | ACCGCCGG GCCGAAAGGCGAGUCAAGGUCU GGAGAAUG | 1037 |
| 2976 | CCUGACCU G CUGGAAAA | 453 | UUUUCCAG GCCGAAAGGCGAGUCAAGGUCU AGGUCAGG | 1038 |
| 2997 | GAGCGGCU G CCCCAGCC | 454 | GGCUGGGG GCCGAAAGGCGAGUCAAGGUCU AGCCGCUC | 1039 |
| 3014 | CCCCAUCU G CACCAUUG | 455 | CAAUGGUG GCCGAAAGGCGAGUCAAGGUCU AGAUGGGG | 1040 |
| 3107 | AUUCUCCC G CAUGGCCA | 456 | UGGCCAUG GCCGAAAGGCGAGUCAAGGUCU GGGAGAAU | 1041 |
| 3128 | CCCCCAGC G CUUUGUGG | 457 | CCACAAAG GCCGAAAGGCGAGUCAAGGUCU GCUGGGGG | 1042 |
| 3191 | CUUCUACC G CUCACUGC | 458 | GCAGUGAG GCCGAAAGGCGAGUCAAGGUCU GGUAGAAG | 1043 |
| 3198 | CGCUCACU G CUGGAGGA | 459 | UCCUCCAG GCCGAAAGGCGAGUCAAGGUCU AGUGAGCG | 1044 |
| 3232 | UGGUGGAU G CUGAGGAG | 460 | CUCCUCAG GCCGAAAGGCGAGUCAAGGUCU AUCCACCA | 1045 |

TABLE XVI-continued

Human HER2 Class II (zinzyme) Ribozyme and Target Sequence

| Pos | Substrate | Seq ID | Ribozyme | Seq ID |
|---|---|---|---|---|
| 3280 | CAGACCCU G CCCCGGGC | 461 | GCCCGGGG GCCGAAAGGCGAGUCAAGGUCU AGGGUCUG | 1046 |
| 3289 | CCCCGGGC G CUGGGGGC | 462 | GCCCCCAG GCCGAAAGGCGAGUCAAGGUCU GCCCGGGG | 1047 |
| 3317 | CAGGCACC G CAGCUCAU | 463 | AUGAGCUG GCCGAAAGGCGAGUCAAGGUCU GGUGCCUG | 1048 |
| 3468 | AAGGGGCU G CAAAGCCU | 464 | AGGCUUUG GCCGAAAGGCGAGUCAAGGUCU AGCCCCUU | 1049 |
| 3534 | GUACCCCU G CCCUCUGA | 465 | UCAGAGGG GCCGAAAGGCGAGUCAAGGUCU AGGGGUAC | 1050 |
| 3559 | GCUACGUU G CCCCCCUG | 466 | CAGGGGGG GCCGAAAGGCGAGUCAAGGUCU AACGUAGC | 1051 |
| 3572 | CCUGACCU G CAGCCCCC | 467 | GGGGGCUG GCCGAAAGGCGAGUCAAGGUCU AGGUCAGG | 1052 |
| 3627 | CCCCCUUC G CCCCGAGA | 468 | UCUCGGGG GCCGAAAGGCGAGUCAAGGUCU GAAGGGGG | 1053 |
| 3645 | GGCCCUCU G CCUGCUGC | 469 | GCAGCAGG GCCGAAAGGCGAGUCAAGGUCU AGAGGGCC | 1054 |
| 3649 | CUCUGCCU G CUGCCCGA | 470 | UCGGGCAG GCCGAAAGGCGAGUCAAGGUCU AGGCAGAG | 1055 |
| 3652 | UGCCUGCU G CCCGACCU | 471 | AGGUCGGG GCCGAAAGGCGAGUCAAGGUCU AGCAGGCA | 1056 |
| 3661 | CCCGACCU G CUGGUGCC | 472 | GGCACCAG GCCGAAAGGCGAGUCAAGGUCU AGGUCGGG | 1057 |
| 3667 | CUGCUGGU G CCACUCUG | 473 | CAGAGUGG GCCGAAAGGCGAGUCAAGGUCU ACCAGCAG | 1058 |
| 3730 | ACGUUUUU G CCUUUGGG | 474 | CCCAAAGG GCCGAAAGGCGAGUCAAGGUCU AAAAACGU | 1059 |
| 3742 | UUGGGGGU G CCGUGGAG | 475 | CUCCACGG GCCGAAAGGCGAGUCAAGGUCU ACCCCCAA | 1060 |
| 3784 | GAGGAGCU G CCCCUCAG | 476 | CUGAGGGG GCCGAAAGGCGAGUCAAGGUCU AGCUCCUC | 1061 |
| 3808 | CUCCUCCU G CCUUCAGC | 477 | GCUGAAGG GCCGAAAGGCGAGUCAAGGUCU AGGAGGAG | 1062 |
| 3933 | CUGGACGU G CCAGUGUG | 478 | CACACUGG GCCGAAAGGCGAGUCAAGGUCU ACGUCCAG | 1063 |
| 3960 | CCAAGUCC G CAGAAGCC | 479 | GGCUUCUG GCCGAAAGGCGAGUCAAGGUCU GGACUUGG | 1064 |
| 4007 | UGACUUCU G CUGGCAUC | 480 | GAUGCCAG GCCGAAAGGCGAGUCAAGGUCU AGAAGUCA | 1065 |
| 4056 | GGGAACCU G CCAUGCCA | 481 | UGGCAUGG GCCGAAAGGCGAGUCAAGGUCU AGGUUCCC | 1066 |
| 4061 | CCUGCCAU G CCAGGAAC | 482 | GUUCCUGG GCCGAAAGGCGAGUCAAGGUCU AUGGCAGG | 1067 |
| 4094 | UCCUUCCU G CUUGAGUU | 483 | AACUCAAG GCCGAAAGGCGAGUCAAGGUCU AGGAAGGA | 1068 |
| 4179 | GAGGCCCU G CCCAAUGA | 484 | UCAUUGGG GCCGAAAGGCGAGUCAAGGUCU AGGGCCUC | 1069 |
| 4208 | CAGUGGAU G CCACAGCC | 485 | GGCUGUGG GCCGAAAGGCGAGUCAAGGUCU AUCCACUG | 1070 |
| 4351 | CUAGUACU G CCCCCCAU | 486 | AUGGGGGG GCCGAAAGGCGAGUCAAGGUCU AGUACUAG | 1071 |
| 4406 | UACAGAGU G CUUUUCUG | 487 | CAGAAAAG GCCGAAAGGCGAGUCAAGGUCU ACUCUGUA | 1072 |
| 192 | GCGGCCUU G UGCCGCUG | 488 | CAGCGGCA GCCGAAAGGCGAGUCAAGGUCU AAGGCCGC | 1073 |
| 249 | ACCCAAGU G UGCACCGG | 489 | CCGGUGCA GCCGAAAGGCGAGUCAAGGUCU ACUUGGGU | 1074 |
| 387 | GCCAGCCU G UCCUUCCU | 490 | AGGAAGGA GCCGAAAGGCGAGUCAAGGUCU AGGCUGGC | 1075 |
| 478 | UGCGGAUU G UGCGAGGC | 491 | GCCUCGCA GCCGAAAGGCGAGUCAAGGUCU AAUCCGCA | 1076 |
| 559 | CCACCCCU G UCACAGGG | 492 | CCCUGUGA GCCGAAAGGCGAGUCAAGGUCU AGGGGUGG | 1077 |
| 678 | ACGAUUUU G UGGAAGGA | 493 | UCCUUCCA GCCGAAAGGCGAGUCAAGGUCU AAAAUCGU | 1078 |
| 758 | CCACCCCU G UUCUCCGA | 494 | UCGGAGAA GCCGAAAGGCGAGUCAAGGUCU AGGGGUGG | 1079 |
| 768 | UCUCCGAU G UGUAAGGG | 495 | CCCUUACA GCCGAAAGGCGAGUCAAGGUCU AUCGGAGA | 1080 |
| 770 | UCCGAUGU G UAAGGGCU | 496 | AGCCCUUA GCCGAAAGGCGAGUCAAGGUCU ACAUCGGA | 1081 |
| 809 | UGAGGAUU G UCAGAGCC | 497 | GGCUCUGA GCCGAAAGGCGAGUCAAGGUCU AAUCCUCA | 1082 |
| 829 | CGCGCACU G UCUGUGCC | 498 | GGCACAGA GCCGAAAGGCGAGUCAAGGUCU AGUGCGCG | 1083 |
| 833 | CACUGUCU G UGCCGGUG | 499 | CACCGGCA GCCGAAAGGCGAGUCAAGGUCU AGACAGUG | 1084 |
| 845 | CGGUGGCU G UGCCCGCU | 500 | AGCGGGCA GCCGAAAGGCGAGUCAAGGUCU AGCCACCG | 1085 |
| 893 | UGAGCAGU G UGCUGCCG | 501 | CGGCAGCA GCCGAAAGGCGAGUCAAGGUCU ACUGCUCA | 1086 |
| 965 | UGGCAUCU G UGAGCUGC | 502 | GCAGCUCA GCCGAAAGGCGAGUCAAGGUCU AGAUGCCA | 1087 |
| 1058 | CGCCAGCU G UGUGACUG | 503 | CAGUCACA GCCGAAAGGCGAGUCAAGGUCU AGCUGGCG | 1088 |
| 1060 | CCAGCUGU G UGACUGCC | 504 | GGCAGUCA GCCGAAAGGCGAGUCAAGGUCU ACAGCUGG | 1089 |
| 1070 | GACUGCCU G UCCCUACA | 505 | UGUAGGGA GCCGAAAGGCGAGUCAAGGUCU AGGCAGUC | 1090 |
| 1166 | ACAGCGGU G UGAGAAGU | 506 | ACUUCUCA GCCGAAAGGCGAGUCAAGGUCU ACCGCUGU | 1091 |
| 1187 | CAAGCCCU G UGCCCGAG | 507 | CUCGGGCA GCCGAAAGGCGAGUCAAGGUCU AGGGCUUG | 1092 |
| 1197 | GCCCGAGU G UGCUAUGG | 508 | CCAUAGCA GCCGAAAGGCGAGUCAAGGUCU ACUCGGGC | 1093 |
| 1371 | CUCCAAGU G UUUGAGAC | 509 | GUCUCAAA GCCGAAAGGCGAGUCAAGGUCU ACUUGGAG | 1094 |
| 1685 | GGACGAGU G UGUGGGCG | 510 | CGCCCACA GCCGAAAGGCGAGUCAAGGUCU ACUCGUCC | 1095 |
| 1687 | ACGAGUGU G UGGGCGAG | 511 | CUCGCCCA GCCGAAAGGCGAGUCAAGGUCU ACACUCGU | 1096 |
| 1716 | CACCAGCU G UGCGCCCG | 512 | CGGGCGCA GCCGAAAGGCGAGUCAAGGUCU AGCUGGUG | 1097 |
| 1757 | CACCCAGU G UGUCAACU | 513 | AGUUGACA GCCGAAAGGCGAGUCAAGGUCU ACUGGGUG | 1098 |
| 1759 | CCCAGUGU G UCAACUGC | 514 | GCAGUUGA GCCGAAAGGCGAGUCAAGGUCU ACACUGGG | 1099 |
| 1837 | GGGAGUAU G UGAAUGCC | 515 | GGCAUUCA GCCGAAAGGCGAGUCAAGGUCU AUACUCCC | 1100 |
| 1853 | CAGGCACU G UUUGCCGU | 516 | ACGGCAAA GCCGAAAGGCGAGUCAAGGUCU AGUGCCUG | 1101 |
| 1874 | CCCUGAGU G UCAGCCCC | 517 | GGGGCUGA GCCGAAAGGCGAGUCAAGGUCU ACUCAGGG | 1102 |
| 1901 | AGUGACCU G UUUUGGAC | 518 | GUCCAAAA GCCGAAAGGCGAGUCAAGGUCU AGGUCACU | 1103 |
| 1925 | UGACCAGU G UGUGGCCU | 519 | AGGCCACA GCCGAAAGGCGAGUCAAGGUCU ACUGGUCA | 1104 |
| 1927 | ACCAGUGU G UGGCCUGU | 520 | ACAGGCCA GCCGAAAGGCGAGUCAAGGUCU ACACUGGU | 1105 |
| 1934 | UGUGGCCU G UGCCCACU | 521 | AGUGGGCA GCCGAAAGGCGAGUCAAGGUCU AGGCCACA | 1106 |
| 1984 | CCAGCGGU G UGAAACCU | 522 | AGGUUUCA GCCGAAAGGCGAGUCAAGGUCU ACCGCUGG | 1107 |
| 2075 | CCACUCCU G UGUGGACC | 523 | GGUCCACA GCCGAAAGGCGAGUCAAGGUCU AGGAGUGG | 1108 |
| 2077 | ACUCCUGU G UGGACCUG | 524 | CAGGUCCA GCCGAAAGGCGAGUCAAGGUCU ACAGGAGU | 1109 |
| 2410 | GGGAGAAU G UGAAAAUU | 525 | AAUUUUCA GCCGAAAGGCGAGUCAAGGUCU AUUCUCCC | 1110 |
| 2436 | AUCAAAGU G UUGAGGGA | 526 | UCCCUCAA GCCGAAAGGCGAGUCAAGGUCU ACUUUGAU | 1111 |
| 2503 | UGGCUGGU G UGGGCUCC | 527 | GGAGCCCA GCCGAAAGGCGAGUCAAGGUCU ACCAGCCA | 1112 |
| 2518 | CCCCAUAU G UCUCCCGC | 528 | GCGGGAGA GCCGAAAGGCGAGUCAAGGUCU AUAUGGGG | 1113 |
| 2602 | UAGACCAU G UCCGGGAA | 529 | UUCCCGGA GCCGAAAGGCGAGUCAAGGUCU AUGGUCUA | 1114 |
| 2651 | GAACUGGU G UAUGCAGA | 530 | UCUGCAUA GCCGAAAGGCGAGUCAAGGUCU ACCAGUUC | 1115 |
| 2689 | UGGAGGAU G UGCGGCUC | 531 | GAGCCGCA GCCGAAAGGCGAGUCAAGGUCU AUCCUCCA | 1116 |
| 2749 | CCAACCAU G UCAAAAUU | 532 | AAUUUUGA GCCGAAAGGCGAGUCAAGGUCU AUGGUUGG | 1117 |
| 2887 | AGAGUGAU G UGUGGAGU | 533 | ACUCCACA GCCGAAAGGCGAGUCAAGGUCU AUCACUCU | 1118 |
| 2889 | AGUGAUGU G UGGAGUUA | 534 | UAACUCCA GCCGAAAGGCGAGUCAAGGUCU ACAUCACU | 1119 |
| 2902 | GUUAUGGU G UGACUGUG | 535 | CACAGUCA GCCGAAAGGCGAGUCAAGGUCU ACCAUAAC | 1120 |

TABLE XVI-continued

Human HER2 Class II (zinzyme) Ribozyme and Target Sequence

| Pos | Substrate | Seq ID | Ribozyme | Seq ID |
|---|---|---|---|---|
| 2908 | GUGUGACU G UGUGGGAG | 536 | CUCCCACA GCCGAAAGGCGAGUCAAGGUCU AGUCACAC | 1121 |
| 2910 | GUGACUGU G UGGGAGCU | 537 | AGCUCCCA GCCGAAAGGCGAGUCAAGGUCU ACAGUCAC | 1122 |
| 3025 | CCAUUGAU G UCUACAUG | 538 | CAUGUAGA GCCGAAAGGCGAGUCAAGGUCU AUCAAUGG | 1123 |
| 3047 | GGUCAAAU G UUGGAUGA | 539 | UCAUCCAA GCCGAAAGGCGAGUCAAGGUCU AUUUGACC | 1124 |
| 3068 | CUCUGAAU G UCGGCCAA | 540 | UUGGCCGA GCCGAAAGGCGAGUCAAGGUCU AUUCAGAG | 1125 |
| 3093 | GAGUUGGU G UCUGAAUU | 541 | AAUUCAGA GCCGAAAGGCGAGUCAAGGUCU ACCAACUC | 1126 |
| 3133 | AGCGCUUU G UGGUCAUC | 542 | GAUGACCA GCCGAAAGGCGAGUCAAGGUCU AAAGCGCU | 1127 |
| 3269 | CUUCUUCU G UCCAGACC | 543 | GGUCUGGA GCCGAAAGGCGAGUCAAGGUCU AGAAGAAG | 1128 |
| 3427 | GCUCCGAU G UAUUUGAU | 544 | AUCAAAUA GCCGAAAGGCGAGUCAAGGUCU AUCGGAGC | 1129 |
| 3592 | CUGAAUAU G UGAACCAG | 545 | CUGGUUCA GCCGAAAGGCGAGUCAAGGUCU AUAUUCAG | 1130 |
| 3607 | AGCCAGAU G UUCGGCCC | 546 | GGGCCGAA GCCGAAAGGCGAGUCAAGGUCU AUCUGGCU | 1131 |
| 3939 | GUGCCAGU G UGAACCAG | 547 | CUGGUUCA GCCGAAAGGCGAGUCAAGGUCU ACUGGCAC | 1132 |
| 3974 | GCCCUGAU G UGUCCUCA | 548 | UGAGGACA GCCGAAAGGCGAGUCAAGGUCU AUCAGGGC | 1133 |
| 3976 | CCUGAUGU G UCCUCAGG | 549 | CCUGAGGA GCCGAAAGGCGAGUCAAGGUCU ACAUCAGG | 1134 |
| 4072 | AGGAACCU G UCCUAAGG | 550 | CCUUAGGA GCCGAAAGGCGAGUCAAGGUCU AGGUUCCU | 1135 |
| 4162 | GAGUCUUU G UGGAUUCU | 551 | AGAAUCCA GCCGAAAGGCGAGUCAAGGUCU AAAGACUC | 1136 |
| 4300 | AAGGGAGU G UCUAAGAA | 552 | UUCUUAGA GCCGAAAGGCGAGUCAAGGUCU ACUCCCUU | 1137 |
| 4332 | CAGAGACU G UCCCUGAA | 553 | UUCAGGGA GCCGAAAGGCGAGUCAAGGUCU AGUCUCUG | 1138 |
| 4380 | GCAAUGGU G UCAGUAUC | 554 | GAUACUGA GCCGAAAGGCGAGUCAAGGUCU ACCAUUGC | 1139 |
| 4397 | CAGGCUUU G UACAGAG | 555 | ACUCUGUA GCCGAAAGGCGAGUCAAGGUCU AAAGCCUG | 1140 |
| 4414 | GCUUUUCU G UUUAGUUU | 556 | AAACUAAA GCCGAAAGGCGAGUCAAGGUCU AGAAAAGC | 1141 |
| 4434 | CUUUUUUU G UUUUGUUU | 557 | AAACAAAA GCCGAAAGGCGAGUCAAGGUCU AAAAAAAG | 1142 |
| 4439 | UUUGUUUU G UUUUUUUA | 558 | UAAAAAAA GCCGAAAGGCGAGUCAAGGUCU AAAACAAA | 1143 |
| 9 | AAGGGGAG G UAACCCUG | 559 | CAGGGUUA GCCGAAAGGCGAGUCAAGGUCU CUCCCCUU | 1144 |
| 18 | UAACCCUG G CCCCUUUG | 560 | CAAAGGGG GCCGAAAGGCGAGUCAAGGUCU CAGGGUUA | 1145 |
| 27 | CCCCUUUG G UCGGGGCC | 561 | GGCCCCGA GCCGAAAGGCGAGUCAAGGUCU CAAAGGGG | 1146 |
| 33 | UGGUCGGG G CCCCGGGC | 562 | GCCCGGGG GCCGAAAGGCGAGUCAAGGUCU CCCGACCA | 1147 |
| 40 | GGCCCCGG G CAGCCGCG | 563 | CGCGGCUG GCCGAAAGGCGAGUCAAGGUCU CCGGGGCC | 1148 |
| 43 | CCCGGGCA G CCGCGCGC | 564 | GCGCGCGG GCCGAAAGGCGAGUCAAGGUCU UGCCCGGG | 1149 |
| 65 | CCCACGGG G CCCUUUAC | 565 | GUAAAGGG GCCGAAAGGCGAGUCAAGGUCU CCCGUGGG | 1150 |
| 89 | CGCGCCCG G CCCCCACC | 566 | GGUGGGGG GCCGAAAGGCGAGUCAAGGUCU CGGGCGCG | 1151 |
| 105 | CCCUCGCA G CACCCCGC | 567 | GCGGGGUG GCCGAAAGGCGAGUCAAGGUCU UGCGAGGG | 1152 |
| 130 | CCCUCCCA G CCGGGUCC | 568 | GGACCCGG GCCGAAAGGCGAGUCAAGGUCU UGGGAGGG | 1153 |
| 135 | CCAGCCGG G UCCAGCCG | 569 | CGGCUGGA GCCGAAAGGCGAGUCAAGGUCU CCGGCUGG | 1154 |
| 140 | CGGGUCCA G CCGGAGCC | 570 | GGCUCCGG GCCGAAAGGCGAGUCAAGGUCU UGGACCCG | 1155 |
| 146 | CAGCCGGA G CCAUGGGG | 571 | CCCCAUGG GCCGAAAGGCGAGUCAAGGUCU UCCGGCUG | 1156 |
| 154 | GCCAUGGG G CCGGAGCC | 572 | GGCUCCGG GCCGAAAGGCGAGUCAAGGUCU CCCAUGGC | 1157 |
| 160 | GGGCCGGA G CCGCAGUG | 573 | CACUGCGG GCCGAAAGGCGAGUCAAGGUCU UCCGGCCC | 1158 |
| 166 | GAGCCGCA G UGAGCACC | 574 | GGUGCUCA GCCGAAAGGCGAGUCAAGGUCU UGCGGCUC | 1159 |
| 170 | CGCAGUGA G CACCAUGG | 575 | CCAUGGUG GCCGAAAGGCGAGUCAAGGUCU UCACUGCG | 1160 |
| 180 | ACCAUGGA G CUGGCGGC | 576 | GCCGCCAG GCCGAAAGGCGAGUCAAGGUCU UCCAUGGU | 1161 |
| 184 | UGGAGCUG G CGGCCUUG | 577 | CAAGGCCG GCCGAAAGGCGAGUCAAGGUCU CAGCUCCA | 1162 |
| 187 | AGCUGGCG G CCUUGUGC | 578 | GCACAAGG GCCGAAAGGCGAGUCAAGGUCU CGCCAGCU | 1163 |
| 204 | CGCUGGGG G CUCCUCCU | 579 | AGGAGGAG GCCGAAAGGCGAGUCAAGGUCU CCCCAGCG | 1164 |
| 232 | CCCCCGGA G CCGCGAGC | 580 | GCUCGCGG GCCGAAAGGCGAGUCAAGGUCU UCCGGGGG | 1165 |
| 239 | AGCCGCGA G CACCCAAG | 581 | CUUGGGUG GCCGAAAGGCGAGUCAAGGUCU UCGCGGCU | 1166 |
| 247 | GCACCCAA G UGUGCACC | 582 | GGUGCACA GCCGAAAGGCGAGUCAAGGUCU UUGGGUGC | 1167 |
| 257 | GUGCACCG G CACAGACA | 583 | UGUCUGUG GCCGAAAGGCGAGUCAAGGUCU CGGUGCAC | 1168 |
| 270 | GACAUGAA G CUGCGGCU | 584 | AGCCGCAG GCCGAAAGGCGAGUCAAGGUCU UUCAUGUC | 1169 |
| 276 | AAGCUGCG G CUCCCUGC | 585 | GCAGGGAG GCCGAAAGGCGAGUCAAGGUCU CGCAGCUU | 1170 |
| 287 | CCCUGCCA G UCCCGAGA | 586 | UCUCGGGA GCCGAAAGGCGAGUCAAGGUCU UGGCAGGG | 1171 |
| 329 | CUACCAGG G CUGCCAGG | 587 | CCUGGCAG GCCGAAAGGCGAGUCAAGGUCU CCUGGUAG | 1172 |
| 337 | GCUGCCAG G UGGUGCAG | 588 | CUGCACCA GCCGAAAGGCGAGUCAAGGUCU CUGGCAGC | 1173 |
| 340 | GCCAGGUG G UGCAGGGA | 589 | UCCCUGCA GCCGAAAGGCGAGUCAAGGUCU CACCUGGC | 1174 |
| 383 | CAAUGCCA G CCUGUCCU | 590 | AGGACAGG GCCGAAAGGCGAGUCAAGGUCU UGGCAUUG | 1175 |
| 412 | UCCAGGAG G UGCAGGGC | 591 | GCCCUGCA GCCGAAAGGCGAGUCAAGGUCU CUCCUGGA | 1176 |
| 419 | GGUGCAGG G CUACGUGC | 592 | GCACGUAG GCCGAAAGGCGAGUCAAGGUCU CCUGCACC | 1177 |
| 424 | AGGGCUAC G UGCUCAUC | 593 | GAUGAGCA GCCGAAAGGCGAGUCAAGGUCU GUAGCCCU | 1178 |
| 445 | ACAACCAA G UGAGGCAG | 594 | CUGCCUCA GCCGAAAGGCGAGUCAAGGUCU UUGGUUGU | 1179 |
| 450 | CAAGUGAG G CAGGUCCC | 595 | GGGACCUG GCCGAAAGGCGAGUCAAGGUCU CUCACUUG | 1180 |
| 454 | UGAGGCAG G UCCCACUG | 596 | CAGUGGGA GCCGAAAGGCGAGUCAAGGUCU CUGCCUCA | 1181 |
| 468 | CUGCAGAG G CUGCGGAU | 597 | AUCCGCAG GCCGAAAGGCGAGUCAAGGUCU CUCUGCAG | 1182 |
| 485 | UGUGCGAG G CACCCAGC | 598 | GCUGGGUG GCCGAAAGGCGAGUCAAGGUCU CUCGCACA | 1183 |
| 492 | GGCACCCA G CUCUUUGA | 599 | UCAAAGAG GCCGAAAGGCGAGUCAAGGUCU UGGGUGCC | 1184 |
| 517 | AUGCCCUG G CCGUGCUA | 600 | UAGCACGG GCCGAAAGGCGAGUCAAGGUCU CAGGGCAU | 1185 |
| 520 | CCCUGGCC G UGCUAGAC | 601 | GUCUAGCA GCCGAAAGGCGAGUCAAGGUCU GGCCAGGG | 1186 |
| 568 | UCACAGGG G CCUCCCCA | 602 | UGGGGAGG GCCGAAAGGCGAGUCAAGGUCU CCCUGUGA | 1187 |
| 581 | CCCAGGAG G CCUGCGGG | 603 | CCCGCAGG GCCGAAAGGCGAGUCAAGGUCU CUCCUGGG | 1188 |
| 591 | CUGCGGGA G CUGCAGCU | 604 | AGCUGCAG GCCGAAAGGCGAGUCAAGGUCU UCCCGCAG | 1189 |
| 597 | GAGCUGCA G CUUCGAAG | 605 | CUUCGAAG GCCGAAAGGCGAGUCAAGGUCU UGCAGCUC | 1190 |
| 605 | GCUUCGAA G CCUCACAG | 606 | CUGUGAGG GCCGAAAGGCGAGUCAAGGUCU UUCGAAGC | 1191 |
| 631 | AAGGAGGG G UCUUGAUC | 607 | GAUCAAGA GCCGAAAGGCGAGUCAAGGUCU CCCUCCUU | 1192 |
| 642 | UUGAUCCA G CGGAACCC | 608 | GGGUUCCG GCCGAAAGGCGAGUCAAGGUCU UGGAUCAA | 1193 |
| 654 | AACCCCCA G CUCUGCUA | 609 | UAGCAGAG GCCGAAAGGCGAGUCAAGGUCU UGGGGGUU | 1194 |
| 708 | AACAACCA G CUGGCUCU | 610 | AGAGCCAG GCCGAAAGGCGAGUCAAGGUCU UGGUUGUU | 1195 |

TABLE XVI-continued

Human HER2 Class II (zinzyme) Ribozyme and Target Sequence

| Pos | Substrate | Seq ID | Ribozyme | Seq ID |
|---|---|---|---|---|
| 712 | ACCAGCUG G CUCUCACA | 611 | UGUGAGAG GCCGAAAGGCGAGUCAAGGUCU CAGCUGGU | 1196 |
| 745 | GCUCUCGG G CCUGCCAC | 612 | GUGGCAGG GCCGAAAGGCGAGUCAAGGUCU CCGAGAGC | 1197 |
| 776 | GUGUAAGG G CUCCCGCU | 613 | AGCGGGAG GCCGAAAGGCGAGUCAAGGUCU CCUUACAC | 1198 |
| 797 | GGGAGAGA G UUCUGAGG | 614 | CCUCAGAA GCCGAAAGGCGAGUCAAGGUCU UCUCUCCC | 1199 |
| 815 | UUGUCAGA G CCUGACGC | 615 | GCGUCAGG GCCGAAAGGCGAGUCAAGGUCU UCUGACAA | 1200 |
| 839 | CUGUGCCG G UGGCUGUG | 616 | CACAGCCA GCCGAAAGGCGAGUCAAGGUCU CGGCACAG | 1201 |
| 842 | UGCCGGUG G CUGUGCCC | 617 | GGGCACAG GCCGAAAGGCGAGUCAAGGUCU CACCGGCA | 1202 |
| 861 | UGCAAGGG G CCACUGCC | 618 | GGCAGUGG GCCGAAAGGCGAGUCAAGGUCU CCCUUGCA | 1203 |
| 888 | UGCCAUGA G CAGUGUGC | 619 | GCACACUG GCCGAAAGGCGAGUCAAGGUCU UCAUGGCA | 1204 |
| 891 | CAUGAGCA G UGUGCUGC | 620 | GCAGCACA GCCGAAAGGCGAGUCAAGGUCU UGCUCAUG | 1205 |
| 902 | UGCUGCCG G CUGCACGG | 621 | CCGUGCAG GCCGAAAGGCGAGUCAAGGUCU CGGCAGCA | 1206 |
| *911 | CUGCACGG G CCCCAAGC | 622 | GCUUGGGG GCCGAAAGGCGAGUCAAGGUCU CCGUGCAG | 1207 |
| 918 | GGCCCCAA G CACUCUGA | 623 | UCAGAGUG GCCGAAAGGCGAGUCAAGGUCU UUGGGGCC | 1208 |
| 934 | ACUGCCUG G CCUGCCUC | 624 | GAGGCAGG GCCGAAAGGCGAGUCAAGGUCU CAGGCAGU | 1209 |
| 956 | CAACCACA G UGGCAUCU | 625 | AGAUGCCA GCCGAAAGGCGAGUCAAGGUCU UGUGGUUG | 1210 |
| 959 | CCACAGUG G CAUCUGUG | 626 | CACAGAUG GCCGAAAGGCGAGUCAAGGUCU CACUGUGG | 1211 |
| 969 | AUCUGUGA G CUGCACUG | 627 | CAGUGCAG GCCGAAAGGCGAGUCAAGGUCU UCACAGAU | 1212 |
| 982 | ACUGCCCA G CCCUGGUC | 628 | GACCAGGG GCCGAAAGGCGAGUCAAGGUCU UGGGCAGU | 1213 |
| 988 | CAGCCCUG G UCACCUAC | 629 | GUAGGUGA GCCGAAAGGCGAGUCAAGGUCU CAGGGCUG | 1214 |
| 1008 | ACAGACAC G UUUGAGUC | 630 | GACUCAAA GCCGAAAGGCGAGUCAAGGUCU GUGUCUGU | 1215 |
| 1014 | ACGUUUGA G UCCAUGCC | 631 | GGCAUGGA GCCGAAAGGCGAGUCAAGGUCU UCAAACGU | 1216 |
| 1034 | UCCCGAGG G CCGGUAUA | 632 | UAUACCGG GCCGAAAGGCGAGUCAAGGUCU CCUCGGGA | 1217 |
| 1038 | GAGGGCCG G UAUACAUU | 633 | AAUGUAUA GCCGAAAGGCGAGUCAAGGUCU CGGCCCUC | 1218 |
| 1049 | UACAUUCG G CGCCAGCU | 634 | AGCUGGCG GCCGAAAGGCGAGUCAAGGUCU CGAAUGUA | 1219 |
| 1055 | CGGCGCCA G CUGUGUGA | 635 | UCACACAG GCCGAAAGGCGAGUCAAGGUCU UGGCGCCG | 1220 |
| 1096 | CUACGGAC G UGGGAUCC | 636 | GGAUCCCA GCCGAAAGGCGAGUCAAGGUCU GUCCGUAG | 1221 |
| 1114 | GCACCCUC G UCUGCCCC | 637 | GGGGCAGA GCCGAAAGGCGAGUCAAGGUCU GAGGGUGC | 1222 |
| 1138 | ACCAAGAG G UGACAGCA | 638 | UGCUGUCA GCCGAAAGGCGAGUCAAGGUCU CUCUUGGU | 1223 |
| 1144 | AGGUGACA G CAGAGGAU | 639 | AUCCUCUG GCCGAAAGGCGAGUCAAGGUCU UGUCACCU | 1224 |
| 1161 | GGAACACA G CGGUGUGA | 640 | UCACACCG GCCGAAAGGCGAGUCAAGGUCU UGUGUUCC | 1225 |
| 1164 | ACACAGCG G UGUGAGAA | 641 | UUCUCACA GCCGAAAGGCGAGUCAAGGUCU CGCUGUGU | 1226 |
| 1173 | UGUGAGAA G UGCAGCAA | 642 | UUGCUGCA GCCGAAAGGCGAGUCAAGGUCU UUCUCACA | 1227 |
| 1178 | GAAGUGCA G CAAGCCCU | 643 | AGGGCUUG GCCGAAAGGCGAGUCAAGGUCU UGCACUUC | 1228 |
| 1182 | UGCAGCAA G CCCUGUGC | 644 | GCACAGGG GCCGAAAGGCGAGUCAAGGUCU UUGCUGCA | 1229 |
| 1195 | GUGCCCGA G UGUGCUAU | 645 | AUAGCACA GCCCAAAGGCGAGUCAAGGUCU UCGGGCAC | 1230 |
| 1205 | GUGCUAUG G UCUGGGCA | 646 | UGCCCAGA GCCGAAAGGCGAGUCAAGGUCU CAUAGCAC | 1231 |
| 1211 | UGGUCUGG G CAUGGAGC | 647 | GCUCCAUG GCCGAAAGGCGAGUCAAGGUCU CCAGACCA | 1232 |
| 1218 | GGCAUGGA G CACUUGCG | 648 | CGCAAGUG GCCGAAAGGCGAGUCAAGGUCU UCCAUGCC | 1233 |
| 1231 | UGCGAGAG G UGAGGGCA | 649 | UGCCCUCA GCCGAAAGGCGAGUCAAGGUCU CUCUCGCA | 1234 |
| 1237 | AGGUGAGG G CAGUUACC | 650 | GGUAACUG GCCGAAAGGCGAGUCAAGGUCU CCUCACCU | 1235 |
| 1240 | UGAGGGCA G UUACCAGU | 651 | ACUGGUAA GCCGAAAGGCGAGUCAAGGUCU UGCCCUCA | 1236 |
| 1247 | AGUUACCA G UGCCAAUA | 652 | UAUUGGCA GCCGAAAGGCGAGUCAAGGUCU UGGUAACU | 1237 |
| 1263 | AUCCAGGA G UUUGCUGG | 653 | CCAGCAAA GCCGAAAGGCGAGUCAAGGUCU UCCUGGAU | 1238 |
| 1271 | GUUUGCUG G CUGCAAGA | 654 | UCUUGCAG GCCGAAAGGCGAGUCAAGGUCU CAGCAAAC | 1239 |
| 1292 | CUUUGGGA G CCUGGCAU | 655 | AUGCCAGG GCCCAAAGGCGAGUCAAGGUCU UCCCAAAG | 1240 |
| 1297 | GGAGCCUG G CAUUUCUG | 656 | CAGAAAUG GCCGAAAGGCGAGUCAAGGUCU CAGGCUCC | 1241 |
| 1313 | GCCGGAGA G CUUUGAUG | 657 | CAUCAAAG GCCGAAAGGCGAGUCAAGGUCU UCUCCGGC | 1242 |
| 1330 | GGGACCCA G CCUCCAAC | 658 | GUUGGAGG GCCGAAAGGCGAGUCAAGGUCU UGGGUCCC | 1243 |
| 1353 | CCGCUCCA G CCAGAGCA | 659 | UGCUCUGG GCCGAAAGGCGAGUCAAGGUCU UGGAGCGG | 1244 |
| 1359 | CAGCCAGA G CAGCUCCA | 660 | UGGAGCUG GCCGAAAGGCGAGUCAAGGUCU UCUGGCUG | 1245 |
| i362 | CCAGAGCA G CUCCAAGU | 661 | ACUUGGAG GCCGAAAGGCGAGUCAAGGUCU UGCUCUGG | 1246 |
| i369 | AGCUCCAA G UGUUUGAG | 662 | CUCAAACA GCCGAAAGGCGAGUCAAGGUCU UUGGAGCU | 1247 |
| i397 | GAUCACAG G UUACCUAU | 663 | AUAGGUAA GCCGAAAGGCGAGUCAAGGUCU CUGUGAUC | 1248 |
| i4i4 | ACAUCUCA G CAUGGCCG | 664 | CGGCCAUG GCCGAAAGGCGAGUCAAGGUCU UGAGAUGU | 1249 |
| i4i9 | UCAGCAUG G CCGGACAG | 665 | CUGUCCGG GCCGAAAGGCGAGUCAAGGUCU CAUGCUGA | 1250 |
| i427 | GCCGGACA G CCUGCCUG | 666 | CAGGCAGG GCCGAAAGGCGAGUCAAGGUCU UGUCCGGC | 1251 |
| i442 | UGACCUCA G CGUCUUCC | 667 | GGAAGACG GCCGAAAGGCGAGUCAAGGUCU UGAGGUCA | 1252 |
| i444 | ACCUCAGC G UCUUCCAG | 668 | CUGGAAGA GCCGAAAGGCGAGUCAAGGUCU GCUGAGGU | 1253 |
| i462 | ACCUGCAA G UAAUCCGG | 669 | CCGGAUUA GCCGAAAGGCGAGUCAAGGUCU UUGCAGGU | 1254 |
| i490 | GCACAAUG G CGCCUACU | 670 | AGUAGGCG GCCGAAAGGCGAGUCAAGGUCU CAUUGUGC | 1255 |
| i5i5 | CUGCAAGG G CUGGGCAU | 671 | AUGCCCAG GCCGAAAGGCGAGUCAAGGUCU CCUUGCAG | 1256 |
| i520 | AGGGCUGG G CAUCAGCU | 672 | AGCUGAUG GCCGAAAGGCGAGUCAAGGUCU CCAGCCCU | 1257 |
| i526 | GGGCAUCA G CUGGCUGG | 673 | CCAGCCAG GCCGAAAGGCGAGUCAAGGUCU UGAUGCCC | 1258 |
| i530 | AUCAGCUG G CUGGGGCU | 674 | AGCCCCAG GCCGAAAGGCGAGUCAAGGUCU CAGCUGAU | 1259 |
| i536 | UGGCUGGG G CUGCGCUC | 675 | GAGCGCAG GCCGAAAGGCGAGUCAAGGUCU CCCAGCCA | 1260 |
| i559 | GGAACUGG G CAGUGGAC | 676 | GUCCACUG GCCGAAAGGCGAGUCAAGGUCU CCAGUUCC | 1261 |
| i562 | ACUGGGCA G UGGACUGG | 677 | CCAGUCCA GCCGAAAGGCGAGUCAAGGUCU UGCCCAGU | 1262 |
| i570 | GUGGACUG G CCCUCAUC | 678 | GAUGAGGG GCCGAAAGGCGAGUCAAGGUCU CAGUCCAC | 1263 |
| i603 | UCUGCUUC G UGCACACG | 679 | CGUGUGCA GCCGAAAGGCGAGUCAAGGUCU GAAGCAGA | 1264 |
| i6i2 | UGCACACG G UGCCCUGG | 680 | CCAGGGCA GCCGAAAGGCGAGUCAAGGUCU CGUGUGCA | 1265 |
| i626 | UGGGACCA G CUCUUUCG | 681 | CGAAAGAG GCCGAAAGGCGAGUCAAGGUCU UGGUCCCA | 1266 |
| i648 | CGCACCAA G CUCUGCUC | 682 | GAGCAGAG GCCGAAAGGCGAGUCAAGGUCU UUGGUGCG | 1267 |
| i67i | GCCAACCG G CCAGAGGA | 683 | UCCUCUGG GCCGAAAGGCGAGUCAAGGUCU CGGUUGGC | 1268 |
| i683 | GAGGACGA G UGUGUGGG | 684 | CCCACACA GCCGAAAGGCGAGUCAAGGUCU UCGUCCUC | 1269 |
| i69i | GUGUGUGG G CGAGGGCC | 685 | GGCCCUCG GCCGAAAGGCGAGUCAAGGUCU CCACACAC | 1270 |

TABLE XVI-continued

Human HER2 Class II (zinzyme) Ribozyme and Target Sequence

| Pos | Substrate | Seq ID | Ribozyme | Seq ID |
|---|---|---|---|---|
| i697 | GGGCGAGG G CCUGGCCU | 686 | AGGCCAGG GCCGAAAGGCGAGUCAAGGUCU CCUCGCCC | 1271 |
| i702 | AGGGCCUG G CCUGCCAC | 687 | GUGGCAGG GCCGAAAGGCGAGUCAAGGUCU CAGGCCCU | 1272 |
| i7i3 | UGCCACCA G CUGUGCGC | 688 | GCGCACAG GCCGAAAGGCGAGUCAAGGUCU UGGUGGCA | 1273 |
| i728 | GCCCGAGG G CACUGCUG | 689 | CAGCAGUG GCCGAAAGGCGAGUCAAGGUCU CCUCGGGC | 1274 |
| 1739 | CUGCUGGG G UCCAGGGC | 690 | GCCCUGGA GCCGAAAGGCGAGUCAAGGUCU CCCAGCAG | 1275 |
| 1746 | GGUCCAGG G CCCACCCA | 691 | UGGGUGGG GCCGAAAGGCGAGUCAAGGUCU CCUGGACC | 1276 |
| 1755 | CCCACCCA G UGUGUCAA | 692 | UUGACACA GCCGAAAGGCGAGUCAAGGUCU UGGGUGGG | 1277 |
| 1769 | CAACUGCA G CCAGUUCC | 693 | GGAACUGG GCCGAAAGGCGAGUCAAGGUCU UGCAGUUG | 1278 |
| 1773 | UGCAGCCA G UUCCUUCG | 694 | CGAAGGAA GCCGAAAGGCGAGUCAAGGUCU UGGCUGCA | 1279 |
| 1784 | CCUUCGGG G CCAGGAGU | 695 | ACUCCUGG GCCGAAAGGCGAGUCAAGGUCU CCCGAAGG | 1280 |
| 1791 | GGCCAGGA G UGCGUGGA | 696 | UCCACGCA GCCGAAAGGCGAGUCAAGGUCU UCCUGGCC | 1281 |
| 1795 | AGGAGUGC G UGGAGGAA | 697 | UUCCUCCA GCCGAAAGGCGAGUCAAGGUCU GCACUCCU | 1282 |
| 1810 | AAUGCCGA G UACUGCAG | 698 | CUGCAGUA GCCGAAAGGCGAGUCAAGGUCU UCGGCAUU | 1283 |
| 1821 | CUGCAGGG G CUCCCCAG | 699 | CUGGGGAG GCCGAAAGGCGAGUCAAGGUCU CCCUGCAG | 1284 |
| 1833 | CCCAGGGA G UAUGUGAA | 700 | UUCACAUA GCCGAAAGGCGAGUCAAGGUCU UCCCUGGG | 1285 |
| 1848 | AAUGCCAG G CACUGUUU | 701 | AAACAGUG GCCGAAAGGCGAGUCAAGGUCU CUGGCAUU | 1286 |
| 1860 | UGUUUGCC G UGCCACCC | 702 | GGGUGGCA GCCGAAAGGCGAGUCAAGGUCU GGCAAACA | 1287 |
| 1872 | CACCCUGA G UGUCAGCC | 703 | GGCUGACA GCCGAAAGGCGAGUCAAGGUCU UCAGGGUG | 1288 |
| 1878 | GAGUGUCA G CCCCAGAA | 704 | UUCUGGGG GCCGAAAGGCGAGUCAAGGUCU UGACACUC | 1289 |
| 1889 | CCAGAAUG G CUCAGUGA | 705 | UCACUGAG GCCGAAAGGCGAGUCAAGGUCU CAUUCUGG | 1290 |
| 1894 | AUGGCUCA G UGACCUGU | 706 | ACAGGUCA GCCGAAAGGCGAGUCAAGGUCU UGAGCCAU | 1291 |
| 1915 | GACCGGAG G CUGACCAG | 707 | CUGGUCAG GCCGAAAGGCGAGUCAAGGUCU CUCCGGUC | 1292 |
| 1923 | GCUGACCA G UGUGUGGC | 708 | GCCACACA GCCGAAAGGCGAGUCAAGGUCU UGGUCAGC | 1293 |
| 1930 | AGUGUGUG G CCUGUGCC | 709 | GGCACAGG GCCGAAAGGCGAGUCAAGGUCU CACACACU | 1294 |
| 1963 | CCUUCUGC G UGGCCCGC | 710 | GCGGGCCA GCCGAAAGGCGAGUCAAGGUCU GCAGAAGG | 1295 |
| 1966 | UCUGCGUG G CCCGCUGC | 711 | GCAGCGGG GCCGAAAGGCGAGUCAAGGUCU CACGCAGA | 1296 |
| 1979 | CUGCCCCA G CGGUGUGA | 712 | UCACACCG GCCGAAAGGCGAGUCAAGGUCU UGGGGCAG | 1297 |
| 1982 | CCCCAGCG G UGUGAAAC | 713 | GUUUCACA GCCGAAAGGCGAGUCAAGGUCU CGCUGGGG | 1298 |
| 2019 | AUCUGGAA G UUUCCAGA | 714 | UCUGGAAA GCCGAAAGGCGAGUCAAGGUCU UUCCAGAU | 1299 |
| 2036 | UGAGGAGG G CGCAUGCC | 715 | GGCAUGCG GCCGAAAGGCGAGUCAAGGUCU CCUCCUCA | 1300 |
| 2046 | GCAUGCCA G CCUUGCCC | 716 | GGGCAAGG GCCGAAAGGCGAGUCAAGGUCU UGGCAUGC | 1301 |
| 2096 | UGACAAGG G CUGCCCCG | 717 | CGGGGCAG GCCGAAAGGCGAGUCAAGGUCU CCUUGUCA | 1302 |
| 2109 | CCCGCCGA G CAGAGAGC | 718 | GCUCUCUG GCCGAAAGGCGAGUCAAGGUCU UCGGCGGG | 1303 |
| 2116 | AGCAGAGA G CCAGCCCU | 719 | AGGGCUGG GCCGAAAGGCGAGUCAAGGUCU UCUCUGCU | 1304 |
| 2120 | GAGAGCCA G CCCUCUGA | 720 | UCAGAGGG GCCGAAAGGCGAGUCAAGGUCU UGGCUCUC | 1305 |
| 2130 | CCUCUGAC G UCCAUCAU | 721 | AUGAUGGA GCCGAAAGGCGAGUCAAGGUCU GUCAGAGG | 1306 |
| 2146 | UCUCUGCG G UGGUUGGC | 722 | GCCAACCA GCCGAAAGGCGAGUCAAGGUCU CGCAGAGA | 1307 |
| 2149 | CUGCGGUG G UUGGCAUU | 723 | AAUGCCAA GCCGAAAGGCGAGUCAAGGUCU CACCGCAG | 1308 |
| 2153 | GGUGGUUG G CAUUCUGC | 724 | GCAGAAUG GCCGAAAGGCGAGUCAAGGUCU CAACCACC | 1309 |
| 2164 | UUCUGCUG G UCGUGGUC | 725 | GACCACGA GCCGAAAGGCGAGUCAAGGUCU CAGCAGAA | 1310 |
| 2167 | UGCUGGUC G UGGUCUUG | 726 | CAAGACCA GCCGAAAGGCGAGUCAAGGUCU GACCAGCA | 1311 |
| 2170 | UGGUCGUG G UCUUGGGG | 727 | CCCCAAGA GCCGAAAGGCGAGUCAAGGUCU CACGACCA | 1312 |
| 2179 | UCUUGGGG G UGGUCUUU | 728 | AAAGACCA GCCGAAAGGCGAGUCAAGGUCU CCCCAAGA | 1313 |
| 2182 | UGGGGGUG G UCUUUGGG | 729 | CCCAAAGA GCCGAAAGGCGAGUCAAGGUCU CACCCCCA | 1314 |
| 2202 | CUCAUCAA G CGACGGCA | 730 | UGCCGUCG GCCGAAAGGCGAGUCAAGGUCU UUGAUGAG | 1315 |
| 2208 | AAGCGACG GCAGCAGAA | 731 | UUCUGCUG GCCGAAAGGCGAGUCAAGGUCU CGUCGCUU | 1316 |
| 2211 | CGACGGCA G CAGAAGAU | 732 | AUCUUCUG GCCGAAAGGCGAGUCAAGGUCU UGCCGUCG | 1317 |
| 2226 | AUCCGGAA G UACACGAU | 733 | AUCGUGUA GCCGAAAGGCGAGUCAAGGUCU UUCCGGAU | 1318 |
| 2259 | GAAACGGA G CUGGUGGA | 734 | UCCACCAG GCCGAAAGGCGAGUCAAGGUCU UCCGUUUC | 1319 |
| 2263 | CGGAGCUG G UGGAGCCG | 735 | CGGCUCCA GCCGAAAGGCGAGUCAAGGUCU CAGCUCCG | 1320 |
| 2268 | CUGGUGGA G CCGCUGAC | 736 | GUCAGCGG GCCGAAAGGCGAGUCAAGGUCU UCCACCAG | 1321 |
| 2282 | GACACCUA G CGGAGCGA | 737 | UCGCUCCG GCCGAAAGGCGAGUCAAGGUCU UAGGUGUC | 1322 |
| 2287 | CUAGCGGA G CGAUGCCC | 738 | GGGCAUCG GCCGAAAGGCGAGUCAAGGUCU UCCGCUAG | 1323 |
| 2302 | CCAACCAG G CGCAGAUG | 739 | CAUCUGCG GCCGAAAGGCGAGUCAAGGUCU CUGGUUGG | 1324 |
| 2331 | GAGACGGA G CUGAGGAA | 740 | UUCCUCAG GCCGAAAGGCGAGUCAAGGUCU UCCGUCUC | 1325 |
| 2341 | UGAGGAAG G UGAAGGUG | 741 | CACCUUCA GCCGAAAGGCGAGUCAAGGUCU CUUCCUCA | 1326 |
| 2347 | AGGUGAAG G UGCUUGGA | 742 | UCCAAGCA GCCGAAAGGCGAGUCAAGGUCU CUUCACCU | 1327 |
| 2360 | UGGAUCUG G CGCUUYUG | 743 | CAAAAGCG GCCGAAAGGCGAGUCAAGGUCU CAGAUCCA | 1328 |
| 2369 | CGCUUUUG G CACAGUCU | 744 | AGACUGUG GCCGAAAGGCGAGUCAAGGUCU CAAAAGCG | 1329 |
| 2374 | UUGGCACA G UCUACAAG | 745 | CUUGUAGA GCCGAAAGGCGAGUCAAGGUCU UGUGCCAA | 1330 |
| 2384 | CUACAAGG G CAUCUGGA | 746 | UCCAGAUG GCCGAAAGGCGAGUCAAGGUCU CCUUGUAG | 1331 |
| 2422 | AAAUUCCA G UGGCCAUC | 747 | GAUGGCCA GCCGAAAGGCGAGUCAAGGUCU UGGAAUUU | 1332 |
| 2425 | UUCCAGUG G CCAUCAAA | 748 | UUUGAUGG GCCGAAAGGCGAGUCAAGGUCU CACUGGAA | 1333 |
| 2434 | CCAUCAAA G UGUUGAGG | 749 | CCUCAACA GCCGAAAGGCGAGUCAAGGUCU UUUGAUGG | 1334 |
| 2461 | CCCCCAAA G CCAACAAA | 750 | UUUGUUGG GCCGAAAGGCGAGUCAAGGUCU UUUGGGGG | 1335 |
| 2485 | UAGACGAA G CAUACGUG | 751 | CACGUAUG GCCGAAAGGCGAGUCAAGGUCU UUCGUCUA | 1336 |
| 2491 | AAGCAUAC G UGAUGGCU | 752 | AGCCAUCA GCCGAAAGGCGAGUCAAGGUCU GUAUGCUU | 1337 |
| 2497 | ACGUGAUG G CUGGUGUG | 753 | CACACCAG GCCGAAAGGCGAGUCAAGGUCU CAUCACGU | 1338 |
| 2501 | GAUGGCUG G UGUGGGCU | 754 | AGCCCACA GCCGAAAGGCGAGUCAAGGUCU CAGCCAUC | 1339 |
| 2507 | UGGUGUGG G CUCCCCAU | 755 | AUGGGGAG GCCGAAAGGCGAGUCAAGGUCU CCACACCA | 1340 |
| 2534 | CCUUCUGG G CAUCUGCC | 756 | GGCAGAUG GCCGAAAGGCGAGUCAAGGUCU CCAGAAGG | 1341 |
| 2554 | CAUCCACG G UGCAGCUG | 757 | CAGCUGCA GCCGAAAGGCGAGUCAAGGUCU CGUGGAUG | 1342 |
| 2559 | ACGGUGCA G CUGGUGAC | 758 | GUCACCAG GCCGAAAGGCGAGUCAAGGUCU UGCACCGU | 1343 |
| 2563 | UGCAGCUG G UGACACAG | 759 | CUGUGUCA GCCGAAAGGCGAGUCAAGGUCU CAGCUGCA | 1344 |
| 2571 | GUGACACA G CUUAUGCC | 760 | GGCAUAAG GCCGAAAGGCGAGUCAAGGUCU UGUGUCAC | 1345 |

TABLE XVI-continued

Human HER2 Class II (zinzyme) Ribozyme and Target Sequence

| Pos | Substrate | Seq ID | Ribozyme | Seq ID |
|---|---|---|---|---|
| 2585 | GCCCUAUG G CUGCCUCU | 761 | AGAGGCAG GCCGAAAGGCGAGUCAAGGUCU CAUAGGGC | 1346 |
| 2627 | ACGCCUGG G CUCCCAGG | 762 | CCUGGGAG GCCGAAAGGCGAGUCAAGGUCU CCAGGCGU | 1347 |
| 2649 | CUGAACUG G UGUAUGCA | 763 | UGCAUACA GCCGAAAGGCGAGUCAAGGUCU CAGUUCAG | 1348 |
| 2675 | GGGGAUGA G CUACCUGG | 764 | CCAGGUAG GCCGAAAGGCGAGUCAAGGUCU UCAUCCCC | 1349 |
| 2694 | GAUGUGCG G CUCGUACA | 765 | UGUACGAG GCCGAAAGGCGAGUCAAGGUCU CGCACAUC | 1350 |
| 2698 | UGCGGCUC G UACACAGG | 766 | CCUGUGUA GCCGAAAGGCGAGUCAAGGUCU GAGCCGCA | 1351 |
| 2713 | GGGACUUG G CCGCUCGG | 767 | CCGAGCGG GCCGAAAGGCGAGUCAAGGUCU CAAGUCCC | 1352 |
| 2725 | CUCGGAAC G UGCUGGUC | 768 | GACCAGCA GCCGAAAGGCGAGUCAAGGUCU GUUCCGAG | 1353 |
| 2731 | ACGUGCUG G UCAAGAGU | 769 | ACUCUUGA GCCGAAAGGCGAGUCAAGGUCU CAGCACGU | 1354 |
| 2738 | GGUCAAGA G UCCCAACC | 770 | GGUUGGGA GCCGAAAGGCGAGUCAAGGUCU UCUUGACC | 1355 |
| 2769 | GACUUCGG G CUGGCUCG | 771 | CGAGCCAG GCCGAAAGGCGAGUCAAGGUCU CCGAAGUC | 1356 |
| 2773 | UCGGGCUG G CUCGGCUG | 772 | CAGCCGAG GCCGAAAGGCGAGUCAAGGUCU CAGCCCGA | 1357 |
| 2778 | CUGGCUCG G CUGCUGGA | 773 | UCCAGCAG GCCGAAAGGCGAGUCAAGGUCU CGAGCCAG | 1358 |
| 2802 | GAGACAGA G UACCAUGC | 774 | GCAUGGUA GCCGAAAGGCGAGUCAAGGUCU UCUGUCUC | 1359 |
| 2819 | AGAUGGGG G CAAGGUGC | 775 | GCACCUUG GCCGAAAGGCGAGUCAAGGUCU CCCCAUCU | 1360 |
| 2824 | GGGGCAAG G UGCCCAUC | 776 | GAUGGGCA GCCGAAAGGCGAGUCAAGGUCU CUUGCCCC | 1361 |
| 2835 | CCCAUCAA G UGGAUGGC | 777 | GCCAUCCA GCCGAAAGGCGAGUCAAGGUCU UUGAUGGG | 1362 |
| 2842 | AGUGGAUG G CGCUGGAG | 778 | CUCCAGCG GCCGAAAGGCGAGUCAAGGUCU CAUCCACU | 1363 |
| 2850 | GCGCUGGA G UCCAUUCU | 779 | AGAAUGGA GCCGAAAGGCGAGUCAAGGUCU UCCAGCGC | 1364 |
| 2865 | CUCCGCCG G CGGUUCAC | 780 | GUGAACCG GCCGAAAGGCGAGUCAAGGUCU CGGCGGAG | 1365 |
| 2868 | CGCCGGCG G UUCACCCA | 781 | UGGGUGAA GCCGAAAGGCGAGUCAAGGUCU CGCCGGCG | 1366 |
| 2882 | CCACCAGA G UGAUGUGU | 782 | ACACAUCA GCCGAAAGGCGAGUCAAGGUCU UCUGGUGG | 1367 |
| 2894 | UGUGUGGA G UUAUGGUG | 783 | CACCAUAA GCCGAAAGGCGAGUCAAGGUCU UCCACACA | 1368 |
| 2900 | GAGUUAUG G UGUGACUG | 784 | CAGUCACA GCCGAAAGGCGAGUCAAGGUCU CAUAACUC | 1369 |
| 2916 | GUGUGGGA G CUGAUGAC | 785 | GUCAUCAG GCCGAAAGGCGAGUCAAGGUCU UCCCACAC | 1370 |
| 2932 | CUUUUGGG G CCAAACCU | 786 | AGGUUUGG GCCGAAAGGCGAGUCAAGGUCU CCCAAAAG | 1371 |
| 2956 | GGAUCCCA G CCCGGGAG | 787 | CUCCCGGG GCCGAAAGGCGAGUCAAGGUCU UGGGAUCC | 1372 |
| 2991 | AAGGGGGA G CGGCUGCC | 788 | GGCAGCCG GCCGAAAGGCGAGUCAAGGUCU UCCCCCUU | 1373 |
| 2994 | GGGGAGCG G CUGCCCCA | 789 | UGGGGCAG GCCGAAAGGCGAGUCAAGGUCU CGCUCCCC | 1374 |
| 3003 | CUGCCCCA G CCCCCCAU | 790 | AUGGGGGG GCCGAAAGGCGAGUCAAGGUCU UGGGGCAG | 1375 |
| 3040 | UGAUCAUG G UCAAAUGU | 791 | ACAUUUGA GCCGAAAGGCGAGUCAAGGUCU CAUGAUCA | 1376 |
| 3072 | GAAUGUCG G CCAAGAUU | 792 | AAUCUUGG GCCGAAAGGCGAGUCAAGGUCU CGACAUUC | 1377 |
| 3087 | UUCCGGGA G UUGGUGUC | 793 | GACACCAA GCCGAAAGGCGAGUCAAGGUCU UCCCGGAA | 1378 |
| 3091 | GGGAGUUG G UGUCUGAA | 794 | UUCAGACA GCCGAAAGGCGAGUCAAGGUCU CAACUCCC | 1379 |
| 3112 | CCCGCAUG G CCAGGGAC | 795 | GUCCCUGG GCCGAAAGGCGAGUCAAGGUCU CAUGCGGG | 1380 |
| 3126 | GACCCCCA G CGCUUUGU | 796 | ACAAAGCG GCCGAAAGGCGAGUCAAGGUCU UGGGGGUC | 1381 |
| 3136 | GCUUUGUG G UCAUCCAG | 797 | CUGGAUGA GCCGAAAGGCGAGUCAAGGUCU CACAAAGC | 1382 |
| 3158 | GGACUUGG G CCCAGCCA | 798 | UGGCUGGG GCCGAAAGGCGAGUCAAGGUCU CCAAGUCC | 1383 |
| 3163 | UGGGCCCA G CCAGUCCC | 799 | GGGACUGG GCCGAAAGGCGAGUCAAGGUCU UGGGCCCA | 1384 |
| 3167 | CCCAGCCA G UCCCUUGG | 800 | CCAAGGGA GCCGAAAGGCGAGUCAAGGUCU UGGCUGGG | 1385 |
| 3179 | CUUGGACA G CACCUUCU | 801 | AGAAGGUG GCCGAAAGGCGAGUCAAGGUCU UGUCCAAG | 1386 |
| 3226 | GGGACCUG G UGGAUGCU | 802 | AGCAUCCA GCCGAAAGGCGAGUCAAGGUCU CAGGUCCC | 1387 |
| 3240 | GCUGAGGA G UAUCUGGU | 803 | ACCAGAUA GCCGAAAGGCGAGUCAAGGUCU UCCUCAGC | 1388 |
| 3247 | AGUAUCUG G UACCCCAG | 804 | CUGGGGUA GCCGAAAGGCGAGUCAAGGUCU CAGAUACU | 1389 |
| 3255 | GUACCCCA G CAGGGCUU | 805 | AAGCCCUG GCCGAAAGGCGAGUCAAGGUCU UGGGGUAC | 1390 |
| 3260 | CCAGCAGG G CUUCUUCU | 806 | AGAAGAAG GCCGAAAGGCGAGUCAAGGUCU CCUGCUGG | 1391 |
| 3287 | UGCCCCGG G CGCUGGGG | 807 | CCCCAGCG GCCGAAAGGCGAGUCAAGGUCU CCGGGGCA | 1392 |
| 3296 | CGCUGGGG G CAUGGUCC | 808 | GGACCAUG GCCGAAAGGCGAGUCAAGGUCU CCCCAGCG | 1393 |
| 3301 | GGGGCAUG G UCCACCAC | 809 | GUGGUGGA GCCGAAAGGCGAGUCAAGGUCU CAUGCCCC | 1394 |
| 3312 | CACCACAG G CACCGCAG | 810 | CUGCGGUG GCCGAAAGGCGAGUCAAGGUCU CUGUGGUG | 1395 |
| 3320 | GCACCGCA G CUCAUCUA | 811 | UAGAUGAG GCCGAAAGGCGAGUCAAGGUCU UGCGGUGC | 1396 |
| 3335 | UACCAGGA G UGGCGGUG | 812 | CACCGCCA GCCGAAAGGCGAGUCAAGGUCU UCCUGGUA | 1397 |
| 3338 | CAGGAGUG G CGGUGGGG | 813 | CCCCACCG GCCGAAAGGCGAGUCAAGGUCU CACUCCUG | 1398 |
| 3341 | GAGUGGCG G UGGGGACC | 814 | GGUCCCCA GCCGAAAGGCGAGUCAAGGUCU CGCCACUC | 1399 |
| 3360 | ACACUAGG G CUGGAGCC | 815 | GGCUCCAG GCCGAAAGGCGAGUCAAGGUCU CCUAGUGU | 1400 |
| 3366 | GGGCUGGA G CCCUCUGA | 816 | UCAGAGGG GCCGAAAGGCGAGUCAAGGUCU UCCAGCCC | 1401 |
| 3382 | AAGAGGAG G CCCCCAGG | 817 | CCUGGGGG GCCGAAAGGCGAGUCAAGGUCU CUCCUCUU | 1402 |
| 3390 | GCCCCCAG G UCUCCACU | 818 | AGUGGAGA GCCGAAAGGCGAGUCAAGGUCU CUGGGGGC | 1403 |
| 3400 | CUCCACUG G CACCCUCC | 819 | GGAGGGUG GCCGAAAGGCGAGUCAAGGUCU CAGUGGAG | 1404 |
| 3415 | CCGAAGGG G CUGGCUCC | 820 | GGAGCCAG GCCGAAAGGCGAGUCAAGGUCU CCCUUCGG | 1405 |
| 3419 | AGGGGCUG G CUCCGAUG | 821 | CAUCGGAG GCCGAAAGGCGAGUCAAGGUCU CAGCCCCU | 1406 |
| 3437 | AUUUGAUG G UGACCUGG | 822 | CCAGGUCA GCCGAAAGGCGAGUCAAGGUCU CAUCAAAU | 1407 |
| 3454 | GAAUGGGG G CAGCCAAG | 823 | CUUGGCUG GCCGAAAGGCGAGUCAAGGUCU CCCCAUUC | 1408 |
| 3457 | UGGGGGCA G CCAAGGGG | 824 | CCCCUUGG GCCGAAAGGCGAGUCAAGGUCU UGCCCCCA | 1409 |
| 3465 | GCCAAGGG G CUGCAAAG | 825 | CUUUGCAG GCCGAAAGGCGAGUCAAGGUCU CCCUUGGC | 1410 |
| 3473 | GCUGCAAA G CCUCCCCA | 826 | UGGGGAGG GCCGAAAGGCGAGUCAAGGUCU UUUGCAGC | 1411 |
| 3494 | UGACCCCA G CCCUCUAC | 827 | GUAGAGGG GCCGAAAGGCGAGUCAAGGUCU UGGGGUCA | 1412 |
| 3504 | CCUCUACA G CGGUACAG | 828 | CUGUACCG GCCGAAAGGCGAGUCAAGGUCU UGUAGAGG | 1413 |
| 3507 | CUACAGCG G UACAGUGA | 829 | UCACUGUA GCCGAAAGGCGAGUCAAGGUCU CGCUGUAG | 1414 |
| 3512 | GCGGUACA G UGAGGACC | 830 | GGUCCUCA GCCGAAAGGCGAGUCAAGGUCU UGUACCGC | 1415 |
| 3526 | ACCCCACA G UACCCCUG | 831 | CAGGGGUA GCCGAAAGGCGAGUCAAGGUCU UGUGGGGU | 1416 |
| 3551 | GACUGAUG G CUACGUUG | 832 | CAACGUAG GCCGAAAGGCGAGUCAAGGUCU CAUCAGUC | 1417 |
| 3556 | AUGGCUAC G UUGCCCCC | 833 | GGGGGCAA GCCGAAAGGCGAGUCAAGGUCU GUAGCCAU | 1418 |
| 3575 | GACCUGCA G CCCCCAGC | 834 | GCUGGGGG GCCGAAAGGCGAGUCAAGGUCU UGCAGGUC | 1419 |
| 3582 | AGCCCCCA G CCUGAAUA | 835 | UAUUCAGG GCCGAAAGGCGAGUCAAGGUCU UGGGGGCU | 1420 |

TABLE XVI-continued

Human HER2 Class II (zinzyme) Ribozyme and Target Sequence

| Pos | Substrate | Seq ID | Ribozyme | Seq ID |
|---|---|---|---|---|
| 3600 | GUGAACCA G CCAGAUGU | 836 | ACAUCUGG GCCGAAAGGCGAGUCAAGGUCU UGGUUCAC | 1421 |
| 3612 | GAUGUUCG G CCCCAGCC | 837 | GGCUGGGG GCCGAAAGGCGAGUCAAGGUCU CGAACAUC | 1422 |
| 3618 | CGGCCCCA G CCCCCUUC | 838 | GAAGGGGG GCCGAAAGGCGAGUCAAGGUCU UGGGGCCG | 1423 |
| 3638 | CCGAGAGG G CCCUCUGC | 839 | GCAGAGGG GCCGAAAGGCGAGUCAAGGUCU CCUCUCGG | 1424 |
| 3665 | ACCUGCUG G UGCCACUC | 840 | GAGUGGCA GCCGAAAGGCGAGUCAAGGUCU CAGCAGGU | 1425 |
| 3681 | CUGGAAAG G CCCAAGAC | 841 | GUCUUGGG GCCGAAAGGCGAGUCAAGGUCU CUUUCCAG | 1426 |
| 3712 | AGAAUGGG G UCGUCAAA | 842 | UUUGACGA GCCGAAAGGCGAGUCAAGGUCU CCCAUUCU | 1427 |
| 3715 | AUGGGGUC G UCAAAGAC | 843 | GUCUUUGA GCCGAAAGGCGAGUCAAGGUCU GACCCCAU | 1428 |
| 3724 | UCAAAGAC G UUUUUGCC | 844 | GGCAAAAA GCCGAAAGGCGAGUCAAGGUCU GUCUUUGA | 1429 |
| 3740 | CUUUGGGG G UGCCGUGG | 845 | CCACGGCA GCCGAAAGGCGAGUCAAGGUCU CCCCAAAG | 1430 |
| 3745 | GGGGUGCC G UGGAGAAC | 846 | GUUCUCCA GCCGAAAGGCGAGUCAAGGUCU GGCACCCC | 1431 |
| 3759 | AACCCCGA G UACUUGAC | 847 | GUCAAGUA GCCGAAAGGCGAGUCAAGGUCU UCGGGGUU | 1432 |
| 3781 | AGGGAGGA G CUGCCCCU | 848 | AGGGGCAG GCCGAAAGGCGAGUCAAGGUCU UCCUCCCU | 1433 |
| 3792 | GCCCCUCA G CCCCACCC | 849 | GGGUGGGG GCCGAAAGGCGAGUCAAGGUCU UGAGGGGC | 1434 |
| 3815 | UGCCUUCA G CCCAGCCU | 850 | AGGCUGGG GCCGAAAGGCGAGUCAAGGUCU UGAAGGCA | 1435 |
| 3820 | UCAGCCCA G CCUUCGAC | 851 | GUCGAAGG GCCGAAAGGCGAGUCAAGGUCU UGGGCUGA | 1436 |
| 3861 | CCACCAGA G CGGGGGGC | 852 | GCCCCCCG GCCGAAAGGCGAGUCAAGGUCU UCUGGUGG | 1437 |
| 3868 | AGCGGGGG G CUCCACCC | 853 | GGGUGGAG GCCGAAAGGCGAGUCAAGGUCU CCCCCGCU | 1438 |
| 3878 | UCCACCCA G CACCUUCA | 854 | UGAAGGUG GCCGAAAGGCGAGUCAAGGUCU UGGGUGGA | 1439 |
| 3901 | CACCUACG G CAGAGAAC | 855 | GUUCUCUG GCCGAAAGGCGAGUCAAGGUCU CGUAGGUG | 1440 |
| 3915 | AACCCAGA G UACCUGGG | 856 | CCCAGGUA GCCGAAAGGCGAGUCAAGGUCU UCUGGGUU | 1441 |
| 3923 | GUACCUGG G UCUGGACG | 857 | CGUCCAGA GCCGAAAGGCGAGUCAAGGUCU CCAGGUAC | 1442 |
| 3931 | GUCUGGAC G UGCCAGUG | 858 | CACUGGCA GCCGAAAGGCGAGUCAAGGUCU GUCCAGAC | 1443 |
| 3937 | ACGUGCCA G UGUGAACC | 859 | GGUUCACA GCCGAAAGGCGAGUCAAGGUCU UGGCACGU | 1444 |
| 3951 | ACCAGAAG G CCAAGUCC | 860 | GGACUUGG GCCGAAAGGCGAGUCAAGGUCU CUUCUGGU | 1445 |
| 3956 | AAGGCCAA G UCCGCAGA | 861 | UCUGCGGA GCCGAAAGGCGAGUCAAGGUCU UUGGCCUU | 1446 |
| 3966 | CCGCAGAA G CCCUGAUG | 862 | CAUCAGGG GCCGAAAGGCGAGUCAAGGUCU UUCUGCGG | 1447 |
| 3987 | CUCAGGGA G CAGGGAAG | 863 | CUUCCCUG GCCGAAAGGCGAGUCAAGGUCU UCCCUGAG | 1448 |
| 3996 | CAGGGAAG G CCUGACUU | 864 | AAGUCAGG GCCGAAAGGCGAGUCAAGGUCU CUUCCCUG | 1449 |
| 4011 | UUCUGCUG G CAUCAAGA | 865 | UCUUGAUG GCCGAAAGGCGAGUCAAGGUCU CAGCAGAA | 1450 |
| 4021 | AUCAAGAG G UGGGAGGG | 866 | CCCUCCCA GCCGAAAGGCGAGUCAAGGUCU CUCUUGAU | 1451 |
| 4029 | GUGGGAGG G CCCUCCGA | 867 | UCGGAGGG GCCGAAAGGCGAGUCAAGGUCU CCUCCCAC | 1452 |
| 4100 | CUGCUUGA G UUCCCAGA | 868 | UCUGGGAA GCCGAAAGGCGAGUCAAGGUCU UCAAGCAG | 1453 |
| 4111 | CCCAGAUG G CUGGAAGG | 869 | CCUUCCAG GCCGAAAGGCGAGUCAAGGUCU CAUCUGGG | 1454 |
| 4121 | UGGAAGGG G UCCAGCCU | 870 | AGGCUGGA GCCGAAAGGCGAGUCAAGGUCU CCCUUCCA | 1455 |
| 4126 | GGGGUCCA G CCUCGUUG | 871 | CAACGAGG GCCGAAAGGCGAGUCAAGGUCU UGGACCCC | 1456 |
| 4131 | CCAGCCUC G UUGGAAGA | 872 | UCUUCCAA GCCGAAAGGCGAGUCAAGGUCU GAGGCUGG | 1457 |
| 4146 | GAGGAACA G CACUGGGG | 873 | CCCCAGUG GCCGAAAGGCGAGUCAAGGUCU UGUUCCUC | 1458 |
| 4156 | ACUGGGGA G UCUUUGUG | 874 | CACAAAGA GCCGAAAGGCGAGUCAAGGUCU UCCCCAGU | 1459 |
| 4174 | AUUCUGAG G CCCUGCCC | 875 | GGGCAGGG GCCGAAAGGCGAGUCAAGGUCU CUCAGAAU | 1460 |
| 4197 | ACUCUAGG G UCCAGUGG | 876 | CCACUGGA GCCGAAAGGCGAGUCAAGGUCU CCUAGAGU | 1461 |
| 4202 | AGGGUCCA G UGGAUGCC | 877 | GGCAUCCA GCCGAAAGGCGAGUCAAGGUCU UGGACCCU | 1462 |
| 4214 | AUGCCACA G CCCAGCUU | 878 | AAGCUGGG GCCGAAAGGCGAGUCAAGGUCU UGUGGCAU | 1463 |
| 4219 | ACAGCCCA G CUUGGCCC | 879 | GGGCCAAG GCCGAAAGGCGAGUCAAGGUCU UGGGCUGU | 1464 |
| 4224 | CCAGCUUG G CCCUUUCC | 880 | GGAAAGGG GCCGAAAGGCGAGUCAAGGUCU CAAGCUGG | 1465 |
| 4246 | GAUCCUGG G UACUGAAA | 881 | UUUCAGUA GCCGAAAGGCGAGUCAAGGUCU CCAGGAUC | 1466 |
| 4255 | UACUGAAA G CCUUAGGG | 882 | CCCUAAGG GCCGAAAGGCGAGUCAAGGUCU UUUCAGUA | 1467 |
| 4266 | UUAGGGAA G CUGGCCUG | 883 | CAGGCCAG GCCGAAAGGCGAGUCAAGGUCU UUCCCUAA | 1468 |
| 4270 | GGAAGCUG G CCUGAGAG | 884 | CUCUCAGG GCCGAAAGGCGAGUCAAGGUCU CAGCUUCC | 1469 |
| 4284 | GAGGGGAA G CGGCCCUA | 885 | UAGGGCCG GCCGAAAGGCGAGUCAAGGUCU UUCCCCUC | 1470 |
| 4287 | GGGAAGCG G CCCUAAGG | 886 | CCUUAGGG GCCGAAAGGCGAGUCAAGGUCU CGCUUCCC | 1471 |
| 4298 | CUAAGGGA G UGUCUAAG | 887 | CUUAGACA GCCGAAAGGCGAGUCAAGGUCU UCCCUUAG | 1472 |
| 4314 | GAACAAAA G CGACCCAU | 888 | AUGGGUCG GCCGAAAGGCGAGUCAAGGUCU UUUUGUUC | 1473 |
| 4346 | GAAACCUA G UACUGCCC | 889 | GGGCAGUA GCCGAAAGGCGAGUCAAGGUCU UAGGUUUC | 1474 |
| 4372 | AAGGAACA G CAAUGGUG | 890 | CACCAUUG GCCGAAAGGCGAGUCAAGGUCU UGUUCCUU | 1475 |
| 4378 | CAGCAAUG G UGUCAGUA | 891 | UACUGACA GCCGAAAGGCGAGUCAAGGUCU CAUUGCUG | 1476 |
| 4384 | UGGUGUCA G UAUCCAGG | 892 | CCUGGAUA GCCGAAAGGCGAGUCAAGGUCU UGACACCA | 1477 |
| 4392 | GUAUCCAG G CUUUGUAC | 893 | GUACAAAG GCCGAAAGGCGAGUCAAGGUCU CUGGAUAC | 1478 |
| 4404 | UGUACAGA G UGCUJUUC | 894 | GAAAAGCA GCCGAAAGGCGAGUCAAGGUCU UCUGUACA | 1479 |
| 4419 | UCUGUUUA G UUUUUACU | 895 | AGUAAAAA GCCGAAAGGCGAGUCAAGGUCU UAAACAGA | 1480 |

Input Sequence = HSERB2R. Cut Site = G/Y
Stem Length = 8. Core Sequence = GCcgaaagGCGaGuCaaGGuCu
HSERB2R (Human c-erb-B-2 mRNA; 4473 bp)

TABLE XVII

Substrate Specificity for Class I Ribozymes

| Substrate sequence | SEQ ID NO | 1-9t mutation | $k_{rel}$ |
|---|---|---|---|
| 5'-GCCGU G GGUUGCAC ACCUUUCC-3' | 1481 | w.t. | 1.00 |
| 5'-GCCG**U** G GGUUGCAC ACCUUUCC-3' | 1481 | A57G | 2.5 |
| 5'-GCCG**A** G GGUUGCAC ACCUUUCC-3' | 1482 | A57U | 0.24 |
| 5'-GCCG**C** G GGUUGCAC ACCUUUCC-3' | 1483 | A57G | 0.66 |
| 5'-GCCG**G** G GGUUGCAC ACCUUUCC-3' | 1484 | AS7C | 0.57 |
| 5'-GCCGU **U** GGUUGCAC ACCUUUCC-3' | 1485 | w.t. | 0.17 |
| 5'-GCCGU **A** GGUUGCAC ACCUUUCC-3' | 1486 | w.t. | n.d. |
| 5'-GCCGU **C** GGUUGCAC ACCUUUCC-3' | 1487 | w.t. | n.d. |
| 5'-GCCGU G GGUUGCAC ACCUUUCC-3' | 1481 | C16U | 0.98 |
| 5'-GCCGU G **U**GUUGCAC ACCUUUCC-3' | 1488 | C16G | n.d. |
| 5'-GCCGU G **U**GUUGCAC ACCUUUCC-3' | 1488 | C16A | 0.65 |
| 5'-GCCGU G **A**GUUGCAC ACCUUUCC-3' | 1489 | C16U | 0.45 |
| 5'-GCCGU G **C**GUUGCAC ACCUUUCC-3' | 1490 | C16G | 0.73 |
| 5'-GCCGU G GGUUGCAC ACCUUU-3' | 1491 | w.t. | 0.89 |
| 5'-GCCGU G GGUUGCAC ACCU-3' | 1492 | w.t. | 1.0 |
| 5'-GCCGU G GGUUGCAC AC-3' | 1493 | w.t. | 0.67 |

TABLE XVIII

Random region alignments/mutations for Class I ribozyme

| | Random region alignments/mutations position | | | | | | | | | | | | | | | | | | | | |
|---|---|---|---|---|---|---|---|---|---|---|---|---|---|---|---|---|---|---|---|---|---|
| clone (#'s) | 1<br>7 | | | 2<br>0 | | | | | | | | | | | 3<br>0 | | | | | | |
| 1–9 motif (42) | G | G | U | G | U | C | A | U | C | A | U | A | | A | U | G | G | C | A | C | C | C |
| 1.1 (39) | | | A | | | | | | | | | | | | | | | | U | | |
| 1.6 | | | | | | | | | | | | | | | | | | | | | |
| 1.27 | | | A | | C | | | | | | | | | | | | | | U | | |
| 1.14 (8) | | | | | | | | | | | | | | | | | A | | | | |
| 1.16 (5) | | | A | | | | | | | | C | | | | | | | | U | | |
| 1.20. | | | A | | A | | | | | | | | | | | | | | U | | |
| 1.24 | | | | | | | | | | | | | U | G | | | | | | | |
| 1.30. | | | A | | | | | | | | | | | | | | | | U | | |
| 2.1 | | | | | C | | | C | | | | | | | | | | | | | |
| 2.13 | | | A | | | | | | | | | | | | | | | | U | | |
| 2.18 (3) | | | A | | | | | | | | | | | | | | | | A | | |
| 2.34 | | | | | | | | | | | | | | | | | A | | | | A |
| 2.21 | | | | | | | | | | | | | | | C | | A | | | | |
| 2.23 (2) | | | | | | | | | | U | | | | | | | | | | | |
| 2.27 | | | A | | C | | G | | | | | | | | | | | | U | | |
| 2.31 | | | | | | | | | | | | | | | | | | | | | |
| 2.35 | | | A | | C | | | C | | | | | | | | | | | U | | |
| 2.36 | | | A | | | | | | | | | | | | | | | | U | | |
| 2.38 (2) | | | A | | | | | | | | | | | G | | | | | U | | |
| 2.45 (2) | | | A | | | | | C | | | | | | | | | | | U | | |
| 3.3 | | | | | | | | C | | | | | | G | | | | | | | |
| 3.6 | | | | | | | | A | | | | | | | | | A | | | | |
| 3.7 | | | A | | | | | C | | | | | | | | | A | | U | | |
| 3.9 | | | | | | | | | | | | | | | | | | | | | |
| 3.26 | | | A | | | — | | C | | | | | | | | | | | U | | |
| 3.27 (2) | | | | | | | | | | | | | | | | | | | U | | |
| 3.28 (2) | | | | | | | | | | G | | | | | | | | | | | |
| 4.13 (3) | | | A | | | | | | | | | | | | | | A | | U | | |
| 4.19 | | | | | | | | | | | | | | | | | | | | | |
| 4.34 (2) | | | A | | | | | | | | | | | | | | | | U | | |
| 4.38 (3) | | | | | | | | | | | | | | | | | | | | | |

mutation maintains base pair

| | Random region alignments/mutations position | | | |
|---|---|---|---|---|
| clone (#'s) | 4<br>0 | 5<br>0 | 5<br>6 | Krel |

TABLE XVIII-continued

Random region alignments/mutations for Class I ribozyme

| | | | | | | | | | | | | | | | | | | | | |
|---|---|---|---|---|---|---|---|---|---|---|---|---|---|---|---|---|---|---|---|---|
| 1–9 motif (42) | U | U | C | A | A | G | G | A | C | A | U | C | G | U | C | C | G | G | G | 1.01 |
| 1.1 (39) | | | | | | | | | | | | | | | | | | | | 0.89 |
| 1.6 | | | | | | | | | | | | A | | | | | | | | 1.06 |
| 1.27 | | | | | | | | | | | | | | | | | | | | 0.95 |
| 1.14 (8) | | | | | | | | | | | | | | | | | | | | 0.82 |
| 1.16 (5) | | | | | | | | | | | | | | | | | | | | 0.66 |
| 1.20. | | | | | | A | | | | | | | | | | | | | | 0.61 |
| 1.24 | | | | | | | | | | | | | | | | | | | | 0.75 |
| 1.30. | | | | | | | | | | | | U | | | | | | | | 0.81 |
| 2.1 | | | | | | | | | | | | | | | | | | | | 0.24 |
| 2.13 | | | | | | | | G | | | | | | | | | | | | 0.19 |
| 2.18 (3) | | | | | | | | | | | | | | | | | | | | 0.02 |
| 2.34 | | | | | | | | | | | | | | | | | | | | 0.62 |
| 2.21 | C | | | | | | | | | | | | | | | | | | | 0.25 |
| 2.23 (2) | | | | | | | | | | | | | | | | | | | | 0.9 |
| 2.27 | | | | | | | | | | | | | | | | | | | | 0.78 |
| 2.31 | | | | | | | | | | | | U | | | | | | | | 1.1 |
| 2.35 | | | | | | | | | | | | | | | | | | | | 0.84 |
| 2.36 | A | | | | | | | | | | | | | | | | | | | 0.31 |
| 2.38 (2) | | | | | | | | | | | | | | | | | | | | 0.81 |
| 2.45 (2) | | | | | | | | | | | | | | | | | | | | 0.36 |
| 3.3 | | | | | | | | | | | | | | | | | | | | 0.6 |
| 3.6 | | | | | | | | | | | | | | | | | | | | 1.11 |
| 3.7 | | | | | | | | | | | | | | | | | | | | 0.98 |
| 3.9 | | | | | | | | | | | | | | | U | | | | | 0.86 |
| 3.26 | | | | | | | | | | | | | | | | | | | | 1.51 |
| 3.27 (2) | | | | | | | | | | | | | | | | | | | | 0.22 |
| 3.28 (2) | | | | | | | | | | | | | | | | | | | | 1.1 |
| 4.13 (3) | | | | | | | | | | | | | | | | | | | | 0.95 |
| 4.19 | A | | | | | | | | | | | | | | | | | | | 0.44 |
| 4.34 (2) | C | | | | | | | | | | | | | | | | | | | 0.27 |
| 4.38 (3) | | | | | | | | | | | C | | | | | | | | | 0.97 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6617438B1). An electronic copy of the "Sequence Listing" will also be available from the USPTO upon request and payment of the fee set forth in 37 CFR 1.19(b)(3).

We claim:

1. An enzymatic nucleic acid molecule having formula III namely:

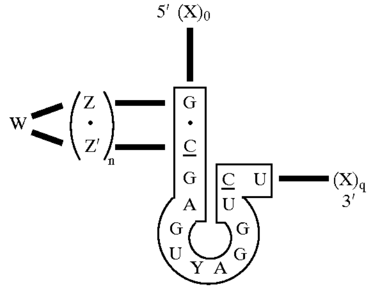

wherein each X, Y, and Z represents independently a nucleotide which may be the same or different; q is an integer selected from the group consisting of 4, 5, 6, 7, 8, 9, 10, 11, 12, and 15; n is an integer ranging from 1 to 10; o is an integer ranging from 3–100; Z' is a nucleotide complementary to Z; each X(q) and X(o) are oligonucleotides which are of sufficient length to stably interact independently with a target nucleic acid sequence; W is a linker ranging from 2 to 70 nucleotides in length or may be a non-nucleotide linker; A, U, G, and C represent nucleotides; C is 2'-amino; and_represents a chemical bond or chemical linkage.

2. The nucleic acid of claim 1, wherein n is selected from the group consisting of 2, 3, 4, 5, 6, and 7.

3. The nucleic acid of claim 1, wherein o is selected from the group consisting of 3, 4, 5, 6, 7, 8, 9, 10, 11, 12, and 15.

4. The enzymatic nucleic acid molecule of claim 1, wherein q and o are of the same length.

5. The enzymatic nucleic acid molecule of claim 1, wherein q and o are of different length.

6. The nucleic acid of claim 1, wherein the target nucleic acid sequence is selected from the group consisting of an RNA, DNA and RNA/DNA mixed polymer.

7. The nucleic acid of claim 1, wherein said chemical linkage is selected from the group consisting of phosphate ester linkage, amide linkage, phosphorothioate, and phosphorodithioate.

8. The enzymatic nucleic acid molecule of claim 1, wherein said enzymatic nucleic acid molecule is chemically synthesized.

9. The enzymatic nucleic acid molecule of claim 1, wherein said enzymatic nucleic acid molecule comprises at least one ribonucleotide.

10. The enzymatic nucleic acid molecule of claim 1, wherein said enzymatic nucleic acid molecule comprises no ribonucleotide residues.

11. The enzymatic nucleic acid molecule of claim 1, wherein said enzymatic nucleic acid molecule comprises at least one 2-amino modification.

12. The enzymatic nucleic acid molecule of claim 1, wherein said enzymatic nucleic acid molecule comprises at least three phosphorothioate modifications.

13. The enzymatic nucleic acid molecule of claim 12, wherein said phosphorothioate modification is at the 5'-end of said enzymatic nucleic acid molecule.

14. The enzymatic nucleic acid molecule of claim 1, wherein said enzymatic nucleic acid molecule comprises a 5'-cap or a 3'-cap or both a 5'-cap and a 3'-cap.

15. The enzymatic nucleic acid molecule of claim 14, wherein said 5-cap is phosphorothioate modification.

16. The enzymatic nucleic acid molecule of claim 14, wherein said 3'-cap is an inverted abasic moiety.

17. The enzymatic nucleic acid molecule of claim 1, wherein said nucleic acid molecule has an endonuclease activity to cleave RNA of HER2 gene.

18. The enzymatic nucleic acid molecule of claim 17, wherein said nucleic acid molecule comprises sequences complementary to any of substrate sequences defined as sequence ID Nos. 85–193 and 310–894.

19. The enzymatic nucleic acid molecule of claim 17, wherein said nucleic acid molecule comprises any of ribozyme sequences defined as sequence ID Nos. 194–309 and 895–1479.

20. The enzymatic nucleic acid molecule of claim 17, wherein said enzymatic nucleic acid molecule comprises a substrate binding region which has between 5 and 30 nucleotides complementary to the RNA.

21. The enzymatic nucleic acid molecule of claim 17, wherein said enzymatic nucleic acid molecule comprises a substrate binding region which has between 7 and 12 nucleotides complementary to the RNA.

22. A composition comprising the enzymatic nucleic acid molecule of claim 1, and a pharmaceutically acceptable carrier.

23. A composition comprising the enzymatic nucleic acid molecule of claim 17, and a pharmaceutically acceptable carrier.

24. The enzymatic nucleic acid molecule of claim 17, wherein said enzymatic nucleic acid molecule comprises at least one sugar modification.

25. The enzymatic nucleic acid molecule of claim 17, wherein said enzymatic nucleic acid molecule comprises at least one nucleic acid base modification.

26. The enzymatic nucleic acid molecule of claim 17, wherein said enzymatic nucleic acid molecule comprises at least one phosphate backbone modification.

27. The enzymatic nucleic acid molecule of claim 17, wherein said phosphate backbone modification is selected from the group consisting of phosphorothioate, phosphorodithioate and amide.

* * * * *